United States Patent
Singh et al.

(10) Patent No.: US 9,458,235 B2
(45) Date of Patent: Oct. 4, 2016

(54) METHOD FOR TREATING A CX3CR1-ASSOCIATED DISEASE WITH CX3CR1-BINDING POLYPEPTIDES

(71) Applicant: Boehringer Ingelheim International GmbH, Ingelheim am Rhein (DE)

(72) Inventors: Sanjaya Singh, Sandy Hook, CT (US); Alisa K. Waterman, Weston, CT (US); Erik Depla, Destelbergen (BE); Toon Laeremans, Dworp (BE); Diane Van Hoorick, Laarne (BE); Cedric Jozef Néotère Ververken, Merelbeke (BE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/682,131

(22) Filed: Apr. 9, 2015

(65) Prior Publication Data

US 2015/0239971 A1    Aug. 27, 2015

Related U.S. Application Data

(62) Division of application No. 13/775,307, filed on Feb. 25, 2013, now Pat. No. 9,035,029.

(60) Provisional application No. 61/603,622, filed on Feb. 27, 2012.

(51) Int. Cl.
| | |
|---|---|
| A61K 39/395 | (2006.01) |
| A61P 13/12 | (2006.01) |
| C07K 16/28 | (2006.01) |
| A61K 39/00 | (2006.01) |

(52) U.S. Cl.
CPC .......... *C07K 16/28* (2013.01); *C07K 16/2866* (2013.01); *A61K 39/3955* (2013.01); *A61K 2039/505* (2013.01); *C07K 2317/22* (2013.01); *C07K 2317/24* (2013.01); *C07K 2317/30* (2013.01); *C07K 2317/52* (2013.01); *C07K 2317/565* (2013.01); *C07K 2317/569* (2013.01); *C07K 2317/76* (2013.01); *C07K 2317/92* (2013.01); *C07K 2317/94* (2013.01); *C07K 2319/00* (2013.01)

(58) Field of Classification Search
None
See application file for complete search history.

(56) References Cited

U.S. PATENT DOCUMENTS

| | | |
|---|---|---|
| 2002/0192212 A1 | 12/2002 | Imai et al. |
| 2010/0113339 A1 | 5/2010 | Beirnaert et al. |
| 2012/0141371 A2 | 6/2012 | Rock et al. |

FOREIGN PATENT DOCUMENTS

| | | |
|---|---|---|
| EP | 1806145 A1 | 7/2007 |
| WO | 0160406 A1 | 8/2001 |

OTHER PUBLICATIONS

D'Haese et al, 2010. Expert Opin Ther Targets. 14(2): 207-219.*
Song et al (2013. Diabetologia. 56: 1661-1669).*
Wong, Brian W.C, et al., "Characterization of fractaline (CX3CL1) and CX3CR1 in human coronary arterise with native atherosclerosis, diabetes mellitus, and transplant vascular disease", Cardiovascular Pathology 2002, pp. 332-338.
Harrison, et al., "Molecular Basis of Cell and Developmental Biology: Mutational Analysis of the Fractaline Chemokine Domain: Basic Amino Acid Residues Differentially contribute to CX3CR1 Binding, Signaling and Cell Adhesion", The Journal of Biological Chemistry, 2001.
Wesolowski, J., et al., "Single Domain Antibodies: promising experimental and therapeutic tools in infection and immunity", Med Microbiol Immunol, 2009, vol. 198, pp. 157-174.
Oh, D., et al., "Fractaline receptor (CXCR1) inhibition is protective against ischemic acute renal failure in mice", American Journal of Physiology-Renal Physiology, 2007.
Muyldermans, S., "Single Domain camel Antibodies: current status", Reviews in Molecular Biology, 2001, pp. 271-302.
Zhang, X., et al., "Involvement of interaction between Fractaline ans CX3Cr1 in cytotoxixity of natural killer cells against tumor cells", Oncology Reports, 2006, pp. 485-488.
Zhou, J., et al., "DEC205-DC targeted DNA vaccines to CX3CR1 and CCL2 are potent and limit macrophage migration", Int. J. Clin. Exp. Med, 2012, pp. 24-33.
Feng, L., et al. "Prevention of crescentic glomerulonephritis by immunoneutralization of the fractaline receptor CX3CR1 Rapid Communnication", Kidney International, 1999, vol. 56, pp. 612-620.
D'Haese, J.,et al., "Fractaline/CX3CR1: why a single chemokine-receptor duo bears a major and unique therapeutic potential", Expert Opinion Therapeutic Targets, 2010, vol. 14, 207-219.
International Search Report, Form PCT/ISA/220, and Written Opinion, Form PCT/ISA/237, for corresponding application PCT/US2013/02780, date of mailing Jun. 27, 2013.
Harrison, Proc. Natl. Acad. Sci., "Role for Neuronally derived fractalkine in mediating interactions between neurons and CX3CR1-exresing microglia", vol. 95, 1998, p. 10896-10901.
Meucci, Dept. of Neurbiology, Pharmacology and Psysiology, "Expression of CX3CR1 chemokine receptors on ieurons and their role in neuronal survival", 2000, p. 1-6.

* cited by examiner

*Primary Examiner* — Zachary Howard
(74) *Attorney, Agent, or Firm* — Michael P. Morris; Edward S. Lazer

(57) ABSTRACT

The present invention relates to CX3CR1-binding polypeptides, in particular polypeptides comprising specific immunoglobulin domains. The invention also relates to nucleic acids encoding such polypeptides; to methods for preparing such polypeptides; to host cells expressing or capable of expressing such polypeptides; to compositions comprising such polypeptides; and to uses of such polypeptides or such compositions, in particular for prophylactic, therapeutic and diagnostic purposes.

2 Claims, No Drawings

US 9,458,235 B2

METHOD FOR TREATING A CX3CR1-ASSOCIATED DISEASE WITH CX3CR1-BINDING POLYPEPTIDES

FIELD OF THE INVENTION

The present invention relates to CX3CR1-binding polypeptides, in particular polypeptides comprising specific immunoglobulin domains. The invention also relates to nucleic acids encoding such polypeptides; to methods for preparing such polypeptides; to host cells expressing or capable of expressing such polypeptides; to compositions comprising such polypeptides; and to uses of such polypeptides or such compositions, in particular for prophylactic, therapeutic and diagnostic purposes.

BACKGROUND OF THE INVENTION

CX3CR1 is a G-protein coupled integral membrane protein, which is a chemokine receptor. It is predominantly expressed on cell types such as monocytes, dendritic cells and T cells that have been associated with the initiation and progression of atherosclerotic plaques. It is upregulated on monocytes by oxidized lipids and mediates migration of these cells into and survival within plaques. Its unique ligand fractalkine (FKN) is expressed on the surface of vascular endothelial and smooth muscle cells in lesions where it modulates leukocyte adhesion. Fractalkine is also released into the circulation by proteolytic cleavage where it functions as a chemotactic agent.

In humans, a CX3CR1 variant (V249I/T280M) with decreased activity has been shown to be associated with a lower risk of cardiovascular disease (coronary heart disease, cerebrovascular disease or peripheral vascular disease) (McDermott, 2001; *Circ Res* 89:401), coronary artery disease (angiographic evidence of stenosis) (McDermott, 2003; *J. Clin. Invest.* 111:1241), and carotid artery occlusive disease (Ghilardi, 2004; *Stroke* 35:1276). CX3CR1 co-localized with fractalkine which showed enhanced immunostaining by polyclonal antibodies within atherosclerotic plaques (Wong, 2002 *Cardiovasc. Path.* 11:332). No fractalkine staining was observed in non-plaque arterial regions.

Several independent mouse genetic studies have shown a beneficial effect of CX3CR1 deficiency on atherosclerosis. A reduction in lesion area in the aortic arch and thoracic aorta as well as a decrease in monocyte/macrophage accumulation in plaques was seen in two independently derived strains of $CX3CR1^{-/-}$ $apoE^{-/-}$ mice fed a high fat diet (Combadière, 2003; *Circulation,* 107:1009, Lesnik, 2003; *J. Clin. Invest.* 111:333).

This shows that CX3CR1 is involved in cardiovascular diseases and the modulation of its activity could provide promising therapies. There is therefore a need for antagonist molecules against CX3CR1 with beneficial pharmacological properties, which can be used as therapeutic agents to treat diseases, in particular cardiovascular diseases in humans.

Accordingly, one aim of the present invention is to provide anti-CX3CR1 antagonist molecules, in particular anti-CX3CR1 antagonist molecules, which have high binding affinity to CX3CR1.

A further aim of the present invention is to provide anti-CX3CR1 antagonist molecules, which have high specificity for CX3CR1.

A further aim of the present invention is to provide anti-CX3CR1 antagonists, which have potent activity.

A further aim of the present invention is to provide anti-CX3CR1 antagonists, which have a favorable bioavailability and half-life.

A further aim of the present invention is to provide anti-CX3CR1 antagonists, which have favorable biophysical properties.

Further aims of the present invention include combinations of any of the aims set forth above.

SUMMARY OF THE INVENTION

The invention provides polypeptides which bind to human CX3CR1 and are capable of blocking the binding of human fractalkine to human CX3CR1. In one aspect, the polypeptide is an immunoglobulin comprising an antigen-binding domain comprising three complementarity determining regions CDR1, CDR2 and CDR3, wherein said immunoglobulin binds to human CX3CR1 and is capable of blocking the binding of human fractalkine to human CX3CR1. In a further aspect, the polypeptide comprises one or more anti-CX3CR1 immunoglobulin single variable domain, wherein said polypeptide is capable of blocking the binding of human fractalkine to human CX3CR1.

In one aspect, a polypeptide of the present invention is characterized by one or more of the following properties:
  Bind with high affinity to human CX3CR1;
  Block the binding of soluble fractalkine to human CX3CR1;
  Inhibit fractalkine induced chemotaxis;
  Inhibit fractalkine induced human CX3CR1 receptor internalization;
  Cross-react with cyno CX3CR1 within 10-fold of $E/IC_{50}$ for human CX3CR1 for binding and functional inhibition.

In a further aspect, a polypeptide of the present invention comprises an anti-CX3CR1 immunoglobulin single variable domain and further comprises a half-life extending moiety, for example an albumin binding moiety, a polyethylene glycol molecule or a Fc domain. In a further aspect, a polypeptide of the present invention comprises two or more anti-CX3CR1 immunoglobulin single variable domains. In one aspect, the two anti-CX3CR1 immunoglobulin single variable domains are covalently linked by a linker peptide. In one aspect, the two anti-CX3CR1 immunoglobulin single variable domains in a polypeptide of the present invention have the same amino acid sequence. In another aspect, the two anti-CX3CR1 immunoglobulin single variable domains in a polypeptide of the present invention have different amino acid sequences. In one aspect, a polypeptide of the present invention comprises two anti-CX3CR1 immunoglobulin single variable domains and further comprises a half-life extending moiety, for example an albumin binding moiety, a polyethylene glycol molecule or a Fc domain.

In one aspect, a polypeptide of the present invention comprises a first anti-CX3CR1 immunoglobulin single variable domain covalently linked to an albumin binding moiety by a first linker peptide, wherein said albumin binding moiety is further covalently linked to a second anti-CX3CR1 immunoglobulin single variable domain by a second linker peptide.

In one aspect, a polypeptide of the present invention comprises an anti-CX3CR1 immunoglobulin single variable domain covalently linked to a Fc domain by a linker peptide. In one aspect, such polypeptide comprising an anti-CX3CR1 immunoglobulin single variable domain covalently linked to a Fc domain by a linker peptide is provided as a dimer, for example through disulfide bridges. The polypeptides of the present invention are used for the prevention, treatment, alleviation and/or diagnosis of CX3CR1-associated diseases, disorders or conditions, in particular cardiovascular diseases, such as atherosclerosis.

In a further aspect, the present invention provides:

Embodiment 1: An immunoglobulin comprising an antigen-binding domain comprising three complementarity determining regions CDR1, CDR2 and CDR3, wherein said immunoglobulin binds to human CX3CR1 and is capable of blocking the binding of human fractalkine to human CX3CR1.

Embodiment 2: A polypeptide comprising one or more anti-CX3CR1 immunoglobulin single variable domain, wherein said polypeptide is capable of blocking the binding of human fractalkine to human CX3CR1.

Embodiment 3: A polypeptide according to embodiment 2, wherein said anti-CX3CR1 immunoglobulin single variable domain consists essentially of four framework regions (FR1, FR2, FR3 and FR4) and three complementary determining regions (CDR1, CDR2 and CDR3).

Embodiment 4: A polypeptide according to embodiment 3, wherein said anti-CX3CR1 immunoglobulin single variable domain has the structure FR1-CDR1-FR2-CDR2-FR3-CDR3-FR4.

Embodiment 5: A polypeptide according to any one of embodiments 2 to 4, wherein said anti-CX3CR1 immunoglobulin single variable domain is an antibody domain.

Embodiment 6: A polypeptide according to embodiment 5, wherein said anti-CX3CR1 immunoglobulin single variable domain is a VH, VL, VHH, camelized VH, or VHH that is optimized for stability, potency, manufacturability and/or similarity to human framework regions.

Embodiment 7: A polypeptide according to any one of embodiments 1 to 6, wherein said polypeptide has an affinity to human CX3CR1 at:
  a) an EC50 of less than or equal to 10 nM, less than or equal to 5 nM, less than or equal to 2.5 nM or less than or equal to 1 nM, as determined by cell binding FACS; or
  b) an IC50 of less than or equal to 10 nM, less than or equal to 5 nM, less than or equal to 2.5 nM or less than or equal to 1 nM, as determined by competition FACS.

Embodiment 8: A polypeptide according to any one of embodiments 1 to 7, wherein said polypeptide blocks the binding of human fractalkine to human CX3CR1 at an IC50 of less than or equal to 300 nM, or less than or equal to 100 nM, or less than or equal to 20 nM, or less than or equal to 10 nM, or less than or equal to 5 nM, or less than or equal to 2.5 nM or less than or equal to 1 nM.

Embodiment 9: A polypeptide according to any one of embodiments 1 to 8, wherein said polypeptide inhibits fractalkine induced chemotaxis mediated by human CX3CR1 at an $IC_{50}$ of less than or equal to 500 nM, or of less than or equal to 100 nM, or of less than or equal to 75 nM, or of less than or equal to 50 nM, or less than or equal to 10 nM or less than or equal to 5 nM.

Embodiment 10: A polypeptide according to any one of embodiments 1 to 9, wherein said polypeptide inhibits fractalkine internalization mediated by human CX3CR1 at an $IC_{50}$ of less than or equal to 10 nM, or less than or equal to 5 nM or or less than or equal to 1 nM.

Embodiment 11: A polypeptide according to any one of embodiments 3 to 10, wherein said CDR3 has the amino acid sequence of Asp-Xaa1-Arg-Arg-Gly-Trp-Xaa2-Xaa3-Xaa4-Xaa5 (SEQ ID NO: 197), wherein:
  Xaa1 is Pro, Ala or Gly;
  Xaa2 is Asp or Asn;
  Xaa3 is Thr or Ser;
  Xaa4 is Arg, Lys, Ala or Gly; and
  Xaa5 is Tyr or Phe.

Embodiment 12: A polypeptide according to any one of embodiments 3 to 11, wherein:
  a)
  Xaa1 is Pro, Ala or Gly;
  Xaa2 is Asp or Asn;
  Xaa3 is Thr;
  Xaa4 is Arg or Lys; and
  Xaa5 is Tyr,
  and/or
  b) wherein said CDR3 is selected from any of SEQ ID No's: 186-190.

Embodiment 13: A polypeptide according to any one of embodiments 3 to 12, wherein said CDR3 has the amino acid sequence of Asp-Pro-Arg-Arg-Gly-Trp-Asp-Thr-Arg-Tyr (SEQ ID NO: 186).

Embodiment 14: A polypeptide according to any one of embodiments 3 to 10, wherein:
  i) said CDR1:
    a) has the amino acid sequence of SEQ ID NO: 141;
    b) has an amino acid sequence that has at least 80% amino acid identity with the amino acid sequence of SEQ ID NO: 141;
    c) has an amino acid sequence that has 2, or 1 amino acid(s) difference with the amino acid sequence of SEQ ID NO: 141, wherein
      at position 2 the S has been changed into T, or G;
      at position 6 the S has been changed into R;
      at position 7 the N has been changed into T; and/or
      at position 9 the M has been changed into K; or
    d) has an amino acid sequence selected from any one of SEQ ID NO's: 141-145 and 213;
  ii) said CDR2:
    a) has the amino acid sequence of SEQ ID NO: 164;
    b) has an amino acid sequence that has at least 70% amino acid identity with the amino acid sequence of SEQ ID NO: 164;
    c) has an amino acid sequence that has 4, 3, 2, or 1 amino acid(s) difference with the amino acid sequence of SEQ ID NO: 164, wherein
      at position 1 the G has been changed into A, L, V or S;
      at position 3 the N has been changed into D, S, Q, G or T;
      at position 4 the S has been changed into T, K, G or P;
      at position 5 the V has been changed into A;
      at position 6 the G has been changed into D;
      at position 7 the I has been changed into T, or V;
      at position 8 the T has been changed into A; and/or
      at position 9 the K has been changed into R; or
    d) has an amino acid sequence selected from any one of SEQ ID NO's: 162-175 and 214-221; and
  iii) said CDR3:
    a) has the amino acid sequence of SEQ ID NO: 186;
    b) has an amino acid sequence that has at least 70% amino acid identity the amino acid sequence of SEQ ID NO: 186;
    c) has an amino acid sequence that has 3, 2, or 1 amino acid(s) difference with the amino acid sequences of SEQ ID NO: 186, wherein
      at position 2 the P has been changed into A, or G;
      at position 7 the D has been changed into N; and/or
      at position 9 the R has been changed into K; or d) has an amino acid sequence selected from any one of SEQ ID NO's: 186-190.

Embodiment 15: A polypeptide according to any one of embodiments 3 to 10, wherein
i) said CDR1 has the amino acid sequence of SEQ ID NO: 146;
ii) said CDR2 has an amino acid sequence that a) has at least 90% amino acid identity with the amino acid sequence of SEQ ID NO: 176 or b) has the amino acid sequence of SEQ ID NO: 176 or 177; and
iii) said CDR3 has the amino acid sequence of SEQ ID NO: 191.

Embodiment 16: A polypeptide according to any one of embodiments 3 to 10, wherein
i) said CDR1:
  a) has the amino acid sequence of SEQ ID NO: 147; or
  b) has an amino acid sequence that has 6, 5, 4, 3, 2, or 1 amino acid(s) difference with the amino acid sequence of SEQ ID NO: 147, wherein
    at position 1 the G has been changed into K, R, or A;
    at position 2 the T has been changed into I, P, S or L;
    at position 3 the I has been changed into V, or T;
    at position 4 the F has been changed into L;
    at position 5 the S has been changed into R, or D;
    at position 6 the N has been changed into S, T, or D; and/or
    at position 7 the N has been changed into T, or Y; or
  c) has an amino acid sequence selected from any one of SEQ ID NO's: 147-161;
ii) said CDR2:
  a) has the amino acid sequence of SEQ ID NO: 179; or
  b) has an amino acid sequences that has 4, 3, 2, or 1 amino acid(s) difference with the amino acid sequence of SEQ ID NO: 179, wherein
    at position 3 the S has been changed into T, or G;
    at position 4 the N has been changed into S, or I;
    at position 5 the S has been changed into T;
    at position 6 the G has been changed into Y; and/or
    at position 8 the T has been changed into A; or
  c) has an amino acid sequence selected from any one of SEQ ID NO's: 178-185; and
iii) said CDR3:
  a) has the amino acid sequence of SEQ ID NO: 192; or
  b) has an amino acid sequence that has at least 80% amino acid identity with the amino acid sequence of SEQ ID NO: 192; or
  c) has an amino acid sequence that has 2, or 1 amino acid(s) difference with the amino acid sequence of SEQ ID NO: 192, wherein
    at position 2 the A has been changed into G;
    at position 8 the T has been changed into S;
    at position 9 the A has been changed into G; and/or
    at position 10 the Y has been changed into F; or
  d) has an amino acid sequence selected from any one of SEQ ID NO's: 192-196.

Embodiment 17: A polypeptide according to embodiment 3, wherein the amino acid sequences of said CDR1, CDR2 and CDR3 are set forth in:
SEQ ID No: 141, 162 and 186, respectively; or
SEQ ID No: 141, 163 and 187, respectively; or
SEQ ID No: 141, 164 and 186, respectively; or
SEQ ID No: 141, 166 and 186, respectively; or
SEQ ID No: 141, 167 and 186, respectively; or
SEQ ID No: 141, 167 and 189, respectively; or
SEQ ID No: 141, 168 and 186, respectively; or
SEQ ID No: 141, 168 and 187, respectively; or
SEQ ID No: 141, 169 and 190, respectively; or
SEQ ID No: 141, 170 and 186, respectively; or
SEQ ID No: 141, 171 and 186, respectively; or
SEQ ID No: 141, 174 and 186, respectively; or
SEQ ID No: 141, 175 and 187, respectively; or
SEQ ID No: 142, 165 and 188, respectively; or
SEQ ID No: 142, 173 and 188, respectively; or
SEQ ID No: 143, 164 and 186, respectively; or
SEQ ID No: 144, 172 and 187, respectively; or
SEQ ID No: 145, 172 and 187, respectively; or
SEQ ID No: 141, 214 and 186, respectively; or
SEQ ID No: 141, 215 and 186, respectively; or
SEQ ID No: 141, 216 and 186, respectively; or
SEQ ID No: 141, 217 and 186, respectively; or
SEQ ID No: 141, 218 and 186, respectively; or
SEQ ID No: 141, 219 and 186, respectively; or
SEQ ID No: 141, 220 and 186, respectively; or
SEQ ID No: 213, 221 and 186, respectively; or
SEQ ID No: 213, 214 and 186, respectively.

Embodiment 18: A polypeptide according to embodiment 3, wherein the amino acid sequences of said CDR1, CDR2 and CDR3 are set forth in:
SEQ ID No: 146, 176 and 191, respectively; or
SEQ ID No: 146, 177 and 191, respectively.

Embodiment 19: A polypeptide according to embodiment 3, wherein the amino acid sequences of said CDR1, CDR2 and CDR3 are set forth in:
SEQ ID No: 147, 178 and 192, respectively; or
SEQ ID No: 147, 179 and 192, respectively; or
SEQ ID No: 147, 179 and 194, respectively; or
SEQ ID No: 148, 179 and 193, respectively; or
SEQ ID No: 149, 179 and 192, respectively; or
SEQ ID No: 149, 180 and 192, respectively; or
SEQ ID No: 149, 181 and 192, respectively; or
SEQ ID No: 149, 183 and 192, respectively; or
SEQ ID No: 149, 185 and 192, respectively; or
SEQ ID No: 150, 179 and 194, respectively; or
SEQ ID No: 150, 182 and 194, respectively; or
SEQ ID No: 151, 179 and 193, respectively; or
SEQ ID No: 151, 182 and 194, respectively; or
SEQ ID No: 151, 184 and 196, respectively; or
SEQ ID No: 152, 179 and 195, respectively; or
SEQ ID No: 153, 179 and 194, respectively; or
SEQ ID No: 154, 182 and 194, respectively; or
SEQ ID No: 155, 179 and 195, respectively; or
SEQ ID No: 156, 181 and 192, respectively; or
SEQ ID No: 157, 179 and 194, respectively; or
SEQ ID No: 158, 179 and 192, respectively; or
SEQ ID No: 159, 178 and 192, respectively; or
SEQ ID No: 160, 179 and 194, respectively; or
SEQ ID No: 161, 179 and 194, respectively.

Embodiment 20: A polypeptide according to embodiment 3, wherein the amino acid sequences of said CDR1, CDR2 and CDR3 are set forth in: SEQ ID NO's: 141, 164 and 186, respectively, or SEQ ID NO's: 141, 162 and 186, respectively.

Embodiment 21: A polypeptide according to embodiment 3, wherein the amino acid sequences of said CDR1, CDR2 and CDR3 are set forth in: SEQ ID NO's: 213, 214 and 186 respectively, SEQ ID NO's: 213, 221 and 186 respectively, or SEQ ID NO's: 141, 162 and 186 respectively.

Embodiment 22: A polypeptide according to any one of embodiments 2 to 10, wherein said anti-CX3CR1 immunoglobulin single variable domain is a VHH domain comprising the sequence set forth in:

a) the amino acid sequence of SEQ ID NO: 3;
b) amino acid sequences that have at least 90% amino acid identity with the amino acid sequences of SEQ ID NO: 3;
c) amino acid sequences that have 11, 10, 9, 8, 7, 6, 5, 4, 3, 2, or 1 amino acid difference with the amino acid sequences of SEQ ID NO: 3; or
d) an amino acid sequence of any one of SEQ ID NO: 1-48, 121-140 or 222-224.

Embodiment 23: A polypeptide according to any one of embodiments 2 to 10, wherein said anti-CX3CR1 immunoglobulin single variable domain is a VHH domain comprising the sequence set forth in:
a) the amino acid sequence of SEQ ID NO: 49;
b) an amino acid sequence that has at least 95% amino acid identity with the amino acid sequences of SEQ ID NO: 49;
c) an amino acid sequence that has 5, 4, 3, 2, or 1 amino acid difference with the amino acid sequences of SEQ ID NO: 49; or
d) an amino acid sequence of any one of SEQ ID NO: 49-52.

Embodiment 24: A polypeptide according to any one of embodiments 2 to 10, wherein said anti-CX3CR1 immunoglobulin single variable domain is a VHH domain comprising the sequence set forth in:
a) the amino acid sequence of SEQ ID NO: 67;
b) an amino acid sequence that has at least 90% amino acid identity with the amino acid sequences of SEQ ID NO: 67;
c) an amino acid sequence that has 12, 11, 10, 9, 8, 7, 6, 5, 4, 3, 2, or 1 amino acid difference with the amino acid sequences of SEQ ID NO: 67; or
d) an amino acid sequence of any one of SEQ ID NO: 53-120.

Embodiment 25: A polypeptide according to embodiment 2, wherein said anti-CX3CR1 immunoglobulin single variable domain comprises the sequence set forth in SEQ ID NO: 1 or SEQ ID NO: 3.

Embodiment 26: A polypeptide according to embodiment 2, wherein said anti-CX3CR1 immunoglobulin single variable domain comprises the sequence set forth in any one of SEQ ID NO: 121-140 or SEQ ID NO: 222-224.

Embodiment 27: A polypeptide according to any of one of the embodiments above, which is humanized and/or optimized for stability, potency, manufacturability and/or similarity to human framework regions.

Embodiment 28: A polypeptide according to embodiment 27, which is humanized and/or sequence optimized in one or more of the following positions (according to Kabat numbering): 1, 11, 14, 16, 74, 83, 108.

Embodiment 29: A polypeptide according to embodiment 28, comprising one or more of the following mutations: E1D, S11L, A14P, E16G, A74S, K83R, Q108L.

Embodiment 30: A polypeptide according to any one of embodiments 3-29, in which:
i) FR1 is selected from SEQ ID NO's: 198-204;
ii) FR2 is selected from SEQ ID NO's: 205-208;
iii) FR3 is selected form SEQ ID NO's: 209-210; and/or
iv) FR4 is selected from SEQ ID NO's: 211-212.

Embodiment 31: A polypeptide according to any one of embodiments 3-30, which is humanized and/or sequence optimized in one or more of the following positions (according to Kabat numbering): 52, 53.

Embodiment 32: A polypeptide according to embodiment 31, comprising one or more of the following mutations: N52S, S53T.

Embodiment 33: A polypeptide according to any one of embodiments 3-32, in which CDR2 is selected from SEQ ID NO's: 214-221.

Embodiment 34: A polypeptide according to any one of embodiments 2-33, wherein said anti-CX3CR1 immunoglobulin single variable domain comprises the sequence set forth in any of SEQ ID NO's: 138-140 or 222-224.

Embodiment 35: A polypeptide according to any one of embodiments 22 to 26, wherein said VHH domain consists of any one of said amino acid sequences.

Embodiment 36: A polypeptide according to any one of embodiments 2 to 35, wherein said immunoglobulin single variable domain cross-blocks the binding of at least one of the immunoglobulin single variable domains of SEQ ID NO's: 1-120, 121-140 and 222-224 to CX3CR1.

Embodiment 37: A polypeptide according to any one of embodiments 2 to 35, wherein said immunoglobulin single variable domain is cross-blocked from binding to CX3CR1 by at least one of the amino acid sequences of SEQ ID NO's: 1-120, 121-140 and 222-224.

Embodiment 38: A polypeptide according to any one of embodiments 2 to 37, wherein the polypeptide further comprises a half-life extending moiety.

Embodiment 39: A polypeptide according to embodiment 38, wherein said half-life extending moiety is covalently linked to said polypeptide and is selected from the group consisting of an albumin binding moiety, such as an anti-albumin immunoglobulin domain, a transferrin binding moiety, such as an anti-transferrin immunoglobulin domain, a polyethylene glycol molecule, a recombinant polyethylene glycol molecule, human serum albumin, a fragment of human serum albumin, an albumin binding peptide or a Fc domain.

Embodiment 40: A polypeptide according to embodiment 38 or 39, wherein said half-life extending moiety consists of an anti-albumin immunoglobulin single variable domain.

Embodiment 41: A polypeptide according to embodiment 40, wherein the immunoglobulin single variable domain is selected from a VHH domain, a humanized VHH domain, a camelized VH domain, a domain antibody, a single domain antibody and/or "dAb"s.

Embodiment 42: A polypeptide according to embodiment 41, wherein the anti-albumin immunoglobulin single variable domain is selected from SEQ ID NO's: 230-232.

Embodiment 43: A polypeptide according to any one of embodiment 2 to 39, wherein said polypeptide is linked to an Fc portion (such as a human Fc, for example as set forth in SEQ ID NO: 252), optionally via a suitable linker or hinge region.

Embodiment 44: A polypeptide according to any one of embodiments 2 to 39, wherein said polypeptide is further linked to one or more constant domains (for example, 2 or 3 constant domains that can be used as part of/to form an Fc portion), to an Fc portion and/or to one or more antibody parts, fragments or domains that confer one or more effector functions to the polypeptide of the invention and/or may confer the ability to bind to one or more Fc receptors, optionally via a suitable linker or hinge region.

Embodiment 45: A polypeptide according to any one of embodiments 2 to 37, wherein said polypeptide further comprises a second immunoglobulin single variable domain, preferably a second anti-CX3CR1 immunoglobulin single variable domain.

Embodiment 46: A polypeptide according to embodiment 45, wherein said first and said second immunoglobulin single variable domains are covalently linked by a linker peptide.

Embodiment 47: A polypeptide according to embodiment 45 or 46, wherein said second immunoglobulin single variable domains essentially consist of four framework regions (FR1 to FR4) and three complementary determining regions (CDR1 to CDR3).

Embodiment 48: A polypeptide according to any one of embodiments 45 to 47, wherein said first and said second immunoglobulin single variable domains are antibody domains.

Embodiment 49: A polypeptide according to any one of embodiments 45 to 48, wherein said first and second immunoglobulin single variable domains are a VH, VL, VHH, camelized VH, or VHH that is optimized for stability, potency, manufacturability and/or similarity to human framework regions.

Embodiment 50: A polypeptide according to any one of embodiments 45 to 49, wherein said CDR1 to CDR3 of said second immunoglobulin single variable domain are set forth in any one of embodiments 11 to 21.

Embodiment 51: A polypeptide according to any one of embodiments 45 to 50, wherein said first and said second immunoglobulin single variable domains comprise the same CDR3.

Embodiment 52: A polypeptide according to embodiment 51, wherein said CDR3 is set forth in any one of embodiment 11 to 13.

Embodiment 53: A polypeptide according to any one of embodiments 45 to 53, wherein said first and said second immunoglobulin single variable domains comprise the same CDR1, CDR2 and CDR3.

Embodiment 54: A polypeptide according to embodiment 53, wherein said CDR1 to CDR3 are set forth in any one of embodiments 11 to 21.

Embodiment 55: A polypeptide according to any one of embodiments 45 to 54, wherein said first and said second immunoglobulin single variable domains comprise the same VHH domain.

Embodiment 56: A The polypeptide according to any one of embodiments 45 to 55, wherein said VHH domain is set forth in any one of embodiments 22 to 37.

Embodiment 57: A polypeptide comprising a first immunoglobulin single variable domain comprising the CDR1, CDR2 and CDR3 set forth SEQ ID NO's: 141, 164 and 186 or SEQ ID NO's: 141, 162 and 186 and a second immunoglobulin single variable domain as set forth in any one of embodiments 2 to 37.

Such a polypeptide may in particular be a polypeptide according to any of embodiments 45 to 56.

Embodiment 58: A polypeptide according to embodiment 57, wherein said first immunoglobulin single variable domain comprises the CDR1, CDR2 and CDR3 set forth in SEQ ID NO's: 213, 214 and 186, SEQ ID NO's: 213, 221 and 186 or SEQ ID NO's: 141, 162 and 186.

Embodiment 59: A polypeptide according to embodiment 57 or 58, wherein said second immunoglobulin single variable domain comprises the CDR1, CDR2 and CDR3 set forth SEQ ID NO's: 141, 164 and 186 or SEQ ID NO's: 141, 162 and 186.

Embodiment 60: A polypeptide according to embodiment 57 or 58, wherein said second immunoglobulin single variable domain comprises the CDR1, CDR2 and CDR3 set forth in: SEQ ID NO's: 213, 214 and 186, SEQ ID NO's: 213, 221 and 186 or SEQ ID NO's: 141, 162 and 186.

Embodiment 61: A polypeptide comprising a first immunoglobulin single variable domain, wherein said first immunoglobulin single variable domain is a VHH domain comprising the sequence set forth in SEQ ID NO: 1 or SEQ ID NO: 3 and a second immunoglobulin single variable domain according to any one of embodiments 2 to 37.

Such a polypeptide may in particular be a polypeptide according to any of embodiments 45 to 60.

Embodiment 62: A polypeptide according to embodiment 61, wherein said first immunoglobulin single variable domain is a VHH domain comprising the sequence set forth in any one of SEQ ID NO: 121-140 or 222-224.

Embodiment 63: A polypeptide according to embodiment 61 or 62, wherein said second immunoglobulin single variable domain is a VHH domain comprising the sequence set forth in SEQ ID NO: 1 or SEQ ID NO: 3.

Embodiment 64: A polypeptide according to embodiment 63, wherein said second immunoglobulin single variable domain is a VHH domain comprising the sequence set forth in any one of SEQ ID NO: 121-140 or 222-224.

Embodiment 65: A polypeptide according to any one of embodiments 45 to 64, wherein the polypeptide further comprises a half-life extending moiety.

Embodiment 66: A polypeptide according to embodiment 65, wherein said half-life extending moiety is covalently linked to said polypeptide and is selected from the group consisting of an albumin binding moiety, such as an anti-albumin immunoglobulin domain, a transferrin binding moiety, such as an anti-transferrin immunoglobulin domain, a polyethylene glycol molecule, a recombinant polyethylene glycol molecule, human serum albumin, a fragment of human serum albumin, an albumin binding peptide or a Fc domain.

Embodiment 67: A polypeptide according to embodiment 66, wherein said half-life extending moiety consists of an anti-albumin immunoglobulin single variable domain.

Embodiment 68: A polypeptide according to embodiment 67, wherein the immunoglobulin single variable domain is selected from a VHH domain, a humanized VHH domain, a camelized VH domain, a domain antibody, a single domain antibody and/or "dAb"s.

Embodiment 69: A polypeptide according to embodiment 68, wherein the anti-albumin immunoglobulin single variable domain is selected from SEQ ID NO's: 230-232.

Embodiment 70: A polypeptide according to any one of embodiments 45 to 64, wherein said polypeptide is linked to an Fc portion (such as a human Fc, for example as set forth in SEQ ID NO: 252), optionally via a suitable linker or hinge region.

Embodiment 71: A polypeptide according to any one of embodiments 45 to 66, wherein said polypeptide is further linked to one or more constant domains (for example, 2 or 3 constant domains that can be used as part of/to form an Fc portion), to an Fc portion and/or to one or more antibody parts, fragments or domains that confer one or more effector functions to the polypeptide of the invention and/or may confer the ability to bind to one or more Fc receptors, optionally via a suitable linker or hinge region.

Embodiment 72: A polypeptide comprising the amino acid sequence of any one of SEQ ID NO: 225-227.

Embodiment 73: A polypeptide comprising the amino acid sequence of any one of SEQ ID NO: 249 or 277-281.

Embodiment 74: A polypeptide comprising the amino acid sequence of any one of SEQ ID NO: 257-262.

Embodiment 75: A polypeptide comprising the amino acid sequence of any one of SEQ ID NO: 253 or 254.

Embodiment 76: A polypeptide comprising the amino acid sequence of any one of SEQ ID NO: 263 or 266.

Embodiment 77: A polypeptide comprising the amino acid sequence of any one of SEQ ID NO: 267-276 and 282.

Embodiment 78: A nucleic acid molecule comprising a region encoding a polypeptide according to any one of embodiments 1 to 77.

Embodiment 79: An expression vector comprising a nucleic acid molecule according to embodiment 78.

Embodiment 80: A host cell carrying an expression vector comprising a nucleic acid molecule, said nucleic acid molecule comprising a region encoding a polypeptide according to any one of embodiments 1 to 77, wherein said host cell is capable of expressing a polypeptide according to any one of embodiments 1 to 77, and wherein said host cell is a prokaryotic or a eukaryotic cell.

Embodiment 81: A pharmaceutical composition comprising (i) as the active ingredient, one or more polypeptides according to any one of embodiments 1 to 77, and (ii) a pharmaceutically acceptable carrier, and optionally (iii) a diluent, excipient, adjuvant and/or stabilizer.

Embodiment 82: A method of manufacturing a polypeptide according to any one of embodiments 1 to 77, comprising the steps of
  culturing a host cell under conditions that allow expression of a polypeptide according to any one of embodiments 1 to 77, wherein said host cell carrying an expression vector comprising a nucleic acid molecule, said nucleic acid molecule comprising a region encoding a polypeptide according to any one of embodiments 1 to 77, and wherein said host cell is a prokaryotic or a eukaryotic cell;
  recovering said polypeptide; and
  purifying said polypeptide.

Embodiment 83: A method of using a polypeptide according to any one of embodiments 1 to 77 for the treatment, prevention or alleviation of a disease, disorder or condition, in particular in a human being.

Embodiment 84: The method of embodiment 83, wherein said disease, disorder or condition is a CX3CR1-associated disease, disorder or condition.

Embodiment 85: The method of embodiment 83, wherein said disease, disorder or condition is atherosclerosis.

Embodiment 86: An injectable pharmaceutical composition comprising the polypeptide according to any one of embodiments 1 to 77, said composition being suitable for intravenous or subcutaneous injection in a human being.

Embodiment 87: A method for preventing and/or treating a disease or disorder that is associated with CX3CR1, wherein said method comprises administering to a subject in need thereof a pharmaceutically active amount of at least one polypeptide according to any one of embodiments 1 to 77.

Embodiment 88: A method of embodiment 85, further comprising administering an additional therapeutic agent selected from the group consisting of a statin, an antiplatelet, an anticoagulant, an antidiabetic and an antihypertensive.

Embodiment 89: A method for inhibiting the binding of CX3CR1 to fractalkine in a mammalian cell, comprising administering to the cell a polypeptide according to any one of embodiments 1 to 77, whereby signaling mediated by the fractalkine is inhibited.

Embodiment 90: A method for detecting and/or quantifying CX3CR1 levels in a biological sample by contacting the sample with a polypeptide according to any one of embodiments 1 to 77 and detecting binding of the polypeptide with CX3CR1.

Embodiment 91: A method for diagnosing an CX3CR1-associated disorder or for determining if a subject has an increased risk of developing an CX3CR1-associated disorder, wherein the method comprises contacting a biological sample from a subject with a polypeptide according to any one of embodiments 1 to 77 and detecting binding of the polypeptide to CX3CR1 to determine the expression or concentration of CX3CR1.

Embodiment 92. A polypeptide according to any one of embodiments 1 to 77 for use in the treatment, prevention or alleviation of a disease, disorder or condition, in a human being.

Embodiment 93. The polypeptide for use according to embodiment 92, wherein the disease, disorder or condition is a CX3CR1-associated disease, disorder or condition.

Embodiment 94. The polypeptide for use according to embodiment 92, wherein the disease, disorder or condition is selected from cardio- and cerebrovascular atherosclerotic disorders, peripheral artery disease, restenosis, diabetic nephropathy, glomerulomephritis, human crescentic glomerulonephritis, IgA nephropathy, membranous nephropathy, lupus nephritis, vasculitis including Henoch-Schonlein purpura and Wegener's granulomatosis, rheumatoid arthritis, osteoarthritis, allograft rejection, systemic sclerosis, neurodegenerative disorders and demyelinating disease, multiple sclerosis (MS), Alzheimer's disease, pulmonary diseases such as COPD, asthma, neuropathic pain, inflammatory pain, or cancer.

Embodiment 95. The polypeptide for use according to embodiment 92, wherein the disease, disorder or condition is atherosclerosis.

Embodiment 96. Use of a polypeptide according to any of embodiments 1 to 77 for the manufacture of a medicament for the treatment, prevention or alleviation of a disease, disorder or condition, in a human being.

Embodiment 97. The method according to embodiment 87, wherein the disease or disorder is selected from cardio- and cerebrovascular atherosclerotic disorders, peripheral artery disease, restenosis, diabetic nephropathy, glomerulonephritis, human crescentic glomerulonephritis, IgA nephropathy, membranous nephropathy, lupus nephritis, vasculitis including Henoch-Schonlein purpura and Wegener's granulomatosis, rheumatoid arthritis, osteoarthritis, allograft rejection, systemic sclerosis, neurodegenerative disorders and demyelinating disease, multiple sclerosis (MS), Alzheimer's disease, pulmonary diseases such as COPD, asthma, neuropathic pain, inflammatory pain, or cancer.

Embodiment 98. The method according to embodiment 87, wherein the disease, disorder or condition is atherosclerosis.

Embodiment 99. A diagnostic kit or diagnostic method comprising a polypeptide according to any one of embodiments 1 to 77, or the use thereof.

Embodiment 100. A diagnostic kit or diagnostic method according to embodiment 99, for the diagnosis of at least one of cardio- and cerebrovascular atherosclerotic disorders, peripheral artery disease, restenosis, diabetic nephropathy, glomerulomephritis, human crescentic glomerulonephritis, IgA nephropathy, membranous nephropathy, lupus nephritis, vasculitis including Henoch-Schonlein purpura and Wegener's granulomatosis, rheumatoid arthritis, osteoarthritis, allograft rejection, systemic sclerosis, neurodegenerative disorders and demyelinating disease, multiple sclerosis (MS), Alzheimer's disease, pulmonary diseases such as COPD, asthma, neuropathic pain, inflammatory pain, or cancer.

DETAILED DESCRIPTION OF THE INVENTION

Definitions

The above and other aspects and embodiments of the invention will become clear from the further description herein, in which:

a) Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd Ed.), Vols. 1-3, Cold Spring Harbor Laboratory Press (1989); Lewin, "Genes IV", Oxford University Press, New York, (1990), and Roitt et al., "Immunology" ($2^{nd}$ Ed.), Gower Medical Publishing, London, New York (1989), as well as to the general background art cited herein; Furthermore, unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein;

b) Unless indicated otherwise, the terms "immunoglobulin" and "immunoglobulin sequence"—whether used herein to refer to a heavy chain antibody or to a conventional 4-chain antibody—are used as general terms to include both the full-size antibody, the individual chains thereof, as well as all parts, domains or fragments thereof (including but not limited to antigen-binding domains or fragments such as VHH domains or VH/VL domains, respectively). In addition, the term "sequence" as used herein (for example in terms like "immunoglobulin sequence", "antibody sequence", "(single) variable domain sequence", "VHH sequence" or "protein sequence"), should generally be understood to include both the relevant amino acid sequence as well as nucleic acid sequences or nucleotide sequences encoding the same, unless the context requires a more limited interpretation;

c) The term "domain" (of a polypeptide or protein) as used herein refers to a folded protein structure which has the ability to retain its tertiary structure independently of the rest of the protein. Generally, domains are responsible for discrete functional properties of proteins, and in many cases may be added, removed or transferred to other proteins without loss of function of the remainder of the protein and/or of the domain.

d) The term "immunoglobulin domain" as used herein refers to a globular region of an antibody chain (such as e.g. a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a 2-layer sandwich of about 7 antiparallel beta-strands arranged in two beta-sheets, optionally stabilized by a conserved disulphide bond.

e) The term "immunoglobulin variable domain" as used herein means an immunoglobulin domain essentially consisting of four "framework regions" which are referred to in the art and hereinbelow as "framework region 1" or "FR1"; as "framework region 2" or"FR2"; as "framework region 3" or "FR3"; and as "framework region 4" or "FR4", respectively; which framework regions are interrupted by three "complementarity determining regions" or "CDRs", which are referred to in the art and hereinbelow as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) that confer specificity to an antibody for the antigen by carrying the antigen-binding site.

f) The terms "immunoglobulin single variable domain" and "single variable domain" as used herein mean an immunoglobulin variable domain which is capable of specifically binding to an epitope of the antigen without pairing with an additional variable immunoglobulin domain. One example of immunoglobulin single variable domains in the meaning of the present invention are "domain antibodies", such as the immunoglobulin single variable domains VH and VL (VH domains and VL domains). Another example of immunoglobulin single variable domains are "VHH domains" (or simply "VHHs") from camelids, as defined hereinafter.

In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associating) immunoglobulin domains such as light and heavy chain variable domains, i.e. by a VH-VL pair of immunoglobulin domains, which jointly bind to an epitope of the respective antigen.

f1) "VHH domains", also known as VHHs, $V_HH$ domains, VHH antibody fragments, and VHH antibodies, have originally been described as the antigen binding immunoglobulin (variable) domain of "heavy chain antibodies" (i.e. of "antibodies devoid of light chains"; Hamers-Casterman C, Atarhouch T, Muyldermans S, Robinson G, Hamers C, Songa E B, Bendahman N, Hamers R.: "Naturally occurring antibodies devoid of light chains"; Nature 363, 446-448 (1993)). The term "VHH domain" has been chosen in order to distinguish these variable domains from the heavy chain variable domains that are present in conventional 4-chain antibodies (which are referred to herein as "$V_H$ domains" or "VH domains") and from the light chain variable domains that are present in conventional 4-chain antibodies (which are referred to herein as "$V_L$ domains" or "VL domains"). VHH domains can specifically bind to an epitope without an additional antigen binding domain (as opposed to VH or VL domains in a conventional 4-chain antibody, in which case the epitope is recognized by a VL domain together with a VH domain). VHH domains are small, robust and efficient antigen recognition units formed by a single immunoglobulin domain.

In the context of the present invention, the terms VHH domain, VHH, $V_HH$ domain, VHH antibody fragment, VHH antibody, as well as "Nanobody®" and "Nanobody® domain" ("Nanobody" being a trademark of the company Ablynx N.V.; Ghent; Belgium) are used interchangeably and are representatives of immunoglobulin single variable domains (having the structure: FR1-CDR1-FR2-CDR2-FR3-CDR3-FR4 and specifically binding to an epitope without requiring the presence of a second immunoglobulin variable domain), and which are distinguished from VH domains by the so-called "hallmark residues", as defined in e.g. WO2009/109635, FIG. 1.

The amino acid residues of a VHH domain are numbered according to the general numbering for $V_H$ domains given by Kabat et al. ("Sequence of proteins of immunological interest", US Public Health Services, NIH Bethesda, Md., Publication No. 91), as applied to VHH domains from Camelids, as shown e.g. in FIG. 2 of Riechmann and Muyldermans, J. Immunol. Methods 231, 25-38 (1999). According to this numbering, FR1 comprises the amino acid residues at positions 1-30,
CDR1 comprises the amino acid residues at positions 31-35,
FR2 comprises the amino acids at positions 36-49,
CDR2 comprises the amino acid residues at positions 50-65,
FR3 comprises the amino acid residues at positions 66-94,
CDR3 comprises the amino acid residues at positions 95-102, and
FR4 comprises the amino acid residues at positions 103-113.

However, it should be noted that—as is well known in the art for $V_H$ domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence.

Alternative methods for numbering the amino acid residues of $V_H$ domains, which methods can also be applied in an analogous manner to VHH domains, are known in the art. However, in the present description, claims and figures, the numbering according to Kabat and applied to VHH domains as described above will be followed, unless indicated otherwise.

The total number of amino acid residues in a VHH domain will usually be in the range of from 110 to 120, often between 112 and 115. It should however be noted that smaller and longer sequences may also be suitable for the purposes described herein.

Further structural characteristics and functional properties of VHH domains and polypeptides containing the same can be summarized as follows:

VHH domains (which have been "designed" by nature to functionally bind to an antigen without the presence of, and without any interaction with, a light chain variable domain) can function as a single, relatively small, functional antigen-binding structural unit, domain or polypeptide. This distinguishes the VHH domains from the VH and VL domains of conventional 4-chain antibodies, which by themselves are generally not suited for practical application as single antigen-binding proteins or immunoglobulin single variable domains, but need to be combined in some form or another to provide a functional antigen-binding unit (as in for example conventional antibody fragments such as Fab fragments; in scFv's, which consist of a VH domain covalently linked to a VL domain).

Because of these unique properties, the use of VHH domains—either alone or as part of a larger polypeptide—offers a number of significant advantages over the use of conventional VH and VL domains, scFv's or conventional antibody fragments (such as Fab- or F(ab')2-fragments):

only a single domain is required to bind an antigen with high affinity and with high selectivity, so that there is no need to have two separate domains present, nor to assure that these two domains are present in the right spatial conformation and configuration (i.e. through the use of especially designed linkers, as with scFv's);

VHH domains can be expressed from a single gene and require no post-translational folding or modifications;

VHH domains can easily be engineered into multivalent and multispecific formats (as further discussed herein);

VHH domains are highly soluble and do not have a tendency to aggregate (as with the mouse-derived antigen-binding domains described by Ward et al., Nature 341: 544-546 (1989));

VHH domains are highly stable to heat, pH, proteases and other denaturing agents or conditions and, thus, may be prepared, stored or transported without the use of refrigeration equipments, conveying a cost, time and environmental savings;

VHH domains are easy and relatively cheap to prepare, even on a scale required for production. For example, VHH domains and polypeptides containing the same can be produced using microbial fermentation (e.g. as further described below) and do not require the use of mammalian expression systems, as with for example conventional antibody fragments;

VHH domains are relatively small (approximately 15 kDa, or 10 times smaller than a conventional IgG) compared to conventional 4-chain antibodies and antigen-binding fragments thereof, and therefore
show high(er) penetration into tissues and
can be administered in higher doses
than such conventional 4-chain antibodies and antigen-binding fragments thereof;

VHH domains can show so-called cavity-binding properties (inter alia due to their extended CDR3 loop, compared to conventional VH domains) and can therefore also access targets and epitopes not accessible to conventional 4-chain antibodies and antigen-binding fragments thereof.

Methods of obtaining VHH domains binding to a specific antigen or epitope have been described earlier, e.g. in WO2006/040153 and WO2006/122786. As also described therein in detail, VHH domains derived from camelids can be "humanized" by replacing one or more amino acid residues in the amino acid sequence of the original VHH sequence by one or more of the amino acid residues that occur at the corresponding position(s) in a VH domain from a conventional 4-chain antibody from a human being. A humanized VHH domain can contain one or more fully human framework region sequences, and, in an even more specific embodiment, can contain human framework region sequences derived from DP-29, DP-47, DP-51, or parts thereof, optionally combined with JH sequences, such as JH5.

f2) "Domain antibodies", also known as "Dab"s, "Domain Antibodies", and "dAbs" (the terms "Domain Antibodies" and "dAbs" being used as trademarks by the GlaxoSmithKline group of companies) have been described in e.g. Ward, E. S., et al.: "Binding activities of a repertoire of single immunoglobulin variable domains secreted from *Escherichia coli*"; Nature 341: 544-546 (1989); Holt, L. J. et al.: "Domain antibodies: proteins for therapy"; TRENDS in Biotechnology 21(11): 484-490 (2003); and WO2003/002609.

Domain antibodies essentially correspond to the VH or VL domains of non-camelid mammalians, in particular human 4-chain antibodies. In order to bind an epitope as a single antigen binding domain, i.e. without being paired with a VL or VH domain, respectively, specific selection for such antigen binding properties is required, e.g. by using libraries of human single VH or VL domain sequences. Domain antibodies have, like VHHs, a molecular weight of approximately 13 to approximately 16 kDa and, if derived from fully human sequences, do not require humanization for e.g. therapeutical use in humans. As in the case of VHH domains, they are well expressed also in prokaryotic expression systems, providing a significant reduction in overall manufacturing cost.

Domain antibodies, as well as VHH domains, can be subjected to affinity maturation by introducing one or more alterations in the amino acid sequence of one or more CDRs, which alterations result in an improved affinity of the resulting immunoglobulin single variable domain for its respective antigen, as compared to the respective parent molecule. Affinity-matured immunoglobulin single variable domain molecules of the invention may be prepared by methods known in the art, for example, as described by Marks et al., 1992, Biotechnology 10:779-783, or Barbas, et al., 1994, Proc. Nat. Acad. Sci, USA 91: 3809-3813; Shier et al., 1995, Gene 169:147-155; Yelton et al., 1995, Immunol. 155: 1994-2004; Jackson et al., 1995, J. Immunol. 154(7):3310-9; and Hawkins et al., 1992, J. Mol. Biol. 226(3): 889 896; K S Johnson and R E Hawkins, "Affinity maturation of antibodies using phage display", Oxford University Press 1996.

f3) Furthermore, it will also be clear to the skilled person that it is possible to "graft" one or more of the CDR's mentioned above onto other "scaffolds", including but not limited to human scaffolds or non-immunoglobulin scaffolds. Suitable scaffolds and techniques for such CDR grafting are known in the art.

g) The terms "epitope" and "antigenic determinant", which can be used interchangeably, refer to the part of a macromolecule, such as a polypeptide, that is recognized by antigen-binding molecules, such as conventional antibodies or the polypeptides of the invention, and more particularly by the antigen-binding site of said molecules. Epitopes define the minimum binding site for an immunoglobulin, and thus represent the target of specificity of an immunoglobulin.

The part of an antigen-binding molecule (such as a conventional antibody or a polypeptide of the invention) that recognizes the epitope is called a paratope.

h) The term "biparatopic" (antigen-)binding molecule or "biparatopic" polypeptide as used herein shall mean a polypeptide comprising a first immunoglobulin single variable domain and a second immunoglobulin single variable domain as herein defined, wherein these two variable domains are capable of binding to two different epitopes of one antigen, which epitopes are not normally bound at the same time by one monospecific immunoglobulin, such as e.g. a conventional antibody or one immunoglobulin single variable domain. Biparatopic polypeptides can be composed of variable domains which have different epitope specificities, and do not contain mutually complementary variable domain pairs which bind to the same epitope. The two variable domains do therefore not compete with each other for binding to the target.

i) A polypeptide (such as an immunoglobulin, an antibody, an immunoglobulin single variable domain, a polypeptide of the invention, or generally an antigen binding molecule or a fragment thereof) that can "bind to" or "specifically bind to", that "has affinity for" and/or that "has specificity for" a certain epitope, antigen or protein (or for at least one part, fragment or epitope thereof) is said to be "against" or "directed against" said epitope, antigen or protein or is a "binding" molecule with respect to such epitope, antigen or protein, or is said to be "anti"-epitope, "anti"-antigen or "anti"-protein (e.g anti-CX3CR1).

k) Generally, the term "specificity" refers to the number of different types of antigens or epitopes to which a particular antigen-binding molecule or antigen-binding protein (such as an immunoglobulin, an antibody, an immunoglobulin single variable domain, or a polypeptide of the invention) can bind. The specificity of an antigen-binding protein can be determined based on its affinity and/or avidity. The affinity, represented by the equilibrium constant for the dissociation of an antigen with an antigen-binding protein (KD), is a measure for the binding strength between an epitope and an antigen-binding site on the antigen-binding protein: the lesser the value of the KD, the stronger the binding strength between an epitope and the antigen-binding molecule (alternatively, the affinity can also be expressed as the affinity constant (KA), which is 1/KD). As will be clear to the skilled person (for example on the basis of the further disclosure herein), affinity can be determined in a manner known per se, depending on the specific antigen of interest. Avidity is the measure of the strength of binding between an antigen-binding molecule (such as an immunoglobulin, an antibody, an immunoglobulin single variable domain, or a polypeptide of the invention) and the pertinent antigen. Avidity is related to both the affinity between an epitope and its antigen binding site on the antigen-binding molecule and the number of pertinent binding sites present on the antigen-binding molecule.

l) Amino acid residues will be indicated according to the standard three-letter or one-letter amino acid code, as generally known and agreed upon in the art. When comparing two amino acid sequences, the term "amino acid difference" refers to insertions, deletions or substitutions of the indicated number of amino acid residues at a position of the reference sequence, compared to a second sequence. In case of substitution(s), such substitution(s) will preferably be conservative amino acid substitution(s), which means that an amino acid residue is replaced with another amino acid residue of similar chemical structure and which has little or essentially no influence on the function, activity or other biological properties of the polypeptide. Such conservative amino acid substitutions are well known in the art, for example from WO 98/49185, wherein conservative amino acid substitutions preferably are substitutions in which one amino acid within the following groups (i)-(v) is substituted by another amino acid residue within the same group: (i) small aliphatic, nonpolar or slightly polar residues: Ala, Ser, Thr, Pro and Gly; (ii) polar, negatively charged residues and their (uncharged) amides: Asp, Asn, Glu and Gln; (iii) polar, positively charged residues: His, Arg and Lys; (iv) large aliphatic, nonpolar residues: Met, Leu, Ile, Val and Cys; and (v) aromatic residues: Phe, Tyr and Trp. Particularly preferred conservative amino acid substitutions are as follows:

Ala into Gly or into Ser;
Arg into Lys;
Asn into Gln or into His;
Asp into Glu;
Cys into Ser;
Gln into Asn;
Glu into Asp;
Gly into Ala or into Pro;
His into Asn or into Gln;
Ile into Leu or into Val;
Leu into Ile or into Val;
Lys into Arg, into Gln or into Glu;

Met into Leu, into Tyr or into Ile;
Phe into Met, into Leu or into Tyr;
Ser into Thr;
Thr into Ser;
Trp into Tyr;
Tyr into Trp or into Phe;
Val into Ile or into Leu.

m) A nucleic acid or polypeptide molecule is considered to be "(in) essentially isolated (form)"—for example, when compared to its native biological source and/or the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid or polypeptide molecule is considered "essentially isolated" when it has been purified at least 2-fold, in particular at least 10-fold, more in particular at least 100-fold, and up to 1000-fold or more. A nucleic acid or polypeptide molecule that is "in essentially isolated form" is preferably essentially homogeneous, as determined using a suitable technique, such as a suitable chromatographical technique, such as polyacrylamide-gelelectrophoresis;

n) "Sequence identity" between e.g. two immunoglobulin single variable domain sequences indicates the percentage of amino acids that are identical between these two sequences. It may be calculated or determined as described in paragraph f) on pages 49 and 50 of WO08/020079. "Sequence similarity" indicates the percentage of amino acids that either are identical or that represent conservative amino acid substitutions.

Target Specificity

The polypeptides of the invention have specificity for human CX3CR1. Thus, the polypeptides of the invention preferably bind to human CX3CR1 (SEQ ID NO: 255). In one aspect, the polypeptides of the present invention also bind to cynomolgus CX3CR1 (SEQ ID NO: 256).

Polypeptides of the Invention

The invention provides novel pharmaceutically active agents for the prevention, treatment, alleviation and/or diagnosis of CX3CR1 associated diseases, disorders or conditions, such as cardiovascular diseases. In particular, the invention provides polypeptides which bind to human CX3CR1 and are capable of blocking the binding of human fractalkine to human CX3CR1. In one aspect, the polypeptide is an immunoglobulin comprising an antigen-binding domain comprising three complementarity determining regions CDR1, CDR2 and CDR3, wherein said immunoglobulin binds to human CX3CR1 and is capable of blocking the binding of human fractalkine to human CX3CR1. In a further aspect, the polypeptide comprises one or more anti-CX3CR1 immunoglobulin single variable domain, wherein said polypeptide is capable of blocking the binding of human fractalkine to human CX3CR1.

In one aspect, a polypeptide of the present invention is characterized by one or more of the following properties:

Bind with high affinity to human CX3CR1, for example at an $EC_{50}$ of less than or equal to 10 nM, less than or equal to 5 nM, less than or equal to 2.5 nM or less than or equal to 1 nM, as determined by cell binding FACS;

Block the binding of human fractalkine to human CX3CR1, for example at an IC50 of less than or equal to 300 nM, or less than or equal to 100 nM, or less than or equal to 20 nM, or less than or equal to 10 nM, or less than or equal to 5 nM, or less than or equal to 2.5 nM or less than or equal to 1 nM;

Inhibit fractalkine induced chemotaxis mediated by human CX3CR1, for example at an $IC_{50}$ of less than or equal to 500 nM, or less than or equal to 100 nM, or of less than or equal to 75 nM, or less than or equal to 50 nM, or less than or equal to 10 nM or less than or equal to 5 nM; the obtained efficacy of inhibition is more than or equal to 15%, or more than or equal to 50%, or more than or equal to 80%, or more than or equal to 95%;

Inhibit fractalkine induced internalization mediated by human CX3CR1, for example at an $IC_{50}$ of less than or equal to 10 nM or less than or equal to 5 nM;

Cross-react with cynomolgus CX3CR1, for example within 10-fold of $E/IC_{50}$ for human CX3CR1 for binding and functional inhibition.

In a further aspect, a polypeptide of the present invention further comprises a half-life extending moiety, for example an albumin binding moiety, a polyethylene glycol molecule or a Fc domain. In a further aspect, a polypeptide of the present invention comprises two or more anti-CX3CR1 immunoglobulin single variable domains. In one aspect, the two anti-CX3CR1 immunoglobulin single variable domains are covalently linked by a linker peptide. In one aspect, the two anti-CX3CR1 immunoglobulin single variable domains in a polypeptide of the present invention have the same amino acid sequence. In another aspect, the two anti-CX3CR1 immunoglobulin single variable domains in a polypeptide of the present invention have different amino acid sequences. In one aspect, a polypeptide of the present invention comprises two anti-CX3CR1 immunoglobulin single variable domains and further comprises a half-life extending moiety, for example an albumin binding moiety, a polyethylene glycol molecule or a Fc domain.

In one aspect, a polypeptide of the present invention comprises a first anti-CX3CR1 immunoglobulin single variable domain covalently linked to an albumin binding moiety by a first linker peptide, wherein said albumin binding moiety is further covalently linked to a second anti-CX3CR1 immunoglobulin single variable domain by a second linker peptide.

In one aspect, a polypeptide of the present invention comprises an anti-CX3CR1 immunoglobulin single variable domain covalently linked to a Fc domain by a linker peptide. In one aspect, such polypeptide comprising an anti-CX3CR1 immunoglobulin single variable domain covalently linked to a Fc domain by a linker peptide is provided as a dimer, for example through disulfide bridges.

Polypeptides according to the present invention are obtained as described hereinbelow. In summary, single variable domains of the present invention were identified from a library expressing single variable domains (VHH) derived from a llama immunized with DNA encoding human CX3CR1. The phage library was panned on hCX3CR1 viral lipoparticles and binding phage were screened for their ability to compete for receptor binding with Alexa-fluor labeled fractalkine (AF-FKN). Representative single variable domains of the present invention are described herein in further details.

In one aspect, an immunoglobulin single variable domain of the present invention consists essentially of four framework regions (FR1, FR2, FR3 and FR4) and three complementary determining regions (CDR1, CDR2 and CDR3). In particular, the immunoglobulin single variable domain has the structure FR1-CDR1-FR2-CDR2-FR3-CDR3-FR4. In one aspect, the immunoglobulin single variable domain is an antibody domain.

In one aspect, the CDR3 of a polypeptide of the present invention, in particular a immunoglobulin single domain of the present invention has the amino acid sequence of Asp-Xaa1-Arg-Arg-Gly-Trp-Xaa2-Xaa3-Xaa4-Xaa5 as set forth in SEQ ID NO: 197, wherein:
  Xaa1 is Pro, Ala or Gly;
  Xaa2 is Asp or Asn;
  Xaa3 is Thr or Ser;
  Xaa4 is Arg, Lys, Ala or Gly; and
  Xaa5 is Tyr or Phe.

In one aspect, the CDR3 of a polypeptide of the present invention, in particular a immunoglobulin single domain of the present invention, has the amino acid sequence of Asp-Xaa1-Arg-Arg-Gly-Trp-Xaa2-Xaa3-Xaa4-Xaa5 as set forth in SEQ ID NO: 197, wherein:
  Xaa1 is Pro, Ala or Gly;
  Xaa2 is Asp or Asn;
  Xaa3 is Thr;
  Xaa4 is Arg or Lys; and
  Xaa5 is Tyr.

In one aspect, the CDR3 of a polypeptide of the present invention, in particular an immunoglobuling single domain of the present invention, has the amino acid sequence of Asp-Pro-Arg-Arg-Gly-Trp-Asp-Thr-Arg-Tyr as set forth in SEQ ID NO: 186.

In a further aspect, a polypeptide of the present invention, in particular an immunoglobuling single domain of the present invention, has the following CDR1, CDR2 and CDR3:
  CDR1:
    a) has the amino acid sequence of GSIFSSNAMA (SEQ ID NO: 141); or
    b) has an amino acid sequence that has at least 80% amino acid identity with the amino acid sequence of SEQ ID NO: 141; or
    c) has an amino acid sequence that has 2, or 1 amino acid(s) difference with the amino acid sequence of SEQ ID NO: 141, wherein
      at position 2 the S has been changed into T, or G;
      at position 6 the S has been changed into R;
      at position 7 the N has been changed into T; and/or
      at position 9 the M has been changed into K; or
    d) has an amino acid sequence selected from any one of SEQ ID NO's: 141-145 and 213;
  CDR2:
    a) has the amino acid sequence of GINSVGITK (SEQ ID NO: 164); or
    b) has an amino acid sequence that has at least 70% amino acid identity with the amino acid sequence of SEQ ID NO: 164; or
    c) has an amino acid sequence that has 4, 3, 2, or 1 amino acid(s) difference with the amino acid sequence of SEQ ID NO: 164, wherein
      at position 1 the G has been changed into A, L, V or S;
      at position 3 the N has been changed into D, S, Q, G or T;
      at position 4 the S has been changed into T, K, G or P;
      at position 5 the V has been changed into A;
      at position 6 the G has been changed into D;
      at position 7 the I has been changed into T, or V;
      at position 8 the T has been changed into A; and/or
      at position 9 the K has been changed into R; or
    d) has an amino acid sequence selected from any one of SEQ ID NO's: 162-175 and 214-221; and
  CDR3:
    a) has the amino acid sequence of DPRRGWDTRY (SEQ ID NO: 186); or
    b) has an amino acid sequence that has at least 70% amino acid identity the amino acid sequence of SEQ ID NO: 186; or
    c) has an amino acid sequence that has 3, 2, or 1 amino acid(s) difference with the amino acid sequences of SEQ ID NO: 186, wherein
      at position 2 the P has been changed into A, or G;
      at position 7 the D has been changed into N; and/or
      at position 9 the R has been changed into K; or
    d) has an amino acid sequence selected from any one of SEQ ID NO's: 186-190.

In a further aspect, a polypeptide of the present invention, in particular a immunoglobuling single domain of the present invention, has the following CDR1, CDR2 and CDR3, wherein:
  said CDR1 has the amino acid sequence of GRTFSSYAMG (SEQ ID NO: 146);
  said CDR2 has an amino acid sequence that a) has at least 90% amino acid identity with the amino acid sequence of GISGSASRKY (SEQ ID NO: 176) or b) has the amino acid sequence of SEQ ID NO: 176 or 177; and
  said CDR3 has the amino acid sequence of SNSYPKVQFDY (SEQ ID NO: 191).

In a further aspect, a polypeptide of the present invention, in particular an immunoglobuling single domain of the present invention, has the following CDR1, CDR2 and CDR3:
  said CDR1
    a) has the amino acid sequence of GTIFSNNAMG (SEQ ID NO: 147); or
    b) has an amino acid sequence that has 6, 5, 4, 3, 2, or 1 amino acid(s) difference with the amino acid sequence of SEQ ID NO: 147, wherein
      at position 1 the G has been changed into K, R, or A;
      at position 2 the T has been changed into I, P, S or L;
      at position 3 the I has been changed into V, or T;
      at position 4 the F has been changed into L;
      at position 5 the S has been changed into R, or D;
      at position 6 the N has been changed into S, T, or D; and/or
      at position 7 the N has been changed into T, or Y; or
    c) has an amino acid sequence selected from any one of SEQ ID NO's: 147-161;
  said CDR2:
    a) has the amino acid sequence of SISNSGSTN (SEQ ID NO: 179); or
    b) has an amino acid sequences that has 4, 3, 2, or 1 amino acid(s) difference with the amino acid sequence of SEQ ID NO: 179, wherein
      at position 3 the S has been changed into T, or G;
      at position 4 the N has been changed into S, or I;
      at position 5 the S has been changed into T;
      at position 6 the G has been changed into Y; and/or
      at position 8 the T has been changed into A; or
    c) has an amino acid sequence selected from any one of SEQ ID NO's: 178-185; and
  said CDR3:
    a) has the amino acid sequence of DARRGWNTAY (SEQ ID NO: 192); or
    b) has an amino acid sequence that has at least 80% amino acid identity with the amino acid sequence of SEQ ID NO: 192; or c) has an amino acid sequence that has 2, or 1 amino acid(s) difference with the amino acid sequence of SEQ ID NO: 192, wherein
   at position 2 the A has been changed into G;
   at position 8 the T has been changed into S;
   at position 9 the A has been changed into G; and/or
   at position 10 the Y has been changed into F; or
d) has an amino acid sequence selected from any one of SEQ ID NO's: 192-196.

In a further aspect, a polypeptide of the present invention, in particular an immunoglobuling single domain of the present invention, has the following CDR1, CDR2 and CDR3:
   SEQ ID No: 141, 162 and 186, respectively; or
   SEQ ID No: 141, 163 and 187, respectively; or
   SEQ ID No: 141, 164 and 186, respectively; or
   SEQ ID No: 141, 166 and 186, respectively; or
   SEQ ID No: 141, 167 and 186, respectively; or
   SEQ ID No: 141, 167 and 189, respectively; or
   SEQ ID No: 141, 168 and 186, respectively; or
   SEQ ID No: 141, 168 and 187, respectively; or
   SEQ ID No: 141, 169 and 190, respectively; or
   SEQ ID No: 141, 170 and 186, respectively; or
   SEQ ID No: 141, 171 and 186, respectively; or
   SEQ ID No: 141, 174 and 186, respectively; or
   SEQ ID No: 141, 175 and 187, respectively; or
   SEQ ID No: 142, 165 and 188, respectively; or
   SEQ ID No: 142, 173 and 188, respectively; or
   SEQ ID No: 143, 164 and 186, respectively; or
   SEQ ID No: 144, 172 and 187, respectively; or
   SEQ ID No: 145, 172 and 187, respectively; or
   SEQ ID No: 141, 214 and 186, respectively; or
   SEQ ID No: 141, 215 and 186, respectively; or
   SEQ ID No: 141, 216 and 186, respectively; or
   SEQ ID No: 141, 217 and 186, respectively; or
   SEQ ID No: 141, 218 and 186, respectively; or
   SEQ ID No: 141, 219 and 186, respectively; or
   SEQ ID No: 141, 220 and 186, respectively; or
   SEQ ID No: 213, 221 and 186, respectively; or
   SEQ ID No: 213, 214 and 186, respectively.

In a further aspect, a polypeptide of the present invention, in particular an immunoglobuling single domain of the present invention, has the following CDR1, CDR2 and CDR3:
   SEQ ID No: 146, 176 and 191, respectively; or
   SEQ ID No: 146, 177 and 191, respectively.

In a further aspect, a polypeptide of the present invention, in particular an immunoglobuling single domain of the present invention, has the following CDR1, CDR2 and CDR3:
   SEQ ID No: 147, 178 and 192, respectively; or
   SEQ ID No: 147, 179 and 192, respectively; or
   SEQ ID No: 147, 179 and 194, respectively; or
   SEQ ID No: 148, 179 and 193, respectively; or
   SEQ ID No: 149, 179 and 192, respectively; or
   SEQ ID No: 149, 180 and 192, respectively; or
   SEQ ID No: 149, 181 and 192, respectively; or
   SEQ ID No: 149, 183 and 192, respectively; or
   SEQ ID No: 149, 185 and 192, respectively; or
   SEQ ID No: 150, 179 and 194, respectively; or
   SEQ ID No: 150, 182 and 194, respectively; or
   SEQ ID No: 151, 179 and 193, respectively; or
   SEQ ID No: 151, 182 and 194, respectively; or
   SEQ ID No: 151, 184 and 196, respectively; or
   SEQ ID No: 152, 179 and 195, respectively; or
   SEQ ID No: 153, 179 and 194, respectively; or
   SEQ ID No: 154, 182 and 194, respectively; or
   SEQ ID No: 155, 179 and 195, respectively; or
   SEQ ID No: 156, 181 and 192, respectively; or
   SEQ ID No: 157, 179 and 194, respectively; or
   SEQ ID No: 158, 179 and 192, respectively; or
   SEQ ID No: 159, 178 and 192, respectively; or
   SEQ ID No: 160, 179 and 194, respectively; or
   SEQ ID No: 161, 179 and 194, respectively.

In a further aspect, a polypeptide of the present invention, in particular an immunoglobuling single domain of the present invention, has the CDR1, CDR2 and CDR3 set forth in:
   SEQ ID NO's: 141, 164 and 186; or
   SEQ ID NO's: 141, 162 and 186.

In a further aspect, a polypeptide of the present invention, in particular an immunoglobuling single domain of the present invention, has the CDR1, CDR2 and CDR3 set forth in:
   SEQ ID NO's: 213, 214 and 186; or
   SEQ ID NO's: 213, 221 and 186; or
   SEQ ID NO's: 141, 162 and 186.

Representative polypeptides of the present invention having the CDRs described above are shown in Tables 1, 2, 3 (representative polypeptides of families 101, 9 and 13, respectively) and 4 (representative polypeptides of optimized variants of family 101.

TABLE 1

Family 101

| Nanobody | SEQ CDR1* | SEQ CDR1 | CDR2* | SEQ CDR2 | CDR3* | SEQ CDR3 |
|---|---|---|---|---|---|---|
| CX3CR1BIIPMP66B02 | 1 | GSIFSSNAMA | 141 | AINSVGVTK | 162 | DPRRGWDTRY | 186 |
| CX3CR1BIIPMP54A12 | 2 | GSIFSSNAMA | 141 | VINSVGITK | 163 | DARRGWDTRY | 187 |
| CX3CR1BIIPMP54A3 | 3 | GSIFSSNAMA | 141 | GINSVGITK | 164 | DPRRGWDTRY | 186 |
| CX3CR1BIIPMP54A4 | 4 | GSIFSSNAMA | 141 | GINSVGITK | 164 | DPRRGWDTRY | 186 |
| CX3CR1BIIPMP54A5 | 5 | GSIFSSNAMA | 141 | GINSVGITK | 164 | DPRRGWDTRY | 186 |
| CX3CR1BIIPMP54A7 | 6 | GTIFSSNAMA | 142 | GINSVDITK | 165 | DPRRGWNTRY | 188 |

TABLE 1-continued

Family 101

| Nanobody | SEQ | CDR1* | SEQ CDR1 | CDR2* | SEQ CDR2 | CDR3* | SEQ CDR3 |
|---|---|---|---|---|---|---|---|
| CX3CR1BIIPMP54B1 | 7 | GSIFSSNAMA | 141 | GINSVGITK | 164 | DPRRGWDTRY | 186 |
| CX3CR1BIIPMP54B2 | 8 | GTIFSSNAMA | 142 | GINSVDITK | 165 | DPRRGWNTRY | 188 |
| CX3CR1BIIPMP54B3 | 9 | GSIFSSNAMA | 141 | AINSVGITK | 166 | DPRRGWDTRY | 186 |
| CX3CR1BIIPMP54B5 | 10 | GSIFSSNAMA | 141 | GINSVGITK | 164 | DPRRGWDTRY | 186 |
| CX3CR1BIIPMP54D5 | 11 | GSIFSSNAMA | 141 | LINSVGITK | 167 | DGRRGWDTRY | 189 |
| CX3CR1BIIPMP54D8 | 12 | GSIFSSNAMA | 141 | GINSVGITK | 164 | DPRRGWDTRY | 186 |
| CX3CR1BIIPMP54F6 | 13 | GSIFSSNAMA | 141 | AINSVGITK | 166 | DPRRGWDTRY | 186 |
| CX3CR1BIIPMP54G3 | 14 | GSIFSSNAMA | 141 | LINSVGITK | 167 | DPRRGWDTRY | 186 |
| CX3CR1BIIPMP54H1 | 15 | GTIFSSNAMA | 142 | GINSVDITK | 165 | DPRRGWNTRY | 188 |
| CX3CR1BIIPMP54H4 | 16 | GSIFSSNAMA | 141 | VINSVGITK | 163 | DARRGWDTRY | 187 |
| CX3CR1BIIPMP61F10 | 17 | GTIFSSNAMA | 142 | GINSVDITK | 165 | DPRRGWNTRY | 188 |
| CX3CR1BIIPMP61D1 | 18 | GSIFSSNAMA | 141 | LINSVGITK | 167 | DPRRGWDTRY | 186 |
| CX3CR1BIIPMP61D5 | 19 | GSIFSSNAMA | 141 | LINSVGITK | 167 | DPRRGWDTRY | 186 |
| CX3CR1BIIPMP61E2 | 20 | GSIFSSNAMA | 141 | GINSVGITK | 164 | DPRRGWDTRY | 186 |
| CX3CR1BIIPMP61F11 | 21 | GSIFSSNAMA | 141 | AINSVGITK | 166 | DPRRGWDTRY | 186 |
| CX3CR1BIIPMP61G2 | 22 | GSIFSSNAMA | 141 | LINSVGITK | 167 | DPRRGWDTRY | 186 |
| CX3CR1BIIPMP61G3 | 23 | GSIFSSNAMA | 141 | AINSVGITK | 166 | DPRRGWDTRY | 186 |
| CX3CR1BIIPMP61G4 | 24 | GSIFSSNAMA | 141 | AINSVGITK | 166 | DPRRGWDTRY | 186 |
| CX3CR1BIIPMP61F4 | 25 | GSIFSSNAMA | 141 | VINTVGITK | 168 | DARRGWDTRY | 187 |
| CX3CR1BIIPMP61A11 | 26 | GSIFSSNAMA | 141 | VINSVGITK | 163 | DARRGWDTRY | 187 |
| CX3CR1BIIPMP61B2 | 27 | GSIFSSNAMA | 141 | VINTVGITK | 168 | DARRGWDTRY | 187 |
| CX3CR1BIIPMP61C9 | 28 | GSIFSSNAMA | 141 | LIDSAGITK | 169 | DARRGWNTKY | 190 |
| CX3CR1BIIPMP65H02 | 29 | GSIFSSNAMA | 141 | AINSVGITK | 166 | DPRRGWDTRY | 186 |
| CX3CR1BIIPMP65E11 | 30 | GSIFSSNAMA | 141 | GINSVGIAK | 170 | DPRRGWDTRY | 186 |
| CX3CR1BIIPMP65E10 | 31 | GSIFSSNAKA | 143 | GINSVGITK | 164 | DPRRGWDTRY | 186 |

TABLE 1-continued

Family 101

| Nanobody | SEQ | CDR1* | SEQ CDR1 | CDR2* | SEQ CDR2 | CDR3* | SEQ CDR3 |
|---|---|---|---|---|---|---|---|
| CX3CR1BIIPMP65E05 | 32 | GSIFSSNAMA | 141 | GINSVGITK | 164 | DPRRGWDTRY | 186 |
| CX3CR1BIIPMP65B11 | 33 | GSIFSSNAMA | 141 | VINKVGITK | 171 | DPRRGWDTRY | 186 |
| CX3CR1BIIPMP65B07 | 34 | GSIFSSNAMA | 141 | AINSVGITK | 166 | DPRRGWDTRY | 186 |
| CX3CR1BIIPMP65B09 | 35 | GSIFSRNAMA | 144 | SINSVGITK | 172 | DARRGWDTRY | 187 |
| CX3CR1BIIPMP65H01 | 36 | GGIFSRNAMA | 145 | SINSVGITK | 172 | DARRGWDTRY | 187 |
| CX3CR1BIIPMP65G07 | 37 | GTIFSSNAMA | 142 | GINSVDITR | 173 | DPRRGWNTRY | 188 |
| CX3CR1BIIPMP66H08 | 38 | GSIFSSNAMA | 141 | LINSVGITK | 167 | DPRRGWDTRY | 186 |
| CX3CR1BIIPMP66H04 | 39 | GSIFSSNAMA | 141 | AINSVGITK | 166 | DPRRGWDTRY | 186 |
| CX3CR1BIIPMP66F02 | 40 | GSIFSSNAMA | 141 | LINSVGITK | 167 | DPRRGWDTRY | 186 |
| CX3CR1BIIPMP66E11 | 41 | GSIFSSNAMA | 141 | AINSVGTTK | 174 | DPRRGWDTRY | 186 |
| CX3CR1BIIPMP66D10 | 42 | GSIFSSNAMA | 141 | LINSVGITK | 167 | DPRRGWDTRY | 186 |
| CX3CR1BIIPMP66D08 | 43 | GSIFSSNAMA | 141 | GINSVGITK | 164 | DPRRGWDTRY | 186 |
| CX3CR1BIIPMP66A04 | 44 | GSIFSSNAMA | 141 | LINSVGITK | 167 | DPRRGWDTRY | 186 |
| CX3CR1BIIPMP66D04 | 45 | GTIFSSNAMA | 142 | GINSVDITK | 165 | DPRRGWNTRY | 188 |
| CX3CR1BIIPMP66D02 | 46 | GSIFSSNAMA | 141 | VINSVGITK | 163 | DARRGWDTRY | 187 |
| CX3CR1BIIPMP66D06 | 47 | GSIFSSNAMA | 141 | SIDSVGITK | 175 | DARRGWDTRY | 187 |
| CX3CR1BIIPMP66G01 | 48 | GSIFSSNAMA | 141 | LINSVGITK | 167 | DGRRGWDTRY | 189 |

*CDR sequences were determined according to Antibody Engineering, vol 2 by Konetermann & Dübel (Eds.), Springer Verlag Heidelberg Berlin, 2010. The sequence numbers in the table (SEQ) refer to the sequences in the sequence listing of the instant application.

TABLE 2

Family 9

| Nanobody | SEQ | CDR1* | SEQ CDR1 | CDR2* | SEQ CDR2 | CDR3* | SEQ CDR3 |
|---|---|---|---|---|---|---|---|
| CX3CR1BIIPMP11H11 | 49 | GRTFSSYAMG | 146 | GISGSASRKY | 176 | SNSYPKVQFDY | 191 |
| CX3CR1BIIPMP12B6 | 50 | GRTFSSYAMG | 146 | GISGSASRKY | 176 | SNSYPKVQFDY | 191 |
| CX3CR1BIIPMP12G9 | 51 | GRTFSSYAMG | 146 | GISGSGSRKY | 177 | SNSYPKVQFDY | 191 |

TABLE 2-continued

| Family 9 | | | | | | | |
|---|---|---|---|---|---|---|---|
| Nanobody | SEQ CDR1 | CDR1* | SEQ CDR2 | CDR2* | SEQ CDR3 | CDR3* | |
| CX3CR1BIIPMP15G11 | 52 | GRTFSSYAMG | 146 | GISGSGSRKY | 177 | SNSYPKVQFDY | 191 |

*CDR sequences were determined according to Antibody Engineering, vol 2 by Konetermann & Dübel (Eds.), Springer Verlag Heidelberg Berlin, 2010. The sequence numbers in the table (SEQ) refer to the sequences in the sequence listing of the instant application.

TABLE 3

| Family 13 | | | | | | | |
|---|---|---|---|---|---|---|---|
| Nanobody | SEQ CDR1 | CDR1* | SEQ CDR2 | CDR2* | SEQ CDR3 | CDR3* | |
| CX3CR1BIIPMP18E6 | 53 | GTIFSNNAMG | 147 | SISSSGSTN | 178 | DARRGWNTAY | 192 |
| CX3CR1BIIPMP12C2 | 54 | GTIFSNTAMG | 148 | SISNSGSTN | 179 | DARRGWNSGY | 193 |
| CX3CR1BIIPMP18A10 | 55 | GIIFSNNAMG | 149 | SISNSGSTN | 179 | DARRGWNTAY | 192 |
| CX3CR1BIIPMP18A2 | 56 | GIIFSNNAMG | 149 | SIGSTYSTN | 180 | DARRGWNTAY | 192 |
| CX3CR1BIIPMP18A8 | 57 | RTIFRSNAMG | 150 | SISNSGSTN | 179 | DARRGWNTGY | 194 |
| CX3CR1BIIPMP18A9 | 58 | GIIFSNNAMG | 149 | SISSTYSTN | 181 | DARRGWNTAY | 192 |
| CX3CR1BIIPMP18B7 | 59 | GTIFRSNAMG | 151 | SISNSGSTN | 179 | DARRGWNSGY | 193 |
| CX3CR1BIIPMP18B9 | 60 | GTIFSNNAMG | 147 | SISSSGSTN | 178 | DARRGWNTAY | 192 |
| CX3CR1BIIPMP18C6 | 61 | GTIFSNNAMG | 147 | SISNSGSTN | 179 | DARRGWNTAY | 192 |
| CX3CR1BIIPMP18C9 | 62 | GIIFSNNAMG | 149 | SISNSGSTN | 179 | DARRGWNTAY | 192 |
| CX3CR1BIIPMP18D1 | 63 | GIIFSNNAMG | 149 | SISNSGSTN | 179 | DARRGWNTAY | 192 |
| CX3CR1BIIPMP18D10 | 64 | GTIFSNNAMG | 147 | SISNSGSTN | 179 | DARRGWNTAY | 192 |
| CX3CR1BIIPMP18D12 | 65 | GTIFSNNAMG | 147 | SISNSGSTN | 179 | DARRGWNTAY | 192 |
| CX3CR1BIIPMP18F1 | 66 | GTIFSNNAMG | 147 | SISNSGSTN | 179 | DARRGWNTAY | 192 |
| CX3CR1BIIPMP18F5 | 67 | GTIFSNNAMG | 147 | SISNSGSTN | 179 | DARRGWNTAY | 192 |
| CX3CR1BIIPMP18F6 | 68 | GTIFSNNAMG | 147 | SISNSGSTN | 179 | DARRGWNTAY | 192 |
| CX3CR1BIIPMP18F9 | 69 | GTIFRTNAMG | 152 | SISNSGSTN | 179 | DGRRGWNTGY | 195 |
| CX3CR1BIIPMP18G5 | 70 | RTIFRSNAMG | 150 | SISNSGSTN | 179 | DARRGWNTGY | 194 |
| CX3CR1BIIPMP18H1 | 71 | GTIFSNNAMG | 147 | SISNSGSTN | 179 | DARRGWNTAY | 192 |
| CX3CR1BIIPMP18H10 | 72 | KTIFRSNAMG | 153 | SISNSGSTN | 179 | DARRGWNTGY | 194 |

TABLE 3-continued

Family 13

| Nanobody | SEQ CDR1 | CDR1* | SEQ CDR2 | CDR2* | SEQ CDR3 | CDR3* |
|---|---|---|---|---|---|---|
| CX3CR1BIIPMP18H7 | 73 | GIIFSNNAMG | 149 | SISNSGSTN | 179 | DARRGWNTAY | 192 |
| CX3CR1BIIPMP18H9 | 74 | GTIFSNNAMG | 147 | SISNSGSTN | 179 | DARRGWNTAY | 192 |
| CX3CR1BIIPMP20B3 | 75 | GIIFSNNAMG | 149 | SIGSTYSTN | 180 | DARRGWNTAY | 192 |
| CX3CR1BIIPMP20C12 | 76 | GTIFRSNAMG | 151 | SISNSGSTN | 179 | DARRGWNSGY | 193 |
| CX3CR1BIIPMP20C3 | 77 | GIIFSNNAMG | 149 | SISNSGSTN | 179 | DARRGWNTAY | 192 |
| CX3CR1BIIPMP20C6 | 78 | GTIFSNNAMG | 147 | SISNSGSTN | 179 | DARRGWNTAY | 192 |
| CX3CR1BIIPMP20D8 | 79 | GTTFRSNAMG | 154 | SITNSGSTN | 182 | DARRGWNTGY | 194 |
| CX3CR1BIIPMP20E11 | 80 | RTIFRSNAMG | 150 | SITNSGSTN | 182 | DARRGWNTGY | 194 |
| CX3CR1BIIPMP20E5 | 81 | GTIFSNNAMG | 147 | SISNSGSTN | 179 | DARRGWNTGY | 194 |
| CX3CR1BIIPMP20F3 | 82 | GTIFSNNAMG | 147 | SISSSGSTN | 178 | DARRGWNTAY | 192 |
| CX3CR1BIIPMP20F4 | 83 | ATIFRSNAMG | 155 | SISNSGSTN | 179 | DGRRGWNTGY | 195 |
| CX3CR1BIIPMP20F5 | 84 | ATIFRSNAMG | 155 | SISNSGSTN | 179 | DGRRGWNTGY | 195 |
| CX3CR1BIIPMP21B6 | 85 | GTIFSNNAMG | 147 | SISNSGSTN | 179 | DARRGWNTAY | 192 |
| CX3CR1BIIPMP24A12 | 86 | GIIFSNNAMG | 149 | SISNSGSAN | 183 | DARRGWNTAY | 192 |
| CX3CR1BIIPMP24A6 | 87 | GTIFSNNAMG | 147 | SISNSGSTN | 179 | DARRGWNTAY | 192 |
| CX3CR1BIIPMP24B9 | 88 | GTIFRSNAMG | 151 | SISISGSTN | 184 | DARRGWNTGF | 196 |
| CX3CR1BIIPMP24D3 | 89 | GIIFSNNAMG | 149 | SISSTYSTN | 181 | DARRGWNTAY | 192 |
| CX3CR1BIIPMP24F7 | 90 | GLIFSNNAMG | 156 | SISSTYSTN | 181 | DARRGWNTAY | 192 |
| CX3CR1BIIPMP28B4 | 91 | ATIFRSNAMG | 155 | SISNSGSTN | 179 | DGRRGWNTGY | 195 |
| CX3CR1BIIPMP28F1 | 92 | GIIFSNNAMG | 149 | SIGSTYSTN | 180 | DARRGWNTAY | 192 |
| CX3CR1BIIPMP28F6 | 93 | GIIFSNNAMG | 149 | SISNSGSTN | 179 | DARRGWNTAY | 192 |
| CX3CR1BIIPMP28F9 | 94 | GTIFSNNAMG | 147 | SISNSGSTN | 179 | DARRGWNTGY | 194 |
| CX3CR1BIIPMP29A5 | 95 | GTIFSNNAMG | 147 | SISNSGSTN | 179 | DARRGWNTAY | 192 |
| CX3CR1BIIPMP29D5 | 96 | GTIFRSNAMG | 151 | SISNSGSTN | 179 | DARRGWNSGY | 193 |
| CX3CR1BIIPMP29E3 | 97 | KTIFRSNAMG | 153 | SISNSGSTN | 179 | DARRGWNTGY | 194 |

TABLE 3-continued

| Family 13 | | | | | | |
|---|---|---|---|---|---|---|
| Nanobody | CDR1* | SEQ CDR1 | CDR2* | SEQ CDR2 | CDR3* | SEQ CDR3 |
| CX3CR1BIIPMP29E7 | KTIFRSNAMG | 98 | SISNSGSTN | 153 | DARRGWNTGY | 179 194 |
| CX3CR1BIIPMP29G10 | GTIFRSNAMG | 99 | SITNSGSTN | 151 | DARRGWNTGY | 182 194 |
| CX3CR1BIIPMP29G7 | GIIFSNNAMG | 100 | SITNTGSTN | 149 | DARRGWNTAY | 185 192 |
| CX3CR1BIIPMP29H1 | GTIFSNNAMG | 101 | SISNSGSTN | 147 | DARRGWNTAY | 179 192 |
| CX3CR1BIIPMP37A8 | RTIFRSNAMG | 102 | SISNSGSTN | 150 | DARRGWNTGY | 179 194 |
| CX3CR1BIIPMP37B9 | GTIFSNNAMG | 103 | SISNSGSTN | 147 | DARRGWNTAY | 179 192 |
| CX3CR1BIIPMP37C12 | GSIFRSNAMG | 104 | SISNSGSTN | 157 | DARRGWNTGY | 179 194 |
| CX3CR1BIIPMP37C7 | RTIFSNNAMG | 105 | SISNSGSTN | 158 | DARRGWNTAY | 179 192 |
| CX3CR1BIIPMP37D9 | GTVFSNNAMG | 106 | SISSSGSTN | 159 | DARRGWNTAY | 178 192 |
| CX3CR1BIIPMP37E12 | KPIFRSNAMG | 107 | SISNSGSTN | 160 | DARRGWNTGY | 179 194 |
| CX3CR1BIIPMP41B10 | GTIFSNNAMG | 108 | SISNSGSTN | 147 | DARRGWNTAY | 179 192 |
| CX3CR1BIIPMP41B11 | GTIFSNNAMG | 109 | SISNSGSTN | 147 | DARRGWNTAY | 179 192 |
| CX3CR1BIIPMP41B8 | GIIFSNNAMG | 110 | SIGSTYSTN | 149 | DARRGWNTAY | 180 192 |
| CX3CR1BIIPMP41C10 | RTIFRSNAMG | 111 | SISNSGSTN | 150 | DARRGWNTGY | 179 194 |
| CX3CR1BIIPMP41F9 | GIIFSNNAMG | 112 | SIGSTYSTN | 149 | DARRGWNTAY | 180 192 |
| CX3CR1BIIPMP41H10 | GLTLDDYAMG | 113 | SISNSGSTN | 161 | DARRGWNTGY | 179 194 |
| CX3CR1BIIPMP46B5 | RTIFRSNAMG | 114 | SISNSGSTN | 150 | DARRGWNTGY | 179 194 |
| CX3CR1BIIPMP46D3 | GTIFSNNAMG | 115 | SISNSGSTN | 147 | DARRGWNTGY | 179 194 |
| CX3CR1BIIPMP46H5 | GIIFSNNAMG | 116 | SISSTYSTN | 149 | DARRGWNTAY | 181 192 |
| CX3CR1BIIPMP48B8 | KTIFRSNAMG | 117 | SISNSGSTN | 153 | DARRGWNTGY | 179 194 |
| CX3CR1BIIPMP48D11 | RTIFRSNAMG | 118 | SISNSGSTN | 150 | DARRGWNTGY | 179 194 |
| CX3CR1BIIPMP48G8 | RTIFRSNAMG | 119 | SISNSGSTN | 150 | DARRGWNTGY | 179 194 |
| CX3CR1BIIPMP48H9 | GTIFSNNAMG | 120 | SISNSGSTN | 147 | DARRGWNTAY | 179 192 |

*CDR sequences were determined according to Antibody Engineering, vol 2 by Konetermann & Dübel (Eds.), Springer Verlag Heidelberg Berlin, 2010. The sequence numbers in the table (SEQ) refer to the sequences in the sequence listing of the instant application.

TABLE 4

Optimized variants

| Nanobody | SEQ CDR1 | CDR1 | SEQ CDR2 | CDR2 | SEQ CDR3 | CDR3 |
|---|---|---|---|---|---|---|
| CX3CR1BIIPMP66B02 | 1 | GSIFSSNAMA | 141 | AINSVGVTK | 162 | DPRRGWDTRY | 186 |
| CX3CR1BII043 | 121 | GSIFSSNAMA | 141 | AINSVGVTK | 162 | DPRRGWDTRY | 186 |
| CX3CR1BII045 | 122 | GSIFSSNAMA | 141 | AINSVGVTK | 162 | DPRRGWDTRY | 186 |
| CX3CR1BII047 | 123 | GSIFSSNAMA | 141 | AINSVGVTK | 162 | DPRRGWDTRY | 186 |
| CX3CR1BII048 | 124 | GSIFSSNAMA | 141 | AINSVGVTK | 162 | DPRRGWDTRY | 186 |
| CX3CR1BII049 | 125 | GSIFSSNAMA | 141 | AINSVGVTK | 162 | DPRRGWDTRY | 186 |
| CX3CR1BII050 | 126 | GSIFSSNAMA | 141 | AINSVGVTK | 162 | DPRRGWDTRY | 186 |
| CX3CR1BII061 | 127 | GSIFSSNAMA | 141 | AINSVGVTK | 162 | DPRRGWDTRY | 186 |
| CX3CR1BII056 | 128 | GSIFSSNAMA | 141 | AINSVGVTK | 162 | DPRRGWDTRY | 186 |
| CX3CR1BII057 | 129 | GSIFSSNAMA | 141 | AINSVGVTK | 162 | DPRRGWDTRY | 186 |
| CX3CR1BII060 | 130 | GSIFSSNAMA | 141 | AINSVGVTK | 162 | DPRRGWDTRY | 186 |
| CX3CR1BII065 | 131 | GSIFSSNAMA | 141 | AISSVGVTK | 214 | DPRRGWDTRY | 186 |
| CX3CR1BII067 | 132 | GSIFSSNAMA | 141 | AIQSVGVTK | 215 | DPRRGWDTRY | 186 |
| CX3CR1BII068 | 133 | GSIFSSNAMA | 141 | AIGSVGVTK | 216 | DPRRGWDTRY | 186 |
| CX3CR1BII074 | 134 | GSIFSSNAMA | 141 | AITSVGVTK | 217 | DPRRGWDTRY | 186 |
| CX3CR1BII118 | 135 | GSIFSSNAMA | 141 | AINTVGVTK | 218 | DPRRGWDTRY | 186 |
| CX3CR1BII129 | 136 | GSIFSSNAMA | 141 | AINGVGVTK | 219 | DPRRGWDTRY | 186 |
| CX3CR1BII158 | 137 | GSIFSSNAMA | 141 | AINPVGVTK | 220 | DPRRGWDTRY | 186 |
| CX3CR1BII306 | 138 | GSIFSSTAMA | 213 | AISSVGVTK | 214 | DPRRGWDTRY | 186 |
| CX3CR1BII307 | 139 | GSIFSSTAMA | 213 | AISTVGVTK | 221 | DPRRGWDTRY | 186 |
| CX3CR1BII308 | 140 | GSIFSSNAMA | 141 | AINSVGVTK | 162 | DPRRGWDTRY | 186 |

*CDR sequences were determined according to Antibody Engineering, vol 2 by Konetermann & Dübel (Eds.), Springer Verlag Heidelberg Berlin, 2010. The sequence numbers in the table (SEQ) refer to the sequences in the sequence listing of the instant application.

In a further aspect, the present invention provides polypeptides having one or more VHH domains.

In one aspect, a VHH domain of the present invention comprises or essentially consists of the sequence set forth in:
a) the amino acid sequence of SEQ ID NO: 3; or
b) amino acid sequences that have at least 90% amino acid identity with the amino acid sequences of SEQ ID NO: 3; or
c) amino acid sequences that have 11, 10, 9, 8, 7, 6, 5, 4, 3, 2, or 1 amino acid difference with the amino acid sequences of SEQ ID NO: 3 or
d) an amino acid sequence of any one of SEQ ID NO: 1-48, or SEQ ID NO: 121-140, or SEQ ID NO: 222-224.

In a further aspect, a VHH domain of the present invention comprises or essentially consists of the sequence set forth in:
a) the amino acid sequence of SEQ ID NO: 49; or
b) an amino acid sequence that has at least 95% amino acid identity with the amino acid sequences of SEQ ID NO: 49; or
c) an amino acid sequence that has 5, 4, 3, 2, or 1 amino acid difference with the amino acid sequences of SEQ ID NO: 49; or
d) an amino acid sequence of any one of SEQ ID NO: 49-52.

In a further aspect, a VHH domain of the present invention comprises or essentially consists of the sequence set forth in:
a) the amino acid sequence of SEQ ID NO: 67; or
b) an amino acid sequence that has at least 90% amino acid identity with the amino acid sequences of SEQ ID NO: 67; or
c) an amino acid sequence that has 12, 11, 10, 9, 8, 7, 6, 5, 4, 3, 2, or 1 amino acid difference with the amino acid sequences of SEQ ID NO: 67; or
d) an amino acid sequence of any one of SEQ ID NO: 53-120.

In a further aspect, a VHH domain of the present invention comprises or essentially consists of the amino acid sequence set forth in any one of SEQ ID NO: 121-140, or SEQ ID NO: 222-224.

In a further aspect, a VHH domain of the present invention comprises or essentially consists of the amino acid sequence set forth in any one of SEQ ID NO: 138-140.

In a further aspect, a VHH domain of the present invention comprises or essentially consists of the amino acid sequence set forth in any one of SEQ ID NO: 222-224.

Representative VHH domains of the present invention are shown in Table 5 and representative optimized VHH domains of the present invention are shown in Table 6 below:

TABLE 5

VHH domains
SEQ ID NO: 1-48 are VHH domains of family 101. SEQ ID
NO: 49-52 are VHH domains of family 9. SEQ ID
NO: 53-120 are VHH domains of family 13.

| | | |
|---|---|---|
| CX3CR1BIIPMP66B02 | EVQLVESGGGSVQAGESLRLSCAASGSIFSSNAM<br>AWYRQAPGKRRDLVAAINSVGVTKYADSVKGRFTI<br>SRDNAKNTVYLQMNSLKPEDTAVYYCTSDPRRGW<br>DTRYWGQGTQVTVSS | SEQ ID<br>NO: 1 |
| CX3CR1BIIPMP54A12 | EVQLVESGGGSVQAGESLRLSCAASGSIFSSNAM<br>AWYRQAPGKQRDLVAVINSVGITKYADSVKGRFTI<br>SGDNAKNTVYLQMNSLKPEDTAVYYCTSDARRGW<br>DTRYWGQGTQVTVSS | SEQ ID<br>NO: 2 |
| CX3CR1BIIPMP54A3 | EVQLVESGGGSVQAGESLRLSCAASGSIFSSNAM<br>AWYRQAPGKQRDLVAGINSVGITKYADSVKGRFTI<br>SRDNAKNTVYLQMNSLKPEDTAVYYCTSDPRRGW<br>DTRYWGQGTQVTVSS | SEQ ID<br>NO: 3 |
| CX3CR1BIIPMP54A4 | EVQLVESGRGSVQAGESLRLSCAASGSIFSSNAM<br>AWYRQAPGKQRDLVAGINSVGITKYADSVKGRFTI<br>SRDNAKNTVYLQMNSLKPEDTAVYYCTSDPRRGW<br>DTRYWGQGTQVTVSS | SEQ ID<br>NO: 4 |
| CX3CR1BIIPMP54A5 | EVQLVESGGGSVQAGESLRLSCAASGSIFSSNAM<br>AWYRQAPGKQRDLVAGINSVGITKYADSVKGRFTI<br>SRDNAKNTVYLQMNSLKPEDTAVYYCTSDPRRGW<br>DTRYWGQGTLVTVSS | SEQ ID<br>NO: 5 |
| CX3CR1BIIPMP54A7 | EVQLVESGGGSVQAGESLRLSCAASGTIFSSNAM<br>AWYRQAPGKQRDLVAGINSVDITKYADSVKGRFTI<br>SRDNAKNTVYLQMNSLKPEDTAVYYCTSDPRRGW<br>NTRYWGQGTQVTVSS | SEQ ID<br>NO: 6 |
| CX3CR1BIIPMP54B1 | EVQLVESGGGSVQAGESLRLSCAASGSIFSSNAM<br>AWYRQAPGKQRDLVAGINSVGITKYADSVKGRFTI<br>SRDNAKNTAYLQMNSLKPEDTAVYYCTSDPRRGW<br>DTRYWGQGTQVTVSS | SEQ ID<br>NO: 7 |
| CX3CR1BIIPMP54B2 | EVQLVESGGGSVQAGESLRLSCAASGTIFSSNAM<br>AWYRQAPGKQRDLVAGINSVDITKYADSVKGRFTI<br>SRDNAKNTVYLQMNSLKPEDTAVYYCTSDPRRGW<br>NTRYWGQGTLVTVSS | SEQ ID<br>NO: 8 |

TABLE 5-continued

VHH domains
SEQ ID NO: 1-48 are VHH domains of family 101. SEQ ID
NO: 49-52 are VHH domains of family 9. SEQ ID
NO: 53-120 are VHH domains of family 13.

| | | |
|---|---|---|
| CX3CR1BIIPMP54B3 | EVQLVESGGGSVQAGESLRLSCAASGSIFSSNAM AWYRQAPGKQRDLVAAINSVGITKYADSVKGRFTI SRDNAKNTVYLQMNSLKPEDTAVYYCTSDPRRGW DTRYWGQGTQVTVSS | SEQ ID NO: 9 |
| CX3CR1BIIPMP54B5 | EVQLVESGGGSVQAGESLRLSCAASGSIFSSNAM AWYRQAPGKQRDLVAGINSVGITKYADSVKGRFTI SRDNAKNTAYLQMNSLKPEDTAVYYCTSDPRRGW DTRYWGQGTLVTVSS | SEQ ID NO: 10 |
| CX3CR1BIIPMP54D5 | EVQLVESGGGSVQAGESLRLSCAASGSIFSSNAM AWYRQAPPGKQRDLVALINSVGITKYADSVKGRFT ISSDNAKNTVYLEMNSLKPEDTAVYYCTSDGRRG WDTRYWGQGTQVTVSS | SEQ ID NO: 11 |
| CX3CR1BIIPMP54D8 | EVQLVESGGGSVQAGGSLRLSCAASGSIFSSNAM AWYRQAPGKQRDLVAGINSVGITKYADSVKGRFTI SRDNAKNTVYLQMNSLKPEDTAVYYCTSDPRRGW DTRYWGQGTLVTVSS | SEQ ID NO: 12 |
| CX3CR1BIIPMP54F6 | KVQLVESGGGSVQAGESLRLSCAASGSIFSSNAM AWYRQAPGKQRDLVAAINSVGITKYADSVKGRFTI SRDNAKNTVYLQMNSLKPEDTAVYYCTSDPRRGW DTRYWGQGTLVTVSS | SEQ ID NO: 13 |
| CX3CR1BIIPMP54G3 | EVQLVESGGGSVQAGESLRLSCAASGSIFSSNAM AWYRQAPGKQRDLVALINSVGITKYADSVKGRFTI SRDNAKNTVYLQMNSLKPEDTAVYYCTSDPRRGW DTRYWGQGTLVTVSS | SEQ ID NO: 14 |
| CX3CR1BIIPMP54H1 | EVQLVESGGGSVQAGESLRLSCAASGTIFSSNAM AWYRQAPGKQRDLVAGINSVDITKYADSVKGRFTV SRDNAKNTVYLQMNSLKPEDTAVYYCTSDPRRGW NTRYWGQGTQVTVSS | SEQ ID NO: 15 |
| CX3CR1BIIPMP54H4 | EVQLVESGGGSVQAGESLRLSCAASGSIFSSNAM AWYRQAPGKQRDLVAVINSVGITKYADSVKGRFTI SGDNAKNTVYLQMNSLKPEDTAVYYCTSDARRGW DTRYWGQGTLVTVSS | SEQ ID NO: 16 |
| CX3CR1BIIPMP61F10 | KVQLVESGGGSVQAGESLRLSCAASGTIFSSNAM AWYRQAPGKQRDLVAGINSVDITKYADSVKGRFTI SRDNAKNTVYLQMNSLKPEDTAVYYCTSDPRRGW NTRYWGQGTQVTVSS | SEQ ID NO: 17 |
| CX3CR1BIIPMP61D1 | EVQLVESGGGSVQAGESLRLSCAASGSIFSSNAM AWYRQAFGKQRDLVALINSVGITKYADSVKGRFTIS RDNAKNTVYLQMNSLKPEDTAVYYCTSDPRRGWD TRYWGQGTQVTVSS | SEQ ID NO: 18 |
| CX3CR1BIIPMP61D5 | KVQLVESGGGSVQAGESLRLSCAASGSIFSSNAM AWYRQAFGKQRDLVALINSVGITKYADSVKGRFTIS RDNAKNTVYLQMNSLKPEDTAVYYCTSDPRRGWD TRYWGQGTQVTVSS | SEQ ID NO: 19 |
| CX3CR1BIIPMP61E2 | EVQLVESGGGSVQAGESLRLSCAASGSIFSSNAM AWYRQAPGKQRDLVAGINSVGITKYADSVKGRFTI SRDNAKNTVYLQMNSLKPEDMAVYYCTSDPRRG WDTRYWGQGTQVTVSS | SEQ ID NO: 20 |
| CX3CR1BIIPMP61F11 | KVQLVESGGGSVQAGESLRLSCAASGSIFSSNAM AWYRQPPGKQRDLVAAINSVGITKYADSVKGRFTI FRDNAKNTVYLQMNSLKPEDTAVYYCTSDPRRGW DTRYWGQGTQVTVSS | SEQ ID NO: 21 |
| CX3CR1BIIPMP61G2 | EVQLVKSGGGSVQAGESLRLSCAASGSIFSSNAM AWYRQAPGKQRDLVALINSVGITKYADSVKGRFTI SRDNAKNTVYLQMNSLKPEDTAVYYCTSDPRRGW DTRYWGQGTQVTVSS | SEQ ID NO: 22 |
| CX3CR1BIIPMP61G3 | KVQLVESGGGSMQAGESLRLSCAASGSIFSSNAM AWYRQAPGKQRDLVAAINSVGITKYADSVKGRFTI SRDNAKNTVYLQMMSLKPEDTAVYYCTSDPRRG WDTRYWGQGTQVTVSS | SEQ ID NO: 23 |

TABLE 5-continued

VHH domains
SEQ ID NO: 1-48 are VHH domains of family 101. SEQ ID
NO: 49-52 are VHH domains of family 9. SEQ ID
NO: 53-120 are VHH domains of family 13.

| | | |
|---|---|---|
| CX3CR1BIIPMP61G4 | KVQLVESGGGSVQAGGSLRLSCAASGSIFSSNAM AWYRQAPGKQRDLVAAINSVGITKYADSVKGRFTI SRDNAKNTVYLQMMSLKPEDTAVYYCTSDPRRG WDTRYWGQGTQVTVSS | SEQ ID NO: 24 |
| CX3CR1BIIPMP61F4 | EVQLVESGGGSVQAGASLRLSCAASGSIFSSNAM AWYRQAPGKQRDLVAVINTVGITKYADSVKGRFTI SRDNAKNTVYLQMNSLKPEDTAVYYCTSDARRGW DTRYWGQGTLVTVSS | SEQ ID NO: 25 |
| CX3CR1BIIPMP61A11 | EVQLVESRGGSVQAGESLRLSCAASGSIFSSNAM AWYRQAPGKQRDLVAVINSVGITKYADSVKGRFTI SGDNAKNTVYLQMNSLKPEDTAVYYCTSDARRGW DTRYWGQGTQVTVSS | SEQ ID NO: 26 |
| CX3CR1BIIPMP61B2 | EVQLVESRGGSVQAGASLRLSCAASGSIFSSNAM AWYRQAPGKQRDLVAVINTVGITKYADSVKGRFTI SRDNAKNTVYLQMNSLKPEDTAVYYCTSDARRGW DTRYWGQGTQVTVSS | SEQ ID NO: 27 |
| CX3CR1BIIPMP61C9 | EVQLVKSGGGSVQAGESLRLSCAASGSIFSSNAM AWYRQALGKQRDLVALIDSAGITKYADSVKGRFTIS RDNAKNTVYLQMNRLKPEDTAVYYCASDARRGW NTKYWGQGTLVTVSS | SEQ ID NO: 28 |
| CX3CR1BIIPMP65H02 | EVQLVESGGGSVQAGESLRLSCAASGSIFSSNAM AWYRQAPGKQRDLVAAINSVGITKYADSVKGRFTI SRDNAKNTVHLQMNSLKPEDTAVYYCTSDPRRGW DTRYWGQGTLVTVSS | SEQ ID NO: 29 |
| CX3CR1BIIPMP65E11 | EVQLVESGGGSVQAGESLRLSCAASGSIFSSNAM AWYRQAPGKQRDLVAGINSVGIAKYADSVKGRFTI SRDNAKNTVYLQMNSLKPEDTAVYYCTSDPRRGW DTRYWGQGTLVTVSS | SEQ ID NO: 30 |
| CX3CR1BIIPMP65E10 | EVQLVESGGGSVQAGESLRLSCAASGSIFSSNAKA WYRQAPGKQRDLVAGINSVGITKYADSVKGRFTIS RDNAKNTVYLQMNSLKPEDTAVYYCTSDPRRGWD TRYWGQGTLVTVSS | SEQ ID NO: 31 |
| CX3CR1BIIPMP65E05 | KVQLVESGGGSVQAGESLRLSCAASGSIFSSNAM AWYRQAPGKQRDLVAGINSVGITKYADSVKGRFTI SRDNAKNTVYLQMNSLKPEDTAVYYCTSDPRRGW DTRYWGQGTLVTVSS | SEQ ID NO: 32 |
| CX3CR1BIIPMP65B11 | EVQLVKSGGGSVQAGESLRLSCAASGSIFSSNAM AWYRQAPGKQRDLVAVINKVGITKYADSVKGRFTI SRDNAKNTVYLQMNSLKPEDTAVYYCTSDPRRGW DTRYWGQGTQVTVSS | SEQ ID NO: 33 |
| CX3CR1BIIPMP65B07 | EVQLVESGGGSVQAGESLRLSCAASGSIFSSNAM AWYRQAPGKQRDLVAAINSVGITKYADSVKGRFTI SRDNAKNTVYLQMNSLKPEDTAVYYCTSDPRRGW DTRYWGQGTLVTVSS | SEQ ID NO: 34 |
| CX3CR1BIIPMP65B09 | EVQLVESGGGSVQAGESLRLSCAASGSIFSRNAM AWYRQAPGKQRDLVASINSVGITKYGDSVKGRFTI SRDNAKNTVYLQMNSLKPEDTAVYYCTSDARRGW DTRYWGQGTLVTVSS | SEQ ID NO: 35 |
| CX3CR1BIIPMP65H01 | EVQLVESGGGSVQAGESLRLSCAASGGIFSRNAM AWYRQAPGKQRDLVASINSVGITKYGDSVKGRFTI SRDNAKNTVYLQMNSLKPEDTAVYYCTSDARRGW DTRYWGQGTQVTVSS | SEQ ID NO: 36 |
| CX3CR1BIIPMP65G07 | EVQLVESGGGSVQAGESLRLSCAASGTIFSSNAM AWYRQAPGKQRDLVAGINSVDITRYADSVKGRFTI SRDNAKNTVYLQMNSLKPEDTAVYYCTSDPRRGW NTRYWGQGTQVTVSS | SEQ ID NO: 37 |
| CX3CR1BIIPMP66H08 | EVQLVESGGGSVQAGESLRLSCAASGSIFSSNAM AWYRQAPGKQRDLVALINSVGITKYADSVKGRFTI SRDNAKNTVYLQMNSLKPEDTAVYYCTSDPRRGW DTRYWGQGTQVTVSS | SEQ ID NO: 38 |

TABLE 5-continued

VHH domains
SEQ ID NO: 1-48 are VHH domains of family 101. SEQ ID
NO: 49-52 are VHH domains of family 9. SEQ ID
NO: 53-120 are VHH domains of family 13.

| | | |
|---|---|---|
| CX3CR1BIIPMP66H04 | EVQLVESGGGSVQAGGSLRLSCAASGSIFSSNAM AWYRQAPGKQRDLVAAINSVGITKYADSVKGRFTI SRDNAKNTVYLQMMSLKPEDTAVYYCTSDPRRG WDTRYWGQGTLVTVSS | SEQ ID NO: 39 |
| CX3CR1BIIPMP66F02 | EVQLVESGGGSVQAGESLRLSCAASGSIFSSNAM AWYRQAPGKQRDLVALINSVGITKYAGSVKGRFTI SRDNAKNTVYLQMNSLKPEDTAVYYCTSDPRRGW DTRYWGQGTQVTVSS | SEQ ID NO: 40 |
| CX3CR1BIIPMP66E11 | EVQLVESGGGSVQAGESLRLSCAASGSIFSSNAM AWYRQAPGKQRDLVAAINSVGTTKYADSVKGRFTI SRDNAKNTVYLQMNSLKPEDTAVYYCTSDPRRGW DTRYWGQGTQVTVSS | SEQ ID NO: 41 |
| CX3CR1BIIPMP66D10 | EVQLVESGGGSVQAGESLRLSCAASGSIFSSNAM AWYRQALGKQRDLVALINSVGITKYADSVKGRFTIS RDNAKNTVYLQMNSLKPEDTAVYYCTSDPRRGWD TRYWGQGTQVTVSS | SEQ ID NO: 42 |
| CX3CR1BIIPMP66D08 | EVQLMESGGGSVQAGESLRLSCAASGSIFSSNAM AWYRQAPGKQRDLVAGINSVGITKYADSVKGRFTI SRDNAKNTVYLQMNSLKPEDTAVYYCTSDPRRGW DTRYWGQGTQVTVSS | SEQ ID NO: 43 |
| CX3CR1BIIPMP66A04 | EVQLVESGGGSVQAGESLRLSCAASGSIFSSNAM AWYRQALGKQRDLVALINSVGITKYADSVKGRFTIS RDNAKNTVYLQMNSLKPEDTAVYYCTSDPRRGWD TRYWGQGTLVTVSS | SEQ ID NO: 44 |
| CX3CR1BIIPMP66D04 | KVQLVESGGGSVQAGESLRLSCAASGTIFSSNAM AWYRQAPGKQRDLVAGINSVDITKYADSVKGRFTI SRDNAKNTVYLQMNSLKPEDTAVYYCTSDPRRGW NTRYWGQGTLVTVSS | SEQ ID NO: 45 |
| CX3CR1BIIPMP66D02 | EVQLVESGGGSVQAGESLRLSCAASGSIFSSNAM AWYRQAPGKQRDLVAVINSVGITKYADSVKGRFTT SGDNAKNTVYLQMNSLKPEDTAVYYCTSDARRGW DTRYWGQGTQVTVSS | SEQ ID NO: 46 |
| CX3CR1BIIPMP66D06 | EVQLVESGGGSVQAGESLRLSCAASGSIFSSNAM AWYRQAPGKQRDLVASIDSVGITKYRDSVKGRFTI SRDNAKNTVYLQMNSLKPEDTAVYYCTSDARRGW DTRYWGQGTQVTVSS | SEQ ID NO: 47 |
| CX3CR1BIIPMP66G01 | EMQLVESGGGSVQAGESLRLSCAASGSIFSSNAM AWYRQAPGKQRDLVALINSVGITKYADSVKGRFTI SRDNAKNTVYLQMNSLKPEDTAVYYCTSDGRRG WDTRYWGQGTQVTVSS | SEQ ID NO: 48 |
| CX3CR1BIIPMP11H11 | EVQLVESGGGLVQAGGSLRLSCVASGRTFSSYAM GWFRQAPGKERAFVAGISGSASRKYYADSVKGRF TVSRDNARNTVYLQMNSLKPEDTAVYYCAASNSY PKVQFDYYGQGTQVTVSS | SEQ ID NO: 49 |
| CX3CR1BIIPMP12B6 | EVQLVQSGGGLVQAGGSLRLSCVASGRTFSSYAM GWFRQAPGRERAFVAGISGSASRKYYADSVKGRF TVSRDNARNTVYLQMNSLKPEDTAVYYCAASNSY PKVQFDYYGQGTQVTVSS | SEQ ID NO: 50 |
| CX3CR1BIIPMP12G9 | EVQLVESGGGLVQPGGSLRLSCVASGRTFSSYAM GWFRQAPGKEREFVAGISGSGSRKYYADSVKGRF TISRDNARNTVYLQMNSLKPEDRAVYYCAASNSYP KVQFDYYGQGTQVTVSS | SEQ ID NO: 51 |
| CX3CR1BIIPMP15G11 | EVQLVESGGGLVQAGGSLRLSCVASGRTFSSYAM GWFRQAPGKEREFVAGISGSGSRKYYADSVKGRF TISRDNARNTVYLQMNSLKPEDRAVYYCAASNSYP KVQFDYYGQGTQVTVSS | SEQ ID NO: 52 |
| CX3CR1BIIPMP18E6 | KVQLVESGGGLVQPGGSLRLSCATSGTIFSNNAM GWYRQAPGKKRDLVASISSSGSTNYADSVKGRFT VSRDNDKNTGYLQMNSLKPEDTGVYYCTLDARRG WNTAYWGQGAQVTVSS | SEQ ID NO: 53 |

TABLE 5-continued

VHH domains
SEQ ID NO: 1-48 are VHH domains of family 101. SEQ ID
NO: 49-52 are VHH domains of family 9. SEQ ID
NO: 53-120 are VHH domains of family 13.

| | | |
|---|---|---|
| CX3CR1BIIPMP12C2 | EVQLVESGGGLVQPGGSLRLSCATSGTIFSNTAM GWYRQAPGKKRDLVASISNSGSTNYADSVKGRFT VSRDNDKNTGYLQMNSLKPEDTGVYYCTVDARRG WNSGYWGQGTQVTSS | SEQ ID NO: 54 |
| CX3CR1BIIPMP18A10 | EVQLVESGGGLVQPGGSLRLSCATSGIIFSNNAMG WYRQAPGKKRDLVASISNSGSTNYADSAKGRFTV SRDNDKNTGYLQMNSLKPEDTGVYYCTVDARRG WNTAYWGQGTQVTVSS | SEQ ID NO: 55 |
| CX3CR1BIIPMP18A2 | EVQLVESGGGVVQPGGSLRLSCVTSGIIFSNNAMG WYRQGPGKKRDLVASIGSTYSTNYADSVKGRFTV SRDNDKNTGYLQMNSLKPEDTGVYYCTIDARRGW NTAYWGQGTPVTVSS | SEQ ID NO: 56 |
| CX3CR1BIIPMP18A8 | EVQLVESGGGLVQPGGSLRLSCATSRTIFRSNAM GWYRQAPGKKRDLVASISNSGSTNYADSVKGRFT VSRDNDKNTGYLQMNSLKPEDTGVYYCTIDARRG WNTGYWGQGTQVTVSS | SEQ ID NO: 57 |
| CX3CR1BIIPMP18A9 | EVQLVESGGGVVQPGGSLRLSCVTSGIIFSNNAMG WYRQGPGKKRDLVASISSTYSTNYADSVKGRFTV SRDNDKNTGYLQMNSLKPEDTGVYYCTIDARRGW NTAYWGQGTPVTVSS | SEQ ID NO: 58 |
| CX3CR1BIIPMP18B7 | EVQLVESGGGLVQPGGSLRLSCATSGTIFRSNAM GWYRQAPGKKRDLVASISNSGSTNYADSVKGRFT VSRDNDKNTGYLQMNSLKPEDTGVYYCTVDARRG WNSGYWGQGTQVTVSS | SEQ ID NO: 59 |
| CX3CR1BIIPMP18B9 | EVQLVESRGGLVQPGGSLRLSCATSGTIFSNNAM GWYRQAPGKKRDLVASISSSGSTNYADSVKGRFT VSRDNDKNTGYLQMNSLKPEDTGVYYCTLDARRG WNTAYWGQGTQVTVSS | SEQ ID NO: 60 |
| CX3CR1BIIPMP18C6 | EVQLMESGGGLVQPGGSLRLSCATSGTIFSNNAM GWYRQAPGKKRDLVASISNSGSTNYADSVKGRFT VSRDNDKNTGYLQMNSLKPEDTGVYYCTVDARRG WNTAYWGQGTQVTVSS | SEQ ID NO: 61 |
| CX3CR1BIIPMP18C9 | EVQLVESGGGLVQPGGSLRLSCATSGIIFSNNAMG WYRQAPGKKRDLVASISNSGSTNYADSVKGRFTV SRDNDKNTGYLQMNSLKPEDTGVYYCTVDARRG WNTAYWGQGTQVTVSS | SEQ ID NO: 62 |
| CX3CR1BIIPMP18D1 | EVQLVESGGGLVQPGGSLRLSCATSGIIFSNNAMG WYRQAPGKKRDLVASISNSGSTNYADSVKGRFTV SRDNDKSTGYLQMNSLKPEDTGVYYCTVDARRG WNTAYWGQGTQVTVSS | SEQ ID NO: 63 |
| CX3CR1BIIPMP18D10 | EVQLVESGGGLVQPGGSLGLSCATSGTIFSNNAM GWYRQAPGKKRDLVASISNSGSTNYADSVKGRFT VSRDNDKNTGYLQMNSLKPEDTGVYYCTVDARRG WNTAYWGQGTQVTVSS | SEQ ID NO: 64 |
| CX3CR1BIIPMP18D12 | EVQLVESGGGLVQPGGSLRLSCTTSGTIFSNNAM GWYRQAPGKKRDLVASISNSGSTNYADSVKGRFT VSRDNDKNTGYLQMNNLKPEDTGVYYCTLDARRG WNTAYWGQGTQVTVSS | SEQ ID NO: 65 |
| CX3CR1BIIPMP18F1 | KVQLVESGGGLVQPGGSLRLSCATSGTIFSNNAM GWYRQAPGKKRDLVASISNSGSTNYADSVKGRFT VSRDNDKNTGYLQMNSLKPEDTGVYYCTVDARRG WNTAYWGQGTQVTVSS | SEQ ID NO: 66 |
| CX3CR1BIIPMP18F5 | EVQLVESGGGLVQPGGSLRLSCATSGTIFSNNAM GWYRQAPGKKRDLVASISNSGSTNYADSVKGRFT VSRDNDKNTGYLQMNSLKPEDTGVYYCTVDARRG WNTAYWGQGTQVTVSS | SEQ ID NO: 67 |
| CX3CR1BIIPMP18F6 | EVQLVDSGGGLVQPGGSLRLSCATSGTIFSNNAM GWYRQAPGKKRDLVASISNSGSTNYADSVKGRFT VSRDNDKNTGYLQMNSLKPEDTGVYYCTVDARRG WNTAYWGQGTQVTVSS | SEQ ID NO: 68 |

TABLE 5-continued

VHH domains
SEQ ID NO: 1-48 are VHH domains of family 101. SEQ ID
NO: 49-52 are VHH domains of family 9. SEQ ID
NO: 53-120 are VHH domains of family 13.

| | | |
|---|---|---|
| CX3CR1BIIPMP18F9 | EVQLVESGGGLVQPGGSLRLSCATSGTIFRTNAM GWYRQAPGKKRDLVASISNSGSTNYADSVKGRFT VSRDNDKNTAYLQMNSLKPEDTGVYYCTIDGRRG WNTGYWGQGTQVTVSS | SEQ ID NO: 69 |
| CX3CR1BIIPMP18G5 | EVQLVESGGGLVQPGGSLRLSCATSRTIFRSNAM GWYRQAPGKKRDLVASISNSGSTNYADSVKGRFT VSRDNDKNTGYLQMNSLKPEDTGVYYCTVDARRG WNTGYWGQGTQVTVSS | SEQ ID NO: 70 |
| CX3CR1BIIPMP18H1 | EVQLVESGGGLVQPGGSLRLSCATSGTIFSNNAM GWYRQALGKKRDLVASISNSGSTNYADSVKGRFT VSRDNDKNTGYLQMNSLKPEDTGVYYCTVDARRG WNTAYWGQGTQVTVSS | SEQ ID NO: 71 |
| CX3CR1BIIPMP18H10 | EVQLVESGGGLVQPGGSLRLSCATSKTIFRSNAM GWYRQAPGKKRDLVASISNSGSTNYADSVKGRFT VSRDNDKNTGYLQMNSLKPEDTGVYYCTVDARRG WNTGYWGQGTQVTVSS | SEQ ID NO: 72 |
| CX3CR1BIIPMP18H7 | EVQLVESRGGLVQPGGSLRLSCATSGIIFSNNAMG WYRQAPGKKRDLVASISNSGSTNYADSVKGRFTV SRDNDKNTGYLQMNSLKPEDTGVYYCTVDARRG WNTAYWGQGTQVTVSS | SEQ ID NO: 73 |
| CX3CR1BIIPMP18H9 | EVQLVKSGGGLVQPGGSLRLSCTTSGTIFSNNAM GWYRQAPGKKRDLVASISNSGSTNYADSVKGRFT VSRDNDKNTGYLQMNNLKPEDTGVYYCTLDARRG WNTAYWGQGTQVTVSS | SEQ ID NO: 74 |
| CX3CR1BIIPMP20B3 | EVQLVESGGGLVQAGGSLRLSCVTSGIIFSNNAMG WYRQGPGKKRDLVASIGSTYSTNYADSVKGRFTV SRDNDKNTGYLQMNSLKPEDTGVYYCTIDARRGW NTAYWGQGTPVTVSS | SEQ ID NO: 75 |
| CX3CR1BIIPMP20C12 | EVQLVESGGGLVQPGGSLRLSCATSGTIFRSNAM GWYRQAPGKKRDLVASISNSGSTNYADSVKGRFT VSRDNDKNTGYLQMNSLKPEDTGVYYCTVDARRG WNSGYWGQGTRVTVSS | SEQ ID NO: 76 |
| CX3CR1BIIPMP20C3 | KVQLVESGGGLVQPGGSLRLSCATSGIIFSNNAMG WYRQAPGKKRDLVASISNSGSTNYADSVKGRFTV SRDNDKNTGYLQMNSLKPEDTGVYYCTVDARRG WNTAYWGQGTQVTVSS | SEQ ID NO: 77 |
| CX3CR1BIIPMP20C6 | EVQLVESGGGLVQAGGSLRLSCATSGTIFSNNAM GWYRQAPGKKRDLVASISNSGSTNYADSVKGRFT VSRDNDKNTGYLQMNSLKPEDTGVYYCTVDARRG WNTAYWGQGTQVTVSS | SEQ ID NO: 78 |
| CX3CR1BIIPMP20D8 | EVQLVESGGGLVQPGRSLRLSCATSGTTFRSNAM GWYRQGPGKKRDLVASITNSGSTNYADSVKGRFT VSRDNDKNTGYLQMSSLKPEDTGVYYCTLDARRG WNTGYWGQGTQVTVSS | SEQ ID NO: 79 |
| CX3CR1BIIPMP20E11 | EVQLVESGGGLVQPGGSLRLSCATSRTIFRSNAM GWYRQGPGKKRDLVASITNSGSTNYADSVKGRFT VSRDNDRNTGYLQMNSLKPEDTGVYYCTVDARRG WNTGYWGQGTQVTVSS | SEQ ID NO: 80 |
| CX3CR1BIIPMP20E5 | KVQLVESGGGLVQPGGSLRLSCATSGTIFSNNAM GWYRQVPGKKRDLVASISNSGSTNYADSVKGRFT VSRDNDKNTGYLQMNSLKPEDTGVYYCTVDARRG WNTGYWGQGTQVTVSS | SEQ ID NO: 81 |
| CX3CR1BIIPMP20F3 | EVQLVESGGGLVQPGGSLRLSCATSGTIFSNNAM GWYRQAPGKKRDLVASISSSGSTNYADSVKGRFT VSRDNDKNTGYLQMNSLKPEDTGVYYCTLDARRG WNTAYWGQGTQVTVSS | SEQ ID NO: 82 |
| CX3CR1BIIPMP20F4 | EVQLVESGGGLVQPGGSLRLSCATSATIFRSNAM GWYRQAPGKKRDLVASISNSGSTNYADSVKGRFT VSRDNDKNTAYLQMNSLKPEDTGVYYCTIDGRRG WNTGYWGQGTQVTVSS | SEQ ID NO: 83 |

TABLE 5-continued

VHH domains
SEQ ID NO: 1-48 are VHH domains of family 101. SEQ ID
NO: 49-52 are VHH domains of family 9. SEQ ID
NO: 53-120 are VHH domains of family 13.

| | | |
|---|---|---|
| CX3CR1BIIPMP20F5 | EVQLVESGGGLVQPGGSLRLSCATSATIFRSNAM GWYRQAPGKKRDLVASISNSGSTNYADSVKGRST VSRDNDKNTAYLQMNSLKPEDTGVYYCTIDGRRG WNTGYWGQGTQVTSS | SEQ ID NO: 84 |
| CX3CR1BIIPMP21B6 | EVQLVESGGGLVQPGGSLRLSCATSGTIFSNNAM GWYRQAPGKKRDLVASISNSGSTNYADSVKGRFT VSRDNDKNTGYLQMNSLKPEDMGVYYCTVDARR GWNTAYWGQGTQVTSS | SEQ ID NO: 85 |
| CX3CR1BIIPMP24A12 | EVQLVESGGGLVQPGGSLRLSCATSGIIFSNNAMG WYRQAPGKKRDLVASISNSGSANYADSVKGRFTV SRDNDKNTGYLQMNSLKPEDTGVYYCTVDARRG WNTAYWGQGTQVTSS | SEQ ID NO: 86 |
| CX3CR1BIIPMP24A6 | EVQLVESGGGLVQPGGSLRLSCTTSGTIFSNNAM GWYRQAPGKKRDLVASISNSGSTNYADSVKGRFT VSGDNDKNTGYLQMNNLKPEDTGVYYCTLDARRG WNTAYWGQGTQVTSS | SEQ ID NO: 87 |
| CX3CR1BIIPMP24B9 | EVQLVESGGGLVQPGGSLRLSCATSGTIFRSNAM GWYRQAPGKKRDLVASISISGSTNYADSVKGRFTV SRDNDKNTGYLQMNSLKPEDTGVYYCTVDARRG WNTGFWGQGTQVTSS | SEQ ID NO: 88 |
| CX3CR1BIIPMP24D3 | EVQLVESGGGLVQPGGSLRLSCVTSGIIFSNNAMG WYRQGPGKKRDLVASISSTYSTNYADSVKGRFTV SRDNDKNTGYLQMNSLKPEDTGVYYCTIDARRGW NTAYWGQGTPVTSS | SEQ ID NO: 89 |
| CX3CR1BIIPMP24F7 | EVQLMESGGGMVQVGGSLRLSCTASGLIFSNNAM GWYRQGPGKKRDLVASISSTYSTNYADSVKGRFT VSRDNDKNTGYLQMNSLKPEDTGVYYCTIDARRG WNTAYWGQGTPVTSS | SEQ ID NO: 90 |
| CX3CR1BIIPMP28B4 | EVQLVESGGGLVQPGGSLRLSCAISATIFRSNAMG WYRQAPGKKRDLVASISNSGSTNYADSVKGRFTV SRDNDKNTAYLQMNSLKPEDTGVYYCTIDGRRGW NTGYWGQGTQVTSS | SEQ ID NO: 91 |
| CX3CR1BIIPMP28F1 | EMQLVESGGGVVQPGGSLRLSCVTSGIIFSNNAM GWYRQGPGKKRDLVASIGSTYSTNYADSVKGRFT VSRDNDKNTGYLQMNSLKPEDTGVYYCTIDARRG WNTAYWGQGTPVTSS | SEQ ID NO: 92 |
| CX3CR1BIIPMP28F6 | EVQLVESGGGLVQPGGSLRLSCATSGIIFSNNAMG WYRQAPGKKRDLVASISNSGSTNHADSVKGRFTV SRDNDKNTGYLQMNSLKPEDTGVYYCTVDARRG WNTAYWGQGTQVTSS | SEQ ID NO: 93 |
| CX3CR1BIIPMP28F9 | EVQLVESGGGLVQPGGSLRLSCATSGTIFSNNAM GWYRQVPGKKRDLVASISNSGSTNYADSVKGRFT VSRDNDKNTGYLQMNSLKPEDTGVYYCTVDARRG WNTAYWGQGTQVTSS | SEQ ID NO: 94 |
| CX3CR1BIIPMP29A5 | EVQLVESRGGLVQPGGSLRLSCATSGTIFSNNAM GWYRQAPGKKRDLVASISNSGSTNYADSVKGRFT VSRDNDKNTGYLQMNSLKPEDTGVYYCTVDARRG WNTAYWGQGTQVTSS | SEQ ID NO: 95 |
| CX3CR1BIIPMP29D5 | KVQLVESGGGLVQPGGSLRLSCATSGTIFRSNAM GWYRQAPGKKRDLVASISNSGSTNYADSVKGRFT VSRDNDKNTGYLQMNSLKPEDTGVYYCTVDARRG WNSGYWGQGTQVTSS | SEQ ID NO: 96 |
| CX3CR1BIIPMP29E3 | EVQLVESEGGLVQPGGSLRLPCATSKTIFRSNAMG WYRQAPGKKRDLVASISNSGSTNYADSVKGRFTV SRDNDKNTGYLQMNSLKPEDTGVYYCTVDARRG WNTGYWGQGTQVTSS | SEQ ID NO: 97 |
| CX3CR1BIIPMP29E7 | EVQLVESGGGLVQPGGSLRLSCATSKTIFRSNAM GWYRQAPGKKRGLVASISNSGSTNYADSVKGRFT VSRDNDKNTGYLQMNSLKPEDTGVYYCTVDARRG WNTGYWGQGTQVTSS | SEQ ID NO: 98 |

TABLE 5-continued

VHH domains
SEQ ID NO: 1-48 are VHH domains of family 101. SEQ ID
NO: 49-52 are VHH domains of family 9. SEQ ID
NO: 53-120 are VHH domains of family 13.

| | | |
|---|---|---|
| CX3CR1BIIPMP29G10 | EVQLMESGGGLVQPGGSLRLSCATSGTIFRSNAM GWYRQGPGKKRDLVASITNSGSTNYADSVKGRFT VSRDNDKNTGYLQMSSLKPEDTGVYYCTLDARRG WNTGYWGQGTQVTVSS | SEQ ID NO: 99 |
| CX3CR1BIIPMP29G7 | EVQLVESGGGLVQPGGSLRLSCATSGIIFSNNAMG WYRQGPGKKRDLVASITNTGSTNYADSVKGRFTV SRDNDRNTVYLQMNSLKPEDTGVYYCTVDARRG WNTAYWGQGTQVTVSS | SEQ ID NO: 100 |
| CX3CR1BIIPMP29H1 | EVQLVESGGGLVQAGGSLRLSCTTSGTIFSNNAM GWYRQAPGKKRDLVASISNSGSTNYADSVKGRFT VSRDNDKNTGYLQMNNLKPEDTGVYYCTLDARRG WNTAYWGQGTQVTVSS | SEQ ID NO: 101 |
| CX3CR1BIIPMP37A8 | EVQLVESGGGLVQPGGSLRLSCATSRTIFRSNAM GWYRQAPGKKRDLVASISNSGSTNYADSAKGRFT VSRDNDKNTGYLQMNSLKPEDTGVYYCTVDARRG WNTGYWGQGTQVTVSS | SEQ ID NO: 102 |
| CX3CR1BIIPMP37B9 | EVQLVESGGLVQPGGSLRLSCATSGTIFSNNAMG WYRQAPGKKRDLVASISNSGSTNYADSVKGRFTV SRDNDKNTGYLQMNSLKPEDTGVYYCTVDARRG WNTAYWGQGTQVTVSS | SEQ ID NO: 103 |
| CX3CR1BIIPMP37C12 | EVQLVESGGGLVQAGGSLRLSCVASGSIFRSNAM GWYRQAPGKKRDLVASISNSGSTNYADSVKGRFT VSRDNDKNTGYLQMNSLKPEDTGVYYCTIDARRG WNTGYWGQGTQVTVSS | SEQ ID NO: 104 |
| CX3CR1BIIPMP37C7 | EVQLVESGGGLVQPGGSLRLSCATSRTIFSNNAM GWYRQAPGKKRDLVASISNSGSTNYADSVKGRFT VSRDNDKNTGYLQMNSLKPEDTGVYYCTVDARRG WNTAYWGQGTQVTVSS | SEQ ID NO: 105 |
| CX3CR1BIIPMP37D9 | EVQLVESGGGLVQPGGSLRLSCATSGTVFSNNAM GWYRQAPGKKRDLVASISSSGSTNYADSVKGRFT VSRDNDKNTGYLQMNSLKPEDTGVYYCTLDARRG WNTAYWGQGTQVTVSS | SEQ ID NO: 106 |
| CX3CR1BIIPMP37E12 | EVQLVESGGGLVQPGGSLRLSCATSKPIFRSNAM GWYRQAPGKKRDLVASISNSGSTNYADSVKGRFT VSRDNDKNTGYLQMNSLKPEDTGVYYCTVDARRG WNTAYWGQGTQVTVSS | SEQ ID NO: 107 |
| CX3CR1BIIPMP41B10 | EVQLVESEGGLVQPGGSLRLSCTTSGTIFSNNAMG WYRQAPGKKRDLVASISNSGSTNYADSVKGRFTV SRDNDKNTGYLQMNNLKPEDTGVYYCTLDARRG WNTAYWGQGTQVTVSS | SEQ ID NO: 108 |
| CX3CR1BIIPMP41B11 | EVQLVESGGGLVQPGGSLRLSCATSGTIFSNNAM GWYRQAPGKKRDLVASISNSGSTNYADSVKGRFT VSRDNDKNTGYLQMNSPKPEDTGVYYCTVDARR GWNTAYWGQGTQVTVSS | SEQ ID NO: 109 |
| CX3CR1BIIPMP41B8 | EVQLVESEGGVVQPGGSLRLSCVTSGIIFSNNAMG WYRQGPGKKRDLVASIGSTYSTNYADSVKGRFTV SRDNDKNTGYLQMNSLKPEDTGVYYCTIDARRGW NTAYWGQGTPVTVSS | SEQ ID NO: 110 |
| CX3CR1BIIPMP41C10 | EMQLVESGGGLVQPGGSLRLSCATSRTIFRSNAM GWYRQAPGKKRDLVASISNSGSTNYADSVKGRFT VSRDNDKSTGYLQMNSLKPEDTGVYYCTVDARRG WNTGYWGQGTQVTVSS | SEQ ID NO: 111 |
| CX3CR1BIIPMP41F9 | EVQLVESGGGVVQPGESLRLSCVTSGIIFSNNAMG WYRQGPGKKRDLVASIGSTYSTNYADSVKGRFTV SRDNDKNTGYLQMNSLKPEDTGVYYCTIDARRGW NTAYWGQGTPVTVSS | SEQ ID NO: 112 |
| CX3CR1BIIPMP41H10 | KVQLVESGGGLVQPGDSLRLSCAASGLTLDDYAM GWYRQAPGKKRDLVASISNSGSTNYADSVKGRFT VSRDNDKNTGYLQMNSLKPEDTGVYYCTIDARRG WNTGYWGQGTQVTVSS | SEQ ID NO: 113 |

TABLE 5-continued

VHH domains
SEQ ID NO: 1-48 are VHH domains of family 101. SEQ ID
NO: 49-52 are VHH domains of family 9. SEQ ID
NO: 53-120 are VHH domains of family 13.

| | | |
|---|---|---|
| CX3CR1BIIPMP46B5 | KVQLVESGGGLVQPGGSLRLSCATSRTIFRSNAM GWYRQAPGKKRDLVASISNSGSTNYADSVKGRFT VSRDNDKNTGYLQMNSLKPEDTGVYYCTIDARRG WNTGYWGQGTQVTVSS | SEQ ID NO: 114 |
| CX3CR1BIIPMP46D3 | EVQLVESGGGLVQPGGSLRLSCATSGTIFSNNAM GWYRQVPGKKRDLVASISNSGSTNYADSVKGRFT VSRDNDKNTGYLRMNSLKPEDTGVYYCTVDARRG WNTGYWGQGTQVTVSS | SEQ ID NO: 115 |
| CX3CR1BIIPMP46H5 | EVQLVESGGGLVQAGGSLRLSCVTSGIIFSNNAMG WYRQGPGKKRDLVASISSTYSTNYADSVKGRFTV SRDNDKNTGYLQMNSLKPEDTGVYYCTIDARRGW NTAYWGQGTPVTVSS | SEQ ID NO: 116 |
| CX3CR1BIIPMP48B8 | EVQLVESGGGLVQPGGSLRLSCATSKTIFRSNAM GWYRQAPGKKRDLVASISNSGSTNYTDSVKGRFT VSRDNDKNTGYLQMNSLKPEDTGVYYCTVDARRG WNTGYWGQGTQVTVSS | SEQ ID NO: 117 |
| CX3CR1BIIPMP48D11 | KVQLVESGGGLVQPGGSLRLSCATSRTIFRSNAM GWYRQAPGKKRDLVASISNSGSTNYADSVKGRFT VSRDNDKNTGYLQMNSLKPEDTGVYYCTVDARRG WNTGYWGQGTQVTVSS | SEQ ID NO: 118 |
| CX3CR1BIIPMP48G8 | EVQLVESGGGLVQPGGSLRLSCATSRTIFRSNAM GWYRQAPGKKRDLVASISNSGSTNYADSVKGRFA VSRDNDKNTGYLQMNSLKPEDTGVYYCTVDARRG WNTGYWGQGTQVTVSS | SEQ ID NO: 119 |
| CX3CR1BIIPMP48H9 | EVQLVESGGGLVQPGGSLRLSCATSGTIFSNNAM GWYRQAPGKKRDLVASISNSGSTNYADFVKGRFT VSRDNDKNTGYLQMNSLKPEDTGVYYCTVDARRG WNTAYWGQGTQVTVSS | SEQ ID NO: 120 |

TABLE 6

Optimized VHH domains

| | | |
|---|---|---|
| CX3CR1BII043 | EVQLVESGGGSVQPGESLRLSCAASGSIFSSNAM AWYRQAPGKRRDLVAAINSVGVTKYADSVKGRFTI SRDNSKNTVYLQMNSLRPEDTAVYYCTSDPRRGW DTRYWGQGTLVTVSS | SEQ ID NO: 121 |
| CX3CR1BII045 | DVQLVESGGGSVQPGESLRLSCAASGSIFSSNAM AWYRQAPGKRRDLVAAINSVGVTKYADSVKGRFTI SRDNSKNTVYLQMNSLRPEDTAVYYCTSDPRRGW DTRYWGQGTLVTVSS | SEQ ID NO: 122 |
| CX3CR1BII047 | EVQLVESGGGLVQPGESLRLSCAASGSIFSSNAMA WYRQAPGKRRDLVAAINSVGVTKYADSVKGRFTIS RDNSKNTVYLQMNSLRPEDTAVYYCTSDPRRGW DTRYWGQGTLVTVSS | SEQ ID NO: 123 |
| CX3CR1BII048 | EVQLVESGGGSVQPGGSLRLSCAASGSIFSSNAM AWYRQAPGKRRDLVAAINSVGVTKYADSVKGRFTI SRDNSKNTVYLQMNSLRPEDTAVYYCTSDPRRGW DTRYWGQGTLVTVSS | SEQ ID NO: 124 |
| CX3CR1BII049 | EVQLVESGGGSVQPGESLRLSCAASGSIFSSNAM AWYRQAPGKQRDLVAAINSVGVTKYADSVKGRFTI SRDNSKNTVYLQMNSLRPEDTAVYYCTSDPRRGW DTRYWGQGTLVTVSS | SEQ ID NO: 125 |
| CX3CR1BII050 | EVQLVESGGGSVQPGESLRLSCAASGSIFSSNAM AWYRQAPGKRRELVAAINSVGVTKYADSVKGRFTI SRDNSKNTVYLQMNSLRPEDTAVYYCTSDPRRGW DTRYWGQGTLVTVSS | SEQ ID NO: 126 |

TABLE 6-continued

Optimized VHH domains

| CX3CR1BII061 | EVQLVESGGGLVQPGGSLRLSCAASGSIFSSNAM AWYRQAPGKRRDLVAAINSVGVTKYADSVKGRFTI SRDNSKNTVYLQMNSLRPEDTAVYYCTSDPRRGW DTRYWGQGTLVTVSS | SEQ ID NO: 127 |
|---|---|---|
| CX3CR1BII056 | EVQLVESGGGLVQPGGSLRLSCAASGSIFSSNAM AWYRQAPGKQRDLVAAINSVGVTKYADSVKGRFTI SRDNSKNTVYLQMNSLRPEDTAVYYCTSDPRRGW DTRYWGQGTLVTVSS | SEQ ID NO: 128 |
| CX3CR1BII057 | EVQLVESGGGLVQPGGSLRLSCAASGSIFSSNAM AWYRQAPGKRRELVAAINSVGVTKYADSVKGRFTI SRDNSKNTVYLQMNSLRPEDTAVYYCTSDPRRGW DTRYWGQGTLVTVSS | SEQ ID NO: 129 |
| CX3CR1BII060 | EVQLVESGGGLVQPGGSLRLSCAASGSIFSSNAM AWYRQAPGKQRELVAAINSVGVTKYADSVKGRFTI SRDNSKNTVYLQMNSLRPEDTAVYYCTSDPRRGW DTRYWGQGTLVTVSS | SEQ ID NO: 130 |
| CX3CR1BII065 | EVQLVESGGGSVQAGESLRLSCAASGSIFSSNAM AWYRQAPGKRRDLVAAISSVGVTKYADSVKGRFTI SRDNAKNTVYLQMNSLKPEDTAVYYCTSDPRRGW DTRYWGQGTLVTVSS | SEQ ID NO: 131 |
| CX3CR1BII067 | EVQLVESGGGSVQAGESLRLSCAASGSIFSSNAM AWYRQAPGKRRDLVAAIQSVGVTKYADSVKGRFTI SRDNAKNTVYLQMNSLKPEDTAVYYCTSDPRRGW DTRYWGQGTLVTVSS | SEQ ID NO: 132 |
| CX3CR1BII068 | EVQLVESGGGSVQAGESLRLSCAASGSIFSSNAM AWYRQAPGKRRDLVAAIGSVGVTKYADSVKGRFTI SRDNAKNTVYLQMNSLKPEDTAVYYCTSDPRRGW DTRYWGQGTLVTVSS | SEQ ID NO: 133 |
| CX3CR1BII074 | EVQLVESGGGSVQAGESLRLSCAASGSIFSSNAM AWYRQAPGKRRDLVAAITSVGVTKYADSVKGRFTI SRDNAKNTVYLQMNSLKPEDTAVYYCTSDPRRGW DTRYWGQGTLVTVSS | SEQ ID NO: 134 |
| CX3CR1BII118 | EVQLVESGGGSVQAGESLRLSCAASGSIFSSNAM AWYRQAPGKRRDLVAAINTVGVTKYADSVKGRFTI SRDNAKNTVYLQMNSLKPEDTAVYYCTSDPRRGW DTRYWGQGTLVTVSS | SEQ ID NO: 135 |
| CX3CR1BII129 | EVQLVESGGGSVQAGESLRLSCAASGSIFSSNAM AWYRQAPGKRRDLVAAINGVGVTKYADSVKGRFTI SRDNAKNTVYLQMNSLKPEDTAVYYCTSDPRRGW DTRYWGQGTLVTVSS | SEQ ID NO: 136 |
| CX3CR1BII158 | EVQLVESGGGSVQAGESLRLSCAASGSIFSSNAM AWYRQAPGKRRDLVAAINPVGVTKYADSVKGRFTI SRDNAKNTVYLQMNSLKPEDTAVYYCTSDPRRGW DTRYWGQGTLVTVSS | SEQ ID NO: 137 |
| CX3CR1BII306 | DVQLVESGGGLVQPGGSLRLSCAASGSIFSSTAM AWYRQAPGKRRDLVAAISSVGVTKYADSVKGRFTI SRDNSKNTVYLQMNSLRPEDTAVYYCTSDPRRGW DTRYWGQGTLVTVSS | SEQ ID NO: 138 |
| CX3CR1BII307 | DVQLVESGGGLVQPGGSLRLSCAASGSIFSSTAM AWYRQAPGKRRDLVAAISTVGVTKYADSVKGRFTI SRDNSKNTVYLQMNSLRPEDTAVYYCTSDPRRGW DTRYWGQGTLVTVSS | SEQ ID NO: 139 |
| CX3CR1BII308 | DVQLVESGGGLVQPGGSLRLSCAASGSIFSSNAM AWYRQAPGKRRDLVAAINSVGVTKYADSVKGRFTI SRDNSKNTVYLQMNSLRPEDTAVYYCTSDPRRGW DTRYWGQGTLVTVSS | SEQ ID NO: 140 |
| CX3CR1BII00306 (D1E) | EVQLVESGGGLVQPGGSLRLSCAASGSIFSSTAMA WYRQAPGKRRDLVAAISSVGVTKYADSVKGRFTIS RDNSKNTVYLQMNSLRPEDTAVYYCTSDPRRGW DTRYWGQGTLVTVSS | SEQ ID NO: 222 |

TABLE 6-continued

Optimized VHH domains

| | | |
|---|---|---|
| CX3CR1BII00307 (D1E) | EVQLVESGGGLVQPGGSLRLSCAASGSIFSSTAMA WYRQAPGKRRDLVAAISTVGVTKYADSVKGRFTIS RDNSKNTVYLQMNSLRPEDTAVYYCTSDPRRGW DTRYWGQGTLVTVSS | SEQ ID NO: 223 |
| CX3CR1BII00308 (D1E) | EVQLVESGGGLVQPGGSLRLSCAASGSIFSSNAM AWYRQAPGKRRDLVAAINSVGVTKYADSVKGRFTI SRDNSKNTVYLQMNSLRPEDTAVYYCTSDPRRGW DTRYWGQGTLVTVSS | SEQ ID NO: 224 |

In a further aspect, a polypeptide according to the present invention, in particular an immunoglobulin single variable domain of the present invention, is humanized and/or optimized for stability, potency, manufacturability and/or similarity to human framework regions. For example, the polypeptide is humanized and/or sequence optimized in one or more of the following positions (according to Kabat numbering): 1, 11, 14, 16, 74, 83, 108. In one aspect, the polypeptide comprises one or more of the following mutations: E1D, S11L, A14P, E16G, A74S, K83R, Q108L.

In one aspect, one or more framework regions of a polypeptide according to the present invention, in particular an immunoglobulin single variable domain of the present invention, are humanized and/or sequence optimized. In one aspect, a polypeptide according to the present invention, in particular an immunoglobulin single variable domain of the present invention, comprises framework regions (FR) for example as set forth below:
i) FR1 is selected from any one of SEQ ID NO's: 198-204;
ii) FR2 is selected from any one of SEQ ID NO's: 205-208;
iii) FR3 is selected form any one of SEQ ID NO's: 209-210; and/or
iv) FR4 is selected from any one of SEQ ID NO's: 211-212.

Human immunoglobulin framework region sequences (FR) that can also be used as framework region sequences for the immunoglobulin single variable domains as described above are known in the art. Also known in the art are methods for humanizing framework regions of immunoglobulin single variable domains derived from species other than humans.

In a further aspect, one or more CDR regions of a polypeptide according to the present invention, in particular an immunoglobulin single variable domain of the present invention, is humanized and/or sequence optimized. In one aspect, a polypeptide according to the present invention, in particular an immunoglobulin single variable domain of the present invention, is humanized and/or sequence optimized in one or more of the following positions (according to Kabat numbering): 52, 53.

In a further aspect, a polypeptide according to the present invention, in particular an immunoglobulin single variable domain of the present invention, comprises one or more of the following mutations: N52S, S53T.

In a further aspect, a polypeptide according to the present invention, in particular an immunoglobulin single variable domain of the present invention, comprises a CDR2 selected from any one of SEQ ID NO's: 214-221.

Representative humanized and/or optimized sequences of the present invention are shown in Table 4 and 6 hereinabove and in Table 7 herein below.

Table 7: Sequence Optimized Variants

Table 7a shows the FR1-CDR1-FR2-CRD2 of the sequence optimized variants, table 7b shows FR3-CDR3-FR4-CDR4 of said variants. The sequence numbers in the tables (SEQ) refer to the sequences in the sequence listing of the instant application.

TABLE 7a

Sequence optimized variants (FR1-CDR1-FR2-CDR2)

| Nano body | SEQ FR1 | FR1 | SEQ CDR1 | CDR1 | FR2 | SEQ FR2 | CDR2 | SEQ CDR2 |
|---|---|---|---|---|---|---|---|---|
| CX3CR1BIIPMP66B02 | 1 | EVQLVES GGGSVQ AGESLRL SCAAS | 198 | GSIFS SNAMA | 141 | WYRQ APGKR RDLVA | 205 | AINSV GVTK | 162 |
| CX3CR1BII043 | 121 | EVQLVES GGGSVQ PGESLRL SCAAS | 199 | GSIFS SNAMA | 141 | WYRQ APGKR RDLVA | 205 | AINSV GVTK | 162 |
| CX3CR1BII045 | 122 | DVQLVES GGGSVQ PGESLRL SCAAS | 200 | GSIFS SNAMA | 141 | WYRQ APGKR RDLVA | 205 | AINSV GVTK | 162 |
| CX3CR1BII047 | 123 | EVQLVES GGGLVQ PGESLRL SCAAS | 201 | GSIFS SNAMA | 141 | WYRQ APGKR RDLVA | 205 | AINSV GVTK | 162 |

TABLE 7a-continued

Sequence optimized variants (FR1-CDR1-FR2-CDR2)

| Nano body | SEQ FR1 | FR1 | SEQ CDR1 | CDR1 | SEQ FR2 | FR2 | SEQ CDR2 | CDR2 | SEQ CDR2 |
|---|---|---|---|---|---|---|---|---|---|
| CX3CR1BII048 | 124 | EVQLVES GGGSVQ PGGSLRL SCAAS | 202 | GSIFS SNAMA | 141 | WYRQ APGKR RDLVA | 205 | AINSV GVTK | 162 |
| CX3CR1BII049 | 125 | EVQLVES GGGSVQ PGESLRL SCAAS | 199 | GSIFS SNAMA | 141 | WYRQ APGK QRDLVA | 206 | AINSV GVTK | 162 |
| CX3CR1BII050 | 126 | EVQLVES GGGSVQ PGESLRL SCAAS | 199 | GSIFS SNAMA | 141 | WYRQ APGKR RELVA | 207 | AINSV GVTK | 162 |
| CX3CR1BII061 | 127 | EVQLVES GGGLVQ PGGSLRL SCAAS | 203 | GSIFS SNAMA | 141 | WYRQ APGKR RDLVA | 205 | AINSV GVTK | 162 |
| CX3CR1BII056 | 128 | EVQLVES GGGLVQ PGGSLRL SCAAS | 203 | GSIFS SNAMA | 141 | WYRQ APGK QRDLVA | 206 | AINSV GVTK | 162 |
| CX3CR1BII057 | 129 | EVQLVES GGGLVQ PGGSLRL SCAAS | 203 | GSIFS SNAMA | 141 | WYRQ APGKR RELVA | 207 | AINSV GVTK | 162 |
| CX3CR1BII060 | 130 | EVQLVES GGGLVQ PGGSLRL SCAAS | 203 | GSIFS SNAMA | 141 | WYRQ APGK QRELVA | 208 | AINSV GVTK | 162 |
| CX3CR1BII065 | 131 | EVQLVES GGGSVQ AGESLRL SCAAS | 198 | GSIFS SNAMA | 141 | WYRQ APGKR RDLVA | 205 | AISSV GVTK | 214 |
| CX3CR1BII067 | 132 | EVQLVES GGGSVQ AGESLRL SCAAS | 198 | GSIFS SNAMA | 141 | WYRQ APGKR RDLVA | 205 | AIGSV GVTK | 215 |
| CX3CR1BII068 | 133 | EVQLVES GGGSVQ AGESLRL SCAAS | 198 | GSIFS SNAMA | 141 | WYRQ APGKR RDLVA | 205 | AIGSV GVTK | 216 |
| CX3CR1BII074 | 134 | EVQLVES GGGSVQ AGESLRL SCAAS | 198 | GSIFS SNAMA | 141 | WYRQ APGKR RDLVA | 205 | AITSV GVTK | 217 |
| CX3CR1BII118 | 135 | EVQLVES GGGSVQ AGESLRL SCAAS | 198 | GSIFS SNAMA | 141 | WYRQ APGKR RDLVA | 205 | AINTV GVTK | 218 |
| CX3CR1BII129 | 136 | EVQLVES GGGSVQ AGESLRL SCAAS | 198 | GSIFS SNAMA | 141 | WYRQ APGKR RDLVA | 205 | AING VGVTK | 219 |
| CX3CR1BII158 | 137 | EVQLVES GGGSVQ AGESLRL SCAAS | 198 | GSIFS SNAMA | 141 | WYRQ APGKR RDLVA | 205 | AINPV GVTK | 220 |
| CX3CR1BII306 | 138 | DVQLVES GGGLVQ PGGSLRL SCAAS | 204 | GSIFS STAMA | 213 | WYRQ APGKR RDLVA | 205 | AISSV GVTK | 214 |

TABLE 7a-continued

Sequence optimized variants (FR1-CDR1-FR2-CDR2)

| Nano body | SEQ FR1 | SEQ FR1 CDR1 | SEQ CDR1 | FR2 | SEQ FR2 CDR2 | SEQ CDR2 |
|---|---|---|---|---|---|---|
| CX3CR1BII307 | 139 DVQLVES GGGLVQ PGGSLRL SCAAS | 204 GSIFS STAMA | 213 | WYRQ APGKR RDLVA | 205 AISTV GVTK | 221 |
| CX3CR1BII308 | 140 DVQLVES GGGLVQ PGGSLRL SCAAS | 204 GSIFS SNAMA | 141 | WYRQ APGKR RDLVA | 205 AINSV GVTK | 162 |

TABLE 7b

Sequence optimized variants (FR3-CDR3-FR4)

| Nano body | SEQ FR3 | SEQ FR3 | CDR3 | SEQ CDR3 | FR4 | SEQ FR4 |
|---|---|---|---|---|---|---|
| CX3CR1BIIPMP66B02 | 1 YADSVKGRFTI SRDNAKNTVYL QMNSLKPEDTA VYYCTS | 209 | DPRRGW DTRY | 186 | WGQGTQ VTVSS | 211 |
| CX3CR1BII043 | 121 YADSVKGRFTI SRDNSKNTVYL QMNSLRPEDT AVYYCTS | 210 | DPRRGW DTRY | 186 | WGQGTL VTVSS | 212 |
| CX3CR1BII045 | 122 YADSVKGRFTI SRDNSKNTVYL QMNSLRPEDT AVYYCTS | 210 | DPRRGW DTRY | 186 | WGQGTL VTVSS | 212 |
| CX3CR1BII047 | 123 YADSVKGRFTI SRDNSKNTVYL QMNSLRPEDT AVYYCTS | 210 | DPRRGW DTRY | 186 | WGQGTL VTVSS | 212 |
| CX3CR1BII048 | 124 YADSVKGRFTI SRDNSKNTVYL QMNSLRPEDT AVYYCTS | 210 | DPRRGW DTRY | 186 | WGQGTL VTVSS | 212 |
| CX3CR1BII049 | 125 YADSVKGRFTI SRDNSKNTVYL QMNSLRPEDT AVYYCTS | 210 | DPRRGW DTRY | 186 | WGQGTL VTVSS | 212 |
| CX3CR1BII050 | 126 YADSVKGRFTI SRDNSKNTVYL QMNSLRPEDT AVYYCTS | 210 | DPRRGW DTRY | 186 | WGQGTL VTVSS | 212 |
| CX3CR1BII061 | 127 YADSVKGRFTI SRDNSKNTVYL QMNSLRPEDT AVYYCTS | 210 | DPRRGW DTRY | 186 | WGQGTL VTVSS | 212 |
| CX3CR1BII056 | 128 YADSVKGRFTI SRDNSKNTVYL QMNSLRPEDT AVYYCTS | 210 | DPRRGW DTRY | 186 | WGQGTL VTVSS | 212 |
| CX3CR1BII057 | 129 YADSVKGRFTI SRDNSKNTVYL QMNSLRPEDT AVYYCTS | 210 | DPRRGW DTRY | 186 | WGQGTL VTVSS | 212 |
| CX3CR1BII060 | 130 YADSVKGRFTI SRDNSKNTVYL QMNSLRPEDT AVYYCTS | 210 | DPRRGW DTRY | 186 | WGQGTL VTVSS | 212 |

TABLE 7b-continued

Sequence optimized variants (FR3-CDR3-FR4)

| Nanobody | SEQ | FR3 | SEQ FR3 | CDR3 | SEQ CDR3 | FR4 | SEQ FR4 |
|---|---|---|---|---|---|---|---|
| CX3CR1BII065 | 131 | YADSVKGRFTISRDNAKNTVYLQMNSLKPEDTAVYYCTS | 209 | DPRRGWDTRY | 186 | WGQGTLVTVSS | 212 |
| CX3CR1BII067 | 132 | YADSVKGRFTISRDNAKNTVYLQMNSLKPEDTAVYYCTS | 209 | DPRRGWDTRY | 186 | WGQGTLVTVSS | 212 |
| CX3CR1BII068 | 133 | YADSVKGRFTISRDNAKNTVYLQMNSLKPEDTAVYYCTS | 209 | DPRRGWDTRY | 186 | WGQGTLVTVSS | 212 |
| CX3CR1BII074 | 134 | YADSVKGRFTISRDNAKNTVYLQMNSLKPEDTAVYYCTS | 209 | DPRRGWDTRY | 186 | WGQGTLVTVSS | 212 |
| CX3CR1BII118 | 135 | YADSVKGRFTISRDNAKNTVYLQMNSLKPEDTAVYYCTS | 209 | DPRRGWDTRY | 186 | WGQGTLVTVSS | 212 |
| CX3CR1BII129 | 136 | YADSVKGRFTISRDNAKNTVYLQMNSLKPEDTAVYYCTS | 209 | DPRRGWDTRY | 186 | WGQGTLVTVSS | 212 |
| CX3CR1BII158 | 137 | YADSVKGRFTISRDNAKNTVYLQMNSLKPEDTAVYYCTS | 209 | DPRRGWDTRY | 186 | WGQGTLVTVSS | 212 |
| CX3CR1BII306 | 138 | YADSVKGRFTISRDNSKNTVYLQMNSLRPEDTAVYYCTS | 210 | DPRRGWDTRY | 186 | WGQGTLVTVSS | 212 |
| CX3CR1BII307 | 139 | YADSVKGRFTISRDNSKNTVYLQMNSLRPEDTAVYYCTS | 210 | DPRRGWDTRY | 186 | WGQGTLVTVSS | 212 |
| CX3CR1BII308 | 140 | YADSVKGRFTISRDNSKNTVYLQMNSLRPEDTAVYYCTS | 210 | DPRRGWDTRY | 186 | WGQGTLVTVSS | 212 |

In one aspect of the present invention, a polypeptide of the invention can additionally contain modifications such as glycosyl residues, modified amino acid side chains, and the like.

It will be clear to the skilled person that for pharmaceutical uses in humans, the polypeptides of the invention are preferably directed against human CX3CR1, whereas for veterinary purposes, the polypeptides of the invention are preferably directed against CX3CR1 from the species to be treated.

It will also be clear to the skilled person that when used as a therapeutic agent in humans, the immunoglobulin single variable domains comprised in the polypeptides according to the invention are preferably humanized immunoglobulin single variable domains.

According to the invention, an immunoglobulin single variable domain can be a domain antibody, i.e. VL or VH antibody, and/or VHH domains as described above, and/or any other sort of immunoglobulin single variable domain, for example camelized VH, provided that these immunoglobulin single variable domains are anti-CX3CR1 immunoglobulin single variable domains.

In one aspect of the invention, the immunoglobulin single variable domain essentially consists of either a domain antibody sequence or a VHH domain sequence as described above. In particular, the immunoglobulin single variable domain essentially consists of a VHH domain sequences.

In a further aspect, a polypeptide of the present invention comprises two or more anti-CX3CR1 immunoglobulin single variable domains. In a further aspect, a polypeptide of the present invention comprises two anti-CX3CR1 immunoglobulin single variable domains, for example anti-CX3CR1 VHHs. In one aspect, the two anti-CX3CR1 immunoglobulin single variable domains in a polypeptide of the present invention have the same amino acid sequence. In another aspect, the two anti-CX3CR1 immunoglobulin single variable domains in a polypeptide of the present invention have different amino acid sequences.

According to another embodiment of the invention, the at least two immunoglobulin single variable domains present in a polypeptide of the invention can be linked to each other directly (i.e. without use of a linker) or via a linker. The linker is preferably a linker peptide and will, according to the invention, be selected so as to allow binding of the at least two immunoglobulin single variable domains to CX3CR1, either within one and the same CX3CR1 molecule, or within two different molecules.

Suitable linkers will inter alia depend on the epitopes and, specifically, the distance between the epitopes on CX3CR1 to which the immunoglobulin single variable domains bind, and will be clear to the skilled person based on the disclosure herein, optionally after some limited degree of routine experimentation.

Also, when the two or more anti-CX3CR1 immunoglobulin single variable domains are domain antibodies or VHH domains, they may also be linked to each other via a third domain antibody or VHH domain (in which the two or more immunoglobulin single variable domains may be linked directly to the third domain antibody or VHH domain or via suitable linkers). Such a third domain antibody or VHH domain may for example be a domain antibody or VHH domain that provides for an increased half-life, as further described herein. For example, the latter domain antibody or VHH domain may be a domain antibody or VHH domain that is capable of binding to a (human) serum protein such as (human) serum albumin or (human) transferrin, as further described herein.

Alternatively, the two or more anti-CX3CR1 immunoglobulin single variable domains may be linked in series (either directly or via a suitable linker) and the third (single) domain antibody or VHH domain (which may provide for increased half-life, as described above) may be connected directly or via a linker to one of these two or more aforementioned immunoglobulin sequences.

Suitable linkers are described herein in connection with specific polypeptides of the invention and may—for example and without limitation—comprise an amino acid sequence, which amino acid sequence preferably has a length of 5 or more amino acids, 7 or more amino acids, 9 or more amino acids, 11 or more amino acids, 15 or more amino acids or at least 17 amino acids, such as about 20 to 40 amino acids. However, the upper limit is not critical but is chosen for reasons of convenience regarding e.g. biopharmaceutical production of such polypeptides.

The linker sequence may be a naturally occurring sequence or a non-naturally occurring sequence. If used for therapeutical purposes, the linker is preferably non-immunogenic in the subject to which the polypeptide of the invention is administered.

One useful group of linker sequences are linkers derived from the hinge region of heavy chain antibodies as described in WO 96/34103 and WO 94/04678.

Other examples are poly-alanine linker sequences such as Ala-Ala-Ala.

Further preferred examples of linker sequences are Gly/Ser linkers of different length such as $(gly_x ser_y)_z$ linkers, including $(gly_4 ser)_3$, $(gly_4 ser)_4$, $(gly_4 ser)$, $(gly_3 ser)$, $gly_3$, and $(gly_3 ser_2)_3$.

If the polypeptide of the invention is modified by the attachment of a polymer, for example a polyethylene glycol (PEG) moiety, the linker sequence preferably includes an amino acid residue, such as a cysteine or a lysine, allowing such modification, e.g. PEGylation, in the linker region.

Examples of linkers are:

GGGGS (5 GS linker, SEQ ID NO: 233)

SGGSGGS (7GS linker, SEQ ID NO: 234)

GGGGCGGGS (8GS linker, SEQ ID NO: 235)

GGGGSGGGS (9GS linker, SEQ ID NO: 236)

GGGGSGGGGS (10GS linker, SEQ ID NO: 237)

GGGGSGGGGSGGGGS (15GS linker, SEQ ID NO: 238)

GGGGSGGGGSGGGGGGS (18GS linker, SEQ ID NO: 239)

GGGGSGGGGSGGGGSGGGGS (20GS linker, SEQ ID NO: 240)

GGGGSGGGGSGGGGSGGGGSGGGGS (25GS linker, SEQ ID NO: 241)

GGGGSGGGGSGGGGSGGGGSGGGGSGGGGS (30GS linker, SEQ ID NO: 242)

GGGGSGGGGSGGGGSGGGGSGGGGSGGGGSGGGGS (35GS linker, SEQ ID NO: 243)

EPKSCDKTHTCPPCP (G1 hinge linker, SEQ ID NO: 244)

GGGGSGGGSEPKSCDKTHTCPPCP (9GS-G1 hinge linker, SEQ ID NO: 245)

EPKTPKPQPAAA (Llama upper long hinge region, SEQ ID NO: 246)

ELKTPLGDTTHTCPRCPEPKSCDTPPPCPRCPEPKSCDTPPPCPRCPEPKSCDTPPPCPRCP (G3 hinge, SEQ ID NO: 247)

AAA (Ala linker, SEQ ID NO: 248)

Furthermore, the linker may also be a poly(ethylene glycol) moiety, as shown in e.g. WO04/081026.

Non-limiting examples of polypeptides comprising or consisting of two or more anti-CX3CR1 immunoglobulin single variable domains are given in Table 8a.

TABLE 8a

Bivalent anti-CX3CR1 polypeptides

| | | |
|---|---|---|
| CX3CR1BII007 | EVQLVESGGGLVQAGGSLRLSCVASGRTFSSYAMG WFRQAPGKERAFVAGISGSASRKYYADSVKGRFTV SRDNARNTVYLQMNSLKPEDTAVYYCAASNSYPKV QFDYYGQGTQVTVSSGGGGSGGGGSGGGGSGGG GSGGGGSGGGGSGGGGSKVQLVESGGGLVQPGG | SEQ ID NO: 267 |

TABLE 8a-continued

| Bivalent anti-CX3CR1 polypeptides | | |
|---|---|---|
| | SLRLSCATSGTIFSNNAMGWYRQAPGKKRDLVASIS<br>SSGSTNYADSVKGRFTVSRDNDKNTGYLQMNSLKP<br>EDTGVYYCTLDARRGWNTAYWGQGAQVTVSS | |
| CX3CR1BII009 | KVQLVESGGGLVQPGGSLRLSCATSGTIFSNNAMG<br>WYRQAPGKKRDLVASISSSGSTNYADSVKGRFTVS<br>RDNDKNTGYLQMNSLKPEDTGVYYCTLDARRGWNT<br>AYWGQGAQVTVSSGGGGSGGGGSGGGGSGGGG<br>SGGGGSGGGGSGGGGSEVQLVESGGGLVQAGGS<br>LRLSCVASGRTFSSYAMGWFRQAPGKERAFVAGIS<br>GSASRKYYADSVKGRFTVSRDNARNTVYLQMNSLK<br>PEDTAVYYCAASNSYPKVQFDYYGQGTQVTVSS | SEQ ID<br>NO: 268 |
| CX3CR1BII012 | EVQLVESGGGSVQAGGSLRLSCAASGSIFSSNAMA<br>WYRQAPGKQRDLVAGINSVGITKYADSVKGRFTISR<br>DNAKNTVYLQMNSLKPEDTAVYYCTSDPRRGWDTR<br>YWGQGTLVTVSSGGGGSGGGGSGGGGSGGGGSG<br>GGGSGGGGSGGGGSKVQLVESGGGLVQPGGSLRL<br>SCATSGTIFSNNAMGWYRQAPGKKRDLVASISSSGS<br>TNYADSVKGRFTVSRDNDKNTGYLQMNSLKPEDTG<br>VYYCTLDARRGWNTAYWGQGAQVTVSS | SEQ ID<br>NO: 269 |
| CX3CR1BII016 | EVQLVESGGGSVQAGESLRLSCAASGSIFSSNAMA<br>WYRQAPGKQRDLVAVINSVGITKYADSVKGRFTISG<br>DNAKNTVYLQMNSLKPEDTAVYYCTSDARRGWDTR<br>YWGQGTQVTVSSGGGGSGGGGSGGGGSGGGGS<br>GGGGSGGGGSGGGGSEVQLVESGGGSVQAGESL<br>RLSCAASGSIFSSNAMAWYRQAPGKQRDLVAVINSV<br>GITKYADSVKGRFTISGDNAKNTVYLQMNSLKPEDT<br>AVYYCTSDARRGWDTRYWGQGTQVTVSS | SEQ ID<br>NO: 270 |
| CX3CR1BII017 | EVQLVESGGGSVQAGESLRLSCAASGSIFSSNAMA<br>WYRQAPPGKQRDLVALINSVGITKYADSVKGRFTISS<br>DNAKNTVYLEMNSLKPEDTAVYYCTSDGRRGWDTR<br>YWGQGTQVTVSSGGGGSGGGGSGGGGSGGGGS<br>GGGGSGGGGSGGGGSEVQLVESGGGSVQAGESL<br>RLSCAASGSIFSSNAMAWYRQAPPGKQRDLVALINS<br>VGITKYADSVKGRFTISSDNAKNTVYLEMNSLKPEDT<br>AVYYCTSDGRRGWDTRYWGQGTQVTVSS | SEQ ID<br>NO: 271 |
| CX3CR1BII018 | EVQLVESGGGSVQAGESLRLSCAASGSIFSSNAMA<br>WYRQAPGKRRDLVAAINSVGVTKYADSVKGRFTISR<br>DNAKNTVYLQMNSLKPEDTAVYYCTSDPRRGWDTR<br>YWGQGTQVTVSSGGGGSGGGGSGGGGSGGGGS<br>GGGGSGGGGSGGGGSEVQLVESGGGSVQAGESL<br>RLSCAASGSIFSSNAMAWYRQAPGKRRDLVAAINSV<br>GVTKYADSVKGRFTISRDNAKNTVYLQMNSLKPEDT<br>AVYYCTSDPRRGWDTRYWGQGTQVTVSS | SEQ ID<br>NO: 272 |
| CX3CR1BII019 | EMQLVESGGGSVQAGESLRLSCAASGSIFSSNAMA<br>WYRQAPGKQRDLVALINSVGITKYADSVKGRFTISR<br>DNAKNTVYLQMNSLKPEDTAVYYCTSDGRRGWDTR<br>YWGQGTQVTVSSGGGGSGGGGSGGGGSGGGGS<br>GGGGSGGGGSGGGGSEMQLVESGGGSVQAGESL<br>RLSCAASGSIFSSNAMAWYRQAPGKQRDLVALINSV<br>GITKYADSVKGRFTISRDNAKNTVYLQMNSLKPEDTA<br>VYYCTSDGRRGWDTRYWGQGTQVTVSS | SEQ ID<br>NO: 273 |
| CX3CR1BII020 | EVQLVESGGGSVQAGESLRLSCAASGSIFSSNAMA<br>WYRQAPGKQRDLVAGINSVGITKYADSVKGRFTISR<br>DNAKNTAYLQMNSLKPEDTAVYYCTSDPRRGWDTR<br>YWGQGTLVTVSSGGGGSGGGGSGGGGSGGGGSG<br>GGGSGGGGSGGGGSEVQLVESGGGSVQAGESLRL<br>SCAASGSIFSSNAMAWYRQAPGKQRDLVAGINSVGI<br>TKYADSVKGRFTISRDNAKNTAYLQMNSLKPEDTAV<br>YYCTSDPRRGWDTRYWGQGTLVTVSS | SEQ ID<br>NO: 274 |
| CX3CR1BII026 | EVQLVESGGGLVQAGGSLRLSCVASGRTFSSYAMG<br>WFRQAPGKERAFVAGISGSASRKYYADSVKGRFTV<br>SRDNARNTVYLQMNSLKPEDTAVYYCAASNSYPKV<br>QFDYYGQGTQVTVSSGGGGSGGGGSGGGGSGGG<br>GSGGGGSGGGGSGGGGSEVQLVESGGGSVQAGE<br>SLRLSCAASGSIFSSNAMAWYRQAPGKRRDLVAAIN<br>SVGVTKYADSVKGRFTISRDNAKNTVYLQMNSLKPE<br>DTAVYYCTSDPRRGWDTRYWGQGTQVTVSS | SEQ ID<br>NO: 275 |
| CX3CR1BII027 | EVQLVESGGGLVQAGGSLRLSCVASGRTFSSYAMG<br>WFRQAPGKERAFVAGISGSASRKYYADSVKGRFTV<br>SRDNARNTVYLQMNSLKPEDTAVYYCAASNSYPKV | SEQ ID<br>NO: 276 |

TABLE 8a-continued

Bivalent anti-CX3CR1 polypeptides

|  | | |
|---|---|---|
| | QFDYYGQGTQVTVSSGGGGSGGGGSGGGGSGGG<br>GSGGGGSGGGGSGGGGSEVQLVESGGGSVQAGE<br>SLRLSCAASGSIFSSNAMAWYRQAPGKQRDLVAGIN<br>SVGITKYADSVKGRFTISRDNAKNTAYLQMNSLKPE<br>DTAVYYCTSDPRRGWDTRYWGQGTLVTVSS | |
| CX3CR1BII006 | EVQLVESGGGLVQAGGSLRLSCVASGRTFSSYAMG<br>WFRQAPGKERAFVAGISGSASRKYYADSVKGRFTV<br>SRDNARNTVYLQMNSLKPEDTAVYYCAASNSYPKV<br>QFDYYGQGTLVTVSSGGGGSGGGGSGGGGSGGG<br>GSGGGGSGGGGSGGGGSEVQLVESGGGLVQAGG<br>SLRLSCVASGRTFSSYAMGWFRQAPGKERAFVAGI<br>SGSASRKYYADSVKGRFTVSRDNARNTVYLQMNSL<br>KPEDTAVYYCAASNSYPKVQFDYYGQGTLVTVSS | SEQ ID<br>NO: 282 |

In another embodiment, the at least two immunoglobulin single variable domains of the polypeptide of the invention are linked to each other via another moiety (optionally via one or two linkers), such as another polypeptide which, in a preferred but non-limiting embodiment, may be a further immunoglobulin single variable domain as already described above. Such moiety may either be essentially inactive or may have a biological effect such as improving the desired properties of the polypeptide or may confer one or more additional desired properties to the polypeptide. For example, and without limitation, the moiety may improve the half-life of the protein or polypeptide, and/or may reduce its immunogenicity or improve any other desired property.

In one aspect, a polypeptide of the invention includes, especially when used as a therapeutic agent, a moiety which extends the half-life of the polypeptide of the invention in serum or other body fluids of a patient. The term "half-life" means the time taken for the serum concentration of the (modified) polypeptide to reduce by 50%, in vivo, for example due to degradation of the polypeptide and/or clearance and/or sequestration by natural mechanisms.

According to a further embodiment of the invention, the two immunoglobulin single variable domains may be fused to a serum albumin molecule, such as described e.g. in WO01/79271 and WO03/59934.

Alternatively, such half-life extending moiety can be covalently linked or fused to said polypeptide and may be, without limitation, an Fc portion, an albumin moiety, a fragment of an albumin moiety, an albumin binding moiety, such as an anti-albumin immunoglobulin single variable domain, a transferrin binding moiety, such as an anti-transferrin immunoglobulin single variable domain, a polyoxyalkylene molecule, such as a polyethylene glycol molecule, an albumin binding peptide, or hydroxyethyl starch (HES) derivatives.

In another aspect, the polypeptide of the invention comprises a moiety which binds to an antigen found in blood, such as serum albumin, serum immunoglobulins, thyroxine-binding protein, fibrinogen or transferrin, thereby conferring an increased half-life in vivo to the resulting polypeptide of the invention. According to one embodiment, such moiety is an albumin-binding immunoglobulin and, in particular, an albumin-binding immunoglobulin single variable domain such as an albumin-binding VHH domain.

In another embodiment, the polypeptide of the invention comprises a moiety which binds to serum albumin, wherein such moiety is an albumin binding peptide, as described e.g. in international patent publications WO2008/068280 and WO2009/127691.

If intended for use in humans, such albumin-binding immunoglobulin single variable domain (also called anti-albumin immunoglobulin single variable domain) will preferably bind to human serum albumin and will preferably be a humanized albumin-binding VHH domain.

Immunoglobulin single variable domains binding to human serum albumin are known in the art and are described in further detail in e.g. WO2006/122786. A specifically useful albumin binding VHH domain consists of or contains the amino acid sequence as set forth in any one of SEQ ID NO: 230-232:

TABLE 8b

| ALB-1 | AVQLVESGGGLVQPGNSLRLSCAASGFTFRSFG<br>MSWVRQAPGKEPEWVSSISGSGSDTLYADSVK<br>GRFTISRDNAKTTLYLQMNSLKPEDTAVYYCTIG<br>GSLSRSSQGTQVTVSS | SEQ<br>ID<br>NO: | 230 |
|---|---|---|---|
| ALB-11<br>(human-<br>ized<br>ALB-1) | EVQLVESGGGLVQPGNSLRLSCAASGFTFSSFG<br>MSWVRQAPGKGLEWVSSISGSGSDTLYADSVK<br>GRFTISRDNAKTTLYLQMNSLRPEDTAVYYCTIG<br>GSLSRSSQGTLVTVSS | SEQ<br>ID<br>NO: | 231 |
| ALB-2 | AVQLVESGGGLVQGGGSLRLACAASERIFDLNL<br>MGWYRQGPGNERELVATCITVGDSTNYADSVK<br>GRFTISMDYTKQTVYLHMNSLRPEDTGLYYCKIR<br>RTWHSELWGQGTQVTVSS | SEQ<br>ID<br>NO: | 232 |

According to one embodiment, a polypeptide of the invention may be linked to one or more antibody parts, fragments or domains that confer one or more effector functions to the polypeptide of the invention and/or may confer the ability to bind to one or more Fc receptors. For example, for this purpose, and without being limited thereto, the antibody parts may be or may comprise CH2 and/or CH3 domains of an antibody, such as from a heavy chain antibody (as described hereabove) and more preferably from a conventional human 4-chain antibody; specifically, the polypeptide of the invention may be linked to an Fc region, for example from human IgG, from human IgE or from another human Ig. For example, WO 94/04678 describes heavy chain antibodies comprising a Camelid VHH domain or a humanized derivative thereof, in which the Camelidae CH2 and/or CH3 domain have been replaced by human CH2 and/or CH3 domains, so as to provide an immunoglobulin that consists of 2 heavy chains each comprising a—optionally humanized—VHH domain and human CH2 and CH3 domains (but no CH1 domain), which immunoglobulin has the effector function provided by the CH2 and CH3 domains, can function without the presence of any light chains, and has an increased half-life as compared to the corresponding VHH domains without such modification.

In one aspect, a polypeptide of the present invention comprises two anti-CX3CR1 VHHs and a VHH capable of binding to serum albumin. In one aspect, the VHHs are fused using linker peptides. Representative examples of such polypeptides of the present invention are shown hereinbelow.

In one aspect, a polypeptide of the present invention comprises a first anti-CX3CR1 VHH fused to a first linker peptide, which is itself fused to a VHH capable of binding to serum albumin, which is itself fused to a second linker peptide, which is itself fused to a second anti-CX3CR1 VHH. In one aspect, the first or the second linker peptide is a 9GS linker, in one aspect, the first and the second linker peptide is a 9GS linker. In one aspect, the VHH capable of binding to serum albumin is capable of binding to human serum albumin. In one aspect, the VHH capable of binding to serum albumin has the amino acid sequence set forth in SEQ ID NO: 231. In one aspect, the first and the second anti-CX3CR1 VHH have the same amino acid sequence. In one aspect, the first or the second anti-CX3CR1 VHH has the CDR1, CDR2 and CDR3 set forth in:
SEQ ID NO's: 213, 214 and 186; or
SEQ ID NO's: 213, 221 and 186; or
SEQ ID NO's: 141, 162 and 186.

In one aspect, the first and the second anti-CX3CR1 VHH have the CDR1, CDR2 and CDR3 set forth in:
SEQ ID NO's: 213, 214 and 186; or
SEQ ID NO's: 213, 221 and 186; or
SEQ ID NO's: 141, 162 and 186.

In one aspect, the first or the second anti-CX3CR1 VHH has the amino acid sequence set forth in any one of SEQ ID NO: 138 to 140 or SEQ ID NO: 222 to 224. In one aspect, the first and the second anti-CX3CR1 VHH have the same amino acid sequence, wherein said amino acid sequence is the sequence set forth in any one of SEQ ID NO: 138 to 140 or SEQ ID NO: 222 to 224.

Non-limiting examples of polypeptides of the present invention are the polypeptides of any one of SEQ ID NO: 225 to 227, 249 or 277 to 281.

TABLE 9

| | | |
|---|---|---|
| CX3CR1BII00312 | DVQLVESGGGLVQPGGSLRLSCAASGSIFSSTA MAWYRQAPGKRRDLVAAISSVGVTKYADSVKGR FTISRDNSKNTVYLQMNSLRPEDTAVYYCTSDPR RGWDTRYWGQGTLVTVSSGGGGSGGGSEVQL VESGGGLVQPGNSLRLSCAASGFTFSSFGMSW VRQAPGKGLEWVSSISGSGSDTLYADSVKGRFTI SRDNAKTTLYLQMNSLRPEDTAVYYCTIGGSLSR SSQGTLVTVSSGGGGSGGGSEVQLVESGGGLV QPGGSLRLSCAASGSIFSSTAMAWYRQAPGKRR DLVAAISSVGVTKYADSVKGRFTISRDNSKNTVYL QMNSLRPEDTAVYYCTSDPRRGWDTRYWGQG TLVTVSS | SEQ ID NO: 225 |
| CX3CR1BII00313 | DVQLVESGGGLVQPGGSLRLSCAASGSIFSSTA MAWYRQAPGKRRDLVAAISTVGVTKYADSVKGR FTISRDNSKNTVYLQMNSLRPEDTAVYYCTSDPR RGWDTRYWGQGTLVTVSSGGGGSGGGSEVQL VESGGGLVQPGNSLRLSCAASGFTFSSFGMSW VRQAPGKGLEWVSSISGSGSDTLYADSVKGRFTI SRDNAKTTLYLQMNSLRPEDTAVYYCTIGGSLSR SSQGTLVTVSSGGGGSGGGSEVQLVESGGGLV QPGGSLRLSCAASGSIFSSTAMAWYRQAPGKRR DLVAAISTVGVTKYADSVKGRFTISRDNSKNTVYL QMNSLRPEDTAVYYCTSDPRRGWDTRYWGQG TLVTVSS | SEQ ID NO: 226 |
| CX3CR1BII00314 | DVQLVESGGGLVQPGGSLRLSCAASGSIFSSNA MAWYRQAPGKRRDLVAAINSVGVTKYADSVKGR FTISRDNSKNTVYLQMNSLRPEDTAVYYCTSDPR RGWDTRYWGQGTLVTVSSGGGGSGGGSEVQL VESGGGLVQPGNSLRLSCAASGFTFSSFGMSW VRQAPGKGLEWVSSISGSGSDTLYADSVKGRFTI SRDNAKTTLYLQMNSLRPEDTAVYYCTIGGSLSR SSQGTLVTVSSGGGGSGGGSEVQLVESGGGLV QPGGSLRLSCAASGSIFSSNAMAWYRQAPGKR RDLVAAINSVGVTKYADSVKGRFTISRDNSKNTV YLQMNSLRPEDTAVYYCTSDPRRGWDTRYWGQ GTLVTVSS | SEQ ID NO: 227 |
| CX3CR1BII032 | EVQLVESGGGSVQAGESLRLSCAASGSIFSSNA MAWYRQAPGKRRDLVAAINSVGVTKYADSVKGR FTISRDNAKNTVYLQMNSLKPEDTAVYYCTSDPR RGWDTRYWGQGTQVTVSSGGGGSGGGSEVQL VESGGGSVQAGESLRLSCAASGSIFSSNAMAWY RQAPGKRRDLVAAINSVGVTKYADSVKGRFTISR DNAKNTVYLQMNSLKPEDTAVYYCTSDPRRGW DTRYWGQGTQVTVSSGGGGSGGGSEVQLVES GGGLVQPGNSLRLSCAASGFTFSSFGMSWVRQ APGKGLEWVSSISGSGSDTLYADSVKGRFTISRD NAKTTLYLQMNSLRPEDTAVYYCTIGGSLSRSSQ GTLVTVSS | SEQ ID NO: 277 |

TABLE 9-continued

| | | |
|---|---|---|
| CX3CR1BII034 | EVQLVESGGGSVQAGESLRLSCAASGSIFSSNA MAWYRQAPGKRRDLVAAINSVGVTKYADSVKGR FTISRDNAKNTVYLQMNSLKPEDTAVYYCTSDPR RGWDTRYWGQGTQVTVSSGGGGSGGGGSGG GGSGGGGSGGGGSGGGGSGGGGSEVQLVES GGGSVQAGESLRLSCAASGSIFSSNAMAWYRQ APGKRRDLVAAINSVGVTKYADSVKGRFTISRDN AKNTVYLQMNSLKPEDTAVYYCTSDPRRGWDTR YWGQGTQVTVSSGGGGSGGGSEVQLVESGGG LVQPGNSLRLSCAASGFTFSSFGMSWVRQAPG KGLEWVSSISGSGSDTLYADSVKGRFTISRDNAK TTLYLQMNSLRPEDTAVYYCTIGGSLSRSSQGTL VTVSS | SEQ ID NO: 278 |
| CX3CR1BII036 | EVQLVESGGGSVQAGESLRLSCAASGSIFSSNA MAWYRQAPGKRRDLVAAINSVGVTKYADSVKGR FTISRDNAKNTVYLQMNSLKPEDTAVYYCTSDPR RGWDTRYWGQGTLVTVSSGGGGSGGGSEVQL VESGGGLVQPGNSLRLSCAASGFTFSSFGMSW VRQAPGKGLEWVSSISGSGSDTLYADSVKGRFTI SRDNAKTTLYLQMNSLRPEDTAVYYCTIGGSLSR SSQGTLVTVSSGGGGSGGGSEVQLVESGGGSV QAGESLRLSCAASGSIFSSNAMAWYRQAPGKRR DLVAAINSVGVTKYADSVKGRFTISRDNAKNTVY LQMNSLKPEDTAVYYCTSDPRRGWDTRYWGQG TLVTVSS | SEQ ID NO: 249 |
| CX3CR1BII040 | EVQLVESGGGSVQAGESLRLSCAASGSIFSSNA MAWYRQAPGKRRDLVAAINSVGVTKYADSVKGR FTISRDNAKNTVYLQMNSLKPEDTAVYYCTSDPR RGWDTRYWGQGTQVTVSSGGGGSGGGSEVQL VESGGGSVQAGESLRLSCAASGSIFSSNAMAWY RQAPGKRRDLVAAINSVGVTKYADSVKGRFTISR DNAKNTVYLQMNSLKPEDTAVYYCTSDPRRGW DTRYWGQGTQVTVSSGGGGSGGGGSGGGGS GGGGSGGGGSGGGGSGGGGSEVQLVESGGGL VQPGNSLRLSCAASGFTFSSFGMSWVRQAPGK GLEWVSSISGSGSDTLYADSVKGRFTISRDNAKT TLYLQMNSLRPEDTAVYYCTIGGSLSRSSQGTLV TVSS | SEQ ID NO: 279 |
| CX3CR1BII041 | EVQLVESGGGSVQAGESLRLSCAASGSIFSSNA MAWYRQAPGKRRDLVAAINSVGVTKYADSVKGR FTISRDNAKNTVYLQMNSLKPEDTAVYYCTSDPR RGWDTRYWGQGTQVTVSSGGGGSGGGGSGG GGSGGGGSGGGGSGGGGSGGGGSEVQLVES GGGSVQAGESLRLSCAASGSIFSSNAMAWYRQ APGKRRDLVAAINSVGVTKYADSVKGRFTISRDN AKNTVYLQMNSLKPEDTAVYYCTSDPRRGWDTR YWGQGTQVTVSSGGGGSGGGGSGGGGSGGG GSGGGGSGGGGSGGGGSEVQLVESGGGLVQP GNSLRLSCAASGFTFSSFGMSWVRQAPGKGLE WVSSISGSGSDTLYADSVKGRFTISRDNAKTTLY LQMNSLRPEDTAVYYCTIGGSLSRSSQGTLVTVSS | SEQ ID NO: 280 |
| CX3CR1BII042 | EVQLVESGGGSVQAGESLRLSCAASGSIFSSNA MAWYRQAPGKRRDLVAAINSVGVTKYADSVKGR FTISRDNAKNTVYLQMNSLKPEDTAVYYCTSDPR RGWDTRYWGQGTQVTVSSGGGGSGGGGSGG GGSGGGGSGGGGSGGGGSGGGGSEVQLVES GGGLVQPGNSLRLSCAASGFTFSSFGMSWVRQ APGKGLEWVSSISGSGSDTLYADSVKGRFTISRD NAKTTLYLQMNSLRPEDTAVYYCTIGGSLSRSSQ GTLVTVSSGGGGSGGGGSGGGGSGGGGSGGG GSGGGGSGGGGSEVQLVESGGGSVQAGESLRL SCAASGSIFSSNAMAWYRQAPGKRRDLVAAINS VGVTKYADSVKGRFTISRDNAKNTVYLQMNSLKP EDTAVYYCTSDPRRGWDTRYWGQGTQVTVSS | SEQ ID NO: 281 |

In another aspect, a polypeptide of the present invention comprises an anti-CX3CR1 VHH and a Fc domain. In one aspect, a polypeptide of the present invention comprises an anti-CX3CR1 VHH fused to a linker peptide, which is itself fused to a Fc domain. In one aspect, the linker peptide is a 15GS linker. In one aspect, the Fc domain has the amino acid sequence set forth in SEQ ID NO: 250 or 252. In one aspect, the VHH has the CDR1, CDR2 and CDR3 set forth in:

SEQ ID NO's: 213, 214 and 186; or
SEQ ID NO's: 213, 221 and 186; or
SEQ ID NO's: 141, 162 and 186.

In one aspect, the VHH has the amino acid sequence set forth in any one of SEQ ID NO: 138 to 140 or SEQ ID NO: 222 to 224. In one aspect the polypeptide is in the form of a dimer, for example wherein the dimer is formed by one or more disulfide bridge.

Non-limiting examples of polypeptides of the present invention are the polypeptides of SEQ ID NO: 251, 253 or 254.

TABLE 10

| | | |
|---|---|---|
| Mouse Fc domain | PPCKCPAPNLLGGPSVFIFPPKIKDVLMISLSPIVT CVVVAVSEDDPDVQISWFVNNVEVHTAQTQTHR EDYNSTLRVVSALPIQHQDWMSGKEFKCKVNNK DLPAPIERTISKPKGSVRAPQVYVLPPPEEEMTK KQVTLTCMVTDFMPEDIYVEWTNNGKTELNYKN TEPVLDSDGSYFMYSKLRVEKKNWVERNSYSCS VVHEGLHNHHTTKSFSRTPGK | SEQ ID NO: 250 |
| 66B02-mFc | EVQLVESGGGSVQAGESLRLSCAASGSIFSSNA MAWYRQAPGKRRDLVAAINSVGVTKYADSVKGR FTISRDNAKNTVYLQMNSLKPEDTAVYYCTSDPR RGWDTRYWGQGTLVTVSSGGGGSGGGGSGG GGSPPCKCPAPNLLGGPSVFIFPPKIKDVLMISLS PIVTCVVVAVSEDDPDVQISWFVNNVEVHTAQTQ THREDYNSTLRVVSALPIQHQDWMSGKEFKCKV NNKDLPAPIERTISKPKGSVRAPQVYVLPPPEEE MTKKQVTLTCMVTDFMPEDIYVEWTNNGKTELN YKNTEPVLDSDGSYFMYSKLRVEKKNWVERNSY SCSVVHEGLHNHHTTKSFSRTPGK | SEQ ID NO: 251 |
| Human Fc Domain | CPPCPAPEAAGGPSVFLFPPKPKDTLMISRTPEV TCVVVDVSHEDPEVKFNWYVDGVEVHNAKTKPR EEQYNSTYRVVSVLTVLHQDWLNGKEYKCKVSN KALPAPIEKTISKAKGQPREPQVYTLPPSREEMT KNQVSLTCLVKGFYPSDIAVEWESNGQPENNYK TTPPVLDSDGSFFLYSKLTVDKSRWQQGNVFSC SVMHEALHNHYTQKSLSLSPGK | SEQ ID NO: 252 |
| 306D-hFc | DVQLVESGGGLVQPGGSLRLSCAASGSIFSSTA MAWYRQAPGKRRDLVAAISSVGVTKYADSVKGR FTISRDNSKNTVYLQMNSLRPEDTAVYYCTSDPR RGWDTRYWGQGTLVTVSSGGGGSGGGGSGG GGSCPPCPAPEAAGGPSVFLFPPKPKDTLMISRT PEVTCVVVDVSHEDPEVKFNWYVDGVEVHNAKT KPREEQYNSTYRVVSVLTVLHQDWLNGKEYKCK VSNKALPAPIEKTISKAKGQPREPQVYTLPPSREE MTKNQVSLTCLVKGFYPSDIAVEWESNGQPENN YKTTPPVLDSDGSFFLYSKLTVDKSRWQQGNVF SCSVMHEALHNHYTQKSLSLSPGK | SEQ ID NO: 253 |
| 307D-hFc | DVQLVESGGGLVQPGGSLRLSCAASGSIFSSTA MAWYRQAPGKRRDLVAAISTVGVTKYADSVKGR FTISRDNSKNTVYLQMNSLRPEDTAVYYCTSDPR RGWDTRYWGQGTLVTVSSGGGGSGGGGSGG GGSCPPCPAPEAAGGPSVFLFPPKPKDTLMISRT PEVTCVVVDVSHEDPEVKFNWYVDGVEVHNAKT KPREEQYNSTYRVVSVLTVLHQDWLNGKEYKCK VSNKALPAPIEKTISKAKGQPREPQVYTLPPSREE MTKNQVSLTCLVKGFYPSDIAVEWESNGQPENN YKTTPPVLDSDGSFFLYSKLTVDKSRWQQGNVF SCSVMHEALHNHYTQKSLSLSPGK | SEQ ID NO: 254 |

A polypeptide of the invention may be modified to improve its properties. In one aspect, a polypeptide of the present invention may be modified to increase its stability upon storage. In one aspect, a polypeptide of the present invention may be modified to facilitate its expression in a particular host system. For example, the first codon of a polypeptide of the present invention may be modified. In one aspect, a polypeptide of the present invention begins with a glutamic acid (glu) as its first amino acid. In another aspect, a polypeptide of the present invention begins with an aspartic acid (asp) as its first amino acid, for example to reduce pyroglutamate formation at the N-terminus during storage and hence increase product stability. In another aspect, a polypeptide of the present invention begins with an alanine (ala) or a valine (val) as its first amino acid, for example to facilitate the expression of the polypeptide in a prokaryotic expression system, such as *Escherichia coli*. Such modification of a polypeptide according to the present invention are made using techniques known in the art.

Representative examples of polypeptides according to the present invention with a modified first codon are set forth in any one of SEQ ID NO: 257-262 and 263-266 and are shown in Tables 11 and 12 below:

TABLE 11

| | | |
|---|---|---|
| CX3CR1BII00312 (D1A) | AVQLVESGGGLVQPGGSLRLSCAASGSIFSSTA MAWYRQAPGKRRDLVAAISSVGVTKYADSVKGR FTISRDNSKNTVYLQMNSLRPEDTAVYYCTSDPR RGWDTRYWGQGTLVTVSSGGGGSGGGSEVQL VESGGGLVQPGNSLRLSCAASGFTFSSFGMSW VRQAPGKGLEWVSSISGSGSDTLYADSVKGRFTI SRDNAKTTLYLQMNSLRPEDTAVYYCTIGGSLSR SSQGTLVTVSSGGGGSGGGSEVQLVESGGGLV QPGGSLRLSCAASGSIFSSTAMAWYRQAPGKRR DLVAAISSVGVTKYADSVKGRFTISRDNSKNTVYL QMNSLRPEDTAVYYCTSDPRRGWDTRYWGQG TLVTVSS | SEQ ID NO: 257 |
| CX3CR1BII00313 (D1A) | AVQLVESGGGLVQPGGSLRLSCAASGSIFSSTA MAWYRQAPGKRRDLVAAISTVGVTKYADSVKGR FTISRDNSKNTVYLQMNSLRPEDTAVYYCTSDPR RGWDTRYWGQGTLVTVSSGGGGSGGGSEVQL VESGGGLVQPGNSLRLSCAASGFTFSSFGMSW VRQAPGKGLEWVSSISGSGSDTLYADSVKGRFTI SRDNAKTTLYLQMNSLRPEDTAVYYCTIGGSLSR SSQGTLVTVSSGGGGSGGGSEVQLVESGGGLV QPGGSLRLSCAASGSIFSSTAMAWYRQAPGKRR DLVAAISTVGVTKYADSVKGRFTISRDNSKNTVYL QMNSLRPEDTAVYYCTSDPRRGWDTRYWGQG TLVTVSS | SEQ ID NO: 258 |
| CX3CR1BII00314 (D1A) | AVQLVESGGGLVQPGGSLRLSCAASGSIFSSNA MAWYRQAPGKRRDLVAAINSVGVTKYADSVKGR FTISRDNSKNTVYLQMNSLRPEDTAVYYCTSDPR RGWDTRYWGQGTLVTVSSGGGGSGGGSEVQL VESGGGLVQPGNSLRLSCAASGFTFSSFGMSW VRQAPGKGLEWVSSISGSGSDTLYADSVKGRFTI SRDNAKTTLYLQMNSLRPEDTAVYYCTIGGSLSR | SEQ ID NO: 259 |

TABLE 11-continued

| | | |
|---|---|---|
| | SSQGTLVTVSSGGGGSGGGSEVQLVESGGGLV<br>QPGGSLRLSCAASGSIFSSNAMAWYRQAPGKR<br>RDLVAAINSVGVTKYADSVKGRFTISRDNSKNTV<br>YLQMNSLRPEDTAVYYCTSDPRRGWDTRYWGQ<br>GTLVTVSS | |
| CX3CR1BII00312<br>(D1V) | VQLVESGGGLVQPGGSLRLSCAASGSIFSSTAM<br>AWYRQAPGKRRDLVAAISSVGVTKYADSVKGRF<br>TISRDNSKNTVYLQMNSLRPEDTAVYYCTSDPRR<br>GWDTRYWGQGTLVTVSSGGGGSGGGSEVQLV<br>ESGGGLVQPGNSLRLSCAASGFTFSSFGMSWV<br>RQAPGKGLEWVSSISGSGSDTLYADSVKGRFTIS<br>RDNAKTTLYLQMNSLRPEDTAVYYCTIGGSLSRS<br>SQGTLVTVSSGGGGSGGGSEVQLVESGGGLVQ<br>PGGSLRLSCAASGSIFSSTAMAWYRQAPGKRRD<br>LVAAISSVGVTKYADSVKGRFTISRDNSKNTVYL<br>QMNSLRPEDTAVYYCTSDPRRGWDTRYWGQG<br>TLVTVSS | SEQ ID 260<br>NO: |
| CX3CR1BII00313<br>(D1V) | VQLVESGGGLVQPGGSLRLSCAASGSIFSSTAM<br>AWYRQAPGKRRDLVAAISTVGVTKYADSVKGRF<br>TISRDNSKNTVYLQMNSLRPEDTAVYYCTSDPRR<br>GWDTRYWGQGTLVTVSSGGGGSGGGSEVQLV<br>ESGGGLVQPGNSLRLSCAASGFTFSSFGMSWV<br>RQAPGKGLEWVSSISGSGSDTLYADSVKGRFTIS<br>RDNAKTTLYLQMNSLRPEDTAVYYCTIGGSLSRS<br>SQGTLVTVSSGGGGSGGGSEVQLVESGGGLVQ<br>PGGSLRLSCAASGSIFSSTAMAWYRQAPGKRRD<br>LVAAISTVGVTKYADSVKGRFTISRDNSKNTVYLQ<br>MNSLRPEDTAVYYCTSDPRRGWDTRYWGQGTL<br>VTVSS | SEQ ID 261<br>NO: |
| CX3CR1BII00314<br>(D1V) | VQLVESGGGLVQPGGSLRLSCAASGSIFSSNAM<br>AWYRQAPGKRRDLVAAINSVGVTKYADSVKGRF<br>TISRDNSKNTVYLQMNSLRPEDTAVYYCTSDPRR<br>GWDTRYWGQGTLVTVSSGGGGSGGGSEVQLV<br>ESGGGLVQPGNSLRLSCAASGFTFSSFGMSWV<br>RQAPGKGLEWVSSISGSGSDTLYADSVKGRFTIS<br>RDNAKTTLYLQMNSLRPEDTAVYYCTIGGSLSRS<br>SQGTLVTVSSGGGGSGGGSEVQLVESGGGLVQ<br>PGGSLRLSCAASGSIFSSNAMAWYRQAPGKRRD<br>LVAAINSVGVTKYADSVKGRFTISRDNSKNTVYL<br>QMNSLRPEDTAVYYCTSDPRRGWDTRYWGQG<br>TLVTVSS | SEQ ID 262<br>NO: |

TABLE 12

| | | |
|---|---|---|
| 306D-hFc<br>(D1A) | AVQLVESGGGLVQPGGSLRLSCAASGSIFSSTA<br>MAWYRQAPGKRRDLVAAISTVGVTKYADSVKGR<br>FTISRDNSKNTVYLQMNSLRPEDTAVYYCTSDPR<br>RGWDTRYWGQGTLVTVSSGGGGSGGGGSGG<br>GGSCPPCPAPEAAGGPSVFLFPPKPKDTLMISRT<br>PEVTCVVVDVSHEDPEVKFNWYVDGVEVHNAKT<br>KPREEQYNSTYRVVSVLTVLHQDWLNGKEYKCK<br>VSNKALPAPIEKTISKAKGQPREPQVYTLPPSREE<br>MTKNQVSLTCLVKGFYPSDIAVEWESNGQPENN<br>YKTTPPVLDSDGSFFLYSKLTVDKSRWQQGNVF<br>SCSVMHEALHNHYTQKSLSLSPGK | SEQ<br>ID<br>NO: 263 |
| 307D-hFc<br>(D1A) | AVQLVESGGGLVQPGGSLRLSCAASGSIFSSTA<br>MAWYRQAPGKRRDLVAAISTVGVTKYADSVKGR<br>FTISRDNSKNTVYLQMNSLRPEDTAVYYCTSDPR<br>RGWDTRYWGQGTLVTVSSGGGGSGGGGSGG<br>GGSCPPCPAPEAAGGPSVFLFPPKPKDTLMISRT<br>PEVTCVVVDVSHEDPEVKFNWYVDGVEVHNAKT<br>KPREEQYNSTYRVVSVLTVLHQDWLNGKEYKCK<br>VSNKALPAPIEKTISKAKGQPREPQVYTLPPSREE<br>MTKNQVSLTCLVKGFYPSDIAVEWESNGQPENN<br>YKTTPPVLDSDGSFFLYSKLTVDKSRWQQGNVF<br>SCSVMHEALHNHYTQKSLSLSPGK | SEQ<br>ID<br>NO: 264 |
| 306D-hFc<br>(D1V) | VQLVESGGGLVQPGGSLRLSCAASGSIFSSTAM<br>AWYRQAPGKRRDLVAAISSVGVTKYADSVKGRF<br>TISRDNSKNTVYLQMNSLRPEDTAVYYCTSDPRR<br>GWDTRYWGQGTLVTVSSGGGGSGGGGSGGG<br>GSCPPCPAPEAAGGPSVFLFPPKPKDTLMISRTP<br>EVTCVVVDVSHEDPEVKFNWYVDGVEVHNAKTK<br>PREEQYNSTYRVVSVLTVLHQDWLNGKEYKCKV<br>SNKALPAPIEKTISKAKGQPREPQVYTLPPSREE<br>MTKNQVSLTCLVKGFYPSDIAVEWESNGQPENN<br>YKTTPPVLDSDGSFFLYSKLTVDKSRWQQGNVF<br>SCSVMHEALHNHYTQKSLSLSPGK | SEQ<br>ID<br>NO: 265 |
| 307D-hFc<br>(D1V) | VQLVESGGGLVQPGGSLRLSCAASGSIFSSTAM<br>AWYRQAPGKRRDLVAAISTVGVTKYADSVKGRF<br>TISRDNSKNTVYLQMNSLRPEDTAVYYCTSDPRR<br>GWDTRYWGQGTLVTVSSGGGGSGGGGSGGG<br>GSCPPCPAPEAAGGPSVFLFPPKPKDTLMISRTP<br>EVTCVVVDVSHEDPEVKFNWYVDGVEVHNAKTK<br>PREEQYNSTYRVVSVLTVLHQDWLNGKEYKCKV<br>SNKALPAPIEKTISKAKGQPREPQVYTLPPSREE<br>MTKNQVSLTCLVKGFYPSDIAVEWESNGQPENN<br>YKTTPPVLDSDGSFFLYSKLTVDKSRWQQGNVF<br>SCSVMHEALHNHYTQKSLSLSPGK | SEQ<br>ID<br>NO: 266 |

In one further aspect, a polypeptide of the present invention is characterized by one or more of the following properties:

Bind with high affinity to human CX3CR1;
Inhibit binding of soluble fractalkine to human CX3CR1;
Inhibit fractalkine induced chemotaxis;
Inhibit fractalkine induced human CX3CR1 receptor internalization;
Cross-react with cyno CX3CR1 within 10-fold of $E/IC_{50}$ for human CX3CR1 for binding and functional inhibition.

Accordingly, in one aspect, a polypeptide of the present invention has an affinity to human CX3CR1 at an IC50 less than or equal to 10 nM, or less than or equal to 5 nM, or less than or equal to 2.5 nM or less than or equal to 1 nM, as determined by competition FACS.

In a further aspect, a polypeptide of the present invention has an affinity to human CX3CR1 at an EC50 of less than or equal to 10 nM, or less than or equal to 5 nM, or less than or equal to 2.5 nM or less than or equal to 1 nM, as determined by cell binding FACS.

In a further aspect, a polypeptide of the present invention blocks the binding of human CX3CR1 to human fractalkine at or above 50%, or at or above 60%, or at or above 70%, or at or above 80%, or at or above 90%, or at or above 95% as determined by competition FACS with human fractalkine.

In a further aspect, a polypeptide of the present invention blocks the binding of human fractalkine to human CX3CR1 at an IC50 of less than or equal to 300 nM, or less than or equal to 100 nM, or less than or equal to 20 nM, or less than or equal to 10 nM, or less than or equal to 5 nM, less than or equal to 2.5 nM or less than or equal to 1 nM as determined by competition FACS with human fractalkine.

In a further aspect, a polypeptide of the present invention inhibits fractalkine induced chemotaxis mediated by human CX3CR1 at or above 10%, or at or above 30%, or at or above 40%, or at or above 50%, or at or above 60%, or at or above 70%, or at or above 80%, or at or above 90%.

In a further aspect, a polypeptide of the present invention inhibits fractalkine induced chemotaxis mediated by human CX3CR1 at an $IC_{50}$ of less than or equal to 500 nM, or of less than or equal to 100 nM, or less than or equal to 75 nM, or less than or equal to 50 nM, or less than or equal to 10 nM or less than or equal to 5 nM.

In a further aspect, a polypeptide of the present invention inhibits fractalkine induced human CX3CR1 receptor internalization at an $IC_{50}$ of less than or equal to 10 nM, or less than or equal to 5 nM or less than or equal to 1 nM.

According to still another embodiment, a half-life extending modification of a polypeptide of the invention (such modification also reducing immunogenicity of the polypeptide) comprises attachment of a suitable pharmacologically acceptable polymer, such as straight or branched chain poly(ethylene glycol) (PEG) or derivatives thereof (such as methoxypoly(ethylene glycol) or mPEG). Generally, any suitable form of PEGylation can be used, such as the PEGylation used in the art for antibodies and antibody fragments (including but not limited to domain antibodies and scFv's); reference is made, for example, to: Chapman, Nat. Biotechnol., 54, 531-545 (2002); Veronese and Harris, Adv. Drug Deliv. Rev. 54, 453-456 (2003); Harris and Chess, Nat. Rev. Drug. Discov. 2 (2003); WO 04/060965; and U.S. Pat. No. 6,875,841.

Various reagents for PEGylation of polypeptides are also commercially available, for example from Nektar Therapeutics, USA, or NOF Corporation, Japan, such as the Sunbright® EA Series, SH Series, MA Series, CA Series, and ME Series, such as Sunbright® ME-100MA, Sunbright® ME-200MA, and Sunbright® ME-400MA.

Preferably, site-directed PEGylation is used, in particular via a cysteine-residue (see for example Yang et al., Protein Engineering 16, 761-770 (2003)). For example, for this purpose, PEG may be attached to a cysteine residue that naturally occurs in a polypeptide of the invention, a polypeptide of the invention may be modified so as to suitably introduce one or more cysteine residues for attachment of PEG, or an amino acid sequence comprising one or more cysteine residues for attachment of PEG may be fused to the N- and/or C-terminus and/or PEG may be attached to a linker region that bridges two or more functional domains of a polypeptide of the invention, all using techniques of protein engineering known per se to the skilled person.

Preferably, for the polypeptides of the invention, a PEG is used with a molecular weight of more than 5 kDa, such as more than 10 kDa and less than 200 kDa, such as less than 100 kDa; for example in the range of 20 kDa to 80 kDa.

With regard to PEGylation, it should be noted that generally, the invention also encompasses any polypeptide of the invention that has been PEGylated at one or more amino acid positions, preferably in such a way that said PEGylation either (1) increases the half-life in vivo; (2) reduces immunogenicity; (3) provides one or more further beneficial properties known per se for PEGylation; (4) does not essentially affect the affinity of the polypeptide for CX3CR1 (e.g. does not reduce said affinity by more than 50%, and more preferably not by more than 10%, as determined by a suitable assay, such as those described in the Examples below); and/or (4) does not affect any of the other desired properties of the polypeptides of the invention. Suitable PEG-groups and methods for attaching them, either specifically or non-specifically, will be clear to the skilled person.

According to a specifically preferred embodiment of the invention, a PEGylated polypeptide of the invention includes one PEG moiety of linear PEG having a molecular weight of 40 kDa or 60 kDa, wherein the PEG moiety is attached to the polypeptide in a linker region and, specifically, at a Cys residue, for example at position 5 of a GS8-linker peptide as shown in SEQ ID NO:235.

Preferred examples of PEGylated polypeptides of the invention are PEGylated preferably with one of the PEG reagents as mentioned above, such as "Sunbright® ME-400MA" as shown in the following chemical formula:

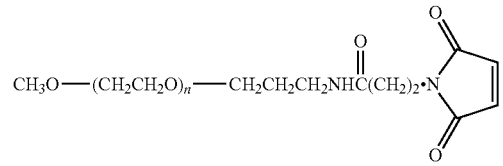

which has an average molecular weight of 40 kDa.

Therapeutic Uses

In one aspect, the present invention provides a polypeptide of the present invention or a pharmaceutical composition comprising said polypeptide for use as a medicament.

In one aspect, the present invention provides the use of a polypeptide of the present invention or a pharmaceutical composition comprising said polypeptide for the treatment or prophylaxis of cardio- and cerebrovascular atherosclerotic disorders, peripheral artery disease, restenosis, diabetic nephropathy, glomerulonephritis, human crescentic glomerulonephritis, IgA nephropathy, membranous nephropathy, lupus nephritis, vasculitis including Henoch-Schonlein purpura and Wegener's granulomatosis, rheumatoid arthritis, osteoarthritis, allograft rejection, systemic sclerosis, neurodegenerative disorders and demyelinating disease, multiple sclerosis (MS), Alzheimer's disease, pulmonary diseases such as COPD, asthma, neuropathic pain, inflammatory pain, or cancer.

In another aspect, the present invention provides the use of a polypeptide of the present invention or a pharmaceutical composition comprising said polypeptide for the treatment or prophylaxis of atherosclerosis.

In another aspect, the present invention provides the use of a polypeptide of the present invention or a pharmaceutical composition comprising said polypeptide for the treatment or prophylaxis of atherosclerosis by preventing and/or reducing the formation of new atherosclerotic lesions or plaques and/or by preventing or slowing progression of existing lesions and plaques.

In another aspect, the present invention provides the use of a polypeptide of the present invention or a pharmaceutical composition comprising said polypeptide for the treatment or prophylaxis of atherosclerosis by changing the composition of the plaques to reduce the risk of plaque rupture and atherothrombotic events.

In one aspect, the present invention also provides a method of treating, or reducing the risk of, cardio- and cerebrovascular atherosclerotic disorders, peripheral artery disease, restenosis, diabetic nephropathy, glomerulonephritis, human crescentic glomerulonephritis, IgA nephropathy, membranous nephropathy, lupus nephritis, vasculitis including Henoch-Schonlein purpura and Wegener's granulomatosis, rheumatoid arthritis, osteoarthritis, allograft rejection, systemic sclerosis, neurodegenerative disorders and demyelinating disease, multiple sclerosis (MS), Alzheimer's disease, pulmonary diseases such as COPD, asthma, neuropathic pain, inflammatory pain, or cancer, in a person suffering from or at risk of, said disease or condition, wherein the method comprises administering to the person a therapeutically effective amount of a polypeptide according to the present invention or a pharmaceutical composition comprising said polypeptide.

In one aspect, the present invention also provides a method of treating, or reducing the risk of atherosclerosis in a person suffering from or at risk of, said disease or condition, wherein the method comprises administering to the person a therapeutically effective amount of polypeptide of the present invention or a pharmaceutical composition comprising said polypeptide.

In one aspect, the present invention also provides a method of treating, or reducing the risk of atherosclerosis by preventing and/or reducing the formation of new atherosclerotic lesions or plaques and/or by preventing or slowing progression of existing lesions and plaques in a person suffering from or at risk of, said disease or condition, wherein the method comprises administering to the person a therapeutically effective amount of polypeptide of the present invention or a pharmaceutical composition comprising said polypeptide.

In one aspect, the present invention also provides a method of treating, or reducing the risk of atherosclerosis by changing the composition of the plaques so as to reduce the risk of plaque rupture and atherothrombotic events in a person suffering from or at risk of, said disease or condition, wherein the method comprises administering to the person a therapeutically effective amount of a polypeptide of the present invention or a pharmaceutical composition comprising said polypeptide.

In one aspect, a polypeptide of the present invention is indicated for use in the treatment or prophylaxis of a disease or disorder that is associated with CX3CR1.

In one aspect, a polypeptide of the present invention is indicated for use in the treatment or prophylaxis of diseases or conditions in which modulation of activity at the CX3CR1 receptor is desirable. In one aspect, the present invention also provides a method of treating, or reducing the risk of, diseases or conditions in which antagonism of the CX3CR1 receptor is beneficial which comprises administering to a person suffering from or at risk of, said disease or condition, a polypeptide of the present invention.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

In the context of the present invention, the term "prevention, treatment and/or alleviation" not only comprises preventing and/or treating and/or alleviating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated will be a mammal, and more in particular a human being. As will be clear to the skilled person, the subject to be treated will in particular be a person suffering from, or at risk from, the diseases, disorders or conditions mentioned herein.

It will also be clear to the skilled person that the above methods of treatment of a disease include the preparation of a medicament for the treatment of said disease. Furthermore, it is clear that the polypeptides of the invention can be used as an active ingredient in a medicament or pharmaceutical composition intended for the treatment of the above diseases. Thus, the invention also relates to the use of a polypeptide of the invention in the preparation of a pharmaceutical composition for the prevention, treatment and/or alleviation of any of the diseases, disorders or conditions mentioned hereinabove. The invention further relates to a polypeptide of the invention for therapeutic or prophylactic use and, specifically, for the prevention, treatment and/or alleviation of any of the diseases, disorders or conditions mentioned hereinabove. The invention further relates to a pharmaceutical composition for the prevention, treatment and/or alleviation of the diseases, disorders or conditions mentioned hereinabove, wherein such composition comprises at least one polypeptide of the invention.

The polypeptides of the invention and/or the compositions comprising the same can be administered to a patient in need thereof in any suitable manner, depending on the specific pharmaceutical formulation or composition to be used. Thus, the polypeptides of the invention and/or the compositions comprising the same can for example be administered intravenously, subcutaneously, intramuscularly, intraperitoneally, transdermally, orally, sublingually (e.g. in the form of a sublingual tablet, spray or drop placed under the tongue and adsorbed through the mucus membranes into the capillary network under the tongue), (intra-)nasally (e.g. in the form of a nasal spray and/or as an aerosol), topically, by means of a suppository, by inhalation, intravitreally (esp. for the treatment of dry AMD or glaucoma), or any other suitable manner in an effective amount or dose.

The polypeptides of the invention and/or the compositions comprising the same are administered according to a regimen of treatment that is suitable for preventing, treating and/or alleviating the disease, disorder or condition to be prevented, treated or alleviated. The clinician will generally be able to determine a suitable treatment regimen, depending on factors such as the disease, disorder or condition to be prevented, treated or alleviated, the severity of the disease, the severity of the symptoms thereof, the specific polypeptide of the invention to be used, the specific route of administration and pharmaceutical formulation or composition to be used, the age, gender, weight, diet, general condition of the patient, and similar factors well known to the clinician. Generally, the treatment regimen will comprise the administration of one or more polypeptides of the invention, or of one or more compositions comprising the same, in therapeutically and/or prophylactically effective amounts or doses.

Generally, for the prevention, treatment and/or alleviation of the diseases, disorders and conditions mentioned herein and depending on the specific disease, disorder or condition to be treated, the potency of the specific polypeptide of the invention to be used, the specific route of administration and the specific pharmaceutical formulation or composition used, the polypeptides of the invention will generally be administered in an amount between 0.005 and 20.0 mg per kilogram of body weight and dose, preferably between 0.05 and 10.0 mg/kg/dose, and more preferably between 0.5 and 10 mg/kg/dose, either continuously (e.g. by infusion) or as single doses (such as e.g. daily, weekly, or monthly doses; cf. below), but can significantly vary, especially, depending on the before-mentioned parameters.

For prophylactic applications, compositions containing the polypeptides of the invention may also be administered in similar or slightly lower dosages. The dosage can also be adjusted by the individual physician in the event of any complication.

Depending on the specific polypeptide of the invention and its specific pharmacokinetic and other properties, it may be administered daily, every second, third, fourth, fifth or sixth day, weekly, monthly, and the like. An administration regimen could include long-term, weekly treatment. By "long-term" is meant at least two weeks and preferably months, or years of duration.

The efficacy of the polypeptides of the invention, and of compositions comprising the same, can be tested using any suitable in vitro assay, cell-based assay, in vivo assay and/or animal model known per se, or any combination thereof, depending on the specific disease involved. Suitable assays and animal models will be clear to the skilled person, and for example include the assays and animal models used in the Examples below.

For pharmaceutical use, the polypeptides of the invention may be formulated as a pharmaceutical preparation comprising (i) at least one polypeptide of the invention and (ii) at least one pharmaceutically acceptable carrier, diluent, excipient, adjuvant, and/or stabilizer, and (iii) optionally one or more further pharmaceutically active polypeptides and/or compounds. By "pharmaceutically acceptable" is meant that the respective material does not show any biological or otherwise undesirable effects when administered to an individual and does not interact in a deleterious manner with any of the other components of the pharmaceutical composition (such as e.g. the pharmaceutically active ingredient) in which it is contained. Specific examples can be found in standard handbooks, such as e.g. Remington's Pharmaceutical Sciences, 18$^{th}$ Ed., Mack Publishing Company, USA (1990). For example, the polypeptides of the invention may be formulated and administered in any manner known per se for conventional antibodies and antibody fragments and other pharmaceutically active proteins. Thus, according to a further embodiment, the invention relates to a pharmaceutical composition or preparation that contains at least one polypeptide of the invention and at least one pharmaceutically acceptable carrier, diluent, excipient, adjuvant and/or stabilizer, and optionally one or more further pharmaceutically active substances.

By means of non-limiting examples, such a formulation may be in a form suitable for oral administration, for parenteral administration (such as by intravenous, intramuscular, subcutaneous, intrathecal, intracavernosal or intraperitoneal injection or intravenous infusion), for topical administration, for sublingual administration, for administration by inhalation, by a skin patch, by an implant, by a suppository, for transdermal, nasal, intravitreal, rectal or vaginal administration, and the like. Such suitable administration forms—which may be solid, semi-solid or liquid, depending on the manner of administration—as well as methods and carriers for use in the preparation thereof, will be clear to the skilled person.

Pharmaceutical preparations for parenteral administration, such as intravenous, intramuscular, subcutaneous injection or intravenous infusion may for example be sterile solutions, suspensions, dispersions, emulsions, or powders which comprise the active ingredient and which are suitable, optionally after a further dissolution or dilution step, for infusion or injection. Suitable carriers or diluents for such preparations for example include, without limitation, sterile water and pharmaceutically acceptable aqueous buffers and solutions such as physiological phosphate-buffered saline, Ringer's solutions, dextrose solution, and Hank's solution; water oils; glycerol; ethanol; glycols such as propylene glycol, as well as mineral oils, animal oils and vegetable oils, for example peanut oil, soybean oil, as well as suitable mixtures thereof.

Solutions of the active compound or its salts may also contain a preservative to prevent the growth of microorganisms, such as antibacterial and antifungal agents, for example, parabens, chlorobutanol, phenol, sorbic acid, thimerosal (thiomersal), and the like. In many cases, it will be preferable to include isotonic agents, for example, sugars, buffers or sodium chloride. The proper fluidity can be maintained, for example, by the formation of liposomes, by the maintenance of the required particle size in the case of dispersions or by the use of surfactants. Other agents delaying absorption, for example, aluminum monostearate and gelatin, may also be added.

In all cases, the ultimate dosage form must be sterile, fluid and stable under the conditions of manufacture and storage. Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Usually, aqueous solutions or suspensions will be preferred. Generally, suitable formulations for therapeutic proteins such as the polypeptides of the invention are buffered protein solutions, such as solutions including the protein in a suitable concentration (such as from 0.001 to 400 mg/ml, preferably from 0.005 to 200 mg/ml, more preferably 0.01 to 200 mg/ml, more preferably 1.0-100 mg/ml, such as 1.0 mg/ml (i.v. administration) or 100 mg/ml (s.c. administration) and an aqueous buffer such as:
  phosphate buffered saline, pH 7.4,
  other phosphate buffers, pH 6.2 to 8.2,
  histidine buffers, pH 5.5 to 7.0,
  succinate buffers, pH 3.2 to 6.6, and
  citrate buffers, pH 2.1 to 6.2,
  and, optionally, salts (e.g. NaCl) and/or sugars or polyalcohols (such as trehalose, mannitol, or glycerol) for providing isotonicity of the solution.

Preferred buffered protein solutions are solutions including about 0.05 mg/ml of the polypeptide of the invention dissolved in 25 mM phosphate buffer, pH 6.5, adjusted to isotonicity by adding 220 mM trehalose. In addition, other agents such as a detergent, e.g. 0.02% Tween-20 or Tween-80, may be included in such solutions. Formulations for subcutaneous application may include significantly higher concentrations of the polypeptide of the invention, such as up to 100 mg/ml or even above 100 mg/ml. However, it will be clear to the person skilled in the art that the ingredients and the amounts thereof as given above do only represent one, preferred option. Alternatives and variations thereof will be immediately apparent to the skilled person, or can easily be conceived starting from the above disclosure.

The polypeptides of the invention may also be administered using suitable depot, slow-release or sustained-release formulations, e.g. suitable for injection, using controlled-release devices for implantation under the skin, and/or using a dosing pump or other devices known per se for the administration of pharmaceutically active substances or principles. In addition, the polypeptides of the invention may be formulated in the form of a gel, cream, spray, drop, patch or film which, if placed on the skin, passes through the skin.

Also, compared to conventional antibodies or antibody fragments, one major advantage of the use of the polypeptides of the invention is that they can also be easily administered via routes other than parenteral administration and can be easily formulated for such administration. For example, as described in the international application WO2004/041867, such polypeptides may be formulated for oral, intranasal, intrapulmonary and transdermal administration.

According to another embodiment of the invention there is provided a pharmaceutical combination comprising at least one polypeptide of the invention as disclosed herein and at least one other therapeutic agent selected from the group consisting of statins, antiplatelets, anticoagulants, antidiabetics and anti hypertensives.

Such pharmaceutical combination may optionally additionally comprise a diluent, excipient, adjuvant and/or stabilizer.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition. Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

Yet, a further embodiment of the invention is a method for treating the diseases and disorders as set out above, comprising administering to an individual, simultaneously, separately or sequentially, an effective amount of at least one polypeptide of the invention and at least one agent selected from the group consisting of a statin, an antiplatelet, an anticoagulant, an antidiabetic and an antihypertensive.

According to a further aspect of the invention, the polypeptide of the invention is prepared to be administered in combination with other drugs used for the treatment of the diseases and disorders set out above, such other drugs being selected from the group consisting of a statin, an antiplatelet, an anticoagulant, an antidiabetic and an antihypertensive.

According to still another aspect of the invention, drugs used for the treatment of the diseases and disorders set out above, such drugs being selected from the group consisting of a statin, an antiplatelet, an anticoagulant, an antidiabetic and an antihypertensive are prepared to be administered in combination with the polypeptide of the invention.

According to a further aspect of the invention, the polypeptide of the invention is used in combination with a device useful for the administration of the polypeptide, such as a syringe, injector pen, or other device.

According to still another embodiment of the invention, there is provided a method of diagnosing a disease, disorder or condition mediated by CX3CR1 dysfunction comprising the steps of:
  a) obtaining a sample from a subject, and
  b) contacting, in vitro, the sample with a polypeptide of the invention as defined above, and
  c) detecting the binding of said polypeptide to said sample, and
  d) comparing the binding detected in step (c) with a standard, wherein a difference in binding relative to said sample is diagnostic of a disease, disorder or condition characterised by CX3CR1 dysfunction.

According to another embodiment of the invention, there is provided a method of diagnosing a disease, disorder or condition mediated by CX3CR1 dysfunction comprising the steps of:
  a) obtaining a sample from a subject, and
  b) contacting the sample with a polypeptide of the invention as defined above;
  c) determining the amount of CX3CR1 in the sample; and
  d) comparing the amount determined in step (c) with a standard, wherein a difference in amount relative to said sample is diagnostic of a disease, disorder or condition characterised by CX3CR1 dysfunction.

The above diagnostic methods can also be used for monitoring the effectiveness of a therapeutic treatment of a subject.

According to another embodiment of the invention, there is provided a kit for diagnosing a disease, disorder or condition mediated by CX3CR1 dysfunction, for use in a method as defined above, such kit comprising at least one polypeptide of the invention and, optionally, one or more media, detection means and/or in vitro or in vivo imaging agents, and, further optionally, instructions of use. Suitable in vivo imaging agents include 99mTc, 111Indium, 123Iodine, and, for magnetic resonance imaging, paramagnetic compounds.

The invention further provides a kit comprising at least one polypeptide of the invention and, additionally, one or more other components selected from the group consisting of other drugs used for the treatment of the diseases and disorders as described above, and devices as described above.

The invention further provides methods of manufacturing a polypeptide of the invention, such methods generally comprising the steps of:
- culturing host cells comprising a nucleic acid capable of encoding a polypeptide of the invention (hereinafter: "nucleic acid of the invention") under conditions that allow expression of the polypeptide of the invention; and,
- recovering or isolating the polypeptide expressed by the host cells from the culture; and
- optionally further purifying and/or modifying and/or formulating the polypeptide of the invention.

A nucleic acid of the invention can be genomic DNA, cDNA or synthetic DNA (such as DNA with a codon usage that has been specifically adapted for expression in the intended host cell or host organism). According to one embodiment of the invention, the nucleic acid of the invention is in essentially isolated form, as defined hereabove.

The nucleic acid of the invention may also be in the form of, be present in and/or be part of a vector, such as for example a plasmid, cosmid or YAC, which again may be in essentially isolated form. The vector may especially be an expression vector, i.e. a vector that can provide for expression of the polypeptide in vitro and/or in vivo (e.g. in a suitable host cell, host organism and/or expression system). Such expression vector generally comprises at least one nucleic acid of the invention that is operably linked to one or more suitable regulatory element(s), such as promoter(s), enhancer(s), terminator(s), and the like. Specific examples of such regulatory elements and other elements, such as integration factor(s), selection marker(s), signal or leader sequence(s), reporter gene(s), and the like, useful or necessary for expressing polypeptides of the invention, are disclosed e.g. on pp. 131 to 133 of WO2006/040153.

The nucleic acids of the invention can be prepared or obtained in a manner known per se (e.g. by automated DNA synthesis and/or recombinant DNA technology), based on the information on the amino acid sequences for the polypeptides of the invention given herein, and/or can be isolated from a suitable natural source.

According to another embodiment, the invention relates to a host or host cell that expresses or is capable of expressing a polypeptide of the invention; and/or that contains a nucleic acid encoding a polypeptide of the invention. According to a particularly preferred embodiment, said host cells are bacterial cells, yeast cells, fungal cells or mammalian cells.

Suitable bacterial cells include cells from gram-negative bacterial strains such as strains of *Escherichia coli, Proteus*, and *Pseudomonas*, and gram-positive bacterial strains such as strains of *Bacillus, Streptomyces, Staphylococcus*, and *Lactococcus*. Suitable fungal cell include cells from species of *Trichoderma, Neurospora*, and *Aspergillus*. Suitable yeast cells include cells from species of *Saccharomyces* (for example *Saccharomyces cerevisiae*), *Schizosaccharomyces* (for example *Schizosaccharomyces pombe*), *Pichia* (for example *Pichia pastoris* and *Pichia methanolica*), and *Hansenula*.

Suitable mammalian cells include for example CHO cells, BHK cells, HeLa cells, COS cells, NS0 cells, HEK cells, and the like. However, amphibian cells, insect cells, plant cells, and any other cells used in the art for the expression of heterologous proteins can be used as well.

For production on industrial scale, preferred heterologous hosts for the (industrial) production of immunoglobulin single variable domain polypeptides and protein therapeutics containing them include strains of *E. coli, Pichia pastoris*, and *S. cerevisiae* that are suitable for large scale expression, production and fermentation, and in particular for large scale (bio-)pharmaceutical expression, production and fermentation.

The choice of the specific expression system would depend in part on the requirement for certain post-translational modifications, more specifically glycosylation. The production of a polypeptide of the invention for which glycosylation is desired or required would necessitate the use of mammalian expression hosts that have the ability to glycosylate the expressed protein. In this respect, it will be clear to the skilled person that the glycosylation pattern obtained (i.e. the kind, number and position of residues attached) will depend on the cell or cell line that is used for the expression.

Polypeptides of the invention produced in a cell as set out above can be produced either intracellularly (e.g. in the cytosol, in the periplasma or in inclusion bodies) and then isolated from the host cells and optionally further purified; or they can be produced extracellularly (secreted into the medium in which the host cells are cultured) and then isolated from the culture medium and optionally further purified.

Further methods and reagents used for the recombinant production of polypeptides, such as suitable expression vectors, transformation or transfection methods, selection markers, methods of induction of protein expression, culture conditions, and the like, are known in the art. Similarly, protein isolation and purification techniques useful in a method of manufacture of a polypeptide of the invention are well known to the skilled person.

Production of the polypeptides of the invention through fermentation in convenient recombinant host organisms such as *E. coli* and yeast is cost-effective, as compared to conventional antibodies which also require expensive mammalian cell culture facilities. Furthermore, achievable levels of expression are high and yields of the polypeptides of the invention are in the range of 1 to 10 g/l (*E. coli*) and up to 10 g/l (yeast) and more.

EXAMPLES

Generation CHO, Baf/3, Caki and HEK293 Cell Lines Overexpressing Human CX3CR1 or Cynomolgus CX3CR1

CHO and Baf/3 cells overexpressing human or cynomolgus CX3CR1 were generated using techniques known in the art. Cells expressing human CCR2 or CCR5 were also generated using techniques known in the art.

The cDNA was cloned into pCDNA3.1(+)-neo for human CX3CR1 whereas pcDNA-DEST40-neo was used for mouse CX3CR1.

The amino acid sequences of human CX3CR1 and cynomolgus CX3CR1 are depicted in SEQ ID NO: 255 and 256, respectively.

To establish Camel Kidney (Caki) cells overexpressing human CX3CR1 or mouse CX3CR1, parental Caki cells were electroporated with pCDNA3.1(+)-neo-hCX3CR1 or pcDNA-DEST40-neo-mCX3CR1, respectively. For all conditions, transfectants were selected by adding 1 mg/mL geneticin (Invitrogen, Carlsbad, Calif., USA).

Human Embyonic Kidney (HEK293) cells overexpressing human CX3CR1 or cynomolgus CX3CR1 were generated by lipid-mediated transfection with Fugene (Roche) of pCDNA3.1(+)-neo-hCX3CR1 or cyCX3CR1 plasmids, respectively, in the HEK293 parental cell line. These cells were used as transient transfectants and as such not put under selection. In brief, 2*10E6 cells were seeded per T75 and incubated overnight before transfection. After removal of the culture medium, cells were transfected with the respective plasmids (9 µg) and Fugene (27 µl) according to manufacturer's instructions. 48 hours post transfection, cells were harvested and frozen for further usage.

Example 1

Immunization with CX3CR1 Induces a Humoral Immune Response in Llama 1.1. Immunizations After approval of the Ethical Committee (University Antwerp, Belgium, UA2008A1, 2008/096, 2007/068), 9 llamas (designated No. 368, 369, 370, 381, 382, 384, 312, 313 and 314) were immunized.

Six llamas (312, 313, 314, 381, 382 and 384) were immunized with 4 intramuscular injections (2 mg/dose at weekly or biweekly intervals) of pVAX1-huCX3CR1 plasmid vector (Invitrogen, Carlsbad, Calif., USA). Three llamas (381, 382 and 384) subsequently received 4 subcutaneous injections of human CX3CR1 overexpressing Caki cells which were established as described above. Cells were re-suspended in D-PBS and kept on ice prior to injection.

Three additional llamas (designated No. 368, 369 and 370) were immunized according to standard protocols with 4 subcutaneous injections of human CX3CR1 overexpressing Caki cells which were established as described above. Cells were re-suspended in D-PBS and kept on ice prior to injection. Subsequently, these llamas were administered two injections with recombinant CX3CR1 NT/EC3 fragment coupled to BSA (Table 13). Peptides were ordered at NeoMPS (Polypeptidegroup, Strasbourg, France) and coupled to BSA according to standard protocols.

TABLE 13

Sequence of peptide fragments used for immunization boost

| Fragment | sequence | SEQ ID NO: |
|---|---|---|
| CX3CR1-NT | Ac-Met-Asp-Gln-Phe-Pro-Glu-Ser-Val-Thr-Glu-Asn-Phe-Glu-Tyr-Asp-Asp-Leu-Ala-Glu-Ala-Cys-NH2 | 228 |
| CX3CR1-EC3 | Ac-Lys-Leu-Tyr-Asp-Phe-Phe-Pro-Ser-Cys-Asp-Met-Arg-Lys-Asp-Leu-Arg-Leu-NH2 | 229 |

The first injection was formulated in Complete Freund's Adjuvant (Difco, Detroit, Mich., USA), while the subsequent injection was formulated in Incomplete Freund's Adjuvant (Difco, Detroit, Mich., USA).

1.2. Evaluation of Induced Immune Responses in Llama

To evaluate the induction of immune responses in the animals against human CX3CR1 by ELISA or FACS, sera were collected from llamas 312, 313 and 314 at day 0 (pre-immune), and different time points in the immunization schedule (time of peripheral blood lymphocyte [PBL] collection).

In short, Neutravidin (2 µg/ml) was immobilized overnight at 4° C. in a 96-well Maxisorb plate (Nunc, Wiesbaden, Germany). Wells were blocked with a casein solution (1%) in PBS. Subsequently biotinylated recombinant NT fragment (Polypeptide, Strasbourg, France) or biotinylated EC3 fragments of CX3CR1 (Polypeptide, Strasbourg, France) were captured at 2 µg/ml. After addition of serum dilutions, specifically bound immunoglobulins were detected using a horseradish peroxidase (HRP)-conjugated goat anti-llama immunoglobulin (Bethyl Laboratories Inc., Montgomery, Tex., USA) and a subsequent enzymatic reaction in the presence of the substrate TMB One (3,3',5,5'-tetramentylbenzidine) (Promega, Mannheim, Germany), showing that a significant antibody-dependent immune response against CX3CR1 was induced after the peptide immunizations.

Additionally, serum titers of cell immunized animals were confirmed by FACS analysis on actively growing human CX3CR1 overexpressing CHO cells. The CX3CR1 serum titer responses for llamas 368, 369 and 370 were determined with serum sampled after 4 cell immunizations (day 49), 4 cell immunizations and 1 peptide boost (day 77) and 4 cell immunizations and 2 peptide boosts (day 81). Cells were harvested and washed before incubation with the serum dilutions. Detection was performed with goat anti-llama IgG (Bethyl, Montgomery, Tex., USA) followed by donkey anti-goat coupled with PE (Jackson Laboratories, Suffolk, UK) and read out by analysis on FACSArray (BD Biosciences). A summary of the obtained serum responses as determined by either ELISA or FACS is shown in Table 14 and Table 15.

TABLE 14

Serum titer analysis for the cell/peptide immunized animals

| | | ELISA | | FACS | |
|---|---|---|---|---|---|
| Llama | Immunogen | Recombinant NT | Recombinant EC3 | After cell immunization | After peptide boosts |
| 368 | Caki-huCX3CR1 + NT/EC3 peptide | + | +/− | − | − |
| 369 | Caki-huCX3CR1 + NT/EC3 peptide | + | +/− | + | + |
| 370 | Caki-huCX3CR1 + NT/EC3 peptide | ++ | ++ | − | + |

TABLE 15

Serum titer analysis for the DNA/cell immunized animals

| Llama | Immunogen | ELISA Recombinant NT | ELISA Recombinant EC3 | FACS After DNA immunization | FACS After Cell boosts |
|---|---|---|---|---|---|
| 381 | DNA + Caki-huCX3CR1 | ++ | + | ++ | ++ |
| 382 | DNA + Caki-huCX3CR1 | + | − | − | − |
| 384 | DNA + Caki-huCX3CR1 | ++ | − | − | − |

For the DNA only immunized llamas (312, 313 and 314) no serum titer was determined.

Example 2

Cloning of the Heavy-Chain Only Antibody Fragment Repertoires and Preparation of Phage Following the final immunogen injection of each subset, immune tissues as the source of B-cells that produce the heavy-chain antibodies were collected from the immunized llamas. For llama 312, 313 and 314, two 150-ml blood samples, collected 4 and 8 days after the last antigen injection were collected per animal. For llamas 368, 369 and 370 four 150 ml blood samples were collected, 5 and 7 days after the last cell immunization and additionally 4 and 8 days after the last peptide immunization. Next to those, two lymph node biopsies were taken, 12 days after the last cell immunization and 12 days after the last peptide immunization. For llamas 381, 382 and 384 five 150 ml blood samples were collected, 8 days after the last DNA immunization and additionally 4 days after the first cell boost, 8 and 11 days after the second cell boost and 8 days after the last cell immunization. Next to those, one lymph node biopsy was taken, 8 days after the second cell immunization.

From the blood samples, peripheral blood lymphocytes (PBLs) were prepared using Ficoll-Hypaque according to the manufacturer's instructions (Amersham Biosciences, Piscataway, N.J., USA). From the PBLs and the lymph node biopsy (LN), total RNA was extracted, which was used as starting material for RT-PCR to amplify the VHH encoding DNA segments.

For each immunized llama, libraries were constructed by pooling the total RNA isolated from samples originating from a certain subset of the immunization schedule i.e. after one type of immunization antigen, and for some llamas samples from the different animals were pooled into one library (Table 16).

TABLE 16

Pooling of the different sample for library construction

| Library Name | Llama | Sample |
|---|---|---|
| 368-PBL1 + 2 + LN-V-100209 | 368 | PBL 1 and 2, LN |
| 369 + 370-PBL1 + 2 + LN-V-100209 | 369, 370 | PBL 1 and 2, LN |
| 368-PBL3 + 4-V-280909 | 368 | PBL 3 and 4 |
| 369-PBL3 + 4-V-070409 | 369 | PBL 3 and 4 |
| 370-PBL3 + 4-V-070409 | 370 | PBL 3 and 4 |
| 381-PBL1-V-180310 | 381 | PBL 1 |
| 382-PBL1-V-180310 | 382 | PBL1 |
| 384-PBL1-V-180310 | 384 | PBL1 |
| 381-PBL1 + 2 + 3 + 4 + 5 + LN-V-280909 | 381 | PBL 1, 2, 3, 4, 5 and LN |
| 382-PBL1 + 2 + 3 + 4 + 5 + LN-V-280909 | 382 | PBL 1, 2, 3, 4, 5 and LN |
| 384-PBL1 + 2 + 3 + 4 + 5 + Ln-V-280909 | 384 | PBL 1, 2, 3, 4, 5 and LN |
| 312 + 313 + 314-PBL1 + 2-V-220210 | 312, 313 and 314 | PBL 1 and 2 |
| 312-PBL1 + 2-V-180310 | 312 | PBL 1 and 2 |
| 313-PBL1 + 2-V-180310 | 313 | PBL 1 and 2 |
| 314-PBL1 + 2-V-180310 | 314 | PBL 1 and 2 |

In short, the PCR-amplified VHH repertoire was cloned via specific restriction sites into a vector designed to facilitate phage display of the VHH library. The vector was derived from pUC119 and contains the LacZ promoter, a M13 phage gIII protein coding sequence, a resistance gene for ampicillin or carbenicillin, a multiple cloning site and a hybrid gIII-pelB leader sequence (pAX050). In frame with the VHH coding sequence, the vector encodes a C-terminal c-myc tag and a His6 tag. Phage were prepared according to standard protocols and stored after filter sterilization at 4° C. or at −80° C. in 20% glycerol for further use.

Example 3

Selection of CX3CR1 Specific VHHs via Phage Display

VHH repertoires obtained from all llamas and cloned as phage library were used in different selection strategies, applying a multiplicity of selection conditions. Variables include i) the presentation form of the CX3CR1 protein (on different cell backgrounds or on liposomes/VLPs), ii) the antigen presentation method (In solution when using cells or coated onto plates when using VLPs), iii) the antigen concentration iv) the orthologue used (human or cynomolgus) v) the number of selection rounds and vi) different elution methods (non-specific via trypsin or specific via the ligand Fractalkine). All solid coated phase selections were done in Maxisorp 96-well plates (Nunc, Wiesbaden, Germany).

Selections were performed as follows: CX3CR1 antigen preparations for solid and solution phase selection formats were presented as described above at multiple concentrations. After 2 h incubation with the phage libraries followed by extensive washing, bound phages were eluted with trypsin (1 mg/mL) for 15 minutes. When trypsin was used for phage elution, the protease activity was immediately neutralized by applying 0.8 mM protease inhibitor ABSF. As control, selections without antigen were performed in parallel.

Phage outputs were used to infect E. coli which were then in turn used to prepare phage for the next selection round (phage rescue) After the second round selection the phage outputs were used to infect E. coli which were then plated on agar plates (LB+carb+glucose$^{2\%}$) for analysis of individual VHH clones. In order to screen a selection output for specific binders, single colonies were picked from the agar plates and grown in 1 mL 96-deep-well plates. LacZ-controlled VHH expression was induced by adding IPTG (1 mM final) in the absence of glucose. Periplasmic extracts (in a volume of ~80 uL) were prepared according to standard protocols.

Example 4

Screening of Periplasmic Extracts in CX3CR1-Fraktalkine Competition FACS Assay Periplasmic extracts were screened in a human CX3CR1/human Fractalkine FACS competition assay to assess the blocking capacity of the expressed VHHs. Human CX3CR1 was presented on CHO cells overexpressing CX3CR1. Both a setup using cells harvested from an actively growing culture and a setup using frozen cells was used. As a detection reagent labeled fractalkine was used (R&D Systems, Minneapolis, Minn., USA) labeled with alexa647 (A647-Fractalkine) at a degree of labeling of 1. To setup the assay, first a titration series of the labeled fractalkine was performed on the CHO-huCX3CR1 cells in order to determine the EC50 value for binding. Initially screening was performed at a higher concentration of fractalkine (3 nM) to increase the assay robustness. To increase the sensitivity of the screening to a maximum, the EC30 concentration (1 nM) was chosen for subsequent screening. In brief 50 µl of periplasmic extract was added to 6 nM labeled fractalkine (50 µl) and 200 000 CHO-huCX3CR1 cells. After one hour incubation at 4 C, cells were washed three times before read out was performed on a FACS Array (Becton Dickinson). First a gate was set on the intact cells as determined from the scatter profile. Next, dead cells were gated out by their fluorescence profile from the PI stain (Sigma, St Louis, US). The fluorescence profile from the alexa647 label was determined for each sample and used for calculation of blocking capacity. As controls, conditions were taken along where there was no VHH present in the peri extract or a known irrelevant VHH and samples were included where excess cold fractalkine was included. For each sample the percentage block was determined using the control samples to determine the assay window.

From this screening, VHHs were selected and sequence analysis revealed 120 unique VHHs belonging to 3 different B-cell lineages. The total number of variants found for each B-cell lineage is depicted in Table 17.

TABLE 17

Selection parameters used for the identification of the humanCX3CR1 specific VHH B-cell lineages

| B-cell lineage | Representative VHH ID | # variants | libraries |
|---|---|---|---|
| 9 | CX3CR1BII11H11 | 4 | 368-PBL1 + 2 + LN-V-100209 |
| 13 | CX3CR1BII18E06 | 68 | 368-PBL1 + 2 + LN-V-100209 368-PBL3 + 4-V-280909 |
| 101 | CX3CR1BII66B02 | 48 | 312 + 313 + 314-PBL1 + 2-V-220210 314-PBL1 + 2-V-180310 |

An overview of the selection procedure and performance during initial screening is given for all VHHs in Table 18.

TABLE 18

Selection conditions and primary screening result for the huCX3CR1 specific VHH

| VHH ID | Family | Library | Selections first round | | Selections second round | | % block |
|---|---|---|---|---|---|---|---|
| CX3CR1BII PMP11H11 | 9 | 368-PBL1 + 2 + LN-V-100209 | BA/F3_hCX3CR1 | total (trypsin) | CHO-K1_hCX3CR1 | total (trypsin) | 99.0 |
| CX3CR1BII PMP18E6 | 13 | 368-PBL3 + 4-V-280909 | BA/F3_hCX3CR1 | total (trypsin) | CHO-K1_hCX3CR1 | total (trypsin) | 53.1 |
| CX3CR1BII PMP54A12 | 101 | 312 + 313 + 314-PBL1 + 2-V-220210 | VLPs-hCX3CR1 (10U) | hFrac (2 µM) | VLPs-hCX3CR1 (10U) | hFrac (2 µM) | 93.8 |
| CX3CR1BII PMP54A3 | 101 | 312 + 313 + 314-PBL1 + 2-V-220210 | VLPs-hCX3CR1 (10U) | hFrac (2 µM) | VLPs-hCX3CR1 (10U) | hFrac (2 µM) | 90.8 |
| CX3CR1BII PMP54A4 | 101 | 312 + 313 + 314-PBL1 + 2-V-220210 | VLPs-hCX3CR1 (10U) | hFrac (2 µM) | VLPs-hCX3CR1 (10U) | hFrac (2 µM) | 86.6 |
| CX3CR1BII PMP54A5 | 101 | 312 + 313 + 314-PBL1 + 2-V-220210 | VLPs-hCX3CR1 (10U) | hFrac (2 µM) | VLPs-hCX3CR1 (10U) | hFrac (2 µM) | 92.5 |
| CX3CR1BII PMP54A7 | 101 | 312 + 313 + 314-PBL1 + 2-V-220210 | VLPs-hCX3CR1 (10U) | total (trypsin) | VLPs-hCX3CR1 (10U) | total (trypsin) | 68.9 |
| CX3CR1BII PMP54B1 | 101 | 312 + 313 + 314-PBL1 + 2-V-220210 | VLPs-hCX3CR1 (10U) | hFrac (2 µM) | VLPs-hCX3CR1 (10U) | hFrac (2 µM) | 92.1 |
| CX3CR1BII PMP54B2 | 101 | 312 + 313 + 314-PBL1 + 2-V-220210 | VLPs-hCX3CR1 (10U) | hFrac (2 µM) | VLPs-hCX3CR1 (10U) | hFrac (2 µM) | 65.3 |
| CX3CR1BII PMP54B3 | 101 | 312 + 313 + 314-PBL1 + 2-V-220210 | VLPs-hCX3CR1 (10U) | hFrac (2 µM) | VLPs-hCX3CR1 (10U) | hFrac (2 µM) | 90.1 |
| CX3CR1BII PMP54B5 | 101 | 312 + 313 + 314-PBL1 + 2-V-220210 | VLPs-hCX3CR1 (10U) | hFrac (2 µM) | VLPs-hCX3CR1 (10U) | hFrac (2 µM) | 92.6 |
| CX3CR1BII PMP54D5 | 101 | 312 + 313 + 314-PBL1 + 2-V-220210 | VLPs-hCX3CR1 (10U) | hFrac (2 µM) | VLPs-hCX3CR1 (10U) | hFrac (2 µM) | 87.8 |

TABLE 18-continued

Selection conditions and primary screening result for the huCX3CR1 specific VHH

| VHH ID | Family | Library | Selections first round | | second round | | % block |
|---|---|---|---|---|---|---|---|
| CX3CR1BII PMP54D8 | 101 | 312 + 313 + 314-PBL1 + 2-V-220210 | VLPs-hCX3CR1 (10U) | total (trypsin) | VLPs-hCX3CR1 (10U) | total (trypsin) | 64.1 |
| CX3CR1BII PMP54F6 | 101 | 312 + 313 + 314-PBL1 + 2-V-220210 | VLPs-hCX3CR1 (10U) | hFrac (2 μM) | VLPs-hCX3CR1 (10U) | hFrac (2 μM) | 96.6 |
| CX3CR1BII PMP54G3 | 101 | 312 + 313 + 314-PBL1 + 2-V-220210 | VLPs-hCX3CR1 (10U) | hFrac (2 μM) | VLPs-hCX3CR1 (10U) | hFrac (2 μM) | 74.7 |
| CX3CR1BII PMP54H1 | 101 | 312 + 313 + 314-PBL1 + 2-V-220210 | VLPs-hCX3CR1 (10U) | hFrac (2 μM) | VLPs-hCX3CR1 (10U) | hFrac (2 μM) | 74.6 |
| CX3CR1BII PMP54H4 | 101 | 312 + 313 + 314-PBL1 + 2-V-220210 | VLPs-hCX3CR1 (10U) | hFrac (2 μM) | VLPs-hCX3CR1 (10U) | hFrac (2 μM) | 96.0 |
| CX3CR1BII PMP61F10 | 101 | 314-PBL1 + 2-V-180310 | VLPs-hCX3CR1 (10U) | hFrac (2 μM) | VLPs-hCX3CR1 (10U) | hFrac (2 μM) | 73.5 |
| CX3CR1BII PMP61D1 | 101 | 314-PBL1 + 2-V-180310 | VLPs-hCX3CR1 (10U) | hFrac (2 μM) | VLPs-hCX3CR1 (10U) | hFrac (2 μM) | 68.4 |
| CX3CR1BII PMP61D5 | 101 | 314-PBL1 + 2-V-180310 | VLPs-hCX3CR1 (10U) | hFrac (2 μM) | VLPs-hCX3CR1 (10U) | hFrac (2 μM) | 94.9 |
| CX3CR1BII PMP61E2 | 101 | 314-PBL1 + 2-V-180310 | VLPs-hCX3CR1 (10U) | hFrac (2 μM) | VLPs-hCX3CR1 (10U) | hFrac (2 μM) | 70.3 |
| CX3CR1BII PMP61F11 | 101 | 314-PBL1 + 2-V-180310 | VLPs-hCX3CR1 (10U) | hFrac (2 μM) | VLPs-hCX3CR1 (10U) | hFrac (2 μM) | 96.5 |
| CX3CR1BII PMP61G2 | 101 | 314-PBL1 + 2-V-180310 | VLPs-hCX3CR1 (10U) | hFrac (2 μM) | VLPs-hCX3CR1 (10U) | hFrac (2 μM) | 82.0 |
| CX3CR1BII PMP61G3 | 101 | 314-PBL1 + 2-V-180310 | VLPs-hCX3CR1 (10U) | hFrac (2 μM) | VLPs-hCX3CR1 (10U) | hFrac (2 μM) | 92.1 |
| CX3CR1BII PMP61G4 | 101 | 314-PBL1 + 2-V-180310 | VLPs-hCX3CR1 (10U) | hFrac (2 μM) | VLPs-hCX3CR1 (10U) | hFrac (2 μM) | 94.5 |
| CX3CR1BII PMP61F4 | 101 | 314-PBL1 + 2-V-180310 | VLPs-hCX3CR1 (10U) | hFrac (2 μM) | VLPs-hCX3CR1 (10U) | hFrac (2 μM) | 94.4 |
| CX3CR1BII PMP61A11 | 101 | 314-PBL1 + 2-V-180310 | VLPs-hCX3CR1 (10U) | hFrac (2 μM) | VLPs-hCX3CR1 (10U) | hFrac (2 μM) | 78.0 |
| CX3CR1BII PMP61B2 | 101 | 314-PBL1 + 2-V-180310 | VLPs-hCX3CR1 (10U) | hFrac (2 μM) | VLPs-hCX3CR1 (10U) | hFrac (2 μM) | 94.5 |
| CX3CR1BII PMP61C9 | 101 | 314-PBL1 + 2-V-180310 | VLPs-hCX3CR1 (10U) | total (trypsin) | VLPs-hCX3CR1 (10U) | total (trypsin) | 69.4 |
| CX3CR1BII PMP65H02 | 101 | 312 + 313 + 314-PBL1 + 2-V-220210 | VLPs-hCX3CR1 (10U) | hFrac (2 μM) | VLPs-hCX3CR1 (10U) | hFrac (2 μM) | #N/A |
| CX3CR1BII PMP65E11 | 101 | 312 + 313 + 314-PBL1 + 2-V-220210 | VLPs-hCX3CR1 (10U) | hFrac (2 μM) | VLPs-hCX3CR1 (10U) | hFrac (2 μM) | #N/A |
| CX3CR1BII PMP65E10 | 101 | 312 + 313 + 314-PBL1 + 2-V-220210 | VLPs-hCX3CR1 (10U) | hFrac (2 μM) | VLPs-hCX3CR1 (10U) | hFrac (2 μM) | #N/A |
| CX3CR1BII PMP65E05 | 101 | 312 + 313 + 314-PBL1 + 2-V-220210 | VLPs-hCX3CR1 (10U) | hFrac (2 μM) | VLPs-hCX3CR1 (10U) | hFrac (2 μM) | #N/A |
| CX3CR1BII PMP65B11 | 101 | 312 + 313 + 314-PBL1 + 2-V-220210 | VLPs-hCX3CR1 (10U) | hFrac (2 μM) | VLPs-hCX3CR1 (10U) | hFrac (2 μM) | #N/A |
| CX3CR1BII PMP65B07 | 101 | 312 + 313 + 314-PBL1 + 2-V-220210 | VLPs-hCX3CR1 (10U) | hFrac (2 μM) | VLPs-hCX3CR1 (10U) | hFrac (2 μM) | #N/A |
| CX3CR1BII PMP65B09 | 101 | 312 + 313 + 314-PBL1 + 2-V-220210 | VLPs-hCX3CR1 (10U) | hFrac (2 μM) | VLPs-hCX3CR1 (10U) | hFrac (2 μM) | #N/A |

TABLE 18-continued

Selection conditions and primary screening result for the huCX3CR1 specific VHH

| VHH ID | Family | Library | Selections first round | | Selections second round | | % block |
|---|---|---|---|---|---|---|---|
| CX3CR1BII PMP65H01 | 101 | 312 + 313 + 314-PBL1 + 2-V-220210 | VLPs-hCX3CR1 (10U) | hFrac (2 μM) | VLPs-hCX3CR1 (10U) | hFrac (2 μM) | #N/A |
| CX3CR1BII PMP65G07 | 101 | 312 + 313 + 314-PBL1 + 2-V-220210 | VLPs-hCX3CR1 (10U) | hFrac (2 μM) | VLPs-hCX3CR1 (10U) | hFrac (2 μM) | #N/A |
| CX3CR1BII PMP66H08 | 101 | 314-PBL1 + 2-V-180310 | VLPs-hCX3CR1 (10U) | hFrac (2 μM) | VLPs-hCX3CR1 (10U) | hFrac (2 μM) | #N/A |
| CX3CR1BII PMP66H04 | 101 | 314-PBL1 + 2-V-180310 | VLPs-hCX3CR1 (10U) | hFrac (2 μM) | VLPs-hCX3CR1 (10U) | hFrac (2 μM) | #N/A |
| CX3CR1BII PMP66F02 | 101 | 314-PBL1 + 2-V-180310 | VLPs-hCX3CR1 (10U) | hFrac (2 μM) | VLPs-hCX3CR1 (10U) | hFrac (2 μM) | #N/A |
| CX3CR1BII PMP66E11 | 101 | 314-PBL1 + 2-V-180310 | VLPs-hCX3CR1 (10U) | hFrac (2 μM) | VLPs-hCX3CR1 (10U) | hFrac (2 μM) | #N/A |
| CX3CR1BII PMP66D10 | 101 | 314-PBL1 + 2-V-180310 | VLPs-hCX3CR1 (10U) | hFrac (2 μM) | VLPs-hCX3CR1 (10U) | hFrac (2 μM) | #N/A |
| CX3CR1BII PMP66D08 | 101 | 314-PBL1 + 2-V-180310 | VLPs-hCX3CR1 (10U) | hFrac (2 μM) | VLPs-hCX3CR1 (10U) | hFrac (2 μM) | #N/A |
| CX3CR1BII PMP66B02 | 101 | 314-PBL1 + 2-V-180310 | VLPs-hCX3CR1 (10U) | hFrac (2 μM) | VLPs-hCX3CR1 (10U) | hFrac (2 μM) | #N/A |
| CX3CR1BII PMP66A04 | 101 | 314-PBL1 + 2-V-180310 | VLPs-hCX3CR1 (10U) | hFrac (2 μM) | VLPs-hCX3CR1 (10U) | hFrac (2 μM) | #N/A |
| CX3CR1BII PMP66D04 | 101 | 314-PBL1 + 2-V-180310 | VLPs-hCX3CR1 (10U) | hFrac (2 μM) | VLPs-hCX3CR1 (10U) | hFrac (2 μM) | #N/A |
| CX3CR1BII PMP66D02 | 101 | 314-PBL1 + 2-V-180310 | VLPs-hCX3CR1 (10U) | hFrac (2 μM) | VLPs-hCX3CR1 (10U) | hFrac (2 μM) | #N/A |
| CX3CR1BII PMP66D06 | 101 | 314-PBL1 + 2-V-180310 | VLPs-hCX3CR1 (10U) | hFrac (2 μM) | VLPs-hCX3CR1 (10U) | hFrac (2 μM) | #N/A |
| CX3CR1BII PMP66G01 | 101 | 314-PBL1 + 2-V-180310 | VLPs-hCX3CR1 (10U) | hFrac (2 μM) | VLPs-hCX3CR1 (10U) | hFrac (2 μM) | #N/A |

The amino acid sequences of all obtained unique VHHs are shown in the Sequence Listing and above (CDRs and framework regions were indicated).

Example 5

Characterization of Purified VHHs

Inhibitory anti-CX3CR1 VHHs selected from the screening described in Example 4 were further purified and characterized. Selected VHHs were expressed in *E. coli* TG1 as c-myc, His6-tagged proteins. Expression was induced by addition of 1 mM IPTG and allowed to continue for 4 hours at 37° C. After spinning the cell cultures, periplasmic extracts were prepared by freeze-thawing the pellets. These extracts were used as starting material and VHHs were purified via IMAC and size exclusion chromatography (SEC) resulting in 95% purity as assessed via SDS-PAGE. Inhibition by Anti-CX3CR1 VHHs of Human Fractalkine Binding to Human CX3CR1 Expressed on the BA/F3 Cells The blocking capacity towards the ligand fractalkine of the VHHs was evaluated in a human CX3CR1 competition FACS as outlined in Example 4. Either CHO-huCX3CR1 cells, BA/F3-huCX3CR1 cells or transiently transfected HEK293T cells were used. The amount of labeled ligand used in the different competition setups was also varied. The $IC_{50}$ values for VHHs blocking the interaction of human fractalkine to human CX3CR1 are depicted in Table 19.

TABLE 19

Potency and efficacy of the VHH in a ligand competition FACS

| VHH ID | Family | Cell line | IC50 | % block | Repeats |
|---|---|---|---|---|---|
| 11H11 | 9 | CHO-huCX3CR1 | 1.7E−8 | 100 | 4 |
| 18E06 | 13 | CHO-huCX3CR1 | 1.8E−9 | 33 | 4 |
| 54A12 | 101 | CHO-huCX3CR1 | 2.1E−9 | 104 | 2 |
| 54D08 | 101 | CHO-huCX3CR1 | 1.5E−8 | 101 | 2 |
| 54A07 | 101 | CHO-huCX3CR1 | 1.1E−8 | 78 | 2 |
| 54D05 | 101 | CHO-huCX3CR1 | 2.7E−9 | 102 | 2 |
| 54B03 | 101 | CHO-huCX3CR1 | 2.5E−8 | 108 | 1 |
| 54G03 | 101 | CHO-huCX3CR1 | 5.6E−8 | 107 | 1 |
| 11H11 | 9 | BA/F3-huCX3CR1 | 8.1E−9 | 100 | 3 |
| 18E06 | 13 | BA/F3-huCX3CR1 | 2.8E−9 | 71 | 3 |
| 54A12 | 101 | BA/F3-huCX3CR1 | 4.0E−9 | 100 | 4 |
| 54D08 | 101 | BA/F3-huCX3CR1 | 3.8E−8 | 99 | 1 |
| 54A07 | 101 | BA/F3-huCX3CR1 | 1.5E−8 | 81 | 4 |
| 54D05 | 101 | BA/F3-huCX3CR1 | 5.5E−9 | 99 | 1 |
| 54B03 | 101 | BA/F3-huCX3CR1 | 3.3E−8 | 99 | 1 |
| 54G03 | 101 | BA/F3-huCX3CR1 | 9.8E−8 | 98 | 1 |

TABLE 19-continued

Potency and efficacy of the VHH in a ligand competition FACS

| VHH ID | Family | Cell line | IC50 | % block | Repeats |
|---|---|---|---|---|---|
| 54A12 | 101 | HEK293-huCX3CR1 | 6.8E−9 | 96 | 5 |
| 54D08 | 101 | HEK293-huCX3CR1 | 8.4E−8 | 95 | 2 |
| 54A07 | 101 | HEK293-huCX3CR1 | 2.3E−8 | 52 | 2 |
| 54D05 | 101 | HEK293-huCX3CR1 | 5.3E−9 | 94 | 5 |
| 54B03 | 101 | HEK293-huCX3CR1 | 6.7E−8 | 92 | 2 |
| 54G03 | 101 | HEK293-huCX3CR1 | 2.7E−7 | 89 | 2 |
| 61E02 | 101 | HEK293-huCX3CR1 | 8.2E−8 | 98 | 2 |
| 61B04 | 101 | HEK293-huCX3CR1 | 5.7E−8 | 97 | 2 |
| 61B02 | 101 | HEK293-huCX3CR1 | 1.0E−8 | 94 | 2 |
| 54H01 | 101 | HEK293-huCX3CR1 | 1.0E−8 | 64 | 2 |
| 54A04 | 101 | HEK293-huCX3CR1 | 4.9E−8 | 100 | 2 |
| 61F11 | 101 | HEK293-huCX3CR1 | 4.6E−8 | 96 | 2 |
| 61G03 | 101 | HEK293-huCX3CR1 | 6.0E−8 | 96 | 2 |
| 61G04 | 101 | HEK293-huCX3CR1 | 4.2E−8 | 96 | 2 |
| 66B02 | 101 | HEK293-huCX3CR1 | 2.5E−9 | 102 | 2 |
| 66G01 | 101 | HEK293-huCX3CR1 | 1.4E−8 | 99 | 2 |

Inhibition by Anti-CX3CR1 VHHs of Human Fractalkine Induced Chemotaxis of BA/F3 Cells Overexpressing Human CX3CR1

To evaluate inhibition of Fractalkine induced chemotaxis, a chemotaxis assay was setup using the ChemoTx disposable chamber with 5 µm poresize (Neuroprobe, Gaithersburg, US). Cells were harvested from an actively growing culture and washed before use in assay medium, RPMI (Gibco, Carlsbad, US) supplemented with 0.1% BSA. The bottom chamber was filled with 320 pM human Fractalkine in a total volume of 300 µl. Upon application of the membrane, 0.13E6 cells were deposited on top of the membrane in a total volume of 70 µl. Chemotaxis was allowed for 3 hours at 37° C. in a humidified chamber with CO2. After this incubation period, the membrane was removed and cells in the bottom chamber were resuspended. The amount of ATP present in the wells was determined using the CellTiter-Glo kit (Promega, Madison Wis., US). Read out was performed on an Envision (Perkin Elmer, Mass., US) with the standard settings for luminescence read out. Titration series were performed in triplicate and each plate contained control samples in triplicate as well. As control, a sample without VHH was included as well as a sample where no human Fractalkine was added to the bottom chamber. A summary of the results is shown in Table 20.

TABLE 20

Potency and efficacy of the VHH in blocking the fractalkine induced chemotaxis

| VHH ID | Fam | IC50 | % block | Repeats |
|---|---|---|---|---|
| 11H11 | 9 | 2E−7 | 89 | 5 |
| 18E06 | 13 | NA | 17 | 4 |
| 54A12 | 101 | 8E−8 | 84 | 6 |
| 54D08 | 101 | NA | 33 | 2 |
| 54A07 | 101 | 5E−8 | 45 | 4 |
| 54D05 | 101 | 7E−8 | 81 | 4 |
| 54B03 | 101 | 1E−7 | 73 | 1 |
| 54G03 | 101 | NA | 40 | 1 |
| 66B02 | 101 | 2E−8 | 87 | 2 |
| 66G01 | 101 | 4E−7 | 54 | 2 |

Evaluation of the Cross Reactivity of the Anti-CX3CR1 VHHs Against Cynomolgus CX3CR1

Initially, a FACS based binding setup was used to evaluate the cynomolgus cross reactivity. For this, the VHHs were incubated with the respective cells for 30 minutes at 4° C. followed by three wash steps and subsequently incubated with the detection reagents. As detection, a mouse anti-cmyc antibody (Serotec, MCA2200) followed by a goat anti-mouse antibody coupled to PE (Jackson 115-116-071) was used, each incubation for 30 minutes at 4° C., followed by three wash steps. Results of the assay are shown in Table 21.

TABLE 21

EC50 value for binding of the respective VHH on human CX3CR1 or on cynomolgus CX3CR1

| VHH ID | Family | EC50 (M) Human | EC50 (M) Cynomolgus | ratio | Repeats |
|---|---|---|---|---|---|
| 11H11 | 9 | 8.0E−10 | NA | NA | 2 |
| 18E06 | 13 | 1.5E−9 | 1.4E−8 | 9 | 2 |
| 54A12 | 101 | 3.5E−8 | 1.1E−7 | 3.3 | 1 |
| 54A07 | 101 | 5.4E−7 | 3.0E−8 | 0.1 | 1 |
| 54D05 | 101 | 8.4E−10 | 5.0E−8 | 59.6 | 1 |

For later identified VHHs, a human Fractalkine competition FACS was set up using human or cynomolgus CX3CR1 expressed in HEK293T cells. Both the human and the cynomolgus receptor was transiently transfected in HEK293T cells and transfections were matched by the binding of the labeled ligand, human fractalkine. The competition was evaluated using the EC30 concentration of fractalkine and as such obtained IC50 values are a good estimate of the Ki value, a measure for affinity (Table 22). The experiment was performed as described in Example 4. The ratio of the IC50 values on cynomolgus monkey and human CX3CR1 was used to evaluate potential differences in affinity for CX3CR1 in both species.

TABLE 22

Efficacy and potency of VHHs in ligand competition FACS towards human and cynomolgus CX3CR1

| VHH ID | Family | Human IC50 (M) | Human % block | Cynomolgus IC50 (M) | Cynomolgus % block | ratio | Repeats |
|---|---|---|---|---|---|---|---|
| 54A12 | 101 | 6.8E−9 | 96 | 6.7E−8 | 94 | 9.85 | 5 |
| 54D08 | 101 | 8.4E−8 | 95 | 7.2E−8 | 91 | 0.85 | 2 |
| 54A07 | 101 | 2.3E−8 | 52 | 2.8E−7 | 69 | 12.3 | 2 |
| 54D05 | 101 | 5.3E−9 | 94 | 6.4E−8 | 91 | 12.25 | 5 |
| 54B03 | 101 | 6.7E−8 | 92 | 4.7E−7 | 95 | 7.05 | 2 |
| 54G03 | 101 | 2.7E−7 | 89 | 4.7E−7 | 89 | 1.74 | 2 |
| 61E02 | 101 | 8.2E−8 | 98 | 4.6E−8 | 96 | 0.55 | 2 |
| 61B04 | 101 | 5.7E−8 | 97 | 8.7E−8 | 93 | 1.53 | 2 |
| 61B02 | 101 | 1.0E−8 | 94 | 4.5E−8 | 92 | 4.37 | 2 |
| 54H01 | 101 | 1.0E−8 | 64 | 6.8E−8 | 92 | 6.48 | 2 |
| 54A04 | 101 | 4.9E−8 | 100 | 3.1E−8 | 91 | 0.64 | 2 |
| 61F11 | 101 | 4.6E−8 | 96 | 1.6E−7 | 95 | 3.58 | 2 |
| 61G03 | 101 | 6.0E−8 | 96 | 3.0E−7 | 89 | 5.02 | 2 |
| 61G04 | 101 | 4.2E−8 | 96 | 2.0E−7 | 100 | 4.8 | 2 |
| 66B02 | 101 | 2.5E−9 | 102 | 1.9E−8 | 97 | 7.5 | 2 |
| 66G01 | 101 | 1.4E−8 | 99 | 1.2E−7 | 100 | 8.29 | 2 |

Binding of the Anti-Human CX3CR1 VHHs to Human CCR2, Human CCR5 or Mouse CX3CR1

Specificity for the huCX3CR1 receptor was evaluated by performing a FACS binding experiment on CHO-K1 parental cells or CHO cells expressing huCCR2, huCCR5 or msCX3CR1. The VHHs were incubated with the respective cell lines for 30 minutes at 4° C. followed by three wash steps and subsequently incubated with the detection reagents. As detection, a mouse anti-cmyc antibody (Serotec, MCA2200) followed by a goat anti-mouse antibody coupled to PE (Jackson 115-116-071) was used, each incubation for 30 minutes at 4° C., followed by three wash steps. For each cell line a quality control with receptor-specific antibody was included. In addition, the highest concentration of each VHH was also incubated with CHO cells expressing huCX3CR1 as a positive control. No binding to msCX3CR1, huCCR2 or huCCR5 could be observed.

Determination of the Epitope Bin

A competitive binding experiment was setup in order to determine whether the VHHs bind overlapping epitopes on CX3CR1. For this, the VHH 66B02 labeled with alexa647 was used in a competition FACS on the BA/F3 cells expressing huCX3CR1. Representative VHHs from the three functional families were used as competitors for the binding of the labeled 66B02. The obtained IC50 values are shown in Table 23.

TABLE 23

Competition FACS based epitope binning

| VHH ID | family | IC50 (M) | % block |
|---|---|---|---|
| 11H11 | 9 | 4.9E−09 | 100 |
| 18E06 | 13 | 2.3E−09 | 100 |
| 66B02 | 101 | 1.5E−09 | 100 |

As a complete inhibition of 66B02 binding could be obtained by all representative VHHs from the different ligand blocking families, it can be concluded that all functional families bind in close enough proximity of each other such that they compete with binding of 66B02.

Example 6

Formatting of VHHs to Bivalency

Construction of Bivalents

In order to increase potency and/or efficacy from a selection of the obtained VHHs, bivalent molecules were constructed by genetic engineering. Two VHHs were genetically linked together with a 35GS linker in between the two building blocks and subsequently expressed in *E. coli* as described above for the monovalent VHHs. Different bivalent constructs were made as listed in Table 24.

TABLE 24

Representative bivalent formats

| Construct ID | VHH identity | Family | Linker | VHH identity | Family |
|---|---|---|---|---|---|
| CX3CR1BII007 | CX3CR1BII11H11 | 9 | 35GS | CX3CR1BII18E6 | 13 |
| CX3CR1BII009 | CX3CR1BII18E6 | 13 | 35GS | CX3CR1BII11H11 | 9 |
| CX3CR1BII012 | CX3CR1BII54D08 | 101 | 35GS | CX3CR1BII18E06 | 101 |
| CX3CR1BII016 | CX3CR1BII54A12 | 101 | 35GS | CX3CR1BII54A12 | 101 |
| CX3CR1BII017 | CX3CR1BII54D5 | 101 | 35GS | CX3CR1BII54D5 | 101 |
| CX3CR1BII018 | CX3CR1BII66B02 | 101 | 35GS | CX3CR1BII66B02 | 101 |
| CX3CR1BII019 | CX3CR1BII66G01 | 101 | 35GS | CX3CR1BII66G01 | 101 |
| CX3CR1BII020 | CX3CR1BII54B5 | 101 | 35GS | CX3CR1BII54B5 | 101 |
| CX3CR1BII026 | CX3CR1BII11H11 | 9 | 35GS | CX3CR1BII66B02 | 101 |
| CX3CR1BII027 | CX3CR1BII11H11 | 9 | 35GS | CX3CR1BII54B5 | 101 |

Inhibition by Anti-CX3CR1 VHHs of Human Fractalkine Binding to Human CX3CR1 Expressed on the BA/F3 Cells The inhibition of ligand binding to human CX3CR1 was investigated for the different formats as described in Example 4. For this characterization the BA/F3-huCX3CR1 cell line was used showing stable expression of the human CX3CR1 receptor. The alexa647 labeled ligand fractalkine was used at its EC30 concentration and thereby obtained IC50 values are reflective of the Ki values. An overview of the obtained data is shown in Table 25.

TABLE 25

Potency of bivalent formats in ligand competition

| Construct ID | Cell line | IC50 (M) | % block | Repeats |
|---|---|---|---|---|
| CX3CR1BII007 | CHO-huCX3CR1 | 3.8E−10 | 100 | 2 |
| CX3CR1BII009 | CHO-huCX3CR1 | 7.0E−10 | 91 | 2 |
| CX3CR1BII012 | CHO-huCX3CR1 | 8.0E−10 | 93 | 1 |
| CX3CR1BII016 | HEK293-huCX3CR1 | 1.9E−10 | 102 | 2 |
| CX3CR1BII017 | HEK293-huCX3CR1 | 3.1E−10 | 99 | 2 |
| CX3CR1BII018 | HEK293-huCX3CR1 | 3.0E−10 | 102 | 2 |
| CX3CR1BII019 | HEK293-huCX3CR1 | 2.9E−10 | 100 | 2 |
| CX3CR1BII020 | HEK293-huCX3CR1 | 2.2E−10 | 102 | 2 |
| CX3CR1BII026 | BA/F3-huCX3CR1 | 7.0E−10 | 100 | 3 |
| CX3CR1BII027 | BA/F3-huCX3CR1 | 6.7E−10 | 100 | 3 |

Inhibition by Anti-CX3CR1 VHHs of Human Fractalkine Induced Chemotaxis of BA/F3 Cells Overexpressing Human CX3CR1

Similar to what was described for the monovalent anti-CX3CR1 VHHs, the inhibition of fractalkine induced chemotaxis on the BA/F3-huCX3CR1 cells was evaluated for the bivalent constructs. An identical assay setup was used as described above and the obtained results are summarized in Table 26.

TABLE 26

Inhibition of fractalkine induced chemotaxis by bivalent VHH constructs

| Construct ID | Cell line | IC50 (M) | % block | Repeats |
|---|---|---|---|---|
| CX3CR1BII007 | BA/F3-huCX3CR1 | 4E−9 | 101 | 5 |
| CX3CR1BII009 | BA/F3-huCX3CR1 | 2E−8 | 79 | 5 |
| CX3CR1BII012 | BA/F3-huCX3CR1 | 4E−9 | 78 | 1 |
| CX3CR1BII016 | BA/F3-huCX3CR1 | 2E−9 | 88 | 3 |
| CX3CR1BII017 | BA/F3-huCX3CR1 | 3E−9 | 89 | 3 |
| CX3CR1BII018 | BA/F3-huCX3CR1 | 6E−10 | 98 | 6 |
| CX3CR1BII019 | BA/F3-huCX3CR1 | 2E−9 | 85 | 3 |
| CX3CR1BII020 | BA/F3-huCX3CR1 | 2E−9 | 85 | 3 |
| CX3CR1BII026 | BA/F3-huCX3CR1 | 3E−10 | 98 | 1 |
| CX3CR1BII027 | BA/F3-huCX3CR1 | 9E−10 | 98 | 1 |

Evaluation of the Cross Reactivity of the Anti-CX3CR1 VHHs Against Cynomolgus CX3CR1

Also for the bivalent constructs the cross reactivity towards cynomolgus CX3CR1 was evaluated and compared with the human reactivity. As described earlier, either a binding setup (Table 27) or a ligand competition setup (Table 28) were applied using transient transfected HEK293T cells. Batches of transient transfected cells were matched by their receptor expression level.

TABLE 27

Binding of bivalent constructs to human or cynomolgus CX3CR1

| Construct ID | Cell line | EC50 (M) Human | EC50 (M) Cynomolgus | ratio | Repeats |
|---|---|---|---|---|---|
| CX3CR1BII007 | HEK293T | 3.1E−10 | 4.8E−8 | 154 | 2 |
| CX3CR1BII009 | HEK293T | 2.0E−9 | 6.8E−9 | 3.3 | 2 |
| CX3CR1BII012 | HEK293T | 5.6E−11 | 6.3E−11 | 1.1 | 1 |

TABLE 28

Ligand competition of bivalent constructs on human or cynomolgus CX3CR1

| Construct ID | Cell line | Human IC50 (M) | Human % block | Cynomolgus IC50 (M) | Cynomolgus % block | ratio | Repeats |
|---|---|---|---|---|---|---|---|
| CX3CR1BII016 | HEK293T | 1.9E−10 | 102 | 6.9E−10 | 98 | 3.67 | 2 |
| CX3CR1BII017 | HEK293T | 3.1E−10 | 99 | 1.6E−9 | 95 | 5.34 | 2 |
| CX3CR1BII018 | HEK293T | 3.0E−11 | 102 | 1.0E−10 | 97 | 3.33 | 2 |
| CX3CR1BII019 | HEK293T | 2.9E−10 | 100 | 8.2E−10 | 96 | 2.86 | 2 |
| CX3CR1BII020 | HEK293T | 2.2E−10 | 102 | 3.2E−10 | 97 | 1.47 | 2 |

Example 7

Exploration of Linker Length and Half Life Extension

Evaluation of the Linker Length and Positioning of the Alb11 VHH

As the linker length used in a bivalent format can impact drastically on the obtained potency, different linker lengths were evaluated.

In addition, Alb11, a Nanobody binding to human serum albumin was included to increase the in vivo half-life of the formatted molecules (WO 06/122787). Different formats were made including variations on the linker lengths used, but also the positioning of the different composing VHHs. A summary of the explored formats is shown in Table 29.

TABLE 29

Exploration of half life extension and linker length Construct

| ID | VHH identity | Linker | VHH identity | Linker | VHH identity |
|---|---|---|---|---|---|
| CX3CR1BII032 | CX3CR1BII66B02 | 9GS | CX3CR1BII66B02 | 9GS | Alb11 |
| CX3CR1BII034 | CX3CR1BII66B02 | 35GS | CX3CR1BII66B02 | 9GS | Alb11 |
| CX3CR1BII036 | CX3CR1BII66B02 | 9GS | Alb11 | 9GS | CX3CR1BII66B02 |
| CX3CR1BII040 | CX3CR1BII66B02 | 9GS | CX3CR1BII66B02 | 35GS | Alb11 |
| CX3CR1BII041 | CX3CR1BII66B02 | 35GS | CX3CR1BII66B02 | 35GS | Alb11 |
| CX3CR1BII042 | CX3CR1BII66B02 | 35GS | Alb11 | 35GS | CX3CR1BII66B02 |

Coding sequences for the formatted VHH were cloned into an in-house constructed plasmid allowing expression in Pichia pastoris and secretion into the cultivation medium. The expression vector was derived from pPICZa (Invitrogen) and contained the AOX1 promoter for tightly regulated, methanol induced expression, a resistance gene for Zeocin™, a multicloning site and the α-factor secretion signal. Upon transformation expression cultures were grown and VHH expression was induced by addition of methanol and allowed to continue for 48 hours at 30° C.

The potency of these different formats was evaluated using the ligand competition assay as described above. Seeing that the ligand concentration used is below the EC50 value, the obtained IC50 values are equivalent to the Ki values. The obtained Ki for the different formats is summarized in Table 30.

TABLE 30

Potency of half life extended formats in ligand competition

| Construct ID | Cell line | IC50 (M) | % block | Repeats |
|---|---|---|---|---|
| CX3CR1BII032 | BA/F3-huCX3CR1 | 5.8E−10 | 99 | 2 |
| CX3CR1BII034 | BA/F3-huCX3CR1 | 5.2E−10 | 99 | 2 |
| CX3CR1BII036 | BA/F3-huCX3CR1 | 5.6E−10 | 99 | 2 |
| CX3CR1BII040 | BA/F3-huCX3CR1 | 5.9E−10 | 104 | 1 |
| CX3CR1BII041 | BA/F3-huCX3CR1 | 6.4E−10 | 102 | 1 |
| CX3CR1BII042 | BA/F3-huCX3CR1 | 8.9E−10 | 100 | 1 |

Impact of Human Serum Albumin on the Potency

The binding of human serum albumin (HSA) to the alb11 VHH could impact on the potency of the format and therefore ligand competition was repeated in presence of HSA. Briefly, to allow the binding of HSA to the alb11 VHH, the constructs under evaluation and fractalkine were pre-incubated with HSA for 30 minutes before addition to the cells. Also the cells were resuspended in FACS buffer supplemented with HSA. The final concentration HSA used was a 50 fold excess above the highest VHH concentration used. Subsequently, competition was allowed for 2 hours and further processing was as described in Example 4.

| Construct ID | Cell line | IC50 (M) | % block | Repeats |
|---|---|---|---|---|
| CX3CR1BII032 | BA/F3-huCX3CR1 | 1.4E−9 | 100 | 2 |
| CX3CR1BII034 | BA/F3-huCX3CR1 | 1.3E−9 | 100 | 2 |
| CX3CR1BII036 | BA/F3-huCX3CR1 | 1.4E−9 | 100 | 2 |

The potential interference of HSA was also evaluated in an adapted chemotaxis setup, including HSA in the different compartments of the assay. The concentration HSA used was again a 50 fold excess over the highest concentration of construct used and constructs were loaded with HSA for 30 minutes before start of the assay. The assay buffer was also supplemented with HSA such that HSA is present during the entire span of the experiment. As described above, the disposable ChemoTx chamber with 5 µm poresize (Neuroprobe, Gaithersburg, Md., USA) was used. Cells were harvested from an actively growing culture and washed before use in assay medium, RPMI (Gibco, Carlsbad, US) supplemented with 0.1% BSA and 62.5 µM HSA (Sigma, A8763). The bottom chamber was filled with 320 pM human Fractalkine in a total volume of 300 µl. Upon application of the membrane, 0.13E6 cells were deposited on top of the membrane in a total volume of 70 µl. Chemotaxis was allowed for 3 hours at 37 C. in a humidified chamber with CO2. After this incubation period, the membrane was removed and cells in the bottom chamber were resuspended.

The amount of ATP present in well was determined using the CellTiter-Glo kit (Promega, Madison Wis., USA). Read out was performed on an Envision (Perkin Elmer, Waltham, Mass., USA) with the standard factory settings for luminescence read out. Titration series were performed in triplicate and each plate contained control samples in triplicate as well. As control, a sample without VHH was included as well as a sample where no human Fractalkine was added to the bottom chamber. The obtained IC50 values are listed in Table 31.

TABLE 31

Fractalkine induced chemotaxis in the presence of HSA

| Construct ID | Cell line | IC50 (M) | % block | Repeats |
|---|---|---|---|---|
| CX3CR1BII032 | BA/F3-huCX3CR1 | 6E−10 | 98 | 2 |
| CX3CR1BII034 | BA/F3-huCX3CR1 | 9E−10 | 100 | 2 |
| CX3CR1BII036 | BA/F3-huCX3CR1 | 6E−10 | 102 | 2 |

Inhibition of Fractalkine Internalization by the Formatted Bivalent Half-Life Extended Polypeptides Additional functional assays were performed to demonstrate the antagonist activity of the bivalent half-life extended polypeptides. The polypeptides were evaluated for their ability to inhibit the internalization of A647-Fractalkine in CHO huCX3CR1 cells. Briefly, 1E4 cells/well were plated in black clear bottom, 96 well plates (BD, Franklin Lakes, N.J., USA) and grown overnight. The cells were washed once and then equilibrated in assay buffer (HBSS with calcium and magnesium (Gibco) supplemented with 10 mM HEPES and 0.1% BSA). The formatted polypeptide constructs were added and the plates were incubated for 15 minutes at 37 C. A647-Fractalkine was then added at a final concentration of 8 nM and the cells were incubated for 60 minutes at 37 C. The media was removed and the cells were fixed for 10 minutes with 3.7% formaldehyde solution (Polysciences, Warrington, Pa., USA). The cells were rinsed once with PBS and the nuclei were labeled with Hoechst dye (Life Technologies, Grand Island, N.Y., USA). To quantitate the internalized labeled Fractalkine, the cells were imaged using the BD Pathway bioimaging system. Image segmentation was performed by identifying the labeled cell nucleus and drawing a 3 pixel ring around that mask. Mean A647 intensity was measured in the cytoplasmic ring. The formatted polypeptides potently inhibited Fractalkine internalization as summarized in Table 32:

TABLE 32

Inhibition of A647-Fractalkine Internalization

| Construct ID | Cell line | IC50 (M) | Repeats |
|---|---|---|---|
| CX3CR1BII032 | CHO-huCX3CR1 | 4.0E−10 | 5 |
| CX3CR1BII034 | CHO-huCX3CR1 | 7.4E−10 | 3 |
| CX3CR1BII036 | CHO-huCX3CR1 | 4.9E−10 | 8 |
| CX3CR1BII040 | CHO-huCX3CR1 | 1.0E−9 | 3 |
| CX3CR1BII041 | CHO-huCX3CR1 | 1.1E−9 | 2 |
| CX3CR1BII042 | CHO-huCX3CR1 | 8.5E−10 | 2 |

An Anti-CX3CR1 Formatted Bivalent Half-Life Extended Polypeptide is Devoid of Agonist Activity In order to confirm that a bivalent anti-CX3CR1 half-life extended polypeptide did not have agonist activity, CX3CR1 BII036 was evaluated for induction of calcium influx in the CHO huCX3CR1 cells. Fractalkine mediated increases in cytosolic calcium levels in these cells in a CX3CR1 dependent manner and CX3CR1 BII036 inhibited this response.

The CHO huCX3CR1 cells were plated at 5E4 cells/well in black clear bottom, 96 well plates (BD) and grown overnight. The cells were incubated with Calcium-4 dye/2 mM probenicid (Molecular Devices, Sunnyvale, Calif., USA) in HBSS supplemented with 20 mM HEPES for 60 minutes at 37° C. For demonstrating polypeptide antagonism, CX3CR1 BII036 was preincubated with the cells for 15 minutes prior to the addition of Fractalkine at its EC80 value. Calcium mobilization was monitored on a FLIPR Tetra system (Molecular Devices) as per the manufacturer's instructions. For determining agonism, there was no preincubation with the polypeptide and instead, CX3CR1BII036 was used in place of Fractalkine stimulation. While CX3CR1BII036 inhibited Fractalkine mediated calcium influx with an IC50 of 1.3 nM, no increase in cytosolic calcium levels were observed when the polypeptide alone was added at concentrations up to 1 µM.

Example 8

Exploration of Half Life Extension Formats Using Mouse Fc

To investigate alternative half-life extension modalities, the 66B02 VHH domain was produced as a fusion protein with a mouse IgG2 Fc domain (66B02-mFc). An aspartic acid to alanine mutation (D265A) was incorporated in the CH2 domain to abrogate potential Fc-mediated effector function in this construct (Baudino, J. Immunol., 181, 6664-6669 (2008)). 66B02-mFc was expressed in HEK293T cells or NS0 cells and purified by Protein A affinity chromatography followed by ion exchange chromatography. This molecule was tested for activity utilizing the assay formats described in Example 7. The results are summarized in Table 33:

TABLE 33

66B02-mFc Activity

| Assay | Cell line | IC50 (M) | Repeats |
|---|---|---|---|
| Ligand competition | BA/F3-huCX3CR1 | 5.7E−10 | 2 |
| Chemotaxis | BA/F3-huCX3CR1 | 8.9E−10 | 3 |
| Ligand internalization | CHO-huCX3CR1 | 5.2E−10 | 5 |
| Calcium influx | CHO-huCX3CR1 | 9.8E−10 | 5 |

While 66B02-mFc potently inhibited Fractalkine mediated CX3CR1 activation, it did not display agonist activity. No increase in cytosolic calcium levels was observed with treatment with up to 1 µM of this molecule.

Example 9

Inhibition of Plaque Progression in a Mouse Atherosclerosis Model Bivalent Half-Life Extended Polypeptides Generation of Human CX3CR1 Knock-in Apo $E^{-/-}$ Mice Given the lack of cross reactivity of the identified VHHs for mouse CX3CR1 (Example 5), a human CX3CR1 knock-in mouse line (hu CX3CR1 KI) was generated at TaconicArtemis (Koeln, Germany) to enable testing of these molecules in mouse disease models. A strategy was employed that allowed the expression of the human chemokine receptor under the control of the corresponding mouse promoter while disrupting the expression of the endogenous mouse protein. Briefly, a targeting vector was constructed where the mouse CX3CR1 coding region in exon 2 was replaced with the complete human CX3CR1 open reading frame and flanked by selection markers and loxP sites. The targeting vector was introduced into mouse ES cells and clones that had successfully undergone homologous recombination were used to generate chimeric mice. These mice were bred to highly efficient Flp-deleter mice to achieve removal of the selection marker and germline transmission. The resulting hu CX3CR1 KI mice in a C57BL/6 background were then crossed to Apo $E^{-/-}$ mice (The Jackson Laboratory, Bar Harbor, Me., USA) to generate hu CX3CR1 KI Apo $E^{-/-}$ mice. The Apo $E^{-/-}$ mouse model provides a robust method to elicit extensive atherosclerotic plaque formation that is grossly similar to the human disease with respect to the site-specific localization of plaque formation, histological composition, and the known risk factors (cholesterol, inflammation, hypertension, etc).

Evaluation of the Anti-CX3CR1 Bivalent Half-Life Extended Polypeptides in the Mouse Apo $E^{-/-}$ Atherosclerosis Model Female hu CX3CR1 KI ApoE$^{-/-}$ mice were fed a high fat/high cholesterol diet containing 1.5% cholesterol for 16 weeks beginning at four weeks of age. After 10 weeks, the animals were administered by i.p. injection vehicle (20 mM NaCitrate pH 6.0, 115 mM NaCl), 10 mg/kg 66B02-mFc once or twice per week or 30 mg/kg CX3CR1BII036 twice per week for 6 weeks. The animals were anesthetized by gas anaesthesia and perfused with 0.9% saline. The descending aorta to the ileac bifurcation was carefully removed and fixed in formalin. It was then opened longitudinally, and stained with Sudan IV for 15 minutes, followed by 70% methanol for 2 minutes. The vessels were washed under running water and covered with PBS. The tissues were photographed with a digital camera using SPOT Advanced software (SPOT Imaging Solutions, Sterling Heights, Mich., USA). The percentage of lipid staining was determined with image analysis software (Image-Pro Plus, MediaCybernetics, Rockville, Md., USA) and expressed as a percentage positive staining of the vessel. The results from this study are summarized in Table 34:

TABLE 34

Quantification of Plaque Size in the Descending Aorta in female hu CX3CR1 KI Apo $E^{-/-}$ Mice

| Group | Dose | # Animals | % Plaque Area | % Reduction in Plaque Area |
|---|---|---|---|---|
| Control (10 weeks) | N/A | 6 | 3.4 | N/A |
| Control (16 weeks) | Vehicle | 17 | 14.8 | N/A |
| 66B02-mFc | 10 mg/kg (1× week) | 17 | 13.0 | 16 |
| 66B02-mFc | 10 mg/kg (2×/week) | 17 | 10.3 | 39 (p < 0.05) |
| CX3CR1BII036 | 30 mg/kg (2×/week) | 17 | 10.1 | 41 (p < 0.05) |

Both 66B02-mFc and CX3CR1 BII036 significantly inhibited plaque progression when dosed twice weekly. This correlated with coverage as plasma levels of these molecules could be confirmed to be maintained throughout the study. For once weekly dosing of 66B02-mFc, detectable plasma levels were not maintained and this correlated with the lack of significant efficacy observed after 6 weeks of treatment. Neither molecule significantly affected plasma cholesterol or triglyceride levels.

Example 10

Sequence Optimization of the Parental VHH

In general, during VHH sequence optimization, parental wild type VHH sequences are mutated to yield VHH sequences that are more identical to human VH3-JH germline consensus sequences. Specific amino acids in the framework regions that differ between the VHH and the human VH3-JH germline consensus are altered to the human counterpart in such a way that the protein structure, activity and stability are kept intact. To investigate this, all sequence optimization variants were compared with the parental VHH in three different assays: (i) determination of the melting temperature (Tm) in a Thermal Shift Assay (TSA), (ii) analysis of in vitro potency in fractalkine competition FACS, and for some constructs (iii) analysis of in vitro potency in the fractalkine induced chemotaxis assay.

Mutation of Framework Residues

For sequence optimization, the following mutations were investigated: E1D, S11L, A14P, E16G, R44Q, D46E, A74S, K83R and Q108L. The individual mutants that were generated in the parental sequence of CX3CR1 BII66B02 are depicted in Table 35:

TABLE 35

Investigated mutations during sequence optimization of 66B02

| Clone number | Mutations introduced |
|---|---|
| C100CX3CR1BII043 | A14P, A74S, K83R, Q108L |
| C100CX3CR1BII045 | E1D, A14P, A74S, K83R, Q108L |
| C100CX3CR1BII047 | S11L, A14P, A74S, K83R, Q108L |
| C100CX3CR1BII048 | A14P, E16G, A74S, K83R, Q108L |
| C100CX3CR1BII049 | A14P, R44Q, A74S, K83R, Q108L |
| C100CX3CR1BII050 | A14P, D46E, A74S, K83R, Q108L |

TABLE 35-continued

Investigated mutations during sequence optimization of 66B02

| Clone number | Mutations introduced |
|---|---|
| C100CX3CR1BII061 | S11L, A14P, E16G, A74S, K83R, Q108L |
| C100CX3CR1BII056 | S11L, A14P, E16G, R44Q, A74S, K83R, Q108L |
| C100CX3CR1BII057 | S11L, A14P, E16G, D46E, A74S, K83R, Q108L |
| C100CX3CR1BII060 | S11L, A14P, E16G, R44Q, D46E, A74S, K83R, Q108L |

All constructs were cloned in an E. coli expression vector, and expressed in E. coli as myc/His-tagged proteins in a culture volume of 0.25 L to 0.5 L TB medium. Expression was induced by addition of 1 mM IPTG and allowed to continue for 4 hours at 37° C. and 250 rpm. Cells were pelleted, and periplasmic extracts were prepared by freeze-thawing and resuspension in dPBS. These extracts were used as starting material for immobilized metal affinity chromatography (IMAC) using Histrap FF crude columns (GE healthcare). Nanobodies were eluted from the column with 250 mM imidazole and subsequently desalted towards dPBS. The purity and integrity of Nanobodies was verified by reducing SDS-PAGE.

As summarized in Table 36, A14P, A74S, K83R and Q108L mutations had no clear effect on potency as determined from competition FACS. Similarly, the additional mutations E1D, S11L and E16G did not affect potency. The introduction of either R44Q or D46E on the other hand resulted in a significant drop in potency that was even more pronounced if both mutations were introduced.

TABLE 36

Potency of sequence optimization constructs determined by ligand competition FACS

| Clone number | IC50 | % block | Tm at pH 7 |
|---|---|---|---|
| CX3CR1BII66B02 | 2.6E−09 | 101.0 | 65.66 |
| C100CX3CR1BII043 | 2.2E−09 | 101 | 66.49 |
| C100CX3CR1BII045 | 2.2E−09 | 101.2 | 66.07 |
| C100CX3CR1BII047 | 2.3E−09 | 101.2 | 66.49 |
| C100CX3CR1BII048 | 1.9E−09 | 101.2 | 67.74 |
| C100CX3CR1BII049 | 1.8E−08 | 101.2 | 66.07 |
| C100CX3CR1BII050 | 1.7E−08 | 101.1 | 71.90 |
| C100CX3CR1BII061 | 1.4E−09 | 98.9 | 68.57 |
| C100CX3CR1BII056 | 1.6E−08 | 101.1 | 68.57 |
| C100CX3CR1BII057 | 1.4E−08 | 99.4 | 74.39 |
| C100CX3CR1BII060 | 1.9E−07 | 98.4 | 74.81 |

Also the melting temperature, predictive for the stability of the VHH, was evaluated. Most individual mutations had limited to no effect except for the D46E mutation which raised the melting temperature by approximately 6° C. The introduction of the combined mutations also enhanced the thermal stability, cfr 057 and 060.

Due to the major effects on the potency in ligand competition FACS, the mutations R44Q and D46E were not included in the final sequence.

Mutation of CDR Residues

Based on the in silico analysis of the parental sequence, a glycosylation site was predicted at position 52. Therefore two libraries were constructed; one for position 52 and one for position 53, which was designed to include all possible amino acids at the respective position. The libraries were screened as periplasmic extracts in a ligand competition FACS. First, a dilution series was made of periplasmic material from the parental sequence and three dilutions were selected for further screening. A first dilution point (two fold) was chosen to give full block of the ligand interaction whereas the other two dilution points (128 and 512 fold) should result in 70% and 40% block respectively. Upon production of the periplasmic extracts from the library, all samples were split in two and one of them was subjected to a heat treatment. Both the non-treated and the heat treated samples were subsequently analyzed in the ligand competition FACS at the three dilution points. The impact of the mutation could be estimated by comparing the obtained blockage with that from the parental sequence. The analysis of the heat treated samples provides a measure for a potential impact on stability of the mutation.

Based upon the initial screening results, seven mutations were selected for further characterization. The obtained potency in ligand competition FACS is shown in Table 37.

TABLE 37

Removal glycosylation site at position 52

| Construct | IC50 (M) | % block | Tm at pH 7 |
|---|---|---|---|
| C100CX3CR1BII66B02 | 2.5E−09 | 98.0 | 65.66 |
| CX3CR1BII66B02 (N52S, Q108L) | 1.7E−09 | 98.0 | 66.07 |
| CX3CR1BII66B02 (N52Q, Q108L) | 2.1E−09 | 97.9 | 59.83 |
| CX3CR1BII66B02 (N52G, Q108L) | 1.1E−09 | 98.0 | 59.83 |
| CX3CR1BII66B02 (N52T, Q108L) | 2.8E−09 | 98.0 | 66.07 |
| CX3CR1BII66B02 (S53T, Q108L) | 1.3E−09 | 98.1 | 66.07 |
| CX TABLE 38-continued Sequence optimized variants of the lead VHH 66B02

| Clone number | Mutation introduced | SEQ ID NO: |
|---|---|---|
| CX3CR1BII00307 | CX3CR1BII66B02(E1D, S11L, A14P, E16G, N32T, N52S, S53T, A74S, K86R, Q113L) | 139 |
| CX3CR1BII00308 | CX3CR1BII66B02(E1D, S11L, A14P, E16G, A74S, K86R, Q113L) | 140 |
| CX3CR1BII00312 | CX3CR1BII66B02(E1D, S11L, A14P, E16G, N32T, N52S, A74S, K86R, Q113L)-9GS-Alb11-9GS-CX3CR1BII66B02(S11L, A14P, E16G, N32T, N52S, A74S, K86R, Q113L) | 225 |
| CX3CR1BII00313 | CX3CR1BII66B02(E1D, S11L, A14P, E16G, N32T, N52S, S53T, A74S, K86R, Q113L)-9GS-Alb11-9GS-CX3CR1BII66B02(S11L, A14P, E16G, N32T, N52S, S53T, A74S, K86R, Q113L) | 226 |
| CX3CR1BII00314 | CX3CR1BII66B02(E1D, S11L, A14P, E16G, A74S, K86R, Q113L)-9GS-Alb11-9GS-CX3CR1BII66B02(S11L, A14P, E16G, A74S, K86R, Q113L) | 227 |

A competition FACS experiment was performed as described above as well as a determination of the melting temperature. The obtained values are represented in Table 39.

TABLE 39

Competition FACS and Tm of the sequence optimized variants

| Construct | IC50 (M) | % block | Tm at pH 7 |
|---|---|---|---|
| C100CX3CR1BII66B02 | 2.5E−09 | 98.0 | 65.05 |
| CX3CR1BII00306 | 1.7E−09 | 97.0 | 68.54 |
| CX3CR1BII00307 | 1.9E−09 | 97.0 | 68.13 |
| CX3CR1BII00308 | 1.6E−09 | 97.0 | 68.13 |
| CX3CR1BII00312 | 4.6E−10 | 100.0 | 59.37 |
| CX3CR1BII00313 | 4.0E−10 | 100.0 | 58.88 |
| CX3CR1BII00314 | 6.5E−10 | 100.0 | 58.40 |

These constructs were also characterized in fractalkine induced chemotaxis as described above (Table 40).

TABLE 40

Ligand induced chemotaxis with sequence optimized variants

| Construct | IC50 (M) | % block | n |
|---|---|---|---|
| C100CX3CR1BII66B02 | 3.6E−08 | 91 | 3 |
| CX3CR1BII00306 | 6.3E−08 | 95 | 2 |
| CX3CR1BII00307 | 6.3E−08 | 100 | 2 |
| CX3CR1BII00308 | 4.4E−08 | 89 | 2 |
| CX3CR1BII00312 | 2.7E−09 | 99 | 3 |
| CX3CR1BII00313 | 2.7E−09 | 99 | 3 |
| CX3CR1BII00314 | 3.6E−09 | 100 | 3 |

Selected constructs were evaluated for inhibition of A647-Fractalkine induced internalization in CHO huCX3CR1 cells. The results are summarized in Table 41:

TABLE 41

Ligand induced internalization with sequence optimized variants

| Construct | IC50 (M) | n |
|---|---|---|
| CX3CR1BII00312 | 5.5E−10 | 1 |
| CX3CR1BII00313 | 3.3E−10 | 6 |

A Sequence Optimized Anti-CX3CR1 Half-Life Extended Polypeptide is Devoid of Agonist Activity In order to confirm that sequence optimized anti-CX3CR1 half-life extended polypeptide does not have agonist activity, CX3CR1BII00313 was evaluated for induction of calcium influx in the CHO huCX3CR1 cells. While preincubation with CX3CR1BII00313 inhibited Fractalkine-mediated calcium influx with an IC50 of 1.3 nM, no increase in cytosolic calcium levels were observed when the polypeptide alone was added at concentrations up to 1 μM.

Example 12

Exploration of Half Life Extension Formats Using Human Fc

To investigate additional half-life extension modalities, the CX3CR1BII00306 and CX3CR1 BII00307 sequence optimized VHH domains were produced as fusion proteins with a human IgG1 Fc domain (306D-hFc and 307D-hFc). Two mutations were incorporated in the CH2 domain to abrogate potential Fc-mediated effector function in this construct. 306D-hFc and 307D-hFc were expressed in HEK293T cells or NS0 cells and purified by Protein A affinity chromatography followed by ion exchange chromatography. These molecules were tested for functional activity utilizing the assay formats described in Example 7. The results are summarized in Table 42:

TABLE 42

Activity of hFc Fusion Proteins

| Assay | Cell line | 306D-hFc IC50 | 306D-hFc Repeats | 307D-hFc IC50 | 307D-hFc Repeats |
|---|---|---|---|---|---|
| Ligand competition | BA/F3-huCX3CR1 | 6.9E−10 | 2 | 7.0E−10 | 2 |
| Chemotaxis | BA/F3-huCX3CR1 | 2.9E−9 | 2 | 3.0E−9 | 3 |
| Ligand internalization | CHO-huCX3CR1 | 4.8E−10 | 3 | 3.7E−10 | 3 |
| Calcium influx | CHO-huCX3CR1 | 1.3E−9 | 3 | 3.2E−9 | 3 |

While these molecules potently inhibited Fractalkine mediated CX3CR1 activation, they did not display agonist activity. No increases in cytosolic calcium levels were observed with treatment with up to 1 μM of these Nanobodies alone.

Example 13

Inhibition of Plaque Progression in a Mouse Atherosclerosis Model by a Sequence Optimized Anti-CX3CR1 Nanobody Female hu CX3CR1 KI ApoE$^{-/-}$ mice were fed a high fat/high cholesterol diet containing 1.5% cholesterol for 16 weeks beginning at four weeks of age. After 10 weeks, the animals were administered by i.p. injection vehicle (20 mM NaCitrate pH 6.0, 115 mM NaCl), 30 mg/kg CX3CR1 BII00313 once or twice per week or 30 mg/kg CX3CR1 BII036 twice per week for 6 weeks. The animals were sacrificed and the percentage of plaque area in the descending aorta was quantitated as described above. The results from this study are summarized in Table 43:

TABLE 43

Quantification of Plaque Size in the Descending Aorta in female hu CX3CR1 KI Apo E$^{-/-}$ Mice

| Group | Dose | # Animals | % Plaque Area | % Reduction in Plaque Area |
|---|---|---|---|---|
| Control (10 weeks) | N/A | 6 | 2.1 | N/A |
| Control (16 weeks) | Vehicle | 18 | 12.0 | N/A |
| CX3CR1BII00313 | 30 mg/kg (1× week) | 17 | 10.7 | 13 |
| CX3CR1BII00313 | 30 mg/kg (2×/week) | 18 | 5.9 | 62 (p < 0.01) |
| CX3CR1BII036 | 30 mg/kg (2×/week) | 17 | 6.8 | 52 (p < 0.01) |

Both CX3CR1 BII00313 and CX3CR1 BII036 significantly inhibited plaque progression when dosed twice weekly. This correlated with coverage as plasma levels of these molecules could be confirmed to be maintained throughout the study. For once weekly dosing of CX3CR1BII00313, detectable plasma levels were not maintained and this correlated with the lack of significant efficacy observed after 6 weeks of treatment. Neither molecule significantly affected plasma cholesterol or triglyceride levels.

Example 14

Nanobody Binding to Primary Human and Cynomolgus Monkey CD14+ Cells in Whole Blood Competition FACS with Formatted Sequence Optimized Anti-CX3CR1 Nanobody To confirm binding of the formatted sequence optimized anti-CX3CR1 Nanobody to human primary cells, CX3CR1BII00313 was demonstrated to compete for the binding of A647 labeled CX3CR1BII018 (A647-018) to CD14+ cells in a competition FACS assay in whole blood. Briefly, a mouse anti-human CD14 antibody conjugated with eFluor 450 (eBioscience, San Diego, Calif., USA) was diluted 1:10 in EDTA treated whole blood from a healthy human donor. 40 µl/well was added to 96 well polystyrene round bottom plate followed by 10 µl/well of CX3CR1BII00313 diluted in Stain Buffer with BSA (BD Pharmingen) at a final concentration ranging from 100 nM to 0.002 pM and the samples were incubated for 20 minutes at room temperature. 10 µl/well of A647-018 in Stain Buffer was then added to yield a final concentration of 1 nM (the EC80 of A647-018 binding) and the samples were incubated for an additional 20 minutes at room temperature. 220 µl/well of 1-Step Fix/Lyse solution (eBioscience) was then added. After a 10 minute room temperature incubation the cells were pelleted, washed twice in Stain buffer and resuspended in this buffer. The samples were analyzed on a BD LSR II flow cytometer. The median fluorescence intensity for AlexaFluor 647 was quantified for the gate CD14 positive cell population. CX3CR1BII00313 potently inhibited the binding of A647-018 to CD14 positive cells in human blood with an IC50 of 0.35 nM (n=8).

To confirm binding of the formatted sequence optimized anti-CX3CR1 Nanobody to cynomolgus monkey primary cells, CX3CR1BII00313 was demonstrated to compete for the binding of A647 labeled CX3CR1BII018 (A647-018) to CD14+ cells in a competition FACS assay in cynomolgus monkey whole blood. The method used was analogous to that outlined above except the final concentration of A647-018 was 3 nM (the EC80 of A647-018 binding) and ACK lysing buffer (Life Technologies) was used instead of the 1-Step Fix/Lyse solution. The cells were resuspended in Stain buffer supplemented with 1% formaldehyde prior to analysis. CX3CR1 BII00313 potently inhibited the binding of A647-018 to CD14 positive cells in cynomolgus monkey blood with an IC50 of 0.43 nM (n=4).

Example 15

Pharmacokinetics (PK) in Cynomolgus Monkeys

A pharmacokinetic study was conducted in naïve male cynomolgus monkeys (*Macaca fascicularis*) 2-5 years of age with a body weight range between 2.4-3.5 kg. The monkeys were divided into four treatment groups. Group 1 (n=3) received 0.2 mg/kg of CX3CR1 BII00313 i.v.; Group 2 (n=3) received 2 mg/kg of CX3CR1 BII00313 i.v.; Group 3 (n=3) received 2 mg/kg CX3CR1 BII00313 s.c. and Group 4 (n=3) received 5 mg/kg CX3CR1 BII00313 i.v. CX3CR1 BII00313 was administered as a 2 mg/ml solution in citrate buffer (20 mM sodium citrate/115 mM sodium chloride, pH 6.0). Blood samples were collected over 6 weeks from a peripheral vein into serum separator tubes for PK analysis.

Serum samples were analyzed using a MSD (Meso Scale Discovery) format. Briefly, a biotinylated anti-Nanobody antibody was bound to a MSD standard streptavidin plate (Meso Scale Discovery, Rockville, Md., USA). The plates were washed with 0.05% Tween 20 in phosphate buffered saline and blocked with 5% w/v of SeraCare BSA (SeraCare Life Sciences, Milford, Mass., USA) prior to incubation with serum samples. CX3CR1 BII00313 was detected utilizing a sulfo-labeled anti-Nanobody Nanobody and the plates were analyzed on a Sector Imager 2400 (Meso Scale Discovery). Varying concentrations of CX3CR1 BII0313 from 5000 to 0.5 ng/ml in 5% monkey serum were used as standards. Target engagement was assessed by monitoring levels of free CX3CR1 on CD14+ gated monocytes. This assay was analogous to the competition FACS assay summarized in Example 14 except no additional CX3CR1 BII00313 was added. Serum samples were also monitored for the presence of primate anti-human antibodies (PAHA) as they may impact assessment of PK and free CX3CR1.

ForteBio RED96 was used for detection of PAHA. Briefly, biotinylated CX3CR1BII0313 was captured over streptavidin sensors. Pooled naïve monkey serum was then used as a negative control to calculate cut-off value (defined as two fold above the average binding signal of naïve sera). All serum samples were diluted 20 fold in buffer and the PAHA response was determined to be positive if the binding signal was greater than the cut-off value.

Data for time points following detection of PAHA were excluded from PK/PD analysis. The PK data are summarized in Table 44 below.

TABLE 44

Pharmacokinetic parameters of CX3CR1BII00313

| Dose (mg/kg) | CL (mL/day/kg) | $T_{1/2}$ (day) | MRT (day) | Dose normalized AUC(0-14 d) (nM · d) | F % |
|---|---|---|---|---|---|
| IV 0.2 | 113 | 1 | 1 | ** | |
| IV 2.0 | 9 ± 1 | 9 ± 2 | 8 ± 2 | 56530 | |
| IV 5.0 | ** | ** | ** | 58604 | |
| SC 2.0 | | | | | 54 |

** insufficient data for characterization of terminal phase

Clearance and half-life at 2.0 mg/kg i.v. were 9.4 mL/d/kg and 9.6 days, respectively. At 0.2 mg/kg i.v., clearance was substantially higher (113 mL/d/kg) consistent with saturable target-mediated disposition (TMD) pharmacokinetics. Dose-adjusted $AUC_{(0-14d)}$ was comparable between the 2 and 5 mg/kg i.v. doses suggesting saturation of TMD at the 2 mg/kg dose. Exposure at 2 weeks following either i.v. or s.c. Nanobody administration was >70 nM and bioavailability after s.c. administration was 54%. Free receptor tracked with exposure with greater than 90% target coverage maintained at exposures >10 nM.

The invention claimed is:

1. A method for the treatment of a CX3CR1-associated disease, disorder or condition selected from diabetic nephropathy, glomerulonephritis, human crescentic glomerulonephritis, IgA nephropathy, membranous nephropathy and lupus nephritis, comprising administering a therapeutic amount of a polypeptide comprising an anti-CX3CR1 (anti-CX3 chemokine receptor 1) immunoglobulin single variable domain, wherein said polypeptide comprises a CDR1, CDR2 and CDR3 having the amino acid sequences set forth in:

SEQ ID No: 141, 162 and 186, respectively; or
SEQ ID No: 141, 163 and 187, respectively; or
SEQ ID No: 141, 164 and 186, respectively; or
SEQ ID No: 141, 166 and 186, respectively; or
SEQ ID No: 141, 167 and 186, respectively; or
SEQ ID No: 141, 167 and 189, respectively; or
SEQ ID No: 141, 168 and 186, respectively; or
SEQ ID No: 141, 168 and 187, respectively; or
SEQ ID No: 141, 169 and 190, respectively; or
SEQ ID No: 141, 170 and 186, respectively; or
SEQ ID No: 141, 171 and 186, respectively; or
SEQ ID No: 141, 174 and 186, respectively; or
SEQ ID No: 141, 175 and 187, respectively; or
SEQ ID No: 142, 165 and 188, respectively; or
SEQ ID No: 142, 173 and 188, respectively; or
SEQ ID No: 143, 164 and 186, respectively; or
SEQ ID No: 144, 172 and 187, respectively; or
SEQ ID No: 145, 172 and 187, respectively; or
SEQ ID No: 141, 214 and 186, respectively; or
SEQ ID No: 141, 215 and 186, respectively; or
SEQ ID No: 141, 216 and 186, respectively; or
SEQ ID No: 141, 217 and 186, respectively; or
SEQ ID No: 141, 218 and 186, respectively; or
SEQ ID No: 141, 219 and 186, respectively; or
SEQ ID No: 141, 220 and 186, respectively; or
SEQ ID No: 213, 221 and 186, respectively; or
SEQ ID No: 213, 214 and 186, respectively;
to a patient in need thereof.

2. The method according to claim 1, wherein the disease, disorder or condition is diabetic nephropathy.

* * * * *

SEQUENCE LISTING

```
<160> NUMBER OF SEQ ID NOS: 282

<210> SEQ ID NO 1
<211> LENGTH: 118
<212> TYPE: PRT
<213> ORGANISM: Artificial Sequence
<220> FEATURE:
<223> OTHER INFORMATION: Nanobody sequence

<400> SEQUENCE: 1

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser
        115

<210> SEQ ID NO 2
<211> LENGTH: 118
<212> TYPE: PRT
<213> ORGANISM: Artificial Sequence
<220> FEATURE:
<223> OTHER INFORMATION: Nanobody sequence

<400> SEQUENCE: 2

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Val Ile Asn Ser Val Gly Ile Thr Lys Tyr Ala Asp Ser Val Lys
    50                  55                  60

Gly Arg Phe Thr Ile Ser Gly Asp Asn Ala Lys Asn Thr Val Tyr Leu
65                  70                  75                  80
```

```
Gln Met Asn Ser Leu Lys Pro Glu Asp Thr Ala Val Tyr Tyr Cys Thr
            85                  90                  95

Ser Asp Ala Arg Arg Gly Trp Asp Thr Arg Tyr Trp Gly Gln Gly Thr
            100                 105                 110

Gln Val Thr Val Ser Ser
            115

<210> SEQ ID NO 3
<211> LENGTH: 118
<212> TYPE: PRT
<213> ORGANISM: Artificial Sequence
<220> FEATURE:
<223> OTHER INFORMATION: Nanobody sequence

<400> SEQUENCE: 3

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
            35                  40                  45

Ala Gly Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65              70                  75                  80

Gln Met Asn Ser Leu Lys Pro Glu Asp Thr Ala Val Tyr Tyr Cys Thr
            85                  90                  95

Ser Asp Pro Arg Arg Gly Trp Asp Thr Arg Tyr Trp Gly Gln Gly Thr
            100                 105                 110

Gln Val Thr Val Ser Ser
            115

<210> SEQ ID NO 4
<211> LENGTH: 118
<212> TYPE: PRT
<213> ORGANISM: Artificial Sequence
<220> FEATURE:
<223> OTHER INFORMATION: Nanobody sequence

<400> SEQUENCE: 4

Glu Val Gln Leu Val Glu Ser Gly Arg Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
            35                  40                  45

Ala Gly Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65              70                  75                  80

Gln Met Asn Ser Leu Lys Pro Glu Asp Thr Ala Val Tyr Tyr Cys Thr
            85                  90                  95

Ser Asp Pro Arg Arg Gly Trp Asp Thr Arg Tyr Trp Gly Gln Gly Thr
            100                 105                 110

Gln Val Thr Val Ser Ser
            115

<210> SEQ ID NO 5
```

```
<211> LENGTH: 118
<212> TYPE: PRT
<213> ORGANISM: Artificial Sequence
<220> FEATURE:
<223> OTHER INFORMATION: Nanobody sequence

<400> SEQUENCE: 5

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 6
<211> LENGTH: 118
<212> TYPE: PRT
<213> ORGANISM: Artificial Sequence
<220> FEATURE:
<223> OTHER INFORMATION: Nanobody sequence

<400> SEQUENCE: 6

Glu Val Gln Leu Val Glu Ser Gly Gly Gly Ser Val Gln Ala Gly Glu
1               5                   10                  15

Ser Leu Arg Leu Ser Cys Ala Ala Ser Gly Thr Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Asp Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asn Thr Arg Tyr Trp Gly Gln Gly Thr
            100                 105                 110

Gln Val Thr Val Ser Ser
        115

<210> SEQ ID NO 7
<211> LENGTH: 118
<212> TYPE: PRT
<213> ORGANISM: Artificial Sequence
<220> FEATURE:
<223> OTHER INFORMATION: Nanobody sequence

<400> SEQUENCE: 7

Glu Val Gln Leu Val Glu Ser Gly Gly Gly Ser Val Gln Ala Gly Glu
1               5                   10                  15
```

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Thr
            85                  90                  95

Ser Asp Pro Arg Arg Gly Trp Asp Thr Arg Tyr Trp Gly Gln Gly Thr
            100                 105                 110

Gln Val Thr Val Ser Ser
            115

<210> SEQ ID NO 8
<211> LENGTH: 118
<212> TYPE: PRT
<213> ORGANISM: Artificial Sequence
<220> FEATURE:
<223> OTHER INFORMATION: Nanobody sequence

<400> SEQUENCE: 8

Glu Val Gln Leu Val Glu Ser Gly Gly Gly Ser Val Gln Ala Gly Glu
1               5                   10                  15

Ser Leu Arg Leu Ser Cys Ala Ala Ser Gly Thr Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Asp Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
            85                  90                  95

Ser Asp Pro Arg Arg Gly Trp Asn Thr Arg Tyr Trp Gly Gln Gly Thr
            100                 105                 110

Leu Val Thr Val Ser Ser
            115

<210> SEQ ID NO 9
<211> LENGTH: 118
<212> TYPE: PRT
<213> ORGANISM: Artificial Sequence
<220> FEATURE:
<223> OTHER INFORMATION: Nanobody sequence

<400> SEQUENCE: 9

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Ala Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

```
Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser
        115

<210> SEQ ID NO 10
<211> LENGTH: 118
<212> TYPE: PRT
<213> ORGANISM: Artificial Sequence
<220> FEATURE:
<223> OTHER INFORMATION: Nanobody sequence

<400> SEQUENCE: 10

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 11
<211> LENGTH: 119
<212> TYPE: PRT
<213> ORGANISM: Artificial Sequence
<220> FEATURE:
<223> OTHER INFORMATION: Nanobody sequence

<400> SEQUENCE: 11

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Pro Gly Lys Gln Arg Asp Leu
        35                  40                  45

Val Ala Leu Ile Asn Ser Val Gly Ile Thr Lys Tyr Ala Asp Ser Val
    50                  55                  60

Lys Gly Arg Phe Thr Ile Ser Asp Asn Ala Lys Asn Thr Val Tyr
65                  70                  75                  80

Leu Glu Met Asn Ser Leu Lys Pro Glu Asp Thr Ala Val Tyr Tyr Cys
                85                  90                  95

Thr Ser Asp Gly Arg Arg Gly Trp Asp Thr Arg Tyr Trp Gly Gln Gly
            100                 105                 110

Thr Gln Val Thr Val Ser Ser
        115
```

```
<210> SEQ ID NO 12
<211> LENGTH: 118
<212> TYPE: PRT
<213> ORGANISM: Artificial Sequence
<220> FEATURE:
<223> OTHER INFORMATION: Nanobody sequence

<400> SEQUENCE: 12

Glu Val Gln Leu Val Glu Ser Gly Gly Gly Ser Val Gln Ala Gly Gly
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 13
<211> LENGTH: 118
<212> TYPE: PRT
<213> ORGANISM: Artificial Sequence
<220> FEATURE:
<223> OTHER INFORMATION: Nanobody sequence

<400> SEQUENCE: 13

Lys Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Ala Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 14
<211> LENGTH: 118
<212> TYPE: PRT
<213> ORGANISM: Artificial Sequence
<220> FEATURE:
<223> OTHER INFORMATION: Nanobody sequence

<400> SEQUENCE: 14

Glu Val Gln Leu Val Glu Ser Gly Gly Gly Ser Val Gln Ala Gly Glu
1               5                   10                  15
```

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Leu Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 15
<211> LENGTH: 118
<212> TYPE: PRT
<213> ORGANISM: Artificial Sequence
<220> FEATURE:
<223> OTHER INFORMATION: Nanobody sequence

<400> SEQUENCE: 15

Glu Val Gln Leu Val Glu Ser Gly Gly Gly Ser Val Gln Ala Gly Glu
1               5                   10                  15

Ser Leu Arg Leu Ser Cys Ala Ala Ser Gly Thr Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Asp Ile Thr Lys Tyr Ala Asp Ser Val Lys
    50                  55                  60

Gly Arg Phe Thr Val Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asn Thr Arg Tyr Trp Gly Gln Gly Thr
            100                 105                 110

Gln Val Thr Val Ser Ser
        115

<210> SEQ ID NO 16
<211> LENGTH: 118
<212> TYPE: PRT
<213> ORGANISM: Artificial Sequence
<220> FEATURE:
<223> OTHER INFORMATION: Nanobody sequence

<400> SEQUENCE: 16

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Val Ile Asn Ser Val Gly Ile Thr Lys Tyr Ala Asp Ser Val Lys
    50                  55                  60

Gly Arg Phe Thr Ile Ser Gly Asp Asn Ala Lys Asn Thr Val Tyr Leu

```
                65                  70                  75                  80
Gln Met Asn Ser Leu Lys Pro Glu Asp Thr Ala Val Tyr Tyr Cys Thr
                85                  90                  95

Ser Asp Ala Arg Arg Gly Trp Asp Thr Arg Tyr Trp Gly Gln Gly Thr
            100                 105                 110

Leu Val Thr Val Ser Ser
        115

<210> SEQ ID NO 17
<211> LENGTH: 118
<212> TYPE: PRT
<213> ORGANISM: Artificial Sequence
<220> FEATURE:
<223> OTHER INFORMATION: Nanobody sequence

<400> SEQUENCE: 17

Lys Val Gln Leu Val Glu Ser Gly Gly Gly Ser Val Gln Ala Gly Glu
1               5                   10                  15

Ser Leu Arg Leu Ser Cys Ala Ala Ser Gly Thr Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Asp Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asn Thr Arg Tyr Trp Gly Gln Gly Thr
            100                 105                 110

Gln Val Thr Val Ser Ser
        115

<210> SEQ ID NO 18
<211> LENGTH: 118
<212> TYPE: PRT
<213> ORGANISM: Artificial Sequence
<220> FEATURE:
<223> OTHER INFORMATION: Nanobody sequence

<400> SEQUENCE: 18

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Phe Gly Lys Gln Arg Asp Leu Val
        35                  40                  45

Ala Leu Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser
        115
```

<210> SEQ ID NO 19
<211> LENGTH: 118
<212> TYPE: PRT
<213> ORGANISM: Artificial Sequence
<220> FEATURE:
<223> OTHER INFORMATION: Nanobody sequence

<400> SEQUENCE: 19

```
Lys Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Phe Gly Lys Gln Arg Asp Leu Val
        35                  40                  45

Ala Leu Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser
        115
```

<210> SEQ ID NO 20
<211> LENGTH: 118
<212> TYPE: PRT
<213> ORGANISM: Artificial Sequence
<220> FEATURE:
<223> OTHER INFORMATION: Nanobody sequence

<400> SEQUENCE: 20

```
Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Met Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser
        115
```

<210> SEQ ID NO 21
<211> LENGTH: 118
<212> TYPE: PRT
<213> ORGANISM: Artificial Sequence
<220> FEATURE:
<223> OTHER INFORMATION: Nanobody sequence

<400> SEQUENCE: 21

Lys Val Gln Leu Val Glu Ser Gly Gly Gly Ser Val Gln Ala Gly Glu

-continued

```
                1               5                  10                  15
Ser Leu Arg Leu Ser Cys Ala Ala Ser Gly Ser Ile Phe Ser Ser Asn
            20                  25                  30

Ala Met Ala Trp Tyr Arg Gln Pro Pro Gly Lys Gln Arg Asp Leu Val
            35                  40                  45

Ala Ala Ile Asn Ser Val Gly Ile Thr Lys Tyr Ala Asp Ser Val Lys
        50                  55                  60

Gly Arg Phe Thr Ile Phe Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser
            115
```

<210> SEQ ID NO 22
<211> LENGTH: 118
<212> TYPE: PRT
<213> ORGANISM: Artificial Sequence
<220> FEATURE:
<223> OTHER INFORMATION: Nanobody sequence

<400> SEQUENCE: 22

```
                1               5                  10                  15
Glu Val Gln Leu Val Lys Ser Gly Gly Gly Ser Val Gln Ala Gly Glu

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
            35                  40                  45

Ala Leu Ile Asn Ser Val Gly Ile Thr Lys Tyr Ala Asp Ser Val Lys
        50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser
            115
```

<210> SEQ ID NO 23
<211> LENGTH: 118
<212> TYPE: PRT
<213> ORGANISM: Artificial Sequence
<220> FEATURE:
<223> OTHER INFORMATION: Nanobody sequence

<400> SEQUENCE: 23

```
                1               5                  10                  15
Lys Val Gln Leu Val Glu Ser Gly Gly Gly Ser Met Gln Ala Gly Glu

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
            35                  40                  45

Ala Ala Ile Asn Ser Val Gly Ile Thr Lys Tyr Ala Asp Ser Val Lys
        50                  55                  60
```

```
Gly Arg Phe Thr Ile Ser Arg Asp Asn Ala Lys Asn Thr Val Tyr Leu
 65                  70                  75                  80

Gln Met Met Ser Leu Lys Pro Glu Asp Thr Ala Val Tyr Tyr Cys Thr
                 85                  90                  95

Ser Asp Pro Arg Arg Gly Trp Asp Thr Arg Tyr Trp Gly Gln Gly Thr
            100                 105                 110

Gln Val Thr Val Ser Ser
            115

<210> SEQ ID NO 24
<211> LENGTH: 118
<212> TYPE: PRT
<213> ORGANISM: Artificial Sequence
<220> FEATURE:
<223> OTHER INFORMATION: Nanobody sequence

<400> SEQUENCE: 24

Lys Val Gln Leu Val Glu Ser Gly Gly Gly Val Gln Ala Gly Gly
 1               5                  10                  15

Ser Leu Arg Leu Ser Cys Ala Ala Ser Gly Ser Ile Phe Ser Ser Asn
                20                  25                  30

Ala Met Ala Trp Tyr Arg Gln Ala Pro Gly Lys Gln Arg Asp Leu Val
            35                  40                  45

Ala Ala Ile Asn Ser Val Gly Ile Thr Lys Tyr Ala Asp Ser Val Lys
        50                  55                  60

Gly Arg Phe Thr Ile Ser Arg Asp Asn Ala Lys Asn Thr Val Tyr Leu
 65                  70                  75                  80

Gln Met Met Ser Leu Lys Pro Glu Asp Thr Ala Val Tyr Tyr Cys Thr
                 85                  90                  95

Ser Asp Pro Arg Arg Gly Trp Asp Thr Arg Tyr Trp Gly Gln Gly Thr
            100                 105                 110

Gln Val Thr Val Ser Ser
            115

<210> SEQ ID NO 25
<211> LENGTH: 118
<212> TYPE: PRT
<213> ORGANISM: Artificial Sequence
<220> FEATURE:
<223> OTHER INFORMATION: Nanobody sequence

<400> SEQUENCE: 25

Glu Val Gln Leu Val Glu Ser Gly Gly Gly Val Gln Ala Gly Ala
 1               5                  10                  15

Ser Leu Arg Leu Ser Cys Ala Ala Ser Gly Ser Ile Phe Ser Ser Asn
                20                  25                  30

Ala Met Ala Trp Tyr Arg Gln Ala Pro Gly Lys Gln Arg Asp Leu Val
            35                  40                  45

Ala Val Ile Asn Thr Val Gly Ile Thr Lys Tyr Ala Asp Ser Val Lys
        50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                 85                  90                  95

Ser Asp Ala Arg Arg Gly Trp Asp Thr Arg Tyr Trp Gly Gln Gly Thr
            100                 105                 110

Leu Val Thr Val Ser Ser
            115
```

```
<210> SEQ ID NO 26
<211> LENGTH: 118
<212> TYPE: PRT
<213> ORGANISM: Artificial Sequence
<220> FEATURE:
<223> OTHER INFORMATION: Nanobody sequence

<400> SEQUENCE: 26

Glu Val Gln Leu Val Glu Ser Arg Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Val Ile Asn Ser Val Gly Ile Thr Lys Tyr Ala Asp Ser Val Lys
    50                  55                  60

Gly Arg Phe Thr Ile Ser Gly Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Ala Arg Arg Gly Trp Asp Thr Arg Tyr Trp Gly Gln Gly Thr
            100                 105                 110

Gln Val Thr Val Ser Ser
        115

<210> SEQ ID NO 27
<211> LENGTH: 118
<212> TYPE: PRT
<213> ORGANISM: Artificial Sequence
<220> FEATURE:
<223> OTHER INFORMATION: Nanobody sequence

<400> SEQUENCE: 27

Glu Val Gln Leu Val Glu Ser Arg Gly Gly Ser Val Gln Ala Gly Ala
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Val Ile Asn Thr Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Ala Arg Arg Gly Trp Asp Thr Arg Tyr Trp Gly Gln Gly Thr
            100                 105                 110

Gln Val Thr Val Ser Ser
        115

<210> SEQ ID NO 28
<211> LENGTH: 118
<212> TYPE: PRT
<213> ORGANISM: Artificial Sequence
<220> FEATURE:
<223> OTHER INFORMATION: Nanobody sequence

<400> SEQUENCE: 28
```

```
Glu Val Gln Leu Val Lys Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Leu Gly Lys Gln Arg Asp Leu Val
        35                  40                  45

Ala Leu Ile Asp Ser Ala Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Arg Leu Lys Pro Glu Asp Thr Ala Val Tyr Tyr Cys Ala
                85                  90                  95

Ser Asp Ala Arg Arg Gly Trp Asn Thr Lys Tyr Trp Gly Gln Gly Thr
            100                 105                 110

Leu Val Thr Val Ser Ser
        115
```

<210> SEQ ID NO 29
<211> LENGTH: 118
<212> TYPE: PRT
<213> ORGANISM: Artificial Sequence
<220> FEATURE:
<223> OTHER INFORMATION: Nanobody sequence

<400> SEQUENCE: 29

```
Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Ala Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val His Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115
```

<210> SEQ ID NO 30
<211> LENGTH: 118
<212> TYPE: PRT
<213> ORGANISM: Artificial Sequence
<220> FEATURE:
<223> OTHER INFORMATION: Nanobody sequence

<400> SEQUENCE: 30

```
Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Gly Ile Ala Lys Tyr Ala Asp Ser Val Lys
    50                  55                  60
```

```
Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                 85                  90                  95

Ser Asp Pro Arg Arg Gly Trp Asp Thr Arg Tyr Trp Gly Gln Gly Thr
            100                 105                 110

Leu Val Thr Val Ser Ser
        115
```

<210> SEQ ID NO 31
<211> LENGTH: 118
<212> TYPE: PRT
<213> ORGANISM: Artificial Sequence
<220> FEATURE:
<223> OTHER INFORMATION: Nanobody sequence

<400> SEQUENCE: 31

```
Glu Val Gln Leu Val Glu Ser Gly Gly Gly Ser Val Gln Ala Gly Glu
 1               5                  10                  15

Ser Leu Arg Leu Ser Cys Ala Ala Ser Gly Ser Ile Phe Ser Ser Asn
                20                  25                  30

Ala Lys Ala Trp Tyr Arg Gln Ala Pro Gly Lys Gln Arg Asp Leu Val
            35                  40                  45

Ala Gly Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                 85                  90                  95

Ser Asp Pro Arg Arg Gly Trp Asp Thr Arg Tyr Trp Gly Gln Gly Thr
            100                 105                 110

Leu Val Thr Val Ser Ser
        115
```

<210> SEQ ID NO 32
<211> LENGTH: 118
<212> TYPE: PRT
<213> ORGANISM: Artificial Sequence
<220> FEATURE:
<223> OTHER INFORMATION: Nanobody sequence

<400> SEQUENCE: 32

```
Lys Val Gln Leu Val Glu Ser Gly Gly Gly Ser Val Gln Ala Gly Glu
 1               5                  10                  15

Ser Leu Arg Leu Ser Cys Ala Ala Ser Gly Ser Ile Phe Ser Ser Asn
                20                  25                  30

Ala Met Ala Trp Tyr Arg Gln Ala Pro Gly Lys Gln Arg Asp Leu Val
            35                  40                  45

Ala Gly Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                 85                  90                  95

Ser Asp Pro Arg Arg Gly Trp Asp Thr Arg Tyr Trp Gly Gln Gly Thr
            100                 105                 110

Leu Val Thr Val Ser Ser
```

-continued

```
<210> SEQ ID NO 33
<211> LENGTH: 118
<212> TYPE: PRT
<213> ORGANISM: Artificial Sequence
<220> FEATURE:
<223> OTHER INFORMATION: Nanobody sequence

<400> SEQUENCE: 33
```

Glu Val Gln Leu Val Lys Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Val Ile Asn Lys Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser
        115

```
<210> SEQ ID NO 34
<211> LENGTH: 118
<212> TYPE: PRT
<213> ORGANISM: Artificial Sequence
<220> FEATURE:
<223> OTHER INFORMATION: Nanobody sequence

<400> SEQUENCE: 34
```

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Ala Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

```
<210> SEQ ID NO 35
<211> LENGTH: 118
<212> TYPE: PRT
<213> ORGANISM: Artificial Sequence
<220> FEATURE:
<223> OTHER INFORMATION: Nanobody sequence

<400> SEQUENCE: 35
```

```
Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Arg Asn
            20                  25                  30

Ala Met Ala Trp Tyr Arg Gln Ala Pro Gly Lys Gln Arg Asp Leu Val
        35                  40                  45

Ala Ser Ile Asn Ser Val Gly Ile Thr Lys Tyr Gly Asp Ser Val Lys
    50                  55                  60

Gly Arg Phe Thr Ile Ser Arg Asp Asn Ala Lys Asn Thr Val Tyr Leu
65              70                  75                  80

Gln Met Asn Ser Leu Lys Pro Glu Asp Thr Ala Val Tyr Tyr Cys Thr
                85                  90                  95

Ser Asp Ala Arg Arg Gly Trp Asp Thr Arg Tyr Trp Gly Gln Gly Thr
            100                 105                 110

Leu Val Thr Val Ser Ser
            115
```

<210> SEQ ID NO 36
<211> LENGTH: 118
<212> TYPE: PRT
<213> ORGANISM: Artificial Sequence
<220> FEATURE:
<223> OTHER INFORMATION: Nanobody sequence

<400> SEQUENCE: 36

```
Glu Val Gln Leu Val Glu Ser Gly Gly Gly Ser Val Gln Ala Gly Glu
1               5                   10                  15

Ser Leu Arg Leu Ser Cys Ala Ala Ser Gly Gly Ile Phe Ser Arg Asn
            20                  25                  30

Ala Met Ala Trp Tyr Arg Gln Ala Pro Gly Lys Gln Arg Asp Leu Val
        35                  40                  45

Ala Ser Ile Asn Ser Val Gly Ile Thr Lys Tyr Gly Asp Ser Val Lys
    50                  55                  60

Gly Arg Phe Thr Ile Ser Arg Asp Asn Ala Lys Asn Thr Val Tyr Leu
65              70                  75                  80

Gln Met Asn Ser Leu Lys Pro Glu Asp Thr Ala Val Tyr Tyr Cys Thr
                85                  90                  95

Ser Asp Ala Arg Arg Gly Trp Asp Thr Arg Tyr Trp Gly Gln Gly Thr
            100                 105                 110

Gln Val Thr Val Ser Ser
            115
```

<210> SEQ ID NO 37
<211> LENGTH: 118
<212> TYPE: PRT
<213> ORGANISM: Artificial Sequence
<220> FEATURE:
<223> OTHER INFORMATION: Nanobody sequence

<400> SEQUENCE: 37

```
Glu Val Gln Leu Val Glu Ser Gly Gly Gly Ser Val Gln Ala Gly Glu
1               5                   10                  15

Ser Leu Arg Leu Ser Cys Ala Ala Ser Gly Thr Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Asp Ile Thr Arg Tyr Ala Asp Ser Val Lys
```

```
                 50                  55                  60
Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                 85                  90                  95

Ser Asp Pro Arg Arg Gly Trp Asn Thr Arg Tyr Trp Gly Gln Gly Thr
                100                 105                 110

Gln Val Thr Val Ser Ser
            115

<210> SEQ ID NO 38
<211> LENGTH: 118
<212> TYPE: PRT
<213> ORGANISM: Artificial Sequence
<220> FEATURE:
<223> OTHER INFORMATION: Nanobody sequence

<400> SEQUENCE: 38

Glu Val Gln Leu Val Glu Ser Gly Gly Gly Ser Val Gln Ala Gly Glu
  1               5                  10                  15

Ser Leu Arg Leu Ser Cys Ala Ala Ser Gly Ser Ile Phe Ser Ser Asn
                 20                  25                  30

Ala Met Ala Trp Tyr Arg Gln Ala Pro Gly Lys Gln Arg Asp Leu Val
             35                  40                  45

Ala Leu Ile Asn Ser Val Gly Ile Thr Lys Tyr Ala Asp Ser Val Lys
         50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                 85                  90                  95

Ser Asp Pro Arg Arg Gly Trp Asp Thr Arg Tyr Trp Gly Gln Gly Thr
                100                 105                 110

Gln Val Thr Val Ser Ser
            115

<210> SEQ ID NO 39
<211> LENGTH: 118
<212> TYPE: PRT
<213> ORGANISM: Artificial Sequence
<220> FEATURE:
<223> OTHER INFORMATION: Nanobody sequence

<400> SEQUENCE: 39

Glu Val Gln Leu Val Glu Ser Gly Gly Gly Ser Val Gln Ala Gly Gly
  1               5                  10                  15

Ser Leu Arg Leu Ser Cys Ala Ala Ser Gly Ser Ile Phe Ser Ser Asn
                 20                  25                  30

Ala Met Ala Trp Tyr Arg Gln Ala Pro Gly Lys Gln Arg Asp Leu Val
             35                  40                  45

Ala Ala Ile Asn Ser Val Gly Ile Thr Lys Tyr Ala Asp Ser Val Lys
         50                  55                  60

Gly Arg Phe Thr Ile Ser Arg Asp Asn Ala Lys Asn Thr Val Tyr Leu
 65                  70                  75                  80

Gln Met Met Ser Leu Lys Pro Glu Asp Thr Ala Val Tyr Tyr Cys Thr
                 85                  90                  95

Ser Asp Pro Arg Arg Gly Trp Asp Thr Arg Tyr Trp Gly Gln Gly Thr
                100                 105                 110
```

Leu Val Thr Val Ser Ser
        115

<210> SEQ ID NO 40
<211> LENGTH: 118
<212> TYPE: PRT
<213> ORGANISM: Artificial Sequence
<220> FEATURE:
<223> OTHER INFORMATION: Nanobody sequence

<400> SEQUENCE: 40

Glu Val Gln Leu Val Glu Ser Gly Gly Gly Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Leu Ile Asn Ser Val Gly Ile Thr Lys Tyr Ala Gly Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser
        115

<210> SEQ ID NO 41
<211> LENGTH: 118
<212> TYPE: PRT
<213> ORGANISM: Artificial Sequence
<220> FEATURE:
<223> OTHER INFORMATION: Nanobody sequence

<400> SEQUENCE: 41

Glu Val Gln Leu Val Glu Ser Gly Gly Gly Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Ala Ile Asn Ser Val Gly Thr Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser
        115

<210> SEQ ID NO 42
<211> LENGTH: 118
<212> TYPE: PRT
<213> ORGANISM: Artificial Sequence
<220> FEATURE:
<223> OTHER INFORMATION: Nanobody sequence -continued

<400> SEQUENCE: 42

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Leu Gly Lys Gln Arg Asp Leu Val
        35                  40                  45

Ala Leu Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser
        115

<210> SEQ ID NO 43
<211> LENGTH: 118
<212> TYPE: PRT
<213> ORGANISM: Artificial Sequence
<220> FEATURE:
<223> OTHER INFORMATION: Nanobody sequence

<400> SEQUENCE: 43

Glu Val Gln Leu Met Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser
        115

<210> SEQ ID NO 44
<211> LENGTH: 118
<212> TYPE: PRT
<213> ORGANISM: Artificial Sequence
<220> FEATURE:
<223> OTHER INFORMATION: Nanobody sequence

<400> SEQUENCE: 44

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Leu Gly Lys Gln Arg Asp Leu Val
        35                  40                  45

```
Ala Leu Ile Asn Ser Val Gly Ile Thr Lys Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                 85                  90                  95

Ser Asp Pro Arg Arg Gly Trp Asp Thr Arg Tyr Trp Gly Gln Gly Thr
                100                 105                 110

Leu Val Thr Val Ser Ser
            115

<210> SEQ ID NO 45
<211> LENGTH: 118
<212> TYPE: PRT
<213> ORGANISM: Artificial Sequence
<220> FEATURE:
<223> OTHER INFORMATION: Nanobody sequence

<400> SEQUENCE: 45

Lys Val Gln Leu Val Glu Ser Gly Gly Gly Ser Val Gln Ala Gly Glu
 1               5                  10                  15

Ser Leu Arg Leu Ser Cys Ala Ala Ser Gly Thr Ile Phe Ser Ser Asn
             20                  25                  30

Ala Met Ala Trp Tyr Arg Gln Ala Pro Gly Lys Gln Arg Asp Leu Val
             35                  40                  45

Ala Gly Ile Asn Ser Val Asp Ile Thr Lys Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                 85                  90                  95

Ser Asp Pro Arg Arg Gly Trp Asn Thr Arg Tyr Trp Gly Gln Gly Thr
                100                 105                 110

Leu Val Thr Val Ser Ser
            115

<210> SEQ ID NO 46
<211> LENGTH: 118
<212> TYPE: PRT
<213> ORGANISM: Artificial Sequence
<220> FEATURE:
<223> OTHER INFORMATION: Nanobody sequence

<400> SEQUENCE: 46

Glu Val Gln Leu Val Glu Ser Gly Gly Gly Ser Val Gln Ala Gly Glu
 1               5                  10                  15

Ser Leu Arg Leu Ser Cys Ala Ala Ser Gly Ser Ile Phe Ser Ser Asn
             20                  25                  30

Ala Met Ala Trp Tyr Arg Gln Ala Pro Gly Lys Gln Arg Asp Leu Val
             35                  40                  45

Ala Val Ile Asn Ser Val Gly Ile Thr Lys Tyr Ala Asp Ser Val Lys
 50                  55                  60

Gly Arg Phe Thr Thr Ser Gly Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                 85                  90                  95

Ser Asp Ala Arg Arg Gly Trp Asp Thr Arg Tyr Trp Gly Gln Gly Thr
                100                 105                 110
```

Gln Val Thr Val Ser Ser
        115

<210> SEQ ID NO 47
<211> LENGTH: 118
<212> TYPE: PRT
<213> ORGANISM: Artificial Sequence
<220> FEATURE:
<223> OTHER INFORMATION: Nanobody sequence

<400> SEQUENCE: 47

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Ser Ile Asp Ser Val Gly Ile Thr Lys Tyr Arg Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Ala Arg Arg Gly Trp Asp Thr Arg Tyr Trp Gly Gln Gly Thr
            100                 105                 110

Gln Val Thr Val Ser Ser
        115

<210> SEQ ID NO 48
<211> LENGTH: 118
<212> TYPE: PRT
<213> ORGANISM: Artificial Sequence
<220> FEATURE:
<223> OTHER INFORMATION: Nanobody sequence

<400> SEQUENCE: 48

Glu Met Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Leu Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Gly Arg Arg Gly Trp Asp Thr Arg Tyr Trp Gly Gln Gly Thr
            100                 105                 110

Gln Val Thr Val Ser Ser
        115

<210> SEQ ID NO 49
<211> LENGTH: 120
<212> TYPE: PRT
<213> ORGANISM: Artificial Sequence
<220> FEATURE:
<223> OTHER INFORMATION: Nanobody sequence

<400> SEQUENCE: 49

Glu Val Gln Leu Val Glu Ser Gly Gly Gly Leu Val Gln Ala Gly Gly
1               5                   10                  15

Ser Leu Arg Leu Ser Cys Val Ala Ser Gly Arg Thr Phe Ser Ser Tyr
            20                  25                  30

Ala Met Gly Trp Phe Arg Gln Ala Pro Gly Lys Glu Arg Ala Phe Val
        35                  40                  45

Ala Gly Ile Ser Gly Ser Ala Ser Arg Lys Tyr Tyr Ala Asp Ser Val
    50                  55                  60

Lys Gly Arg Phe Thr Val Ser Arg Asp Asn Ala Arg Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Asn Ser Tyr Pro Lys Val Gln Phe Asp Tyr Tyr Gly Gln
            100                 105                 110

Gly Thr Gln Val Thr Val Ser Ser
            115                 120

<210> SEQ ID NO 50
<211> LENGTH: 120
<212> TYPE: PRT
<213> ORGANISM: Artificial Sequence
<220> FEATURE:
<223> OTHER INFORMATION: Nanobody sequence

<400> SEQUENCE: 50

Glu Val Gln Leu Val Gln Ser Gly Gly Gly Leu Val Gln Ala Gly Gly
1               5                   10                  15

Ser Leu Arg Leu Ser Cys Val Ala Ser Gly Arg Thr Phe Ser Ser Tyr
            20                  25                  30

Ala Met Gly Trp Phe Arg Gln Ala Pro Gly Arg Glu Arg Ala Phe Val
        35                  40                  45

Ala Gly Ile Ser Gly Ser Ala Ser Arg Lys Tyr Tyr Ala Asp Ser Val
    50                  55                  60

Lys Gly Arg Phe Thr Val Ser Arg Asp Asn Ala Arg Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Asn Ser Tyr Pro Lys Val Gln Phe Asp Tyr Tyr Gly Gln
            100                 105                 110

Gly Thr Gln Val Thr Val Ser Ser
            115                 120

<210> SEQ ID NO 51
<211> LENGTH: 120
<212> TYPE: PRT
<213> ORGANISM: Artificial Sequence
<220> FEATURE:
<223> OTHER INFORMATION: Nanobody sequence

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Val Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

```
Ala Gly Ile Ser Gly Ser Gly Ser Arg Lys Tyr Tyr Ala Asp Ser Val
        50                  55                  60

Lys Gly Arg Phe Thr Ile Ser Arg Asp Asn Ala Arg Asn Thr Val Tyr
 65                  70                  75                  80

Leu Gln Met Asn Ser Leu Lys Pro Glu Asp Arg Ala Val Tyr Tyr Cys
                85                  90                  95

Ala Ala Ser Asn Ser Tyr Pro Lys Val Gln Phe Asp Tyr Tyr Gly Gln
               100                 105                 110

Gly Thr Gln Val Thr Val Ser Ser
            115                 120

<210> SEQ ID NO 52
<211> LENGTH: 120
<212> TYPE: PRT
<213> ORGANISM: Artificial Sequence
<220> FEATURE:
<223> OTHER INFORMATION: Nanobody sequence

<400> SEQUENCE: 52

Glu Val Gln Leu Val Glu Ser Gly Gly Gly Leu Val Gln Ala Gly Gly
 1               5                  10                  15

Ser Leu Arg Leu Ser Cys Val Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Gly Ile Ser Gly Ser Gly Ser Arg Lys Tyr Tyr Ala Asp Ser Val
        50                  55                  60

Lys Gly Arg Phe Thr Ile Ser Arg Asp Asn Ala Arg Asn Thr Val Tyr
 65                  70                  75                  80

Leu Gln Met Asn Ser Leu Lys Pro Glu Asp Arg Ala Val Tyr Tyr Cys
                85                  90                  95

Ala Ala Ser Asn Ser Tyr Pro Lys Val Gln Phe Asp Tyr Tyr Gly Gln
               100                 105                 110

Gly Thr Gln Val Thr Val Ser Ser
            115                 120

<210> SEQ ID NO 53
<211> LENGTH: 118
<212> TYPE: PRT
<213> ORGANISM: Artificial Sequence
<220> FEATURE:
<223> OTHER INFORMATION: Nanobody sequence

<400> SEQUENCE: 53

Lys Val Gln Leu Val Glu Ser Gly Gly Gly Leu Val Gln Pro Gly Gly
 1               5                  10                  15

Ser Leu Arg Leu Ser Cys Ala Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Ser Ser Gly Ser Thr Asn Tyr Ala Asp Ser Val Lys
        50                  55                  60

Gly Arg Phe Thr Val Ser Arg Asp Asn Asp Lys Asn Thr Gly Tyr Leu
 65                  70                  75                  80

Gln Met Asn Ser Leu Lys Pro Glu Asp Thr Gly Val Tyr Tyr Cys Thr
                85                  90                  95

Leu Asp Ala Arg Arg Gly Trp Asn Thr Ala Tyr Trp Gly Gln Gly Ala
```

```
Gln Val Thr Val Ser Ser
        115

<210> SEQ ID NO 54
<211> LENGTH: 118
<212> TYPE: PRT
<213> ORGANISM: Artificial Sequence
<220> FEATURE:
<223> OTHER INFORMATION: Nanobody sequence

<400> SEQUENCE: 54

Glu Val Gln Leu Val Glu Ser Gly Gly Gly Leu Val Gln Pro Gly Gly
1               5                  10                  15

Ser Leu Arg Leu Ser Cys Ala Thr Ser Gly Thr Ile Phe Ser Asn Thr
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Ser Gly Tyr Trp Gly Gln Gly Thr
            100                 105                 110

Gln Val Thr Val Ser Ser
        115

<210> SEQ ID NO 55
<211> LENGTH: 118
<212> TYPE: PRT
<213> ORGANISM: Artificial Sequence
<220> FEATURE:
<223> OTHER INFORMATION: Nanobody sequence

<400> SEQUENCE: 55

Glu Val Gln Leu Val Glu Ser Gly Gly Gly Leu Val Gln Pro Gly Gly
1               5                  10                  15

Ser Leu Arg Leu Ser Cys Ala Thr Ser Gly Ile Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Ala Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 56
<211> LENGTH: 118
<212> TYPE: PRT
<213> ORGANISM: Artificial Sequence
<220> FEATURE:
```

<223> OTHER INFORMATION: Nanobody sequence

<400> SEQUENCE: 56

Glu Val Gln Leu Val Glu Ser Gly Gly Gly Val Val Gln Pro Gly Gly
1               5                   10                  15

Ser Leu Arg Leu Ser Cys Val Thr Ser Gly Ile Ile Phe Ser Asn Asn
            20                  25                  30

Ala Met Gly Trp Tyr Arg Gln Gly Pro Gly Lys Lys Arg Asp Leu Val
        35                  40                  45

Ala Ser Ile Gly Ser Thr Tyr Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Ile Asp Ala Arg Arg Gly Trp Asn Thr Ala Tyr Trp Gly Gln Gly Thr
            100                 105                 110

Pro Val Thr Val Ser Ser
        115

<210> SEQ ID NO 57
<211> LENGTH: 118
<212> TYPE: PRT
<213> ORGANISM: Artificial Sequence
<220> FEATURE:
<223> OTHER INFORMATION: Nanobody sequence

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Thr Ser Arg Thr Ile Phe Arg Ser Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Ile Asp Ala Arg Arg Gly Trp Asn Thr Gly Tyr Trp Gly Gln Gly Thr
            100                 105                 110

Gln Val Thr Val Ser Ser
        115

<210> SEQ ID NO 58
<211> LENGTH: 118
<212> TYPE: PRT
<213> ORGANISM: Artificial Sequence
<220> FEATURE:
<223> OTHER INFORMATION: Nanobody sequence

<400> SEQUENCE: 58

Glu Val Gln Leu Val Glu Ser Gly Gly Gly Val Val Gln Pro Gly Gly
1               5                   10                  15

Ser Leu Arg Leu Ser Cys Val Thr Ser Gly Ile Ile Phe Ser Asn Asn
            20                  25                  30

Ala Met Gly Trp Tyr Arg Gln Gly Pro Gly Lys Lys Arg Asp Leu Val

```
            35                  40                  45
Ala Ser Ile Ser Ser Thr Tyr Ser Thr Asn Tyr Ala Asp Ser Val Lys
         50                  55                  60

Gly Arg Phe Thr Val Ser Arg Asp Asn Asp Lys Asn Thr Gly Tyr Leu
 65                  70                  75                  80

Gln Met Asn Ser Leu Lys Pro Glu Asp Thr Gly Val Tyr Tyr Cys Thr
                 85                  90                  95

Ile Asp Ala Arg Arg Gly Trp Asn Thr Ala Tyr Trp Gly Gln Gly Thr
            100                 105                 110

Pro Val Thr Val Ser Ser
            115

<210> SEQ ID NO 59
<211> LENGTH: 118
<212> TYPE: PRT
<213> ORGANISM: Artificial Sequence
<220> FEATURE:
<223> OTHER INFORMATION: Nanobody sequence

<400> SEQUENCE: 59

Glu Val Gln Leu Val Glu Ser Gly Gly Gly Leu Val Gln Pro Gly Gly
 1               5                  10                  15

Ser Leu Arg Leu Ser Cys Ala Thr Ser Gly Thr Ile Phe Arg Ser Asn
                20                  25                  30

Ala Met Gly Trp Tyr Arg Gln Ala Pro Gly Lys Lys Arg Asp Leu Val
            35                  40                  45

Ala Ser Ile Ser Asn Ser Gly Ser Thr Asn Tyr Ala Asp Ser Val Lys
         50                  55                  60

Gly Arg Phe Thr Val Ser Arg Asp Asn Asp Lys Asn Thr Gly Tyr Leu
 65                  70                  75                  80

Gln Met Asn Ser Leu Lys Pro Glu Asp Thr Gly Val Tyr Tyr Cys Thr
                 85                  90                  95

Val Asp Ala Arg Arg Gly Trp Asn Ser Gly Tyr Trp Gly Gln Gly Thr
            100                 105                 110

Gln Val Thr Val Ser Ser
            115

<210> SEQ ID NO 60
<211> LENGTH: 118
<212> TYPE: PRT
<213> ORGANISM: Artificial Sequence
<220> FEATURE:
<223> OTHER INFORMATION: Nanobody sequence

<400> SEQUENCE: 60

Glu Val Gln Leu Val Glu Ser Arg Gly Gly Leu Val Gln Pro Gly Gly
 1               5                  10                  15

Ser Leu Arg Leu Ser Cys Ala Thr Ser Gly Thr Ile Phe Ser Asn Asn
                20                  25                  30

Ala Met Gly Trp Tyr Arg Gln Ala Pro Gly Lys Lys Arg Asp Leu Val
            35                  40                  45

Ala Ser Ile Ser Ser Ser Gly Ser Thr Asn Tyr Ala Asp Ser Val Lys
         50                  55                  60

Gly Arg Phe Thr Val Ser Arg Asp Asn Asp Lys Asn Thr Gly Tyr Leu
 65                  70                  75                  80

Gln Met Asn Ser Leu Lys Pro Glu Asp Thr Gly Val Tyr Tyr Cys Thr
                 85                  90                  95
```

```
Leu Asp Ala Arg Arg Gly Trp Asn Thr Ala Tyr Trp Gly Gln Gly Thr
            100                 105                 110

Gln Val Thr Val Ser Ser
        115

<210> SEQ ID NO 61
<211> LENGTH: 118
<212> TYPE: PRT
<213> ORGANISM: Artificial Sequence
<220> FEATURE:
<223> OTHER INFORMATION: Nanobody sequence

<400> SEQUENCE: 61

Glu Val Gln Leu Met Glu Ser Gly Gly Gly Leu Val Gln Pro Gly Gly
1               5                   10                  15

Ser Leu Arg Leu Ser Cys Ala Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 62
<211> LENGTH: 118
<212> TYPE: PRT
<213> ORGANISM: Artificial Sequence
<220> FEATURE:
<223> OTHER INFORMATION: Nanobody sequence

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Thr Ser Gly Ile Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 63
<211> LENGTH: 118
<212> TYPE: PRT
<213> ORGANISM: Artificial Sequence
```

<220> FEATURE:
<223> OTHER INFORMATION: Nanobody sequence

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Thr Ser Gly Ile Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Ser Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 64
<211> LENGTH: 118
<212> TYPE: PRT
<213> ORGANISM: Artificial Sequence
<220> FEATURE:
<223> OTHER INFORMATION: Nanobody sequence

<400> SEQUENCE: 64

Glu Val Gln Leu Val Glu Ser Gly Gly Gly Leu Val Gln Pro Gly Gly
1               5                   10                  15

Ser Leu Gly Leu Ser Cys Ala Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 65
<211> LENGTH: 118
<212> TYPE: PRT
<213> ORGANISM: Artificial Sequence
<220> FEATURE:
<223> OTHER INFORMATION: Nanobody sequence

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Thr Thr Ser Gly Thr Ile Phe Ser Asn Asn
            20                  25                  30

```
Ala Met Gly Trp Tyr Arg Gln Ala Pro Gly Lys Lys Arg Asp Leu Val
            35                  40                  45

Ala Ser Ile Ser Asn Ser Gly Ser Thr Asn Tyr Ala Asp Ser Val Lys
 50                      55                  60

Gly Arg Phe Thr Val Ser Arg Asp Asn Asp Lys Asn Thr Gly Tyr Leu
 65                  70                  75                  80

Gln Met Asn Asn Leu Lys Pro Glu Asp Thr Gly Val Tyr Tyr Cys Thr
                 85                  90                  95

Leu Asp Ala Arg Arg Gly Trp Asn Thr Ala Tyr Trp Gly Gln Gly Thr
                100                 105                 110

Gln Val Thr Val Ser Ser
            115

<210> SEQ ID NO 66
<211> LENGTH: 118
<212> TYPE: PRT
<213> ORGANISM: Artificial Sequence
<220> FEATURE:
<223> OTHER INFORMATION: Nanobody sequence

<400> SEQUENCE: 66

Lys Val Gln Leu Val Glu Ser Gly Gly Gly Leu Val Gln Pro Gly Gly
 1               5                  10                  15

Ser Leu Arg Leu Ser Cys Ala Thr Ser Gly Thr Ile Phe Ser Asn Asn
            20                  25                  30

Ala Met Gly Trp Tyr Arg Gln Ala Pro Gly Lys Lys Arg Asp Leu Val
            35                  40                  45

Ala Ser Ile Ser Asn Ser Gly Ser Thr Asn Tyr Ala Asp Ser Val Lys
 50                      55                  60

Gly Arg Phe Thr Val Ser Arg Asp Asn Asp Lys Asn Thr Gly Tyr Leu
 65                  70                  75                  80

Gln Met Asn Ser Leu Lys Pro Glu Asp Thr Gly Val Tyr Tyr Cys Thr
                 85                  90                  95

Val Asp Ala Arg Arg Gly Trp Asn Thr Ala Tyr Trp Gly Gln Gly Thr
                100                 105                 110

Gln Val Thr Val Ser Ser
            115

<210> SEQ ID NO 67
<211> LENGTH: 118
<212> TYPE: PRT
<213> ORGANISM: Artificial Sequence
<220> FEATURE:
<223> OTHER INFORMATION: Nanobody sequence

<400> SEQUENCE: 67

Glu Val Gln Leu Val Glu Ser Gly Gly Gly Leu Val Gln Pro Gly Gly
 1               5                  10                  15

Ser Leu Arg Leu Ser Cys Ala Thr Ser Gly Thr Ile Phe Ser Asn Asn
            20                  25                  30

Ala Met Gly Trp Tyr Arg Gln Ala Pro Gly Lys Lys Arg Asp Leu Val
            35                  40                  45

Ala Ser Ile Ser Asn Ser Gly Ser Thr Asn Tyr Ala Asp Ser Val Lys
 50                      55                  60

Gly Arg Phe Thr Val Ser Arg Asp Asn Asp Lys Asn Thr Gly Tyr Leu
 65                  70                  75                  80

Gln Met Asn Ser Leu Lys Pro Glu Asp Thr Gly Val Tyr Tyr Cys Thr
                 85                  90                  95
```

```
Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 68
<211> LENGTH: 118
<212> TYPE: PRT
<213> ORGANISM: Artificial Sequence
<220> FEATURE:
<223> OTHER INFORMATION: Nanobody sequence

<400> SEQUENCE: 68

Glu Val Gln Leu Val Asp Ser Gly Gly Gly Leu Val Gln Pro Gly Gly
1               5                   10                  15

Ser Leu Arg Leu Ser Cys Ala Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 69
<211> LENGTH: 118
<212> TYPE: PRT
<213> ORGANISM: Artificial Sequence
<220> FEATURE:
<223> OTHER INFORMATION: Nanobody sequence

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Arg Thr Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Ala Tyr Leu
65                  70                  75                  80

Gln Met Asn Ser Leu Lys Pro Glu Asp Thr Gly Val Tyr Tyr Cys Thr
                85                  90                  95

Ile Asp Gly Arg Arg Gly Trp Asn Thr Gly Tyr Trp Gly Gln Gly Thr
            100                 105                 110

Gln Val Thr Val Ser Ser
        115

<210> SEQ ID NO 70
<211> LENGTH: 118
<212> TYPE: PRT
```

```
<213> ORGANISM: Artificial Sequence
<220> FEATURE:
<223> OTHER INFORMATION: Nanobody sequence

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Thr Ser Arg Thr Ile Phe Arg Ser Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Gly Tyr Trp Gly Gln Gly Thr
            100                 105                 110

Gln Val Thr Val Ser Ser
        115

<210> SEQ ID NO 71
<211> LENGTH: 118
<212> TYPE: PRT
<213> ORGANISM: Artificial Sequence
<220> FEATURE:
<223> OTHER INFORMATION: Nanobody sequence

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Ser Asn Asn
            20                  25                  30

Ala Met Gly Trp Tyr Arg Gln Ala Leu Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 72
<211> LENGTH: 118
<212> TYPE: PRT
<213> ORGANISM: Artificial Sequence
<220> FEATURE:
<223> OTHER INFORMATION: Nanobody sequence

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Thr Ser Lys Thr Ile Phe Arg Ser Asn
            20                  25                  30
```

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
 50                  55                  60

Gly Arg Phe Thr Val Ser Arg Asp Asn Asp Lys Asn Thr Gly Tyr Leu
 65                  70                  75                  80

Gln Met Asn Ser Leu Lys Pro Glu Asp Thr Gly Val Tyr Tyr Cys Thr
                 85                  90                  95

Val Asp Ala Arg Arg Gly Trp Asn Thr Gly Tyr Trp Gly Gln Gly Thr
                100                 105                 110

Gln Val Thr Val Ser Ser
        115

<210> SEQ ID NO 73
<211> LENGTH: 118
<212> TYPE: PRT
<213> ORGANISM: Artificial Sequence
<220> FEATURE:
<223> OTHER INFORMATION: Nanobody sequence

<400> SEQUENCE: 73

Glu Val Gln Leu Val Glu Ser Arg Gly Gly Leu Val Gln Pro Gly Gly
 1               5                  10                  15

Ser Leu Arg Leu Ser Cys Ala Thr Ser Gly Ile Ile Phe Ser Asn Asn
                 20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
 50                  55                  60

Gly Arg Phe Thr Val Ser Arg Asp Asn Asp Lys Asn Thr Gly Tyr Leu
 65                  70                  75                  80

Gln Met Asn Ser Leu Lys Pro Glu Asp Thr Gly Val Tyr Tyr Cys Thr
                 85                  90                  95

Val Asp Ala Arg Arg Gly Trp Asn Thr Ala Tyr Trp Gly Gln Gly Thr
                100                 105                 110

Gln Val Thr Val Ser Ser
        115

<210> SEQ ID NO 74
<211> LENGTH: 118
<212> TYPE: PRT
<213> ORGANISM: Artificial Sequence
<220> FEATURE:
<223> OTHER INFORMATION: Nanobody sequence

<400> SEQUENCE: 74

Glu Val Gln Leu Val Lys Ser Gly Gly Gly Leu Val Gln Pro Gly Gly
 1               5                  10                  15

Ser Leu Arg Leu Ser Cys Thr Thr Ser Gly Thr Ile Phe Ser Asn Asn
                 20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
 50                  55                  60

Gly Arg Phe Thr Val Ser Arg Asp Asn Asp Lys Asn Thr Gly Tyr Leu
 65                  70                  75                  80

Gln Met Asn Asn Leu Lys Pro Glu Asp Thr Gly Val Tyr Tyr Cys Thr

```
                    85                  90                  95
Leu Asp Ala Arg Arg Gly Trp Asn Thr Ala Tyr Trp Gly Gln Gly Thr
                100                 105                 110
Gln Val Thr Val Ser Ser
        115

<210> SEQ ID NO 75
<211> LENGTH: 118
<212> TYPE: PRT
<213> ORGANISM: Artificial Sequence
<220> FEATURE:
<223> OTHER INFORMATION: Nanobody sequence

<400> SEQUENCE: 75

Glu Val Gln Leu Val Glu Ser Gly Gly Gly Leu Val Gln Ala Gly Gly
1               5                   10                  15

Ser Leu Arg Leu Ser Cys Val Thr Ser Gly Ile Ile Phe Ser Asn Asn
            20                  25                  30

Ala Met Gly Trp Tyr Arg Gln Gly Pro Gly Lys Lys Arg Asp Leu Val
        35                  40                  45

Ala Ser Ile Gly Ser Thr Tyr Ser Thr Asn Tyr Ala Asp Ser Val Lys
50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Ile Asp Ala Arg Arg Gly Trp Asn Thr Ala Tyr Trp Gly Gln Gly Thr
                100                 105                 110

Pro Val Thr Val Ser Ser
        115

<210> SEQ ID NO 76
<211> LENGTH: 118
<212> TYPE: PRT
<213> ORGANISM: Artificial Sequence
<220> FEATURE:
<223> OTHER INFORMATION: Nanobody sequence

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Arg Ser Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Ser Gly Tyr Trp Gly Gln Gly Thr
                100                 105                 110

Arg Val Thr Val Ser Ser
        115

<210> SEQ ID NO 77
<211> LENGTH: 118
```

```
<212> TYPE: PRT
<213> ORGANISM: Artificial Sequence
<220> FEATURE:
<223> OTHER INFORMATION: Nanobody sequence

<400> SEQUENCE: 77

Lys Val Gln Leu Val Glu Ser Gly Gly Gly Leu Val Gln Pro Gly Gly
1               5                   10                  15

Ser Leu Arg Leu Ser Cys Ala Thr Ser Gly Ile Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 78
<211> LENGTH: 118
<212> TYPE: PRT
<213> ORGANISM: Artificial Sequence
<220> FEATURE:
<223> OTHER INFORMATION: Nanobody sequence

<400> SEQUENCE: 78

Glu Val Gln Leu Val Glu Ser Gly Gly Gly Leu Val Gln Ala Gly Gly
1               5                   10                  15

Ser Leu Arg Leu Ser Cys Ala Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 79
<211> LENGTH: 118
<212> TYPE: PRT
<213> ORGANISM: Artificial Sequence
<220> FEATURE:
<223> OTHER INFORMATION: Nanobody sequence

<400> SEQUENCE: 79

Glu Val Gln Leu Val Glu Ser Gly Gly Gly Leu Val Gln Pro Gly Arg
1               5                   10                  15

Ser Leu Arg Leu Ser Cys Ala Thr Ser Gly Thr Thr Phe Arg Ser Asn
```

```
                 20                  25                  30
Ala Met Gly Trp Tyr Arg Gln Gly Pro Gly Lys Lys Arg Asp Leu Val
             35                  40                  45

Ala Ser Ile Thr Asn Ser Gly Ser Thr Asn Tyr Ala Asp Ser Val Lys
         50                  55                  60

Gly Arg Phe Thr Val Ser Arg Asp Asn Asp Lys Asn Thr Gly Tyr Leu
 65                  70                  75                  80

Gln Met Ser Ser Leu Lys Pro Glu Asp Thr Gly Val Tyr Tyr Cys Thr
                 85                  90                  95

Leu Asp Ala Arg Arg Gly Trp Asn Thr Gly Tyr Trp Gly Gln Gly Thr
             100                 105                 110

Gln Val Thr Val Ser Ser
            115

<210> SEQ ID NO 80
<211> LENGTH: 118
<212> TYPE: PRT
<213> ORGANISM: Artificial Sequence
<220> FEATURE:
<223> OTHER INFORMATION: Nanobody sequence

<400> SEQUENCE: 80

Glu Val Gln Leu Val Glu Ser Gly Gly Gly Leu Val Gln Pro Gly Gly
 1               5                  10                  15

Ser Leu Arg Leu Ser Cys Ala Thr Ser Arg Thr Ile Phe Arg Ser Asn
                 20                  25                  30

Ala Met Gly Trp Tyr Arg Gln Gly Pro Gly Lys Lys Arg Asp Leu Val
             35                  40                  45

Ala Ser Ile Thr Asn Ser Gly Ser Thr Asn Tyr Ala Asp Ser Val Lys
         50                  55                  60

Gly Arg Phe Thr Val Ser Arg Asp Asn Asp Arg Asn Thr Gly Tyr Leu
 65                  70                  75                  80

Gln Met Asn Ser Leu Lys Pro Glu Asp Thr Gly Val Tyr Tyr Cys Thr
                 85                  90                  95

Val Asp Ala Arg Arg Gly Trp Asn Thr Gly Tyr Trp Gly Gln Gly Thr
             100                 105                 110

Gln Val Thr Val Ser Ser
            115

<210> SEQ ID NO 81
<211> LENGTH: 118
<212> TYPE: PRT
<213> ORGANISM: Artificial Sequence
<220> FEATURE:
<223> OTHER INFORMATION: Nanobody sequence

<400> SEQUENCE: 81

Lys Val Gln Leu Val Glu Ser Gly Gly Gly Leu Val Gln Pro Gly Gly
 1               5                  10                  15

Ser Leu Arg Leu Ser Cys Ala Thr Ser Gly Thr Ile Phe Ser Asn Asn
                 20                  25                  30

Ala Met Gly Trp Tyr Arg Gln Val Pro Gly Lys Lys Arg Asp Leu Val
             35                  40                  45

Ala Ser Ile Ser Asn Ser Gly Ser Thr Asn Tyr Ala Asp Ser Val Lys
         50                  55                  60

Gly Arg Phe Thr Val Ser Arg Asp Asn Asp Lys Asn Thr Gly Tyr Leu
 65                  70                  75                  80
```

```
Gln Met Asn Ser Leu Lys Pro Glu Asp Thr Gly Val Tyr Tyr Cys Thr
            85                  90                  95

Val Asp Ala Arg Arg Gly Trp Asn Thr Gly Tyr Trp Gly Gln Gly Thr
        100                 105                 110

Gln Val Thr Val Ser Ser
        115

<210> SEQ ID NO 82
<211> LENGTH: 118
<212> TYPE: PRT
<213> ORGANISM: Artificial Sequence
<220> FEATURE:
<223> OTHER INFORMATION: Nanobody sequence

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Ser Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
            85                  90                  95

Leu Asp Ala Arg Arg Gly Trp Asn Thr Ala Tyr Trp Gly Gln Gly Thr
        100                 105                 110

Gln Val Thr Val Ser Ser
        115

<210> SEQ ID NO 83
<211> LENGTH: 118
<212> TYPE: PRT
<213> ORGANISM: Artificial Sequence
<220> FEATURE:
<223> OTHER INFORMATION: Nanobody sequence

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Thr Ser Ala Thr Ile Phe Arg Ser Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Ala Tyr Leu
65                  70                  75                  80

Gln Met Asn Ser Leu Lys Pro Glu Asp Thr Gly Val Tyr Tyr Cys Thr
            85                  90                  95

Ile Asp Gly Arg Arg Gly Trp Asn Thr Gly Tyr Trp Gly Gln Gly Thr
        100                 105                 110

Gln Val Thr Val Ser Ser
        115

<210> SEQ ID NO 84
```

<211> LENGTH: 118
<212> TYPE: PRT
<213> ORGANISM: Artificial Sequence
<220> FEATURE:
<223> OTHER INFORMATION: Nanobody sequence

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Thr Ser Ala Thr Ile Phe Arg Ser Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Ser Thr Val Ser Arg Asp Asn Asp Lys Asn Thr Ala Tyr Leu
65                  70                  75                  80

Gln Met Asn Ser Leu Lys Pro Glu Asp Thr Gly Val Tyr Tyr Cys Thr
                85                  90                  95

Ile Asp Gly Arg Arg Gly Trp Asn Thr Gly Tyr Trp Gly Gln Gly Thr
            100                 105                 110

Gln Val Thr Val Ser Ser
        115

<210> SEQ ID NO 85
<211> LENGTH: 118
<212> TYPE: PRT
<213> ORGANISM: Artificial Sequence
<220> FEATURE:
<223> OTHER INFORMATION: Nanobody sequence

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Met Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 86
<211> LENGTH: 118
<212> TYPE: PRT
<213> ORGANISM: Artificial Sequence
<220> FEATURE:
<223> OTHER INFORMATION: Nanobody sequence

<400> SEQUENCE: 86

Glu Val Gln Leu Val Glu Ser Gly Gly Gly Leu Val Gln Pro Gly Gly
1               5                   10                  15

```
Ser Leu Arg Leu Ser Cys Ala Thr Ser Gly Ile Ile Phe Ser Asn Asn
                20                  25                  30

Ala Met Gly Trp Tyr Arg Gln Ala Pro Gly Lys Lys Arg Asp Leu Val
            35                  40                  45

Ala Ser Ile Ser Asn Ser Gly Ser Ala Asn Tyr Ala Asp Ser Val Lys
        50                  55                  60

Gly Arg Phe Thr Val Ser Arg Asp Asn Asp Lys Asn Thr Gly Tyr Leu
 65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
            115

<210> SEQ ID NO 87
<211> LENGTH: 118
<212> TYPE: PRT
<213> ORGANISM: Artificial Sequence
<220> FEATURE:
<223> OTHER INFORMATION: Nanobody sequence

<400> SEQUENCE: 87

Glu Val Gln Leu Val Glu Ser Gly Gly Gly Leu Val Gln Pro Gly Gly
 1               5                  10                  15

Ser Leu Arg Leu Ser Cys Thr Thr Ser Gly Thr Ile Phe Ser Asn Asn
                20                  25                  30

Ala Met Gly Trp Tyr Arg Gln Ala Pro Gly Lys Lys Arg Asp Leu Val
            35                  40                  45

Ala Ser Ile Ser Asn Ser Gly Ser Thr Asn Tyr Ala Asp Ser Val Lys
        50                  55                  60

Gly Arg Phe Thr Val Ser Gly Asp Asn Asp Lys Asn Thr Gly Tyr Leu
 65                  70                  75                  80

Gln Met Asn Asn Leu Lys Pro Glu Asp Thr Gly Val Tyr Tyr Cys Thr
                85                  90                  95

Leu Asp Ala Arg Arg Gly Trp Asn Thr Ala Tyr Trp Gly Gln Gly Thr
            100                 105                 110

Gln Val Thr Val Ser Ser
            115

<210> SEQ ID NO 88
<211> LENGTH: 118
<212> TYPE: PRT
<213> ORGANISM: Artificial Sequence
<220> FEATURE:
<223> OTHER INFORMATION: Nanobody sequence

<400> SEQUENCE: 88

Glu Val Gln Leu Val Glu Ser Gly Gly Gly Leu Val Gln Pro Gly Gly
 1               5                  10                  15

Ser Leu Arg Leu Ser Cys Ala Thr Ser Gly Thr Ile Phe Arg Ser Asn
                20                  25                  30

Ala Met Gly Trp Tyr Arg Gln Ala Pro Gly Lys Lys Arg Asp Leu Val
            35                  40                  45

Ala Ser Ile Ser Ile Ser Gly Ser Thr Asn Tyr Ala Asp Ser Val Lys
        50                  55                  60

Gly Arg Phe Thr Val Ser Arg Asp Asn Asp Lys Asn Thr Gly Tyr Leu
 65                  70                  75                  80
```

Gln Met Asn Ser Leu Lys Pro Glu Asp Thr Gly Val Tyr Tyr Cys Thr
                85                  90                  95

Val Asp Ala Arg Arg Gly Trp Asn Thr Gly Phe Trp Gly Gln Gly Thr
            100                 105                 110

Gln Val Thr Val Ser Ser
            115

<210> SEQ ID NO 89
<211> LENGTH: 118
<212> TYPE: PRT
<213> ORGANISM: Artificial Sequence
<220> FEATURE:
<223> OTHER INFORMATION: Nanobody sequence

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Val Thr Ser Gly Ile Ile Phe Ser Asn Asn
            20                  25                  30

Ala Met Gly Trp Tyr Arg Gln Gly Pro Gly Lys Lys Arg Asp Leu Val
        35                  40                  45

Ala Ser Ile Ser Ser Thr Tyr Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Ile Asp Ala Arg Arg Gly Trp Asn Thr Ala Tyr Trp Gly Gln Gly Thr
            100                 105                 110

Pro Val Thr Val Ser Ser
            115

<210> SEQ ID NO 90
<211> LENGTH: 118
<212> TYPE: PRT
<213> ORGANISM: Artificial Sequence
<220> FEATURE:
<223> OTHER INFORMATION: Nanobody sequence

<400> SEQUENCE: 90

Glu Val Gln Leu Met Glu Ser Gly Gly Gly Met Val Gln Val Gly Gly
1               5                   10                  15

Ser Leu Arg Leu Ser Cys Thr Ala Ser Gly Leu Ile Phe Ser Asn Asn
            20                  25                  30

Ala Met Gly Trp Tyr Arg Gln Gly Pro Gly Lys Lys Arg Asp Leu Val
        35                  40                  45

Ala Ser Ile Ser Ser Thr Tyr Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Ile Asp Ala Arg Arg Gly Trp Asn Thr Ala Tyr Trp Gly Gln Gly Thr
            100                 105                 110

Pro Val Thr Val Ser Ser
            115

<210> SEQ ID NO 91
<211> LENGTH: 118
<212> TYPE: PRT
<213> ORGANISM: Artificial Sequence
<220> FEATURE:
<223> OTHER INFORMATION: Nanobody sequence

<400> SEQUENCE: 91

```
Glu Val Gln Leu Val Glu Ser Gly Gly Gly Leu Val Gln Pro Gly Gly
1               5                   10                  15

Ser Leu Arg Leu Ser Cys Ala Ile Ser Ala Thr Ile Phe Arg Ser Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Ala Tyr Leu
65                  70                  75                  80

Gln Met Asn Ser Leu Lys Pro Glu Asp Thr Gly Val Tyr Tyr Cys Thr
                85                  90                  95

Ile Asp Gly Arg Arg Gly Trp Asn Thr Gly Tyr Trp Gly Gln Gly Thr
            100                 105                 110

Gln Val Thr Val Ser Ser
        115
```

<210> SEQ ID NO 92
<211> LENGTH: 118
<212> TYPE: PRT
<213> ORGANISM: Artificial Sequence
<220> FEATURE:
<223> OTHER INFORMATION: Nanobody sequence

<400> SEQUENCE: 92

```
Glu Met Gln Leu Val Glu Ser Gly Gly Gly Val Val Gln Pro Gly Gly
1               5                   10                  15

Ser Leu Arg Leu Ser Cys Val Thr Ser Gly Ile Ile Phe Ser Asn Asn
            20                  25                  30

Ala Met Gly Trp Tyr Arg Gln Gly Pro Gly Lys Lys Arg Asp Leu Val
        35                  40                  45

Ala Ser Ile Gly Ser Thr Tyr Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Ile Asp Ala Arg Arg Gly Trp Asn Thr Ala Tyr Trp Gly Gln Gly Thr
            100                 105                 110

Pro Val Thr Val Ser Ser
        115
```

<210> SEQ ID NO 93
<211> LENGTH: 118
<212> TYPE: PRT
<213> ORGANISM: Artificial Sequence
<220> FEATURE:
<223> OTHER INFORMATION: Nanobody sequence

<400> SEQUENCE: 93

```
Glu Val Gln Leu Val Glu Ser Gly Gly Gly Leu Val Gln Pro Gly Gly
1               5                   10                  15
```

```
Ser Leu Arg Leu Ser Cys Ala Thr Ser Gly Ile Ile Phe Ser Asn Asn
            20                  25                  30

Ala Met Gly Trp Tyr Arg Gln Ala Pro Gly Lys Lys Arg Asp Leu Val
            35                  40                  45

Ala Ser Ile Ser Asn Ser Gly Ser Thr Asn His Ala Asp Ser Val Lys
        50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 94
<211> LENGTH: 118
<212> TYPE: PRT
<213> ORGANISM: Artificial Sequence
<220> FEATURE:
<223> OTHER INFORMATION: Nanobody sequence

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Ser Asn Asn
            20                  25                  30

Ala Met Gly Trp Tyr Arg Gln Val Pro Gly Lys Lys Arg Asp Leu Val
            35                  40                  45

Ala Ser Ile Ser Asn Ser Gly Ser Thr Asn Tyr Ala Asp Ser Val Lys
        50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Gly Tyr Trp Gly Gln Gly Thr
            100                 105                 110

Gln Val Thr Val Ser Ser
        115

<210> SEQ ID NO 95
<211> LENGTH: 118
<212> TYPE: PRT
<213> ORGANISM: Artificial Sequence
<220> FEATURE:
<223> OTHER INFORMATION: Nanobody sequence

<400> SEQUENCE: 95

Glu Val Gln Leu Val Glu Ser Arg Gly Gly Leu Val Gln Pro Gly Gly
1               5                   10                  15

Ser Leu Arg Leu Ser Cys Ala Thr Ser Gly Thr Ile Phe Ser Asn Asn
            20                  25                  30

Ala Met Gly Trp Tyr Arg Gln Ala Pro Gly Lys Lys Arg Asp Leu Val
            35                  40                  45

Ala Ser Ile Ser Asn Ser Gly Ser Thr Asn Tyr Ala Asp Ser Val Lys
        50                  55                  60

Gly Arg Phe Thr Val Ser Arg Asp Asn Asp Lys Asn Thr Gly Tyr Leu
```

```
                65                  70                  75                  80
Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
                100                 105                 110

Gln Val Thr Val Ser Ser
                115

<210> SEQ ID NO 96
<211> LENGTH: 118
<212> TYPE: PRT
<213> ORGANISM: Artificial Sequence
<220> FEATURE:
<223> OTHER INFORMATION: Nanobody sequence

<400> SEQUENCE: 96

Lys Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Arg Ser Asn
                20                  25                  30

Ala Met Gly Trp Tyr Arg Gln Ala Pro Gly Lys Lys Arg Asp Leu Val
                35                  40                  45

Ala Ser Ile Ser Asn Ser Gly Ser Thr Asn Tyr Ala Asp Ser Val Lys
                50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Ser Gly Tyr Trp Gly Gln Gly Thr
                100                 105                 110

Gln Val Thr Val Ser Ser
                115

<210> SEQ ID NO 97
<211> LENGTH: 118
<212> TYPE: PRT
<213> ORGANISM: Artificial Sequence
<220> FEATURE:
<223> OTHER INFORMATION: Nanobody sequence

<400> SEQUENCE: 97

Glu Val Gln Leu Val Glu Ser Glu Gly Gly Leu Val Gln Pro Gly Gly
1               5                   10                  15

Ser Leu Arg Leu Pro Cys Ala Thr Ser Lys Thr Ile Phe Arg Ser Asn
                20                  25                  30

Ala Met Gly Trp Tyr Arg Gln Ala Pro Gly Lys Lys Arg Asp Leu Val
                35                  40                  45

Ala Ser Ile Ser Asn Ser Gly Ser Thr Asn Tyr Ala Asp Ser Val Lys
                50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Gly Tyr Trp Gly Gln Gly Thr
                100                 105                 110

Gln Val Thr Val Ser Ser
                115
```

<210> SEQ ID NO 98
<211> LENGTH: 118
<212> TYPE: PRT
<213> ORGANISM: Artificial Sequence
<220> FEATURE:
<223> OTHER INFORMATION: Nanobody sequence

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ala Thr Ser Lys Thr Ile Phe Arg Ser Asn
            20                  25                  30

Ala Met Gly Trp Tyr Arg Gln Ala Pro Gly Lys Lys Arg Gly Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Gly Tyr Trp Gly Gln Gly Thr
            100                 105                 110

Gln Val Thr Val Ser Ser
        115

<210> SEQ ID NO 99
<211> LENGTH: 118
<212> TYPE: PRT
<213> ORGANISM: Artificial Sequence
<220> FEATURE:
<223> OTHER INFORMATION: Nanobody sequence

<400> SEQUENCE: 99

Glu Val Gln Leu Met Glu Ser Gly Gly Gly Leu Val Gln Pro Gly Gly
1               5                   10                  15

Ser Leu Arg Leu Ser Cys Ala Thr Ser Gly Thr Ile Phe Arg Ser Asn
            20                  25                  30

Ala Met Gly Trp Tyr Arg Gln Gly Pro Gly Lys Lys Arg Asp Leu Val
        35                  40                  45

Ala Ser Ile Thr Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Ser Ser Leu Lys Pro Glu Asp Thr Gly Val Tyr Tyr Cys Thr
                85                  90                  95

Leu Asp Ala Arg Arg Gly Trp Asn Thr Gly Tyr Trp Gly Gln Gly Thr
            100                 105                 110

Gln Val Thr Val Ser Ser
        115

<210> SEQ ID NO 100
<211> LENGTH: 118
<212> TYPE: PRT
<213> ORGANISM: Artificial Sequence
<220> FEATURE:
<223> OTHER INFORMATION: Nanobody sequence

<400> SEQUENCE: 100

Glu Val Gln Leu Val Glu Ser Gly Gly Gly Leu Val Gln Pro Gly Gly

```
                1               5                  10                  15
Ser Leu Arg Leu Ser Cys Ala Thr Ser Gly Ile Ile Phe Ser Asn Asn
            20                  25                  30

Ala Met Gly Trp Tyr Arg Gln Gly Pro Gly Lys Lys Arg Asp Leu Val
            35                  40                  45

Ala Ser Ile Thr Asn Thr Gly Ser Thr Asn Tyr Ala Asp Ser Val Lys
    50                  55                  60

Gly Arg Phe Thr Val Ser Arg Asp Asn Asp Arg Asn Thr Val Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
            115
```

<210> SEQ ID NO 101
<211> LENGTH: 118
<212> TYPE: PRT
<213> ORGANISM: Artificial Sequence
<220> FEATURE:
<223> OTHER INFORMATION: Nanobody sequence

<400> SEQUENCE: 101

```
Glu Val Gln Leu Val Glu Ser Gly Gly Gly Leu Val Gln Ala Gly Gly
1               5                  10                  15

Ser Leu Arg Leu Ser Cys Thr Thr Ser Gly Thr Ile Phe Ser Asn Asn
            20                  25                  30

Ala Met Gly Trp Tyr Arg Gln Ala Pro Gly Lys Lys Arg Asp Leu Val
            35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Asn Leu Lys Pro Glu Asp Thr Gly Val Tyr Tyr Cys Thr
                85                  90                  95

Leu Asp Ala Arg Arg Gly Trp Asn Thr Ala Tyr Trp Gly Gln Gly Thr
            100                 105                 110

Gln Val Thr Val Ser Ser
            115
```

<210> SEQ ID NO 102
<211> LENGTH: 118
<212> TYPE: PRT
<213> ORGANISM: Artificial Sequence
<220> FEATURE:
<223> OTHER INFORMATION: Nanobody sequence

<400> SEQUENCE: 102

```
Glu Val Gln Leu Val Glu Ser Gly Gly Gly Leu Val Gln Pro Gly Gly
1               5                  10                  15

Ser Leu Arg Leu Ser Cys Ala Thr Ser Arg Thr Ile Phe Arg Ser Asn
            20                  25                  30

Ala Met Gly Trp Tyr Arg Gln Ala Pro Gly Lys Lys Arg Asp Leu Val
            35                  40                  45

Ala Ser Ile Ser Asn Ser Gly Ser Thr Asn Tyr Ala Asp Ser Ala Lys
    50                  55                  60
```

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Gly Tyr Trp Gly Gln Gly Thr
            100                 105                 110

Gln Val Thr Val Ser Ser
        115

<210> SEQ ID NO 103
<211> LENGTH: 117
<212> TYPE: PRT
<213> ORGANISM: Artificial Sequence
<220> FEATURE:
<223> OTHER INFORMATION: Nanobody sequence

<400> SEQUENCE: 103

Glu Val Gln Leu Val Glu Ser Gly Gly Leu Val Gln Pro Gly Gly Ser
1               5                   10                  15

Leu Arg Leu Ser Cys Ala Thr Ser Gly Thr Ile Phe Ser Asn Asn Ala
            20                  25                  30

Met Gly Trp Tyr Arg Gln Ala Pro Gly Lys Lys Arg Asp Leu Val Ala
        35                  40                  45

Ser Ile Ser Asn Ser Gly Ser Thr Asn Tyr Ala Asp Ser Val Lys Gly
    50                  55                  60

Arg Phe Thr Val Ser Arg Asp Asn Asp Lys Asn Thr Gly Tyr Leu Gln
65                  70                  75                  80

Met Asn Ser Leu Lys Pro Glu Asp Thr Gly Val Tyr Tyr Cys Thr Val
                85                  90                  95

Asp Ala Arg Arg Gly Trp Asn Thr Ala Tyr Trp Gly Gln Gly Thr Gln
            100                 105                 110

Val Thr Val Ser Ser
        115

<210> SEQ ID NO 104
<211> LENGTH: 118
<212> TYPE: PRT
<213> ORGANISM: Artificial Sequence
<220> FEATURE:
<223> OTHER INFORMATION: Nanobody sequence

<400> SEQUENCE: 104

Glu Val Gln Leu Val Glu Ser Gly Gly Leu Val Gln Ala Gly Gly
1               5                   10                  15

Ser Leu Arg Leu Ser Cys Val Ala Ser Gly Ser Ile Phe Arg Ser Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Ile Asp Ala Arg Arg Gly Trp Asn Thr Gly Tyr Trp Gly Gln Gly Thr
            100                 105                 110

Gln Val Thr Val Ser Ser
        115

-continued

<210> SEQ ID NO 105
<211> LENGTH: 118
<212> TYPE: PRT
<213> ORGANISM: Artificial Sequence
<220> FEATURE:
<223> OTHER INFORMATION: Nanobody sequence

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Thr Ser Arg Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 106
<211> LENGTH: 118
<212> TYPE: PRT
<213> ORGANISM: Artificial Sequence
<220> FEATURE:
<223> OTHER INFORMATION: Nanobody sequence

<400> SEQUENCE: 106

Glu Val Gln Leu Val Glu Ser Gly Gly Gly Leu Val Gln Pro Gly Gly
1               5                   10                  15

Ser Leu Arg Leu Ser Cys Ala Thr Ser Gly Thr Val Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Ser Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Leu Asp Ala Arg Arg Gly Trp Asn Thr Ala Tyr Trp Gly Gln Gly Thr
            100                 105                 110

Gln Val Thr Val Ser Ser
        115

<210> SEQ ID NO 107
<211> LENGTH: 118
<212> TYPE: PRT
<213> ORGANISM: Artificial Sequence
<220> FEATURE:
<223> OTHER INFORMATION: Nanobody sequence

<400> SEQUENCE: 107

Glu Val Gln Leu Val Glu Ser Gly Gly Gly Leu Val Gln Pro Gly Gly
1               5                   10                  15

Ser Leu Arg Leu Ser Cys Ala Thr Ser Lys Pro Ile Phe Arg Ser Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
            85                  90                  95

Val Asp Ala Arg Arg Gly Trp Asn Thr Gly Tyr Trp Gly Gln Gly Thr
        100                 105                 110

Gln Val Thr Val Ser Ser
        115

<210> SEQ ID NO 108
<211> LENGTH: 118
<212> TYPE: PRT
<213> ORGANISM: Artificial Sequence
<220> FEATURE:
<223> OTHER INFORMATION: Nanobody sequence

<400> SEQUENCE: 108

Glu Val Gln Leu Val Glu Ser Glu Gly Gly Leu Val Gln Pro Gly Gly
1               5                   10                  15

Ser Leu Arg Leu Ser Cys Thr Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Asn Leu Lys Pro Glu Asp Thr Gly Val Tyr Tyr Cys Thr
            85                  90                  95

Leu Asp Ala Arg Arg Gly Trp Asn Thr Ala Tyr Trp Gly Gln Gly Thr
        100                 105                 110

Gln Val Thr Val Ser Ser
        115

<210> SEQ ID NO 109
<211> LENGTH: 118
<212> TYPE: PRT
<213> ORGANISM: Artificial Sequence
<220> FEATURE:
<223> OTHER INFORMATION: Nanobody sequence

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Pro Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 110
<211> LENGTH: 118
<212> TYPE: PRT
<213> ORGANISM: Artificial Sequence
<220> FEATURE:
<223> OTHER INFORMATION: Nanobody sequence

<400> SEQUENCE: 110

Glu Val Gln Leu Val Glu Ser Glu Gly Gly Val Val Gln Pro Gly Gly
1               5                   10                  15

Ser Leu Arg Leu Ser Cys Val Thr Ser Gly Ile Ile Phe Ser Asn Asn
            20                  25                  30

Ala Met Gly Trp Tyr Arg Gln Gly Pro Gly Lys Lys Arg Asp Leu Val
        35                  40                  45

Ala Ser Ile Gly Ser Thr Tyr Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Ile Asp Ala Arg Arg Gly Trp Asn Thr Ala Tyr Trp Gly Gln Gly Thr
            100                 105                 110

Pro Val Thr Val Ser Ser
        115

<210> SEQ ID NO 111
<211> LENGTH: 118
<212> TYPE: PRT
<213> ORGANISM: Artificial Sequence
<220> FEATURE:
<223> OTHER INFORMATION: Nanobody sequence

<400> SEQUENCE: 111

Glu Met Gln Leu Val Glu Ser Gly Gly Gly Leu Val Gln Pro Gly Gly
1               5                   10                  15

Ser Leu Arg Leu Ser Cys Ala Thr Ser Arg Thr Ile Phe Arg Ser Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Thr Asn Tyr Ala Asp Ser Val Lys
    50                  55                  60

Gly Arg Phe Thr Val Ser Arg Asp Asn Asp Lys Ser Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Gly Tyr Trp Gly Gln Gly Thr
            100                 105                 110

Gln Val Thr Val Ser Ser

<210> SEQ ID NO 112
<211> LENGTH: 118
<212> TYPE: PRT
<213> ORGANISM: Artificial Sequence
<220> FEATURE:
<223> OTHER INFORMATION: Nanobody sequence

<400> SEQUENCE: 112

```
Glu Val Gln Leu Val Glu Ser Gly Gly Val Val Gln Pro Gly Glu
1               5                   10                  15

Ser Leu Arg Leu Ser Cys Val Thr Ser Gly Ile Ile Phe Ser Asn Asn
            20                  25                  30

Ala Met Gly Trp Tyr Arg Gln Gly Pro Gly Lys Lys Arg Asp Leu Val
        35                  40                  45

Ala Ser Ile Gly Ser Thr Tyr Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Ile Asp Ala Arg Arg Gly Trp Asn Thr Ala Tyr Trp Gly Gln Gly Thr
            100                 105                 110

Pro Val Thr Val Ser Ser
        115
```

<210> SEQ ID NO 113
<211> LENGTH: 118
<212> TYPE: PRT
<213> ORGANISM: Artificial Sequence
<220> FEATURE:
<223> OTHER INFORMATION: Nanobody sequence

<400> SEQUENCE: 113

```
Lys Val Gln Leu Val Glu Ser Gly Gly Gly Leu Val Gln Pro Gly Asp
1               5                   10                  15

Ser Leu Arg Leu Ser Cys Ala Ala Ser Gly Leu Thr Leu Asp Asp Tyr
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Ile Asp Ala Arg Arg Gly Trp Asn Thr Gly Tyr Trp Gly Gln Gly Thr
            100                 105                 110

Gln Val Thr Val Ser Ser
        115
```

<210> SEQ ID NO 114
<211> LENGTH: 118
<212> TYPE: PRT
<213> ORGANISM: Artificial Sequence
<220> FEATURE:
<223> OTHER INFORMATION: Nanobody sequence

<400> SEQUENCE: 114

```
Lys Val Gln Leu Val Glu Ser Gly Gly Gly Leu Val Gln Pro Gly Gly
1               5                   10                  15

Ser Leu Arg Leu Ser Cys Ala Thr Ser Arg Thr Ile Phe Arg Ser Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Ile Asp Ala Arg Arg Gly Trp Asn Thr Gly Tyr Trp Gly Gln Gly Thr
                100                 105                 110

Gln Val Thr Val Ser Ser
            115
```

<210> SEQ ID NO 115
<211> LENGTH: 118
<212> TYPE: PRT
<213> ORGANISM: Artificial Sequence
<220> FEATURE:
<223> OTHER INFORMATION: Nanobody sequence

<400> SEQUENCE: 115

```
Glu Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Ser Asn Asn
            20                  25                  30

Ala Met Gly Trp Tyr Arg Gln Val Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

Arg Met Asn Ser Leu Lys Pro Glu Asp Thr Gly Val Tyr Tyr Cys Thr
                85                  90                  95

Val Asp Ala Arg Arg Gly Trp Asn Thr Gly Tyr Trp Gly Gln Gly Thr
                100                 105                 110

Gln Val Thr Val Ser Ser
            115
```

<210> SEQ ID NO 116
<211> LENGTH: 118
<212> TYPE: PRT
<213> ORGANISM: Artificial Sequence
<220> FEATURE:
<223> OTHER INFORMATION: Nanobody sequence

<400> SEQUENCE: 116

```
Glu Val Gln Leu Val Glu Ser Gly Gly Gly Leu Val Gln Ala Gly Gly
1               5                   10                  15

Ser Leu Arg Leu Ser Cys Val Thr Ser Gly Ile Ile Phe Ser Asn Asn
            20                  25                  30

Ala Met Gly Trp Tyr Arg Gln Gly Pro Gly Lys Lys Arg Asp Leu Val
        35                  40                  45

Ala Ser Ile Ser Ser Thr Tyr Ser Thr Asn Tyr Ala Asp Ser Val Lys
```

```
                    50                  55                  60
Gly Arg Phe Thr Val Ser Arg Asp Asn Asp Lys Asn Thr Gly Tyr Leu
 65                  70                  75                  80

Gln Met Asn Ser Leu Lys Pro Glu Asp Thr Gly Val Tyr Tyr Cys Thr
                     85                  90                  95

Ile Asp Ala Arg Arg Gly Trp Asn Thr Ala Tyr Trp Gly Gln Gly Thr
                100                 105                 110

Pro Val Thr Val Ser Ser
            115
```

<210> SEQ ID NO 117
<211> LENGTH: 118
<212> TYPE: PRT
<213> ORGANISM: Artificial Sequence
<220> FEATURE:
<223> OTHER INFORMATION: Nanobody sequence

<400> SEQUENCE: 117

```
Glu Val Gln Leu Val Glu Ser Gly Gly Gly Leu Val Gln Pro Gly Gly
 1               5                  10                  15

Ser Leu Arg Leu Ser Cys Ala Thr Ser Lys Thr Ile Phe Arg Ser Asn
                20                  25                  30

Ala Met Gly Trp Tyr Arg Gln Ala Pro Gly Lys Lys Arg Asp Leu Val
             35                  40                  45

Ala Ser Ile Ser Asn Ser Gly Ser Thr Asn Tyr Thr Asp Ser Val Lys
         50                  55                  60

Gly Arg Phe Thr Val Ser Arg Asp Asn Asp Lys Asn Thr Gly Tyr Leu
 65                  70                  75                  80

Gln Met Asn Ser Leu Lys Pro Glu Asp Thr Gly Val Tyr Tyr Cys Thr
                 85                  90                  95

Val Asp Ala Arg Arg Gly Trp Asn Thr Gly Tyr Trp Gly Gln Gly Thr
                100                 105                 110

Gln Val Thr Val Ser Ser
            115
```

<210> SEQ ID NO 118
<211> LENGTH: 118
<212> TYPE: PRT
<213> ORGANISM: Artificial Sequence
<220> FEATURE:
<223> OTHER INFORMATION: Nanobody sequence

<400> SEQUENCE: 118

```
Lys Val Gln Leu Val Glu Ser Gly Gly Gly Leu Val Gln Pro Gly Gly
 1               5                  10                  15

Ser Leu Arg Leu Ser Cys Ala Thr Ser Arg Thr Ile Phe Arg Ser Asn
                20                  25                  30

Ala Met Gly Trp Tyr Arg Gln Ala Pro Gly Lys Lys Arg Asp Leu Val
             35                  40                  45

Ala Ser Ile Ser Asn Ser Gly Ser Thr Asn Tyr Ala Asp Ser Val Lys
         50                  55                  60

Gly Arg Phe Thr Val Ser Arg Asp Asn Asp Lys Asn Thr Gly Tyr Leu
 65                  70                  75                  80

Gln Met Asn Ser Leu Lys Pro Glu Asp Thr Gly Val Tyr Tyr Cys Thr
                 85                  90                  95

Val Asp Ala Arg Arg Gly Trp Asn Thr Gly Tyr Trp Gly Gln Gly Thr
                100                 105                 110
```

Gln Val Thr Val Ser Ser
        115

<210> SEQ ID NO 119
<211> LENGTH: 118
<212> TYPE: PRT
<213> ORGANISM: Artificial Sequence
<220> FEATURE:
<223> OTHER INFORMATION: Nanobody sequence

<400> SEQUENCE: 119

Glu Val Gln Leu Val Glu Ser Gly Gly Gly Leu Val Gln Pro Gly Gly
1               5                   10                  15

Ser Leu Arg Leu Ser Cys Ala Thr Ser Arg Thr Ile Phe Arg Ser Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Ser Val Lys
    50                  55                  60

Gly Arg Phe Ala Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Gly Tyr Trp Gly Gln Gly Thr
            100                 105                 110

Gln Val Thr Val Ser Ser
        115

<210> SEQ ID NO 120
<211> LENGTH: 118
<212> TYPE: PRT
<213> ORGANISM: Artificial Sequence
<220> FEATURE:
<223> OTHER INFORMATION: Nanobody sequence

<400> SEQUENCE: 120

Glu Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Asn Ser Gly Ser Thr Asn Tyr Ala Asp Phe Val Lys
    50                  55                  60

Gly Arg Phe Thr Val Ser Arg Asp Asn Asp Lys Asn Thr Gly Tyr Leu
65                  70                  75                  80

Gln Met Asn Ser Leu Lys Pro Glu Asp Thr Gly Val Tyr Tyr Cys Thr
                85                  90                  95

Val Asp Ala Arg Arg Gly Trp Asn Thr Ala Tyr Trp Gly Gln Gly Thr
            100                 105                 110

Gln Val Thr Val Ser Ser
        115

<210> SEQ ID NO 121
<211> LENGTH: 118
<212> TYPE: PRT
<213> ORGANISM: Artificial Sequence
<220> FEATURE:
<223> OTHER INFORMATION: Nanobody sequence

<400> SEQUENCE: 121

Glu Val Gln Leu Val Glu Ser Gly Gly Gly Ser Val Gln Pro Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
            115

<210> SEQ ID NO 122
<211> LENGTH: 118
<212> TYPE: PRT
<213> ORGANISM: Artificial Sequence
<220> FEATURE:
<223> OTHER INFORMATION: Nanobody sequence

<400> SEQUENCE: 122

Asp Val Gln Leu Val Glu Ser Gly Gly Gly Ser Val Gln Pro Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
            115

<210> SEQ ID NO 123
<211> LENGTH: 118
<212> TYPE: PRT
<213> ORGANISM: Artificial Sequence
<220> FEATURE:
<223> OTHER INFORMATION: Nanobody sequence

<400> SEQUENCE: 123

Glu Val Gln Leu Val Glu Ser Gly Gly Gly Leu Val Gln Pro Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

```
Ala Ala Ile Asn Ser Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Val Tyr Tyr Cys Thr
                 85                  90                  95

Ser Asp Pro Arg Arg Gly Trp Asp Thr Arg Tyr Trp Gly Gln Gly Thr
                100                 105                 110

Leu Val Thr Val Ser Ser
                115

<210> SEQ ID NO 124
<211> LENGTH: 118
<212> TYPE: PRT
<213> ORGANISM: Artificial Sequence
<220> FEATURE:
<223> OTHER INFORMATION: Nanobody sequence

<400> SEQUENCE: 124

Glu Val Gln Leu Val Glu Ser Gly Gly Gly Ser Val Gln Pro Gly Gly
 1               5                  10                  15

Ser Leu Arg Leu Ser Cys Ala Ala Ser Gly Ser Ile Phe Ser Ser Asn
                20                  25                  30

Ala Met Ala Trp Tyr Arg Gln Ala Pro Gly Lys Arg Arg Asp Leu Val
                35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Val Tyr Tyr Cys Thr
                 85                  90                  95

Ser Asp Pro Arg Arg Gly Trp Asp Thr Arg Tyr Trp Gly Gln Gly Thr
                100                 105                 110

Leu Val Thr Val Ser Ser
                115

<210> SEQ ID NO 125
<211> LENGTH: 118
<212> TYPE: PRT
<213> ORGANISM: Artificial Sequence
<220> FEATURE:
<223> OTHER INFORMATION: Nanobody sequence

<400> SEQUENCE: 125

Glu Val Gln Leu Val Glu Ser Gly Gly Gly Ser Val Gln Pro Gly Glu
 1               5                  10                  15

Ser Leu Arg Leu Ser Cys Ala Ala Ser Gly Ser Ile Phe Ser Ser Asn
                20                  25                  30

Ala Met Ala Trp Tyr Arg Gln Ala Pro Gly Lys Gln Arg Asp Leu Val
                35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Val Tyr Tyr Cys Thr
                 85                  90                  95

Ser Asp Pro Arg Arg Gly Trp Asp Thr Arg Tyr Trp Gly Gln Gly Thr
                100                 105                 110
```

```
Leu Val Thr Val Ser Ser
        115

<210> SEQ ID NO 126
<211> LENGTH: 118
<212> TYPE: PRT
<213> ORGANISM: Artificial Sequence
<220> FEATURE:
<223> OTHER INFORMATION: Nanobody sequence

<400> SEQUENCE: 126

Glu Val Gln Leu Val Glu Ser Gly Gly Gly Ser Val Gln Pro Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Glu Leu Val
        35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 127
<211> LENGTH: 118
<212> TYPE: PRT
<213> ORGANISM: Artificial Sequence
<220> FEATURE:
<223> OTHER INFORMATION: Nanobody sequence

<400> SEQUENCE: 127

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 128
<211> LENGTH: 118
<212> TYPE: PRT
<213> ORGANISM: Artificial Sequence
<220> FEATURE:
<223> OTHER INFORMATION: Nanobody sequence
```

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 129
<211> LENGTH: 118
<212> TYPE: PRT
<213> ORGANISM: Artificial Sequence
<220> FEATURE:
<223> OTHER INFORMATION: Nanobody sequence

<400> SEQUENCE: 129

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Glu Leu Val
        35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 130
<211> LENGTH: 118
<212> TYPE: PRT
<213> ORGANISM: Artificial Sequence
<220> FEATURE:
<223> OTHER INFORMATION: Nanobody sequence

<400> SEQUENCE: 130

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Glu Leu Val
        35                  40                  45

```
Ala Ala Ile Asn Ser Val Gly Val Thr Lys Tyr Ala Asp Ser Val Lys
        50                  55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Val Tyr Tyr Cys Thr
                 85                  90                  95

Ser Asp Pro Arg Arg Gly Trp Asp Thr Arg Tyr Trp Gly Gln Gly Thr
            100                 105                 110

Leu Val Thr Val Ser Ser
            115

<210> SEQ ID NO 131
<211> LENGTH: 118
<212> TYPE: PRT
<213> ORGANISM: Artificial Sequence
<220> FEATURE:
<223> OTHER INFORMATION: Nanobody sequence

<400> SEQUENCE: 131

Glu Val Gln Leu Val Glu Ser Gly Gly Gly Ser Val Gln Ala Gly Glu
 1               5                  10                  15

Ser Leu Arg Leu Ser Cys Ala Ala Ser Gly Ser Ile Phe Ser Ser Asn
                 20                  25                  30

Ala Met Ala Trp Tyr Arg Gln Ala Pro Gly Lys Arg Arg Asp Leu Val
             35                  40                  45

Ala Ala Ile Ser Ser Val Gly Val Thr Lys Tyr Ala Asp Ser Val Lys
        50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                 85                  90                  95

Ser Asp Pro Arg Arg Gly Trp Asp Thr Arg Tyr Trp Gly Gln Gly Thr
            100                 105                 110

Leu Val Thr Val Ser Ser
            115

<210> SEQ ID NO 132
<211> LENGTH: 118
<212> TYPE: PRT
<213> ORGANISM: Artificial Sequence
<220> FEATURE:
<223> OTHER INFORMATION: Nanobody sequence

<400> SEQUENCE: 132

Glu Val Gln Leu Val Glu Ser Gly Gly Gly Ser Val Gln Ala Gly Glu
 1               5                  10                  15

Ser Leu Arg Leu Ser Cys Ala Ala Ser Gly Ser Ile Phe Ser Ser Asn
                 20                  25                  30

Ala Met Ala Trp Tyr Arg Gln Ala Pro Gly Lys Arg Arg Asp Leu Val
             35                  40                  45

Ala Ala Ile Gln Ser Val Gly Val Thr Lys Tyr Ala Asp Ser Val Lys
        50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                 85                  90                  95

Ser Asp Pro Arg Arg Gly Trp Asp Thr Arg Tyr Trp Gly Gln Gly Thr
```

Leu Val Thr Val Ser Ser
        115

<210> SEQ ID NO 133
<211> LENGTH: 118
<212> TYPE: PRT
<213> ORGANISM: Artificial Sequence
<220> FEATURE:
<223> OTHER INFORMATION: Nanobody sequence

<400> SEQUENCE: 133

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Gly Ser Val Gly Val Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 134
<211> LENGTH: 118
<212> TYPE: PRT
<213> ORGANISM: Artificial Sequence
<220> FEATURE:
<223> OTHER INFORMATION: Nanobody sequence

<400> SEQUENCE: 134

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Thr Ser Val Gly Val Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 135
<211> LENGTH: 118
<212> TYPE: PRT
<213> ORGANISM: Artificial Sequence
<220> FEATURE:

<223> OTHER INFORMATION: Nanobody sequence

<400> SEQUENCE: 135

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Thr Val Gly Val Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 136
<211> LENGTH: 118
<212> TYPE: PRT
<213> ORGANISM: Artificial Sequence
<220> FEATURE:
<223> OTHER INFORMATION: Nanobody sequence

<400> SEQUENCE: 136

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Gly Val Gly Val Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 137
<211> LENGTH: 118
<212> TYPE: PRT
<213> ORGANISM: Artificial Sequence
<220> FEATURE:
<223> OTHER INFORMATION: Nanobody sequence

<400> SEQUENCE: 137

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val

```
                35                  40                  45
Ala Ala Ile Asn Pro Val Gly Val Thr Lys Tyr Ala Asp Ser Val Lys
 50                  55                  60
Gly Arg Phe Thr Ile Ser Arg Asp Asn Ala Lys Asn Thr Val Tyr Leu
 65                  70                  75                  80
Gln Met Asn Ser Leu Lys Pro Glu Asp Thr Ala Val Tyr Tyr Cys Thr
                 85                  90                  95
Ser Asp Pro Arg Arg Gly Trp Asp Thr Arg Tyr Trp Gly Gln Gly Thr
                100                 105                 110
Leu Val Thr Val Ser Ser
            115

<210> SEQ ID NO 138
<211> LENGTH: 118
<212> TYPE: PRT
<213> ORGANISM: Artificial Sequence
<220> FEATURE:
<223> OTHER INFORMATION: Nanobody sequence

<400> SEQUENCE: 138

Asp Val Gln Leu Val Glu Ser Gly Gly Gly Leu Val Gln Pro Gly Gly
 1               5                  10                  15
Ser Leu Arg Leu Ser Cys Ala Ala Ser Gly Ser Ile Phe Ser Ser Thr
                20                  25                  30
Ala Met Ala Trp Tyr Arg Gln Ala Pro Gly Lys Arg Arg Asp Leu Val
                35                  40                  45
Ala Ala Ile Ser Ser Val Gly Val Thr Lys Tyr Ala Asp Ser Val Lys
 50                  55                  60
Gly Arg Phe Thr Ile Ser Arg Asp Asn Ser Lys Asn Thr Val Tyr Leu
 65                  70                  75                  80
Gln Met Asn Ser Leu Arg Pro Glu Asp Thr Ala Val Tyr Tyr Cys Thr
                 85                  90                  95
Ser Asp Pro Arg Arg Gly Trp Asp Thr Arg Tyr Trp Gly Gln Gly Thr
                100                 105                 110
Leu Val Thr Val Ser Ser
            115

<210> SEQ ID NO 139
<211> LENGTH: 118
<212> TYPE: PRT
<213> ORGANISM: Artificial Sequence
<220> FEATURE:
<223> OTHER INFORMATION: Nanobody sequence

<400> SEQUENCE: 139

Asp Val Gln Leu Val Glu Ser Gly Gly Gly Leu Val Gln Pro Gly Gly
 1               5                  10                  15
Ser Leu Arg Leu Ser Cys Ala Ala Ser Gly Ser Ile Phe Ser Ser Thr
                20                  25                  30
Ala Met Ala Trp Tyr Arg Gln Ala Pro Gly Lys Arg Arg Asp Leu Val
                35                  40                  45
Ala Ala Ile Ser Thr Val Gly Val Thr Lys Tyr Ala Asp Ser Val Lys
 50                  55                  60
Gly Arg Phe Thr Ile Ser Arg Asp Asn Ser Lys Asn Thr Val Tyr Leu
 65                  70                  75                  80
Gln Met Asn Ser Leu Arg Pro Glu Asp Thr Ala Val Tyr Tyr Cys Thr
                 85                  90                  95
```

```
Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 140
<211> LENGTH: 118
<212> TYPE: PRT
<213> ORGANISM: Artificial Sequence
<220> FEATURE:
<223> OTHER INFORMATION: Nanobody sequence

<400> SEQUENCE: 140

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 141
<211> LENGTH: 10
<212> TYPE: PRT
<213> ORGANISM: Artificial Sequence
<220> FEATURE:
<223> OTHER INFORMATION: CDR sequence

<400> SEQUENCE: 141

Gly Ser Ile Phe Ser Ser Asn Ala Met Ala
1               5                   10

<210> SEQ ID NO 142
<211> LENGTH: 10
<212> TYPE: PRT
<213> ORGANISM: Artificial Sequence
<220> FEATURE:
<223> OTHER INFORMATION: CDR sequence

<400> SEQUENCE: 142

Gly Thr Ile Phe Ser Ser Asn Ala Met Ala
1               5                   10

<210> SEQ ID NO 143
<211> LENGTH: 10
<212> TYPE: PRT
<213> ORGANISM: Artificial Sequence
<220> FEATURE:
<223> OTHER INFORMATION: CDR sequence

<400> SEQUENCE: 143

Gly Ser Ile Phe Ser Ser Asn Ala Lys Ala
1               5                   10
```

<210> SEQ ID NO 144
<211> LENGTH: 10
<212> TYPE: PRT
<213> ORGANISM: Artificial Sequence
<220> FEATURE:
<223> OTHER INFORMATION: CDR sequence

<400> SEQUENCE: 144

Gly Ser Ile Phe Ser Arg Asn Ala Met Ala
1               5                   10

<210> SEQ ID NO 145
<211> LENGTH: 10
<212> TYPE: PRT
<213> ORGANISM: Artificial Sequence
<220> FEATURE:
<223> OTHER INFORMATION: CDR sequence

<400> SEQUENCE: 145

Gly Gly Ile Phe Ser Arg Asn Ala Met Ala
1               5                   10

<210> SEQ ID NO 146
<211> LENGTH: 10
<212> TYPE: PRT
<213> ORGANISM: Artificial Sequence
<220> FEATURE:
<223> OTHER INFORMATION: CDR sequence

<400> SEQUENCE: 146

Gly Arg Thr Phe Ser Ser Tyr Ala Met Gly
1               5                   10

<210> SEQ ID NO 147
<211> LENGTH: 10
<212> TYPE: PRT
<213> ORGANISM: Artificial Sequence
<220> FEATURE:
<223> OTHER INFORMATION: CDR sequence

<400> SEQUENCE: 147

Gly Thr Ile Phe Ser Asn Asn Ala Met Gly
1               5                   10

<210> SEQ ID NO 148
<211> LENGTH: 10
<212> TYPE: PRT
<213> ORGANISM: Artificial Sequence
<220> FEATURE:
<223> OTHER INFORMATION: CDR sequence

<400> SEQUENCE: 148

Gly Thr Ile Phe Ser Asn Thr Ala Met Gly
1               5                   10

<210> SEQ ID NO 149
<211> LENGTH: 10
<212> TYPE: PRT
<213> ORGANISM: Artificial Sequence
<220> FEATURE:
<223> OTHER INFORMATION: CDR sequence

<400> SEQUENCE: 149

Gly Ile Ile Phe Ser Asn Asn Ala Met Gly
1               5                   10

```
<210> SEQ ID NO 150
<211> LENGTH: 10
<212> TYPE: PRT
<213> ORGANISM: Artificial Sequence
<220> FEATURE:
<223> OTHER INFORMATION: CDR sequence

<400> SEQUENCE: 150

Arg Thr Ile Phe Arg Ser Asn Ala Met Gly
1               5                   10

<210> SEQ ID NO 151
<211> LENGTH: 10
<212> TYPE: PRT
<213> ORGANISM: Artificial Sequence
<220> FEATURE:
<223> OTHER INFORMATION: CDR sequence

<400> SEQUENCE: 151

Gly Thr Ile Phe Arg Ser Asn Ala Met Gly
1               5                   10

<210> SEQ ID NO 152
<211> LENGTH: 10
<212> TYPE: PRT
<213> ORGANISM: Artificial Sequence
<220> FEATURE:
<223> OTHER INFORMATION: CDR sequence

<400> SEQUENCE: 152

Gly Thr Ile Phe Arg Thr Asn Ala Met Gly
1               5                   10

<210> SEQ ID NO 153
<211> LENGTH: 10
<212> TYPE: PRT
<213> ORGANISM: Artificial Sequence
<220> FEATURE:
<223> OTHER INFORMATION: CDR sequence

<400> SEQUENCE: 153

Lys Thr Ile Phe Arg Ser Asn Ala Met Gly
1               5                   10

<210> SEQ ID NO 154
<211> LENGTH: 10
<212> TYPE: PRT
<213> ORGANISM: Artificial Sequence
<220> FEATURE:
<223> OTHER INFORMATION: CDR sequence

<400> SEQUENCE: 154

Gly Thr Thr Phe Arg Ser Asn Ala Met Gly
1               5                   10

<210> SEQ ID NO 155
<211> LENGTH: 10
<212> TYPE: PRT
<213> ORGANISM: Artificial Sequence
<220> FEATURE:
<223> OTHER INFORMATION: CDR sequence

<400> SEQUENCE: 155

Ala Thr Ile Phe Arg Ser Asn Ala Met Gly
1               5                   10

<210> SEQ ID NO 156
```

```
<211> LENGTH: 10
<212> TYPE: PRT
<213> ORGANISM: Artificial Sequence
<220> FEATURE:
<223> OTHER INFORMATION: CDR sequence

<400> SEQUENCE: 156

Gly Leu Ile Phe Ser Asn Asn Ala Met Gly
1               5                   10

<210> SEQ ID NO 157
<211> LENGTH: 10
<212> TYPE: PRT
<213> ORGANISM: Artificial Sequence
<220> FEATURE:
<223> OTHER INFORMATION: CDR sequence

<400> SEQUENCE: 157

Gly Ser Ile Phe Arg Ser Asn Ala Met Gly
1               5                   10

<210> SEQ ID NO 158
<211> LENGTH: 10
<212> TYPE: PRT
<213> ORGANISM: Artificial Sequence
<220> FEATURE:
<223> OTHER INFORMATION: CDR sequence

<400> SEQUENCE: 158

Arg Thr Ile Phe Ser Asn Asn Ala Met Gly
1               5                   10

<210> SEQ ID NO 159
<211> LENGTH: 10
<212> TYPE: PRT
<213> ORGANISM: Artificial Sequence
<220> FEATURE:
<223> OTHER INFORMATION: CDR sequence

<400> SEQUENCE: 159

Gly Thr Val Phe Ser Asn Asn Ala Met Gly
1               5                   10

<210> SEQ ID NO 160
<211> LENGTH: 10
<212> TYPE: PRT
<213> ORGANISM: Artificial Sequence
<220> FEATURE:
<223> OTHER INFORMATION: CDR sequence

<400> SEQUENCE: 160

Lys Pro Ile Phe Arg Ser Asn Ala Met Gly
1               5                   10

<210> SEQ ID NO 161
<211> LENGTH: 10
<212> TYPE: PRT
<213> ORGANISM: Artificial Sequence
<220> FEATURE:
<223> OTHER INFORMATION: CDR sequence

<400> SEQUENCE: 161

Gly Leu Thr Leu Asp Asp Tyr Ala Met Gly
1               5                   10

<210> SEQ ID NO 162
<211> LENGTH: 9
```

```
<212> TYPE: PRT
<213> ORGANISM: Artificial Sequence
<220> FEATURE:
<223> OTHER INFORMATION: CDR sequence

<400> SEQUENCE: 162

Ala Ile Asn Ser Val Gly Val Thr Lys
1               5

<210> SEQ ID NO 163
<211> LENGTH: 9
<212> TYPE: PRT
<213> ORGANISM: Artificial Sequence
<220> FEATURE:
<223> OTHER INFORMATION: CDR sequence

<400> SEQUENCE: 163

Val Ile Asn Ser Val Gly Ile Thr Lys
1               5

<210> SEQ ID NO 164
<211> LENGTH: 9
<212> TYPE: PRT
<213> ORGANISM: Artificial Sequence
<220> FEATURE:
<223> OTHER INFORMATION: CDR sequence

<400> SEQUENCE: 164

Gly Ile Asn Ser Val Gly Ile Thr Lys
1               5

<210> SEQ ID NO 165
<211> LENGTH: 9
<212> TYPE: PRT
<213> ORGANISM: Artificial Sequence
<220> FEATURE:
<223> OTHER INFORMATION: CDR sequence

<400> SEQUENCE: 165

Gly Ile Asn Ser Val Asp Ile Thr Lys
1               5

<210> SEQ ID NO 166
<211> LENGTH: 9
<212> TYPE: PRT
<213> ORGANISM: Artificial Sequence
<220> FEATURE:
<223> OTHER INFORMATION: CDR sequence

<400> SEQUENCE: 166

Ala Ile Asn Ser Val Gly Ile Thr Lys
1               5

<210> SEQ ID NO 167
<211> LENGTH: 9
<212> TYPE: PRT
<213> ORGANISM: Artificial Sequence
<220> FEATURE:
<223> OTHER INFORMATION: CDR sequence

<400> SEQUENCE: 167

Leu Ile Asn Ser Val Gly Ile Thr Lys
1               5

<210> SEQ ID NO 168
<211> LENGTH: 9
<212> TYPE: PRT
```

```
<213> ORGANISM: Artificial Sequence
<220> FEATURE:
<223> OTHER INFORMATION: CDR sequence

<400> SEQUENCE: 168

Val Ile Asn Thr Val Gly Ile Thr Lys
1               5

<210> SEQ ID NO 169
<211> LENGTH: 9
<212> TYPE: PRT
<213> ORGANISM: Artificial Sequence
<220> FEATURE:
<223> OTHER INFORMATION: CDR sequence

<400> SEQUENCE: 169

Leu Ile Asp Ser Ala Gly Ile Thr Lys
1               5

<210> SEQ ID NO 170
<211> LENGTH: 9
<212> TYPE: PRT
<213> ORGANISM: Artificial Sequence
<220> FEATURE:
<223> OTHER INFORMATION: CDR sequence

<400> SEQUENCE: 170

Gly Ile Asn Ser Val Gly Ile Ala Lys
1               5

<210> SEQ ID NO 171
<211> LENGTH: 9
<212> TYPE: PRT
<213> ORGANISM: Artificial Sequence
<220> FEATURE:
<223> OTHER INFORMATION: CDR sequence

<400> SEQUENCE: 171

Val Ile Asn Lys Val Gly Ile Thr Lys
1               5

<210> SEQ ID NO 172
<211> LENGTH: 9
<212> TYPE: PRT
<213> ORGANISM: Artificial Sequence
<220> FEATURE:
<223> OTHER INFORMATION: CDR sequence

<400> SEQUENCE: 172

Ser Ile Asn Ser Val Gly Ile Thr Lys
1               5

<210> SEQ ID NO 173
<211> LENGTH: 9
<212> TYPE: PRT
<213> ORGANISM: Artificial Sequence
<220> FEATURE:
<223> OTHER INFORMATION: CDR sequence

<400> SEQUENCE: 173

Gly Ile Asn Ser Val Asp Ile Thr Arg
1               5

<210> SEQ ID NO 174
<211> LENGTH: 9
<212> TYPE: PRT
<213> ORGANISM: Artificial Sequence
```

```
<220> FEATURE:
<223> OTHER INFORMATION: CDR sequence

<400> SEQUENCE: 174

Ala Ile Asn Ser Val Gly Thr Thr Lys
1               5

<210> SEQ ID NO 175
<211> LENGTH: 9
<212> TYPE: PRT
<213> ORGANISM: Artificial Sequence
<220> FEATURE:
<223> OTHER INFORMATION: CDR sequence

<400> SEQUENCE: 175

Ser Ile Asp Ser Val Gly Ile Thr Lys
1               5

<210> SEQ ID NO 176
<211> LENGTH: 10
<212> TYPE: PRT
<213> ORGANISM: Artificial Sequence
<220> FEATURE:
<223> OTHER INFORMATION: CDR sequence

<400> SEQUENCE: 176

Gly Ile Ser Gly Ser Ala Ser Arg Lys Tyr
1               5                   10

<210> SEQ ID NO 177
<211> LENGTH: 10
<212> TYPE: PRT
<213> ORGANISM: Artificial Sequence
<220> FEATURE:
<223> OTHER INFORMATION: CDR sequence

<400> SEQUENCE: 177

Gly Ile Ser Gly Ser Gly Ser Arg Lys Tyr
1               5                   10

<210> SEQ ID NO 178
<211> LENGTH: 9
<212> TYPE: PRT
<213> ORGANISM: Artificial Sequence
<220> FEATURE:
<223> OTHER INFORMATION: CDR sequence

<400> SEQUENCE: 178

Ser Ile Ser Ser Ser Gly Ser Thr Asn
1               5

<210> SEQ ID NO 179
<211> LENGTH: 9
<212> TYPE: PRT
<213> ORGANISM: Artificial Sequence
<220> FEATURE:
<223> OTHER INFORMATION: CDR sequence

<400> SEQUENCE: 179

Ser Ile Ser Asn Ser Gly Ser Thr Asn
1               5

<210> SEQ ID NO 180
<211> LENGTH: 9
<212> TYPE: PRT
<213> ORGANISM: Artificial Sequence
<220> FEATURE:
```

<223> OTHER INFORMATION: CDR sequence

<400> SEQUENCE: 180

Ser Ile Gly Ser Thr Tyr Ser Thr Asn
1               5

<210> SEQ ID NO 181
<211> LENGTH: 9
<212> TYPE: PRT
<213> ORGANISM: Artificial Sequence
<220> FEATURE:
<223> OTHER INFORMATION: CDR sequence

<400> SEQUENCE: 181

Ser Ile Ser Ser Thr Tyr Ser Thr Asn
1               5

<210> SEQ ID NO 182
<211> LENGTH: 9
<212> TYPE: PRT
<213> ORGANISM: Artificial Sequence
<220> FEATURE:
<223> OTHER INFORMATION: CDR sequence

<400> SEQUENCE: 182

Ser Ile Thr Asn Ser Gly Ser Thr Asn
1               5

<210> SEQ ID NO 183
<211> LENGTH: 9
<212> TYPE: PRT
<213> ORGANISM: Artificial Sequence
<220> FEATURE:
<223> OTHER INFORMATION: CDR sequence

<400> SEQUENCE: 183

Ser Ile Ser Asn Ser Gly Ser Ala Asn
1               5

<210> SEQ ID NO 184
<211> LENGTH: 9
<212> TYPE: PRT
<213> ORGANISM: Artificial Sequence
<220> FEATURE:
<223> OTHER INFORMATION: CDR sequence

<400> SEQUENCE: 184

Ser Ile Ser Ile Ser Gly Ser Thr Asn
1               5

<210> SEQ ID NO 185
<211> LENGTH: 9
<212> TYPE: PRT
<213> ORGANISM: Artificial Sequence
<220> FEATURE:
<223> OTHER INFORMATION: CDR sequence

<400> SEQUENCE: 185

Ser Ile Thr Asn Thr Gly Ser Thr Asn
1               5

<210> SEQ ID NO 186
<211> LENGTH: 10
<212> TYPE: PRT
<213> ORGANISM: Artificial Sequence
<220> FEATURE:
<223> OTHER INFORMATION: CDR sequence

<400> SEQUENCE: 186

Asp Pro Arg Arg Gly Trp Asp Thr Arg Tyr
1               5                   10

<210> SEQ ID NO 187
<211> LENGTH: 10
<212> TYPE: PRT
<213> ORGANISM: Artificial Sequence
<220> FEATURE:
<223> OTHER INFORMATION: CDR sequence

<400> SEQUENCE: 187

Asp Ala Arg Arg Gly Trp Asp Thr Arg Tyr
1               5                   10

<210> SEQ ID NO 188
<211> LENGTH: 10
<212> TYPE: PRT
<213> ORGANISM: Artificial Sequence
<220> FEATURE:
<223> OTHER INFORMATION: CDR sequence

<400> SEQUENCE: 188

Asp Pro Arg Arg Gly Trp Asn Thr Arg Tyr
1               5                   10

<210> SEQ ID NO 189
<211> LENGTH: 10
<212> TYPE: PRT
<213> ORGANISM: Artificial Sequence
<220> FEATURE:
<223> OTHER INFORMATION: CDR sequence

<400> SEQUENCE: 189

Asp Gly Arg Arg Gly Trp Asp Thr Arg Tyr
1               5                   10

<210> SEQ ID NO 190
<211> LENGTH: 10
<212> TYPE: PRT
<213> ORGANISM: Artificial Sequence
<220> FEATURE:
<223> OTHER INFORMATION: CDR sequence

<400> SEQUENCE: 190

Asp Ala Arg Arg Gly Trp Asn Thr Lys Tyr
1               5                   10

<210> SEQ ID NO 191
<211> LENGTH: 11
<212> TYPE: PRT
<213> ORGANISM: Artificial Sequence
<220> FEATURE:
<223> OTHER INFORMATION: CDR sequence

<400> SEQUENCE: 191

Ser Asn Ser Tyr Pro Lys Val Gln Phe Asp Tyr
1               5                   10

<210> SEQ ID NO 192
<211> LENGTH: 10
<212> TYPE: PRT
<213> ORGANISM: Artificial Sequence
<220> FEATURE:
<223> OTHER INFORMATION: CDR sequence

```
<400> SEQUENCE: 192

Asp Ala Arg Arg Gly Trp Asn Thr Ala Tyr
1               5                   10

<210> SEQ ID NO 193
<211> LENGTH: 10
<212> TYPE: PRT
<213> ORGANISM: Artificial Sequence
<220> FEATURE:
<223> OTHER INFORMATION: CDR sequence

<400> SEQUENCE: 193

Asp Ala Arg Arg Gly Trp Asn Ser Gly Tyr
1               5                   10

<210> SEQ ID NO 194
<211> LENGTH: 10
<212> TYPE: PRT
<213> ORGANISM: Artificial Sequence
<220> FEATURE:
<223> OTHER INFORMATION: CDR sequence

<400> SEQUENCE: 194

Asp Ala Arg Arg Gly Trp Asn Thr Gly Tyr
1               5                   10

<210> SEQ ID NO 195
<211> LENGTH: 10
<212> TYPE: PRT
<213> ORGANISM: Artificial Sequence
<220> FEATURE:
<223> OTHER INFORMATION: CDR sequence

<400> SEQUENCE: 195

Asp Gly Arg Arg Gly Trp Asn Thr Gly Tyr
1               5                   10

<210> SEQ ID NO 196
<211> LENGTH: 10
<212> TYPE: PRT
<213> ORGANISM: Artificial Sequence
<220> FEATURE:
<223> OTHER INFORMATION: CDR sequence

<400> SEQUENCE: 196

Asp Ala Arg Arg Gly Trp Asn Thr Gly Phe
1               5                   10

<210> SEQ ID NO 197
<211> LENGTH: 10
<212> TYPE: PRT
<213> ORGANISM: Artificial Sequence
<220> FEATURE:
<223> OTHER INFORMATION: CDR sequence
<220> FEATURE:
<221> NAME/KEY: MISC_FEATURE
<222> LOCATION: (2)..(2)
<223> OTHER INFORMATION: X = Pro, Ala or Gly
<220> FEATURE:
<221> NAME/KEY: MISC_FEATURE
<222> LOCATION: (7)..(7)
<223> OTHER INFORMATION: X = Asp or Asn
<220> FEATURE:
<221> NAME/KEY: MISC_FEATURE
<222> LOCATION: (8)..(8)
<223> OTHER INFORMATION: X = Thr or Ser
<220> FEATURE:
<221> NAME/KEY: MISC_FEATURE
<222> LOCATION: (9)..(9)
```

```
<223> OTHER INFORMATION: X = Arg, Lys, Ala or Gly
<220> FEATURE:
<221> NAME/KEY: MISC_FEATURE
<222> LOCATION: (10)..(10)
<223> OTHER INFORMATION: X = Tyr or Phe

<400> SEQUENCE: 197

Asp Xaa Arg Arg Gly Trp Xaa Xaa Xaa Xaa
1               5                   10

<210> SEQ ID NO 198
<211> LENGTH: 25
<212> TYPE: PRT
<213> ORGANISM: Artificial Sequence
<220> FEATURE:
<223> OTHER INFORMATION: Framework sequence

<400> SEQUENCE: 198

Glu Val Gln Leu Val Glu Ser Gly Gly Gly Ser Val Gln Ala Gly Glu
1               5                   10                  15

Ser Leu Arg Leu Ser Cys Ala Ala Ser
            20                  25

<210> SEQ ID NO 199
<211> LENGTH: 25
<212> TYPE: PRT
<213> ORGANISM: Artificial Sequence
<220> FEATURE:
<223> OTHER INFORMATION: Framework sequence

<400> SEQUENCE: 199

Glu Val Gln Leu Val Glu Ser Gly Gly Gly Ser Val Gln Pro Gly Glu
1               5                   10                  15

Ser Leu Arg Leu Ser Cys Ala Ala Ser
            20                  25

<210> SEQ ID NO 200
<211> LENGTH: 25
<212> TYPE: PRT
<213> ORGANISM: Artificial Sequence
<220> FEATURE:
<223> OTHER INFORMATION: Framework sequence

<400> SEQUENCE: 200

Asp Val Gln Leu Val Glu Ser Gly Gly Gly Ser Val Gln Pro Gly Glu
1               5                   10                  15

Ser Leu Arg Leu Ser Cys Ala Ala Ser
            20                  25

<210> SEQ ID NO 201
<211> LENGTH: 25
<212> TYPE: PRT
<213> ORGANISM: Artificial Sequence
<220> FEATURE:
<223> OTHER INFORMATION: Framework sequence

<400> SEQUENCE: 201

Glu Val Gln Leu Val Glu Ser Gly Gly Gly Leu Val Gln Pro Gly Glu
1               5                   10                  15

Ser Leu Arg Leu Ser Cys Ala Ala Ser
            20                  25

<210> SEQ ID NO 202
<211> LENGTH: 25
<212> TYPE: PRT
```

```
<213> ORGANISM: Artificial Sequence
<220> FEATURE:
<223> OTHER INFORMATION: Framework sequence

<400> SEQUENCE: 202

Glu Val Gln Leu Val Glu Ser Gly Gly Gly Ser Val Gln Pro Gly Gly
1               5                   10                  15

Ser Leu Arg Leu Ser Cys Ala Ala Ser
            20                  25

<210> SEQ ID NO 203
<211> LENGTH: 25
<212> TYPE: PRT
<213> ORGANISM: Artificial Sequence
<220> FEATURE:
<223> OTHER INFORMATION: Framework sequence

<400> SEQUENCE: 203

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 204
<211> LENGTH: 25
<212> TYPE: PRT
<213> ORGANISM: Artificial Sequence
<220> FEATURE:
<223> OTHER INFORMATION: Framework sequence

<400> SEQUENCE: 204

Asp Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 205
<211> LENGTH: 14
<212> TYPE: PRT
<213> ORGANISM: Artificial Sequence
<220> FEATURE:
<223> OTHER INFORMATION: Framework sequence

<400> SEQUENCE: 205

Trp Tyr Arg Gln Ala Pro Gly Lys Arg Arg Asp Leu Val Ala
1               5                   10

<210> SEQ ID NO 206
<211> LENGTH: 14
<212> TYPE: PRT
<213> ORGANISM: Artificial Sequence
<220> FEATURE:
<223> OTHER INFORMATION: Framework sequence

<400> SEQUENCE: 206

Trp Tyr Arg Gln Ala Pro Gly Lys Gln Arg Asp Leu Val Ala
1               5                   10

<210> SEQ ID NO 207
<211> LENGTH: 14
<212> TYPE: PRT
<213> ORGANISM: Artificial Sequence
<220> FEATURE:
<223> OTHER INFORMATION: Framework sequence

<400> SEQUENCE: 207
```

Trp Tyr Arg Gln Ala Pro Gly Lys Arg Arg Glu Leu Val Ala
1               5                   10

<210> SEQ ID NO 208
<211> LENGTH: 14
<212> TYPE: PRT
<213> ORGANISM: Artificial Sequence
<220> FEATURE:
<223> OTHER INFORMATION: Framework sequence

<400> SEQUENCE: 208

Trp Tyr Arg Gln Ala Pro Gly Lys Gln Arg Glu Leu Val Ala
1               5                   10

<210> SEQ ID NO 209
<211> LENGTH: 39
<212> TYPE: PRT
<213> ORGANISM: Artificial Sequence
<220> FEATURE:
<223> OTHER INFORMATION: Framework sequence

<400> SEQUENCE: 209

Tyr Ala Asp Ser Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Thr Ser
        35

<210> SEQ ID NO 210
<211> LENGTH: 39
<212> TYPE: PRT
<213> ORGANISM: Artificial Sequence
<220> FEATURE:
<223> OTHER INFORMATION: Framework sequence

<400> SEQUENCE: 210

Tyr Ala Asp Ser Val Lys Gly Arg Phe Thr Ile Ser Arg Asp Asn Ser
1               5                   10                  15

Lys Asn Thr Val Tyr Leu Gln Met Asn Ser Leu Arg Pro Glu Asp Thr
            20                  25                  30

Ala Val Tyr Tyr Cys Thr Ser
        35

<210> SEQ ID NO 211
<211> LENGTH: 11
<212> TYPE: PRT
<213> ORGANISM: Artificial Sequence
<220> FEATURE:
<223> OTHER INFORMATION: Framework sequence

<400> SEQUENCE: 211

Trp Gly Gln Gly Thr Gln Val Thr Val Ser Ser
1               5                   10

<210> SEQ ID NO 212
<211> LENGTH: 11
<212> TYPE: PRT
<213> ORGANISM: Artificial Sequence
<220> FEATURE:
<223> OTHER INFORMATION: Framework sequence

<400> SEQUENCE: 212

Trp Gly Gln Gly Thr Leu Val Thr Val Ser Ser

```
<210> SEQ ID NO 213
<211> LENGTH: 10
<212> TYPE: PRT
<213> ORGANISM: Artificial Sequence
<220> FEATURE:
<223> OTHER INFORMATION: CDR sequence

<400> SEQUENCE: 213

Gly Ser Ile Phe Ser Ser Thr Ala Met Ala
1               5                   10

<210> SEQ ID NO 214
<211> LENGTH: 9
<212> TYPE: PRT
<213> ORGANISM: Artificial Sequence
<220> FEATURE:
<223> OTHER INFORMATION: CDR sequence

<400> SEQUENCE: 214

Ala Ile Ser Ser Val Gly Val Thr Lys
1               5

<210> SEQ ID NO 215
<211> LENGTH: 9
<212> TYPE: PRT
<213> ORGANISM: Artificial Sequence
<220> FEATURE:
<223> OTHER INFORMATION: CDR sequence

<400> SEQUENCE: 215

Ala Ile Gln Ser Val Gly Val Thr Lys
1               5

<210> SEQ ID NO 216
<211> LENGTH: 9
<212> TYPE: PRT
<213> ORGANISM: Artificial Sequence
<220> FEATURE:
<223> OTHER INFORMATION: CDR sequence

<400> SEQUENCE: 216

Ala Ile Gly Ser Val Gly Val Thr Lys
1               5

<210> SEQ ID NO 217
<211> LENGTH: 9
<212> TYPE: PRT
<213> ORGANISM: Artificial Sequence
<220> FEATURE:
<223> OTHER INFORMATION: CDR sequence

<400> SEQUENCE: 217

Ala Ile Thr Ser Val Gly Val Thr Lys
1               5

<210> SEQ ID NO 218
<211> LENGTH: 9
<212> TYPE: PRT
<213> ORGANISM: Artificial Sequence
<220> FEATURE:
<223> OTHER INFORMATION: CDR sequence

<400> SEQUENCE: 218

Ala Ile Asn Thr Val Gly Val Thr Lys
1               5
```

```
<210> SEQ ID NO 219
<211> LENGTH: 9
<212> TYPE: PRT
<213> ORGANISM: Artificial Sequence
<220> FEATURE:
<223> OTHER INFORMATION: CDR sequence

<400> SEQUENCE: 219

Ala Ile Asn Gly Val Gly Val Thr Lys
1               5

<210> SEQ ID NO 220
<211> LENGTH: 9
<212> TYPE: PRT
<213> ORGANISM: Artificial Sequence
<220> FEATURE:
<223> OTHER INFORMATION: CDR sequence

<400> SEQUENCE: 220

Ala Ile Asn Pro Val Gly Val Thr Lys
1               5

<210> SEQ ID NO 221
<211> LENGTH: 9
<212> TYPE: PRT
<213> ORGANISM: Artificial Sequence
<220> FEATURE:
<223> OTHER INFORMATION: CDR sequence

<400> SEQUENCE: 221

Ala Ile Ser Thr Val Gly Val Thr Lys
1               5

<210> SEQ ID NO 222
<211> LENGTH: 118
<212> TYPE: PRT
<213> ORGANISM: Artificial Sequence
<220> FEATURE:
<223> OTHER INFORMATION: Nanobody sequence

<400> SEQUENCE: 222

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ser Thr
            20                  25                  30

Ala Met Ala Trp Tyr Arg Gln Ala Pro Gly Lys Arg Arg Asp Leu Val
        35                  40                  45

Ala Ala Ile Ser Ser Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 223
<211> LENGTH: 118
<212> TYPE: PRT
<213> ORGANISM: Artificial Sequence
```

<220> FEATURE:
<223> OTHER INFORMATION: Nanobody sequence

<400> SEQUENCE: 223

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ser Thr
            20                  25                  30

Ala Met Ala Trp Tyr Arg Gln Ala Pro Gly Lys Arg Arg Asp Leu Val
        35                  40                  45

Ala Ala Ile Ser Thr Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 224
<211> LENGTH: 118
<212> TYPE: PRT
<213> ORGANISM: Artificial Sequence
<220> FEATURE:
<223> OTHER INFORMATION: Nanobody sequence

<400> SEQUENCE: 224

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser
        115

<210> SEQ ID NO 225
<211> LENGTH: 369
<212> TYPE: PRT
<213> ORGANISM: Artificial Sequence
<220> FEATURE:
<223> OTHER INFORMATION: Nanobody sequence

<400> SEQUENCE: 225

Asp Val Gln Leu Val Glu Ser Gly Gly Gly Leu Val Gln Pro Gly Gly
1               5                   10                  15

Ser Leu Arg Leu Ser Cys Ala Ser Gly Ser Ile Phe Ser Ser Thr
            20                  25                  30

```
Ala Met Ala Trp Tyr Arg Gln Ala Pro Gly Lys Arg Asp Leu Val
         35                  40                  45

Ala Ala Ile Ser Ser Val Gly Val Thr Lys Tyr Ala Asp Ser Val Lys
 50                  55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Val Tyr Tyr Cys Thr
                 85                  90                  95

Ser Asp Pro Arg Arg Gly Trp Asp Thr Arg Tyr Trp Gly Gln Gly Thr
            100                 105                 110

Leu Val Thr Val Ser Ser Gly Gly Gly Ser Gly Gly Gly Ser Glu
        115                 120                 125

Val Gln Leu Val Glu Ser Gly Gly Gly Leu Val Gln Pro Gly Asn Ser
        130                 135                 140

Leu Arg Leu Ser Cys Ala Ala Ser Gly Phe Thr Phe Ser Ser Phe Gly
145                 150                 155                 160

Met Ser Trp Val Arg Gln Ala Pro Gly Lys Gly Leu Glu Trp Val Ser
                165                 170                 175

Ser Ile Ser Gly Ser Gly Ser Asp Thr Leu Tyr Ala Asp Ser Val Lys
            180                 185                 190

Gly Arg Phe Thr Ile Ser Arg Asp Asn Ala Lys Thr Thr Leu Tyr Leu
        195                 200                 205

Gln Met Asn Ser Leu Arg Pro Glu Asp Thr Ala Val Tyr Tyr Cys Thr
    210                 215                 220

Ile Gly Gly Ser Leu Ser Arg Ser Ser Gln Gly Thr Leu Val Thr Val
225                 230                 235                 240

Ser Ser Gly Gly Gly Gly Ser Gly Gly Gly Ser Glu Val Gln Leu Val
                245                 250                 255

Glu Ser Gly Gly Gly Leu Val Gln Pro Gly Gly Ser Leu Arg Leu Ser
            260                 265                 270

Cys Ala Ala Ser Gly Ser Ile Phe Ser Ser Thr Ala Met Ala Trp Tyr
        275                 280                 285

Arg Gln Ala Pro Gly Lys Arg Arg Asp Leu Val Ala Ala Ile Ser Ser
    290                 295                 300

Val Gly Val Thr Lys Tyr Ala Asp Ser Val Lys Gly Arg Phe Thr Ile
305                 310                 315                 320

Ser Arg Asp Asn Ser Lys Asn Thr Val Tyr Leu Gln Met Asn Ser Leu
                325                 330                 335

Arg Pro Glu Asp Thr Ala Val Tyr Tyr Cys Thr Ser Asp Pro Arg Arg
            340                 345                 350

Gly Trp Asp Thr Arg Tyr Trp Gly Gln Gly Thr Leu Val Thr Val Ser
        355                 360                 365

Ser

<210> SEQ ID NO 226
<211> LENGTH: 369
<212> TYPE: PRT
<213> ORGANISM: Artificial Sequence
<220> FEATURE:
<223> OTHER INFORMATION: Nanobody sequence

<400> SEQUENCE: 226

Asp Val Gln Leu Val Glu Ser Gly Gly Gly Leu Val Gln Pro Gly Gly
 1               5                  10                  15

Ser Leu Arg Leu Ser Cys Ala Ala Ser Gly Ser Ile Phe Ser Ser Thr
```

```
            20                  25                  30
Ala Met Ala Trp Tyr Arg Gln Ala Pro Gly Lys Arg Asp Leu Val
            35                  40                  45
Ala Ala Ile Ser Thr Val Gly Val Thr Lys Tyr Ala Asp Ser Val Lys
        50                  55                  60
Gly Arg Phe Thr Ile Ser Arg Asp Asn Ser Lys Asn Thr Val Tyr Leu
65                  70                  75                  80
Gln Met Asn Ser Leu Arg Pro Glu Asp Thr Ala Val Tyr Tyr Cys Thr
                85                  90                  95
Ser Asp Pro Arg Arg Gly Trp Asp Thr Arg Tyr Trp Gly Gln Gly Thr
                100                 105                 110
Leu Val Thr Val Ser Ser Gly Gly Gly Gly Ser Gly Gly Gly Ser Glu
                115                 120                 125
Val Gln Leu Val Glu Ser Gly Gly Gly Leu Val Gln Pro Gly Asn Ser
                130                 135                 140
Leu Arg Leu Ser Cys Ala Ala Ser Gly Phe Thr Phe Ser Ser Phe Gly
145                 150                 155                 160
Met Ser Trp Val Arg Gln Ala Pro Gly Lys Gly Leu Glu Trp Val Ser
                165                 170                 175
Ser Ile Ser Gly Ser Gly Ser Asp Thr Leu Tyr Ala Asp Ser Val Lys
                180                 185                 190
Gly Arg Phe Thr Ile Ser Arg Asp Asn Ala Lys Thr Thr Leu Tyr Leu
                195                 200                 205
Gln Met Asn Ser Leu Arg Pro Glu Asp Thr Ala Val Tyr Tyr Cys Thr
                210                 215                 220
Ile Gly Gly Ser Leu Ser Arg Ser Ser Gln Gly Thr Leu Val Thr Val
225                 230                 235                 240
Ser Ser Gly Gly Gly Gly Ser Gly Gly Gly Ser Glu Val Gln Leu Val
                245                 250                 255
Glu Ser Gly Gly Gly Leu Val Gln Pro Gly Gly Ser Leu Arg Leu Ser
                260                 265                 270
Cys Ala Ala Ser Gly Ser Ile Phe Ser Ser Thr Ala Met Ala Trp Tyr
                275                 280                 285
Arg Gln Ala Pro Gly Lys Arg Arg Asp Leu Val Ala Ala Ile Ser Thr
                290                 295                 300
Val Gly Val Thr Lys Tyr Ala Asp Ser Val Lys Gly Arg Phe Thr Ile
305                 310                 315                 320
Ser Arg Asp Asn Ser Lys Asn Thr Val Tyr Leu Gln Met Asn Ser Leu
                325                 330                 335
Arg Pro Glu Asp Thr Ala Val Tyr Tyr Cys Thr Ser Asp Pro Arg Arg
                340                 345                 350
Gly Trp Asp Thr Arg Tyr Trp Gly Gln Gly Thr Leu Val Thr Val Ser
                355                 360                 365
Ser

<210> SEQ ID NO 227
<211> LENGTH: 369
<212> TYPE: PRT
<213> ORGANISM: Artificial Sequence
<220> FEATURE:
<223> OTHER INFORMATION: Nanobody sequence

<400> SEQUENCE: 227

Asp Val Gln Leu Val Glu Ser Gly Gly Gly Leu Val Gln Pro Gly Gly
1               5                   10                  15
```

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
            35                  40                  45

Ala Ala Ile Asn Ser Val Gly Val Thr Lys Tyr Ala Asp Ser Val Lys
 50                  55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Val Tyr Tyr Cys Thr
             85                  90                  95

Ser Asp Pro Arg Arg Gly Trp Asp Thr Arg Tyr Trp Gly Gln Gly Thr
            100                 105                 110

Leu Val Thr Val Ser Ser Gly Gly Gly Ser Gly Gly Gly Ser Glu
            115                 120                 125

Val Gln Leu Val Glu Ser Gly Gly Gly Leu Val Gln Pro Gly Asn Ser
130                 135                 140

Leu Arg Leu Ser Cys Ala Ala Ser Gly Phe Thr Phe Ser Ser Phe Gly
145                 150                 155                 160

Met Ser Trp Val Arg Gln Ala Pro Gly Lys Gly Leu Glu Trp Val Ser
            165                 170                 175

Ser Ile Ser Gly Ser Gly Ser Asp Thr Leu Tyr Ala Asp Ser Val Lys
            180                 185                 190

Gly Arg Phe Thr Ile Ser Arg Asp Asn Ala Lys Thr Thr Leu Tyr Leu
            195                 200                 205

Gln Met Asn Ser Leu Arg Pro Glu Asp Thr Ala Val Tyr Tyr Cys Thr
            210                 215                 220

Ile Gly Gly Ser Leu Ser Arg Ser Ser Gln Gly Thr Leu Val Thr Val
225                 230                 235                 240

Ser Ser Gly Gly Gly Gly Ser Gly Gly Gly Ser Glu Val Gln Leu Val
            245                 250                 255

Glu Ser Gly Gly Gly Leu Val Gln Pro Gly Gly Ser Leu Arg Leu Ser
            260                 265                 270

Cys Ala Ala Ser Gly Ser Ile Phe Ser Ser Asn Ala Met Ala Trp Tyr
            275                 280                 285

Arg Gln Ala Pro Gly Lys Arg Arg Asp Leu Val Ala Ala Ile Asn Ser
            290                 295                 300

Val Gly Val Thr Lys Tyr Ala Asp Ser Val Lys Gly Arg Phe Thr Ile
305                 310                 315                 320

Ser Arg Asp Asn Ser Lys Asn Thr Val Tyr Leu Gln Met Asn Ser Leu
            325                 330                 335

Arg Pro Glu Asp Thr Ala Val Tyr Tyr Cys Thr Ser Asp Pro Arg Arg
            340                 345                 350

Gly Trp Asp Thr Arg Tyr Trp Gly Gln Gly Thr Leu Val Thr Val Ser
            355                 360                 365

Ser

<210> SEQ ID NO 228
<211> LENGTH: 21
<212> TYPE: PRT
<213> ORGANISM: Artificial Sequence
<220> FEATURE:
<223> OTHER INFORMATION: CX3CR1 N-terminal sequence

<400> SEQUENCE: 228

```
Met Asp Gln Phe Pro Glu Ser Val Thr Glu Asn Phe Glu Tyr Asp Asp
1               5                   10                  15

Leu Ala Glu Ala Cys
            20

<210> SEQ ID NO 229
<211> LENGTH: 17
<212> TYPE: PRT
<213> ORGANISM: Artificial Sequence
<220> FEATURE:
<223> OTHER INFORMATION: CX3CR1-EC3

<400> SEQUENCE: 229

Lys Leu Tyr Asp Phe Phe Pro Ser Cys Asp Met Arg Lys Asp Leu Arg
1               5                   10                  15

Leu

<210> SEQ ID NO 230
<211> LENGTH: 115
<212> TYPE: PRT
<213> ORGANISM: Artificial Sequence
<220> FEATURE:
<223> OTHER INFORMATION: Nanobody sequence

<400> SEQUENCE: 230

Ala Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gly Gly Thr Gln Val Thr
            100                 105                 110

Val Ser Ser
        115

<210> SEQ ID NO 231
<211> LENGTH: 115
<212> TYPE: PRT
<213> ORGANISM: Artificial Sequence
<220> FEATURE:
<223> OTHER INFORMATION: Nanobody sequence

<400> SEQUENCE: 231

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80
```

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 232
<211> LENGTH: 117
<212> TYPE: PRT
<213> ORGANISM: Artificial Sequence
<220> FEATURE:
<223> OTHER INFORMATION: Nanobody sequence

<400> SEQUENCE: 232

Ala Val Gln Leu Val Glu Ser Gly Gly Gly Leu Val Gln Gly Gly Gly
1               5                   10                  15

Ser Leu Arg Leu Ala Cys Ala Ala Ser Glu Arg Ile Phe Asp Leu Asn
            20                  25                  30

Leu Met Gly Trp Tyr Arg Gln Gly Pro Gly Asn Glu Arg Glu Leu Val
        35                  40                  45

Ala Thr Cys Ile Thr Val Gly Asp Ser Thr Asn Tyr Ala Asp Ser Val
    50                  55                  60

Lys Gly Arg Phe Thr Ile Ser Met Asp Tyr Thr Lys Gln Thr Val Tyr
65                  70                  75                  80

Leu His Met Asn Ser Leu Arg Pro Glu Asp Thr Gly Leu Tyr Tyr Cys
                85                  90                  95

Lys Ile Arg Arg Thr Trp His Ser Glu Leu Trp Gly Gln Gly Thr Gln
            100                 105                 110

Val Thr Val Ser Ser
        115

<210> SEQ ID NO 233
<211> LENGTH: 5
<212> TYPE: PRT
<213> ORGANISM: Artificial Sequence
<220> FEATURE:
<223> OTHER INFORMATION: Linker sequence

<400> SEQUENCE: 233

Gly Gly Gly Gly Ser
1               5

<210> SEQ ID NO 234
<211> LENGTH: 7
<212> TYPE: PRT
<213> ORGANISM: Artificial Sequence
<220> FEATURE:
<223> OTHER INFORMATION: Linker sequence

<400> SEQUENCE: 234

Ser Gly Gly Ser Gly Gly Ser
1               5

<210> SEQ ID NO 235
<211> LENGTH: 9
<212> TYPE: PRT
<213> ORGANISM: Artificial Sequence
<220> FEATURE:
<223> OTHER INFORMATION: Linker sequence

<400> SEQUENCE: 235

```
Gly Gly Gly Gly Ser Gly Gly Gly Ser
1               5

<210> SEQ ID NO 236
<211> LENGTH: 9
<212> TYPE: PRT
<213> ORGANISM: Artificial Sequence
<220> FEATURE:
<223> OTHER INFORMATION: Linker sequence

<400> SEQUENCE: 236

Gly Gly Gly Gly Ser Gly Gly Gly Ser
1               5

<210> SEQ ID NO 237
<211> LENGTH: 10
<212> TYPE: PRT
<213> ORGANISM: Artificial Sequence
<220> FEATURE:
<223> OTHER INFORMATION: Linker sequence

<400> SEQUENCE: 237

Gly Gly Gly Gly Ser Gly Gly Gly Gly Ser
1               5                   10

<210> SEQ ID NO 238
<211> LENGTH: 15
<212> TYPE: PRT
<213> ORGANISM: Artificial Sequence
<220> FEATURE:
<223> OTHER INFORMATION: Linker sequence

<400> SEQUENCE: 238

Gly Gly Gly Gly Ser Gly Gly Gly Gly Ser Gly Gly Gly Gly Ser
1               5                   10                  15

<210> SEQ ID NO 239
<211> LENGTH: 18
<212> TYPE: PRT
<213> ORGANISM: Artificial Sequence
<220> FEATURE:
<223> OTHER INFORMATION: Linker sequence

<400> SEQUENCE: 239

Gly Gly Gly Gly Ser Gly Gly Gly Gly Ser Gly Gly Gly Gly Gly
1               5                   10                  15

Gly Ser

<210> SEQ ID NO 240
<211> LENGTH: 20
<212> TYPE: PRT
<213> ORGANISM: Artificial Sequence
<220> FEATURE:
<223> OTHER INFORMATION: Linker sequence

<400> SEQUENCE: 240

Gly Gly Gly Gly Ser Gly Gly Gly Gly Ser Gly Gly Gly Gly Ser Gly
1               5                   10                  15

Gly Gly Gly Ser
            20

<210> SEQ ID NO 241
<211> LENGTH: 25
<212> TYPE: PRT
<213> ORGANISM: Artificial Sequence
```

<220> FEATURE:
<223> OTHER INFORMATION: Linker sequence

<400> SEQUENCE: 241

Gly Gly Gly Gly Ser Gly Gly Gly Ser Gly Gly Gly Ser Gly
1               5                   10                  15

Gly Gly Gly Ser Gly Gly Gly Ser
            20                  25

<210> SEQ ID NO 242
<211> LENGTH: 30
<212> TYPE: PRT
<213> ORGANISM: Artificial Sequence
<220> FEATURE:
<223> OTHER INFORMATION: Linker sequence

<400> SEQUENCE: 242

Gly Gly Gly Gly Ser Gly Gly Gly Ser Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 243
<211> LENGTH: 35
<212> TYPE: PRT
<213> ORGANISM: Artificial Sequence
<220> FEATURE:
<223> OTHER INFORMATION: Linker sequence

<400> SEQUENCE: 243

Gly Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly
            20                  25                  30

Gly Gly Ser
        35

<210> SEQ ID NO 244
<211> LENGTH: 15
<212> TYPE: PRT
<213> ORGANISM: Artificial Sequence
<220> FEATURE:
<223> OTHER INFORMATION: Linker sequence

<400> SEQUENCE: 244

Glu Pro Lys Ser Cys Asp Lys Thr His Thr Cys Pro Pro Cys Pro
1               5                   10                  15

<210> SEQ ID NO 245
<211> LENGTH: 24
<212> TYPE: PRT
<213> ORGANISM: Artificial Sequence
<220> FEATURE:
<223> OTHER INFORMATION: Linker sequence

<400> SEQUENCE: 245

Gly Gly Gly Gly Ser Gly Gly Gly Ser Glu Pro Lys Ser Cys Asp Lys
1               5                   10                  15

Thr His Thr Cys Pro Pro Cys Pro
            20

<210> SEQ ID NO 246
<211> LENGTH: 12
<212> TYPE: PRT

```
<213> ORGANISM: Artificial Sequence
<220> FEATURE:
<223> OTHER INFORMATION: Linker sequence

<400> SEQUENCE: 246

Glu Pro Lys Thr Pro Lys Pro Gln Pro Ala Ala Ala
1               5                   10

<210> SEQ ID NO 247
<211> LENGTH: 62
<212> TYPE: PRT
<213> ORGANISM: Artificial Sequence
<220> FEATURE:
<223> OTHER INFORMATION: Linker sequence

<400> SEQUENCE: 247

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro
    50                  55                  60

<210> SEQ ID NO 248
<211> LENGTH: 3
<212> TYPE: PRT
<213> ORGANISM: Artificial Sequence
<220> FEATURE:
<223> OTHER INFORMATION: Linker sequence

<400> SEQUENCE: 248

Ala Ala Ala
1

<210> SEQ ID NO 249
<211> LENGTH: 369
<212> TYPE: PRT
<213> ORGANISM: Artificial Sequence
<220> FEATURE:
<223> OTHER INFORMATION: Nanobody sequence

<400> SEQUENCE: 249

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser Gly Gly Gly Ser Gly Gly Gly Ser Glu
        115                 120                 125

Val Gln Leu Val Glu Ser Gly Gly Gly Leu Val Gln Pro Gly Asn Ser
```

```
            130                 135                 140
Leu Arg Leu Ser Cys Ala Ala Ser Gly Phe Thr Phe Ser Ser Phe Gly
145                 150                 155                 160

Met Ser Trp Val Arg Gln Ala Pro Gly Lys Gly Leu Glu Trp Val Ser
                165                 170                 175

Ser Ile Ser Gly Ser Gly Ser Asp Thr Leu Tyr Ala Asp Ser Val Lys
            180                 185                 190

Gly Arg Phe Thr Ile Ser Arg Asp Asn Ala Lys Thr Thr Leu Tyr Leu
                195                 200                 205

Gln Met Asn Ser Leu Arg Pro Glu Asp Thr Ala Val Tyr Tyr Cys Thr
        210                 215                 220

Ile Gly Gly Ser Leu Ser Arg Ser Ser Gln Gly Thr Leu Val Thr Val
225                 230                 235                 240

Ser Ser Gly Gly Gly Gly Ser Gly Gly Gly Ser Glu Val Gln Leu Val
                245                 250                 255

Glu Ser Gly Gly Gly Ser Val Gln Ala Gly Glu Ser Leu Arg Leu Ser
            260                 265                 270

Cys Ala Ala Ser Gly Ser Ile Phe Ser Ser Asn Ala Met Ala Trp Tyr
        275                 280                 285

Arg Gln Ala Pro Gly Lys Arg Arg Asp Leu Val Ala Ala Ile Asn Ser
        290                 295                 300

Val Gly Val Thr Lys Tyr Ala Asp Ser Val Lys Gly Arg Phe Thr Ile
305                 310                 315                 320

Ser Arg Asp Asn Ala Lys Asn Thr Val Tyr Leu Gln Met Asn Ser Leu
                325                 330                 335

Lys Pro Glu Asp Thr Ala Val Tyr Tyr Cys Thr Ser Asp Pro Arg Arg
            340                 345                 350

Gly Trp Asp Thr Arg Tyr Trp Gly Gln Gly Thr Leu Val Thr Val Ser
        355                 360                 365

Ser

<210> SEQ ID NO 250
<211> LENGTH: 223
<212> TYPE: PRT
<213> ORGANISM: Artificial Sequence
<220> FEATURE:
<223> OTHER INFORMATION: Mouse Fc domain

<400> SEQUENCE: 250

Pro Pro Cys Lys Cys Pro Ala Pro Asn Leu Leu Gly Gly Pro Ser Val
1               5                   10                  15

Phe Ile Phe Pro Pro Lys Ile Lys Asp Val Leu Met Ile Ser Leu Ser
                20                  25                  30

Pro Ile Val Thr Cys Val Val Val Ala Val Ser Glu Asp Asp Pro Asp
            35                  40                  45

Val Gln Ile Ser Trp Phe Val Asn Asn Val Glu Val His Thr Ala Gln
        50                  55                  60

Thr Gln Thr His Arg Glu Asp Tyr Asn Ser Thr Leu Arg Val Val Ser
65                  70                  75                  80

Ala Leu Pro Ile Gln His Gln Asp Trp Met Ser Gly Lys Glu Phe Lys
                85                  90                  95

Cys Lys Val Asn Asn Lys Asp Leu Pro Ala Pro Ile Glu Arg Thr Ile
            100                 105                 110

Ser Lys Pro Lys Gly Ser Val Arg Ala Pro Gln Val Tyr Val Leu Pro
        115                 120                 125
```

Pro Pro Glu Glu Glu Met Thr Lys Lys Gln Val Thr Leu Thr Cys Met
    130                 135                 140

Val Thr Asp Phe Met Pro Glu Asp Ile Tyr Val Glu Trp Thr Asn Asn
145                 150                 155                 160

Gly Lys Thr Glu Leu Asn Tyr Lys Asn Thr Glu Pro Val Leu Asp Ser
                165                 170                 175

Asp Gly Ser Tyr Phe Met Tyr Ser Lys Leu Arg Val Glu Lys Lys Asn
                180                 185                 190

Trp Val Glu Arg Asn Ser Tyr Ser Cys Ser Val Val His Glu Gly Leu
        195                 200                 205

His Asn His His Thr Thr Lys Ser Phe Ser Arg Thr Pro Gly Lys
    210                 215                 220

<210> SEQ ID NO 251
<211> LENGTH: 356
<212> TYPE: PRT
<213> ORGANISM: Artificial Sequence
<220> FEATURE:
<223> OTHER INFORMATION: Nanobody with Fc domain

<400> SEQUENCE: 251

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Pro Pro Cys Lys Cys Pro Ala Pro Asn Leu Leu
    130                 135                 140

Gly Gly Pro Ser Val Phe Ile Phe Pro Pro Lys Ile Lys Asp Val Leu
145                 150                 155                 160

Met Ile Ser Leu Ser Pro Ile Val Thr Cys Val Val Val Ala Val Ser
                165                 170                 175

Glu Asp Asp Pro Asp Val Gln Ile Ser Trp Phe Val Asn Asn Val Glu
            180                 185                 190

Val His Thr Ala Gln Thr Gln Thr His Arg Glu Asp Tyr Asn Ser Thr
        195                 200                 205

Leu Arg Val Val Ser Ala Leu Pro Ile Gln His Gln Asp Trp Met Ser
    210                 215                 220

Gly Lys Glu Phe Lys Cys Lys Val Asn Asn Lys Asp Leu Pro Ala Pro
225                 230                 235                 240

Ile Glu Arg Thr Ile Ser Lys Pro Lys Gly Ser Val Arg Ala Pro Gln
                245                 250                 255

Val Tyr Val Leu Pro Pro Glu Glu Glu Met Thr Lys Lys Gln Val
            260                 265                 270

```
Thr Leu Thr Cys Met Val Thr Asp Phe Met Pro Glu Asp Ile Tyr Val
        275                 280                 285

Glu Trp Thr Asn Asn Gly Lys Thr Glu Leu Asn Tyr Lys Asn Thr Glu
290                 295                 300

Pro Val Leu Asp Ser Asp Gly Ser Tyr Phe Met Tyr Ser Lys Leu Arg
305                 310                 315                 320

Val Glu Lys Lys Asn Trp Val Glu Arg Asn Ser Tyr Ser Cys Ser Val
                325                 330                 335

Val His Glu Gly Leu His Asn His His Thr Thr Lys Ser Phe Ser Arg
            340                 345                 350

Thr Pro Gly Lys
        355
```

<210> SEQ ID NO 252
<211> LENGTH: 222
<212> TYPE: PRT
<213> ORGANISM: Artificial Sequence
<220> FEATURE:
<223> OTHER INFORMATION: Human Fc domain

<400> SEQUENCE: 252

```
Cys Pro Pro Cys Pro Ala Pro Glu Ala Ala Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220
```

<210> SEQ ID NO 253
<211> LENGTH: 355
<212> TYPE: PRT
<213> ORGANISM: Artificial Sequence
<220> FEATURE:
<223> OTHER INFORMATION: Nanobody with Fc domain

<400> SEQUENCE: 253

Asp Val Gln Leu Val Glu Ser Gly Gly Gly Leu Val Gln Pro Gly Gly
1               5                   10                  15
Ser Leu Arg Leu Ser Cys Ala Ala Ser Gly Ser Ile Phe Ser Ser Thr
            20                  25                  30
Ala Met Ala Trp Tyr Arg Gln Ala Pro Gly Lys Arg Arg Asp Leu Val
        35                  40                  45
Ala Ala Ile Ser Ser Val Gly Val Thr Lys Tyr Ala Asp Ser Val Lys
    50                  55                  60
Gly Arg Phe Thr Ile Ser Arg Asp Asn Ser Lys Asn Thr Val Tyr Leu
65                  70                  75                  80
Gln Met Asn Ser Leu Arg Pro Glu Asp Thr Ala Val Tyr Tyr Cys Thr
                85                  90                  95
Ser Asp Pro Arg Arg Gly Trp Asp Thr Arg Tyr Trp Gly Gln Gly Thr
            100                 105                 110
Leu Val Thr Val Ser Ser Gly Gly Gly Ser Gly Gly Gly Gly Gly Ser
        115                 120                 125
Gly Gly Gly Gly Ser Cys Pro Pro Cys Pro Ala Pro Glu Ala Ala Gly
    130                 135                 140
Gly Pro Ser Val Phe Leu Phe Pro Pro Lys Pro Lys Asp Thr Leu Met
145                 150                 155                 160
Ile Ser Arg Thr Pro Glu Val Thr Cys Val Val Val Asp Val Ser His
                165                 170                 175
Glu Asp Pro Glu Val Lys Phe Asn Trp Tyr Val Asp Gly Val Glu Val
            180                 185                 190
His Asn Ala Lys Thr Lys Pro Arg Glu Glu Gln Tyr Asn Ser Thr Tyr
        195                 200                 205
Arg Val Val Ser Val Leu Thr Val Leu His Gln Asp Trp Leu Asn Gly
    210                 215                 220
Lys Glu Tyr Lys Cys Lys Val Ser Asn Lys Ala Leu Pro Ala Pro Ile
225                 230                 235                 240
Glu Lys Thr Ile Ser Lys Ala Lys Gly Gln Pro Arg Glu Pro Gln Val
                245                 250                 255
Tyr Thr Leu Pro Pro Ser Arg Glu Glu Met Thr Lys Asn Gln Val Ser
            260                 265                 270
Leu Thr Cys Leu Val Lys Gly Phe Tyr Pro Ser Asp Ile Ala Val Glu
        275                 280                 285
Trp Glu Ser Asn Gly Gln Pro Glu Asn Asn Tyr Lys Thr Thr Pro Pro
    290                 295                 300
Val Leu Asp Ser Asp Gly Ser Phe Phe Leu Tyr Ser Lys Leu Thr Val
305                 310                 315                 320
Asp Lys Ser Arg Trp Gln Gln Gly Asn Val Phe Ser Cys Ser Val Met
                325                 330                 335
His Glu Ala Leu His Asn His Tyr Thr Gln Lys Ser Leu Ser Leu Ser
            340                 345                 350
Pro Gly Lys
        355

<210> SEQ ID NO 254
<211> LENGTH: 355
<212> TYPE: PRT
<213> ORGANISM: Artificial Sequence
<220> FEATURE:
<223> OTHER INFORMATION: Nanobody with Fc domain

<400> SEQUENCE: 254

```
Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ser Thr
            20                  25                  30

Ala Met Ala Trp Tyr Arg Gln Ala Pro Gly Lys Arg Arg Asp Leu Val
        35                  40                  45

Ala Ala Ile Ser Thr Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Cys Pro Pro Cys Pro Ala Pro Glu Ala Ala Gly
    130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser His
                165                 170                 175

Glu Asp Pro Glu Val Lys Phe Asn Trp Tyr Val Asp Gly Val Glu Val
            180                 185                 190

His Asn Ala Lys Thr Lys Pro Arg Glu Glu Gln Tyr Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Leu Pro Ala Pro Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Arg Glu Glu Met Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Thr Pro Pro
    290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Phe Ser Cys Ser Val Met
                325                 330                 335

His Glu Ala Leu His Asn His Tyr Thr Gln Lys Ser Leu Ser Leu Ser
            340                 345                 350

Pro Gly Lys
        355
```

<210> SEQ ID NO 255
<211> LENGTH: 355
<212> TYPE: PRT
<213> ORGANISM: Homo sapiens

<400> SEQUENCE: 255

```
Met Asp Gln Phe Pro Glu Ser Val Thr Glu Asn Phe Glu Tyr Asp Asp
  1               5                  10                  15

Leu Ala Glu Ala Cys Tyr Ile Gly Asp Ile Val Val Phe Gly Thr Val
             20                  25                  30

Phe Leu Ser Ile Phe Tyr Ser Val Ile Phe Ala Ile Gly Leu Val Gly
         35                  40                  45

Asn Leu Leu Val Val Phe Ala Leu Thr Asn Ser Lys Lys Pro Lys Ser
     50                  55                  60

Val Thr Asp Ile Tyr Leu Leu Asn Leu Ala Leu Ser Asp Leu Leu Phe
 65                  70                  75                  80

Val Ala Thr Leu Pro Phe Trp Thr His Tyr Leu Ile Asn Glu Lys Gly
                 85                  90                  95

Leu His Asn Ala Met Cys Lys Phe Thr Thr Ala Phe Phe Phe Ile Gly
            100                 105                 110

Phe Phe Gly Ser Ile Phe Phe Ile Thr Val Ile Ser Ile Asp Arg Tyr
        115                 120                 125

Leu Ala Ile Val Leu Ala Ala Asn Ser Met Asn Asn Arg Thr Val Gln
    130                 135                 140

His Gly Val Thr Ile Ser Leu Gly Val Trp Ala Ala Ala Ile Leu Val
145                 150                 155                 160

Ala Ala Pro Gln Phe Met Phe Thr Lys Gln Lys Glu Asn Glu Cys Leu
                165                 170                 175

Gly Asp Tyr Pro Glu Val Leu Gln Glu Ile Trp Pro Val Leu Arg Asn
            180                 185                 190

Val Glu Thr Asn Phe Leu Gly Phe Leu Leu Pro Leu Leu Ile Met Ser
        195                 200                 205

Tyr Cys Tyr Phe Arg Ile Ile Gln Thr Leu Phe Ser Cys Lys Asn His
    210                 215                 220

Lys Lys Ala Lys Ala Ile Lys Leu Ile Leu Leu Val Val Ile Val Phe
225                 230                 235                 240

Phe Leu Phe Trp Thr Pro Tyr Asn Val Met Ile Phe Leu Glu Thr Leu
                245                 250                 255

Lys Leu Tyr Asp Phe Phe Pro Ser Cys Asp Met Arg Lys Asp Leu Arg
            260                 265                 270

Leu Ala Leu Ser Val Thr Glu Thr Val Ala Phe Ser His Cys Cys Leu
        275                 280                 285

Asn Pro Leu Ile Tyr Ala Phe Ala Gly Glu Lys Phe Arg Arg Tyr Leu
    290                 295                 300

Tyr His Leu Tyr Gly Lys Cys Leu Ala Val Leu Cys Gly Arg Ser Val
305                 310                 315                 320

His Val Asp Phe Ser Ser Ser Glu Ser Gln Arg Ser Arg His Gly Ser
                325                 330                 335

Val Leu Ser Ser Asn Phe Thr Tyr His Thr Ser Asp Gly Asp Ala Leu
            340                 345                 350

Leu Leu Leu
        355

<210> SEQ ID NO 256
<211> LENGTH: 355
<212> TYPE: PRT
<213> ORGANISM: Macaca fascicularis

<400> SEQUENCE: 256

Met Asp Pro Phe Pro Glu Ser Val Thr Glu Asn Phe Glu Tyr Asp Asp
  1               5                  10                  15
```

Ser Ala Glu Ala Cys Tyr Ile Gly Asp Ile Val Ala Phe Gly Thr Val
            20                  25                  30

Phe Leu Ser Ile Phe Tyr Ser Val Phe Ala Ile Gly Leu Val Gly
        35                  40                  45

Asn Leu Leu Val Val Phe Ala Leu Thr Asn Ser Lys Lys Pro Lys Ser
 50                  55                  60

Val Thr Asp Ile Tyr Leu Leu Asn Leu Ala Leu Ser Asp Leu Leu Phe
 65                  70                  75                  80

Val Ala Thr Leu Pro Phe Trp Thr His Tyr Val Ile Asn Glu Glu Gly
                85                  90                  95

Leu Gln Asn Ala Met Cys Lys Phe Thr Thr Ala Phe Phe Ile Gly
                100                 105                 110

Phe Phe Gly Ser Ile Phe Phe Ile Thr Ile Ile Ser Ile Asp Arg Tyr
        115                 120                 125

Leu Ala Ile Val Leu Ala Ala Asn Ser Met Asn Asn Arg Thr Val Gln
 130                 135                 140

His Gly Val Thr Ile Ser Leu Gly Val Trp Ala Ala Ile Leu Val
145                 150                 155                 160

Ala Ala Pro Gln Phe Met Phe Thr Lys Gln Lys Glu Asn Glu Cys Leu
                165                 170                 175

Gly Asp Tyr Pro Glu Val Leu Gln Glu Ile Trp Pro Val Leu Arg Asn
                180                 185                 190

Val Glu Ala Asn Phe Leu Gly Phe Leu Leu Pro Leu Leu Ile Met Ser
            195                 200                 205

Tyr Cys Tyr Phe Arg Ile Ile Gln Thr Leu Phe Ser Cys Lys Asn His
 210                 215                 220

Lys Lys Ala Lys Ala Ile Lys Leu Ile Leu Leu Val Val Val Phe
225                 230                 235                 240

Phe Leu Phe Trp Thr Pro Tyr Asn Val Met Ile Phe Leu Glu Thr Leu
                245                 250                 255

Lys Leu Tyr Asp Phe Phe Pro Ser Cys Asp Met Arg Arg Asp Leu Arg
                260                 265                 270

Leu Ala Leu Ser Val Thr Glu Thr Val Ala Phe Ser His Cys Cys Leu
            275                 280                 285

Asn Pro Leu Ile Tyr Ala Phe Ala Gly Glu Lys Phe Arg Arg Tyr Leu
 290                 295                 300

Tyr His Leu Tyr Gly Lys Cys Leu Ala Val Leu Cys Gly Arg Ser Val
305                 310                 315                 320

His Val Asp Phe Ser Pro Ser Glu Ser Gln Arg Ser Arg Gln Gly Ser
                325                 330                 335

Val Leu Ser Ser Asn Phe Thr Tyr His Thr Ser Asp Gly Asp Ala Ser
            340                 345                 350

Leu Leu Leu
        355

<210> SEQ ID NO 257
<211> LENGTH: 369
<212> TYPE: PRT
<213> ORGANISM: Artificial Sequence
<220> FEATURE:
<223> OTHER INFORMATION: Nanobody sequence

<400> SEQUENCE: 257

Ala Val Gln Leu Val Glu Ser Gly Gly Gly Leu Val Gln Pro Gly Gly
1               5                   10                  15

```
Ser Leu Arg Leu Ser Cys Ala Ala Ser Gly Ile Phe Ser Ser Thr
         20                  25                  30

Ala Met Ala Trp Tyr Arg Gln Ala Pro Gly Lys Arg Arg Asp Leu Val
     35                  40                  45

Ala Ala Ile Ser Ser Val Gly Val Thr Lys Tyr Ala Asp Ser Val Lys
 50                  55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Val Tyr Tyr Cys Thr
                 85                  90                  95

Ser Asp Pro Arg Arg Gly Trp Asp Thr Arg Tyr Trp Gly Gln Gly Thr
             100                 105                 110

Leu Val Thr Val Ser Ser Gly Gly Gly Ser Gly Gly Gly Ser Glu
         115                 120                 125

Val Gln Leu Val Glu Ser Gly Gly Leu Val Gln Pro Gly Asn Ser
130                 135                 140

Leu Arg Leu Ser Cys Ala Ala Ser Gly Phe Thr Phe Ser Ser Phe Gly
145                 150                 155                 160

Met Ser Trp Val Arg Gln Ala Pro Gly Lys Gly Leu Glu Trp Val Ser
                 165                 170                 175

Ser Ile Ser Gly Ser Gly Ser Asp Thr Leu Tyr Ala Asp Ser Val Lys
             180                 185                 190

Gly Arg Phe Thr Ile Ser Arg Asp Asn Ala Lys Thr Thr Leu Tyr Leu
         195                 200                 205

Gln Met Asn Ser Leu Arg Pro Glu Asp Thr Ala Val Tyr Tyr Cys Thr
     210                 215                 220

Ile Gly Gly Ser Leu Ser Arg Ser Ser Gln Gly Thr Leu Val Thr Val
225                 230                 235                 240

Ser Ser Gly Gly Gly Gly Ser Gly Gly Gly Ser Glu Val Gln Leu Val
                 245                 250                 255

Glu Ser Gly Gly Gly Leu Val Gln Pro Gly Gly Ser Leu Arg Leu Ser
             260                 265                 270

Cys Ala Ala Ser Gly Ser Ile Phe Ser Ser Thr Ala Met Ala Trp Tyr
         275                 280                 285

Arg Gln Ala Pro Gly Lys Arg Arg Asp Leu Val Ala Ala Ile Ser Ser
     290                 295                 300

Val Gly Val Thr Lys Tyr Ala Asp Ser Val Lys Gly Arg Phe Thr Ile
305                 310                 315                 320

Ser Arg Asp Asn Ser Lys Asn Thr Val Tyr Leu Gln Met Asn Ser Leu
                 325                 330                 335

Arg Pro Glu Asp Thr Ala Val Tyr Tyr Cys Thr Ser Asp Pro Arg Arg
             340                 345                 350

Gly Trp Asp Thr Arg Tyr Trp Gly Gln Gly Thr Leu Val Thr Val Ser
         355                 360                 365

Ser
```

<210> SEQ ID NO 258
<211> LENGTH: 369
<212> TYPE: PRT
<213> ORGANISM: Artificial Sequence
<220> FEATURE:
<223> OTHER INFORMATION: Nanobody sequence

<400> SEQUENCE: 258

```
Ala Val Gln Leu Val Glu Ser Gly Gly Gly Leu Val Gln Pro Gly Gly
 1               5                  10                  15

Ser Leu Arg Leu Ser Cys Ala Ala Ser Gly Ser Ile Phe Ser Ser Thr
            20                  25                  30

Ala Met Ala Trp Tyr Arg Gln Ala Pro Gly Lys Arg Arg Asp Leu Val
            35                  40                  45

Ala Ala Ile Ser Thr Val Gly Val Thr Lys Tyr Ala Asp Ser Val Lys
        50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
            85                  90                  95

Ser Asp Pro Arg Arg Gly Trp Asp Thr Arg Tyr Trp Gly Gln Gly Thr
            100                 105                 110

Leu Val Thr Val Ser Ser Gly Gly Gly Gly Ser Gly Gly Gly Ser Glu
            115                 120                 125

Val Gln Leu Val Glu Ser Gly Gly Leu Val Gln Pro Gly Asn Ser
            130                 135                 140

Leu Arg Leu Ser Cys Ala Ala Ser Gly Phe Thr Phe Ser Ser Phe Gly
145                 150                 155                 160

Met Ser Trp Val Arg Gln Ala Pro Gly Lys Gly Leu Glu Trp Val Ser
            165                 170                 175

Ser Ile Ser Gly Ser Gly Ser Asp Thr Leu Tyr Ala Asp Ser Val Lys
            180                 185                 190

Gly Arg Phe Thr Ile Ser Arg Asp Asn Ala Lys Thr Thr Leu Tyr Leu
            195                 200                 205

Gln Met Asn Ser Leu Arg Pro Glu Asp Thr Ala Val Tyr Tyr Cys Thr
            210                 215                 220

Ile Gly Gly Ser Leu Ser Arg Ser Ser Gln Gly Thr Leu Val Thr Val
225                 230                 235                 240

Ser Ser Gly Gly Gly Gly Ser Gly Gly Gly Ser Glu Val Gln Leu Val
            245                 250                 255

Glu Ser Gly Gly Gly Leu Val Gln Pro Gly Gly Ser Leu Arg Leu Ser
            260                 265                 270

Cys Ala Ala Ser Gly Ser Ile Phe Ser Ser Thr Ala Met Ala Trp Tyr
            275                 280                 285

Arg Gln Ala Pro Gly Lys Arg Arg Asp Leu Val Ala Ala Ile Ser Thr
            290                 295                 300

Val Gly Val Thr Lys Tyr Ala Asp Ser Val Lys Gly Arg Phe Thr Ile
305                 310                 315                 320

Ser Arg Asp Asn Ser Lys Asn Thr Val Tyr Leu Gln Met Asn Ser Leu
            325                 330                 335

Arg Pro Glu Asp Thr Ala Val Tyr Tyr Cys Thr Ser Asp Pro Arg Arg
            340                 345                 350

Gly Trp Asp Thr Arg Tyr Trp Gly Gln Gly Thr Leu Val Thr Val Ser
            355                 360                 365

Ser
```

<210> SEQ ID NO 259
<211> LENGTH: 369
<212> TYPE: PRT
<213> ORGANISM: Artificial Sequence
<220> FEATURE:
<223> OTHER INFORMATION: Nanobody sequence

```
<400> SEQUENCE: 259

Ala Val Gln Leu Val Glu Ser Gly Gly Leu Val Gln Pro Gly Gly
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser Gly Gly Gly Gly Ser Gly Gly Gly Ser Glu
        115                 120                 125

Val Gln Leu Val Glu Ser Gly Gly Gly Leu Val Gln Pro Gly Asn Ser
    130                 135                 140

Leu Arg Leu Ser Cys Ala Ala Ser Gly Phe Thr Phe Ser Ser Phe Gly
145                 150                 155                 160

Met Ser Trp Val Arg Gln Ala Pro Gly Lys Gly Leu Glu Trp Val Ser
                165                 170                 175

Ser Ile Ser Gly Ser Gly Ser Asp Thr Leu Tyr Ala Asp Ser Val Lys
            180                 185                 190

Gly Arg Phe Thr Ile Ser Arg Asp Asn Ala Lys Thr Thr Leu Tyr Leu
        195                 200                 205

Gln Met Asn Ser Leu Arg Pro Glu Asp Thr Ala Val Tyr Tyr Cys Thr
    210                 215                 220

Ile Gly Gly Ser Leu Ser Arg Ser Ser Gln Gly Thr Leu Val Thr Val
225                 230                 235                 240

Ser Ser Gly Gly Gly Gly Ser Gly Gly Gly Ser Glu Val Gln Leu Val
                245                 250                 255

Glu Ser Gly Gly Gly Leu Val Gln Pro Gly Gly Ser Leu Arg Leu Ser
            260                 265                 270

Cys Ala Ala Ser Gly Ser Ile Phe Ser Ser Asn Ala Met Ala Trp Tyr
        275                 280                 285

Arg Gln Ala Pro Gly Lys Arg Arg Asp Leu Val Ala Ala Ile Asn Ser
    290                 295                 300

Val Gly Val Thr Lys Tyr Ala Asp Ser Val Lys Gly Arg Phe Thr Ile
305                 310                 315                 320

Ser Arg Asp Asn Ser Lys Asn Thr Val Tyr Leu Gln Met Asn Ser Leu
                325                 330                 335

Arg Pro Glu Asp Thr Ala Val Tyr Tyr Cys Thr Ser Asp Pro Arg Arg
            340                 345                 350

Gly Trp Asp Thr Arg Tyr Trp Gly Gln Gly Thr Leu Val Thr Val Ser
        355                 360                 365

Ser

<210> SEQ ID NO 260
<211> LENGTH: 368
<212> TYPE: PRT
<213> ORGANISM: Artificial Sequence
<220> FEATURE:
```

<223> OTHER INFORMATION: Nanobody sequence

<400> SEQUENCE: 260

Val Gln Leu Val Glu Ser Gly Gly Gly Leu Val Gln Pro Gly Gly Ser
1               5                   10                  15
Leu Arg Leu Ser Cys Ala Ala Ser Gly Ser Ile Phe Ser Ser Thr Ala
            20                  25                  30
Met Ala Trp Tyr Arg Gln Ala Pro Gly Lys Arg Arg Asp Leu Val Ala
        35                  40                  45
Ala Ile Ser Ser Val Gly Val Thr Lys Tyr Ala Asp Ser Val Lys Gly
    50                  55                  60
Arg Phe Thr Ile Ser Arg Asp Asn Ser Lys Asn Thr Val Tyr Leu Gln
65                  70                  75                  80
Met Asn Ser Leu Arg Pro Glu Asp Thr Ala Val Tyr Tyr Cys Thr Ser
                85                  90                  95
Asp Pro Arg Arg Gly Trp Asp Thr Arg Tyr Trp Gly Gln Gly Thr Leu
            100                 105                 110
Val Thr Val Ser Ser Gly Gly Gly Gly Ser Gly Gly Gly Ser Glu Val
        115                 120                 125
Gln Leu Val Glu Ser Gly Gly Gly Leu Val Gln Pro Gly Asn Ser Leu
    130                 135                 140
Arg Leu Ser Cys Ala Ala Ser Gly Phe Thr Phe Ser Ser Phe Gly Met
145                 150                 155                 160
Ser Trp Val Arg Gln Ala Pro Gly Lys Gly Leu Glu Trp Val Ser Ser
                165                 170                 175
Ile Ser Gly Ser Gly Ser Asp Thr Leu Tyr Ala Asp Ser Val Lys Gly
            180                 185                 190
Arg Phe Thr Ile Ser Arg Asp Asn Ala Lys Thr Thr Leu Tyr Leu Gln
        195                 200                 205
Met Asn Ser Leu Arg Pro Glu Asp Thr Ala Val Tyr Tyr Cys Thr Ile
    210                 215                 220
Gly Gly Ser Leu Ser Arg Ser Ser Gln Gly Thr Leu Val Thr Val Ser
225                 230                 235                 240
Ser Gly Gly Gly Gly Ser Gly Gly Gly Ser Glu Val Gln Leu Val Glu
                245                 250                 255
Ser Gly Gly Gly Leu Val Gln Pro Gly Gly Ser Leu Arg Leu Ser Cys
            260                 265                 270
Ala Ala Ser Gly Ser Ile Phe Ser Ser Thr Ala Met Ala Trp Tyr Arg
        275                 280                 285
Gln Ala Pro Gly Lys Arg Arg Asp Leu Val Ala Ala Ile Ser Ser Val
    290                 295                 300
Gly Val Thr Lys Tyr Ala Asp Ser Val Lys Gly Arg Phe Thr Ile Ser
305                 310                 315                 320
Arg Asp Asn Ser Lys Asn Thr Val Tyr Leu Gln Met Asn Ser Leu Arg
                325                 330                 335
Pro Glu Asp Thr Ala Val Tyr Tyr Cys Thr Ser Asp Pro Arg Arg Gly
            340                 345                 350
Trp Asp Thr Arg Tyr Trp Gly Gln Gly Thr Leu Val Thr Val Ser Ser
        355                 360                 365

<210> SEQ ID NO 261
<211> LENGTH: 368
<212> TYPE: PRT
<213> ORGANISM: Artificial Sequence
<220> FEATURE:

<223> OTHER INFORMATION: Nanobody sequence

<400> SEQUENCE: 261

Val Gln Leu Val Glu Ser Gly Gly Gly Leu Val Gln Pro Gly Gly Ser
1               5                   10                  15
Leu Arg Leu Ser Cys Ala Ala Ser Gly Ser Ile Phe Ser Thr Ala
            20                  25                  30
Met Ala Trp Tyr Arg Gln Ala Pro Gly Lys Arg Arg Asp Leu Val Ala
        35                  40                  45
Ala Ile Ser Thr Val Gly Val Thr Lys Tyr Ala Asp Ser Val Lys Gly
    50                  55                  60
Arg Phe Thr Ile Ser Arg Asp Asn Ser Lys Asn Thr Val Tyr Leu Gln
65                  70                  75                  80
Met Asn Ser Leu Arg Pro Glu Asp Thr Ala Val Tyr Tyr Cys Thr Ser
                85                  90                  95
Asp Pro Arg Arg Gly Trp Asp Thr Arg Tyr Trp Gly Gln Gly Thr Leu
            100                 105                 110
Val Thr Val Ser Ser Gly Gly Gly Ser Gly Gly Ser Glu Val
        115                 120                 125
Gln Leu Val Glu Ser Gly Gly Gly Leu Val Gln Pro Gly Asn Ser Leu
    130                 135                 140
Arg Leu Ser Cys Ala Ala Ser Gly Phe Thr Phe Ser Ser Phe Gly Met
145                 150                 155                 160
Ser Trp Val Arg Gln Ala Pro Gly Lys Gly Leu Glu Trp Val Ser Ser
                165                 170                 175
Ile Ser Gly Ser Gly Ser Asp Thr Leu Tyr Ala Asp Ser Val Lys Gly
            180                 185                 190
Arg Phe Thr Ile Ser Arg Asp Asn Ala Lys Thr Thr Leu Tyr Leu Gln
        195                 200                 205
Met Asn Ser Leu Arg Pro Glu Asp Thr Ala Val Tyr Tyr Cys Thr Ile
    210                 215                 220
Gly Gly Ser Leu Ser Arg Ser Ser Gln Gly Thr Leu Val Thr Val Ser
225                 230                 235                 240
Ser Gly Gly Gly Gly Ser Gly Gly Gly Ser Glu Val Gln Leu Val Glu
                245                 250                 255
Ser Gly Gly Gly Leu Val Gln Pro Gly Gly Ser Leu Arg Leu Ser Cys
            260                 265                 270
Ala Ala Ser Gly Ser Ile Phe Ser Ser Thr Ala Met Ala Trp Tyr Arg
        275                 280                 285
Gln Ala Pro Gly Lys Arg Arg Asp Leu Val Ala Ala Ile Ser Thr Val
    290                 295                 300
Gly Val Thr Lys Tyr Ala Asp Ser Val Lys Gly Arg Phe Thr Ile Ser
305                 310                 315                 320
Arg Asp Asn Ser Lys Asn Thr Val Tyr Leu Gln Met Asn Ser Leu Arg
                325                 330                 335
Pro Glu Asp Thr Ala Val Tyr Tyr Cys Thr Ser Asp Pro Arg Arg Gly
            340                 345                 350
Trp Asp Thr Arg Tyr Trp Gly Gln Gly Thr Leu Val Thr Val Ser Ser
        355                 360                 365

<210> SEQ ID NO 262
<211> LENGTH: 368
<212> TYPE: PRT
<213> ORGANISM: Artificial Sequence
<220> FEATURE:

<223> OTHER INFORMATION: Nanobody sequence

<400> SEQUENCE: 262

Val Gln Leu Val Glu Ser Gly Gly Gly Leu Val Gln Pro Gly Gly Ser
1               5                   10                  15

Leu Arg Leu Ser Cys Ala Ala Ser Gly Ser Ile Phe Ser Ser Asn Ala
            20                  25                  30

Met Ala Trp Tyr Arg Gln Ala Pro Gly Lys Arg Arg Asp Leu Val Ala
        35                  40                  45

Ala Ile Asn Ser Val Gly Val Thr Lys Tyr Ala Asp Ser Val Lys Gly
    50                  55                  60

Arg Phe Thr Ile Ser Arg Asp Asn Ser Lys Asn Thr Val Tyr Leu Gln
65                  70                  75                  80

Met Asn Ser Leu Arg Pro Glu Asp Thr Ala Val Tyr Tyr Cys Thr Ser
                85                  90                  95

Asp Pro Arg Arg Gly Trp Asp Thr Arg Tyr Trp Gly Gln Gly Thr Leu
            100                 105                 110

Val Thr Val Ser Ser Gly Gly Gly Ser Gly Gly Gly Ser Glu Val
        115                 120                 125

Gln Leu Val Glu Ser Gly Gly Gly Leu Val Gln Pro Gly Asn Ser Leu
    130                 135                 140

Arg Leu Ser Cys Ala Ala Ser Gly Phe Thr Phe Ser Ser Phe Gly Met
145                 150                 155                 160

Ser Trp Val Arg Gln Ala Pro Gly Lys Gly Leu Glu Trp Val Ser Ser
                165                 170                 175

Ile Ser Gly Ser Gly Ser Asp Thr Leu Tyr Ala Asp Ser Val Lys Gly
            180                 185                 190

Arg Phe Thr Ile Ser Arg Asp Asn Ala Lys Thr Thr Leu Tyr Leu Gln
        195                 200                 205

Met Asn Ser Leu Arg Pro Glu Asp Thr Ala Val Tyr Tyr Cys Thr Ile
    210                 215                 220

Gly Gly Ser Leu Ser Arg Ser Ser Gln Gly Thr Leu Val Thr Val Ser
225                 230                 235                 240

Ser Gly Gly Gly Gly Ser Gly Gly Gly Ser Glu Val Gln Leu Val Glu
                245                 250                 255

Ser Gly Gly Gly Leu Val Gln Pro Gly Gly Ser Leu Arg Leu Ser Cys
            260                 265                 270

Ala Ala Ser Gly Ser Ile Phe Ser Ser Asn Ala Met Ala Trp Tyr Arg
        275                 280                 285

Gln Ala Pro Gly Lys Arg Arg Asp Leu Val Ala Ala Ile Asn Ser Val
    290                 295                 300

Gly Val Thr Lys Tyr Ala Asp Ser Val Lys Gly Arg Phe Thr Ile Ser
305                 310                 315                 320

Arg Asp Asn Ser Lys Asn Thr Val Tyr Leu Gln Met Asn Ser Leu Arg
                325                 330                 335

Pro Glu Asp Thr Ala Val Tyr Tyr Cys Thr Ser Asp Pro Arg Arg Gly
            340                 345                 350

Trp Asp Thr Arg Tyr Trp Gly Gln Gly Thr Leu Val Thr Val Ser Ser
        355                 360                 365

<210> SEQ ID NO 263
<211> LENGTH: 355
<212> TYPE: PRT
<213> ORGANISM: Artificial Sequence
<220> FEATURE:

<223> OTHER INFORMATION: Nanobody sequence

<400> SEQUENCE: 263

```
Ala Val Gln Leu Val Glu Ser Gly Gly Gly Leu Val Gln Pro Gly Gly
  1               5                  10                  15
Ser Leu Arg Leu Ser Cys Ala Ala Ser Gly Ser Ile Phe Ser Ser Thr
             20                  25                  30
Ala Met Ala Trp Tyr Arg Gln Ala Pro Gly Lys Arg Arg Asp Leu Val
         35                  40                  45
Ala Ala Ile Ser Ser Val Gly Val Thr Lys Tyr Ala Asp Ser Val Lys
     50                  55                  60
Gly Arg Phe Thr Ile Ser Arg Asp Asn Ser Lys Asn Thr Val Tyr Leu
 65                  70                  75                  80
Gln Met Asn Ser Leu Arg Pro Glu Asp Thr Ala Val Tyr Tyr Cys Thr
             85                  90                  95
Ser Asp Pro Arg Arg Gly Trp Asp Thr Arg Tyr Trp Gly Gln Gly Thr
            100                 105                 110
Leu Val Thr Val Ser Ser Gly Gly Gly Ser Gly Gly Gly Gly Ser
            115                 120                 125
Gly Gly Gly Gly Ser Cys Pro Pro Cys Pro Ala Pro Glu Ala Ala Gly
130                 135                 140
Gly Pro Ser Val Phe Leu Phe Pro Pro Lys Pro Lys Asp Thr Leu Met
145                 150                 155                 160
Ile Ser Arg Thr Pro Glu Val Thr Cys Val Val Val Asp Val Ser His
            165                 170                 175
Glu Asp Pro Glu Val Lys Phe Asn Trp Tyr Val Asp Gly Val Glu Val
            180                 185                 190
His Asn Ala Lys Thr Lys Pro Arg Glu Glu Gln Tyr Asn Ser Thr Tyr
        195                 200                 205
Arg Val Val Ser Val Leu Thr Val Leu His Gln Asp Trp Leu Asn Gly
    210                 215                 220
Lys Glu Tyr Lys Cys Lys Val Ser Asn Lys Ala Leu Pro Ala Pro Ile
225                 230                 235                 240
Glu Lys Thr Ile Ser Lys Ala Lys Gly Gln Pro Arg Glu Pro Gln Val
            245                 250                 255
Tyr Thr Leu Pro Pro Ser Arg Glu Glu Met Thr Lys Asn Gln Val Ser
            260                 265                 270
Leu Thr Cys Leu Val Lys Gly Phe Tyr Pro Ser Asp Ile Ala Val Glu
        275                 280                 285
Trp Glu Ser Asn Gly Gln Pro Glu Asn Asn Tyr Lys Thr Thr Pro Pro
    290                 295                 300
Val Leu Asp Ser Asp Gly Ser Phe Phe Leu Tyr Ser Lys Leu Thr Val
305                 310                 315                 320
Asp Lys Ser Arg Trp Gln Gln Gly Asn Val Phe Ser Cys Ser Val Met
            325                 330                 335
His Glu Ala Leu His Asn His Tyr Thr Gln Lys Ser Leu Ser Leu Ser
            340                 345                 350
Pro Gly Lys
        355
```

<210> SEQ ID NO 264
<211> LENGTH: 355
<212> TYPE: PRT
<213> ORGANISM: Artificial Sequence
<220> FEATURE:

<223> OTHER INFORMATION: Nanobody sequence

<400> SEQUENCE: 264

Ala Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ser Thr
            20                  25                  30

Ala Met Ala Trp Tyr Arg Gln Ala Pro Gly Lys Arg Arg Asp Leu Val
        35                  40                  45

Ala Ala Ile Ser Thr Val Gly Val Thr Lys Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Cys Pro Pro Cys Pro Ala Pro Glu Ala Ala Gly
130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser His
            165                 170                 175

Glu Asp Pro Glu Val Lys Phe Asn Trp Tyr Val Asp Gly Val Glu Val
        180                 185                 190

His Asn Ala Lys Thr Lys Pro Arg Glu Glu Gln Tyr Asn Ser Thr Tyr
    195                 200                 205

Arg Val Val Ser Val Leu Thr Val Leu His Gln Asp Trp Leu Asn Gly
210                 215                 220

Lys Glu Tyr Lys Cys Lys Val Ser Asn Lys Ala Leu Pro Ala Pro Ile
225                 230                 235                 240

Glu Lys Thr Ile Ser Lys Ala Lys Gly Gln Pro Arg Glu Pro Gln Val
            245                 250                 255

Tyr Thr Leu Pro Pro Ser Arg Glu Glu Met Thr Lys Asn Gln Val Ser
        260                 265                 270

Leu Thr Cys Leu Val Lys Gly Phe Tyr Pro Ser Asp Ile Ala Val Glu
    275                 280                 285

Trp Glu Ser Asn Gly Gln Pro Glu Asn Asn Tyr Lys Thr Thr Pro Pro
290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Phe Ser Cys Ser Val Met
            325                 330                 335

His Glu Ala Leu His Asn His Tyr Thr Gln Lys Ser Leu Ser Leu Ser
        340                 345                 350

Pro Gly Lys
        355

<210> SEQ ID NO 265
<211> LENGTH: 354
<212> TYPE: PRT
<213> ORGANISM: Artificial Sequence
<220> FEATURE:

```
<223> OTHER INFORMATION: Nanobody sequence

<400> SEQUENCE: 265

Val Gln Leu Val Glu Ser Gly Gly Gly Leu Val Gln Pro Gly Gly Ser
 1               5                  10                  15

Leu Arg Leu Ser Cys Ala Ala Ser Gly Ser Ile Phe Ser Thr Ala
            20                  25                  30

Met Ala Trp Tyr Arg Gln Ala Pro Gly Lys Arg Arg Asp Leu Val Ala
        35                  40                  45

Ala Ile Ser Ser Val Gly Val Thr Lys Tyr Ala Asp Ser Val Lys Gly
    50                  55                  60

Arg Phe Thr Ile Ser Arg Asp Asn Ser Lys Asn Thr Val Tyr Leu Gln
65                  70                  75                  80

Met Asn Ser Leu Arg Pro Glu Asp Thr Ala Val Tyr Tyr Cys Thr Ser
                85                  90                  95

Asp Pro Arg Arg Gly Trp Asp Thr Arg Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Ser Cys Pro Pro Cys Pro Ala Pro Glu Ala Ala Gly Gly
130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
    210                 215                 220

Glu Tyr Lys Cys Lys Val Ser Asn Lys Ala Leu Pro Ala Pro Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Arg Glu Glu Met Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
    290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Ser Leu Ser Pro
            340                 345                 350

Gly Lys

<210> SEQ ID NO 266
<211> LENGTH: 354
<212> TYPE: PRT
<213> ORGANISM: Artificial Sequence
<220> FEATURE:
<223> OTHER INFORMATION: Nanobody sequence
```

<400> SEQUENCE: 266

| | | | | | | | | | | | | |
|---|---|---|---|---|---|---|---|---|---|---|---|---|
| Val | Gln | Leu | Val | Glu | Ser | Gly | Gly | Leu | Val | Gln | Pro | Gly | Gly | Ser |
| 1 | | | | 5 | | | | | 10 | | | | | 15 |
| Leu | Arg | Leu | Ser | Cys | Ala | Ala | Ser | Gly | Ser | Ile | Phe | Ser | Ser | Thr | Ala |
| | | | 20 | | | | | 25 | | | | | 30 | | |
| Met | Ala | Trp | Tyr | Arg | Gln | Ala | Pro | Gly | Lys | Arg | Arg | Asp | Leu | Val | Ala |
| | | | | 35 | | | | | 40 | | | | | 45 | |
| Ala | Ile | Ser | Thr | Val | Gly | Val | Thr | Lys | Tyr | Ala | Asp | Ser | Val | Lys | Gly |
| | 50 | | | | | 55 | | | | | 60 | | | | |
| Arg | Phe | Thr | Ile | Ser | Arg | Asp | Asn | Ser | Lys | Asn | Thr | Val | Tyr | Leu | Gln |
| 65 | | | | | 70 | | | | | 75 | | | | | 80 |
| Met | Asn | Ser | Leu | Arg | Pro | Glu | Asp | Thr | Ala | Val | Tyr | Tyr | Cys | Thr | Ser |
| | | | | 85 | | | | | 90 | | | | | 95 | |
| Asp | Pro | Arg | Arg | Gly | Trp | Asp | Thr | Arg | Tyr | Trp | Gly | Gln | Gly | Thr | Leu |
| | | | 100 | | | | | 105 | | | | | 110 | | |
| Val | Thr | Val | Ser | Ser | Gly | Gly | Gly | Gly | Ser | Gly | Gly | Gly | Gly | Ser | Gly |
| | | | 115 | | | | | 120 | | | | | 125 | | |
| Gly | Gly | Gly | Ser | Cys | Pro | Pro | Cys | Pro | Ala | Pro | Glu | Ala | Ala | Gly | Gly |
| | 130 | | | | | 135 | | | | | 140 | | | | |
| Pro | Ser | Val | Phe | Leu | Phe | Pro | Pro | Lys | Pro | Lys | Asp | Thr | Leu | Met | Ile |
| 145 | | | | | 150 | | | | | 155 | | | | | 160 |
| Ser | Arg | Thr | Pro | Glu | Val | Thr | Cys | Val | Val | Val | Asp | Val | Ser | His | Glu |
| | | | | 165 | | | | | 170 | | | | | 175 | |
| Asp | Pro | Glu | Val | Lys | Phe | Asn | Trp | Tyr | Val | Asp | Gly | Val | Glu | Val | His |
| | | | 180 | | | | | 185 | | | | | 190 | | |
| Asn | Ala | Lys | Thr | Lys | Pro | Arg | Glu | Glu | Gln | Tyr | Asn | Ser | Thr | Tyr | Arg |
| | | | 195 | | | | | 200 | | | | | 205 | | |
| Val | Val | Ser | Val | Leu | Thr | Val | Leu | His | Gln | Asp | Trp | Leu | Asn | Gly | Lys |
| | 210 | | | | | 215 | | | | | 220 | | | | |
| Glu | Tyr | Lys | Cys | Lys | Val | Ser | Asn | Lys | Ala | Leu | Pro | Ala | Pro | Ile | Glu |
| 225 | | | | | 230 | | | | | 235 | | | | | 240 |
| Lys | Thr | Ile | Ser | Lys | Ala | Lys | Gly | Gln | Pro | Arg | Glu | Pro | Gln | Val | Tyr |
| | | | | 245 | | | | | 250 | | | | | 255 | |
| Thr | Leu | Pro | Pro | Ser | Arg | Glu | Glu | Met | Thr | Lys | Asn | Gln | Val | Ser | Leu |
| | | | 260 | | | | | 265 | | | | | 270 | | |
| Thr | Cys | Leu | Val | Lys | Gly | Phe | Tyr | Pro | Ser | Asp | Ile | Ala | Val | Glu | Trp |
| | | | 275 | | | | | 280 | | | | | 285 | | |
| Glu | Ser | Asn | Gly | Gln | Pro | Glu | Asn | Asn | Tyr | Lys | Thr | Thr | Pro | Pro | Val |
| | 290 | | | | | 295 | | | | | 300 | | | | |
| Leu | Asp | Ser | Asp | Gly | Ser | Phe | Phe | Leu | Tyr | Ser | Lys | Leu | Thr | Val | Asp |
| 305 | | | | | 310 | | | | | 315 | | | | | 320 |
| Lys | Ser | Arg | Trp | Gln | Gln | Gly | Asn | Val | Phe | Ser | Cys | Ser | Val | Met | His |
| | | | | 325 | | | | | 330 | | | | | 335 | |
| Glu | Ala | Leu | His | Asn | His | Tyr | Thr | Gln | Lys | Ser | Leu | Ser | Leu | Ser | Pro |
| | | | 340 | | | | | 345 | | | | | 350 | | |
| Gly | Lys | | | | | | | | | | | | | | |

<210> SEQ ID NO 267
<211> LENGTH: 273
<212> TYPE: PRT
<213> ORGANISM: Artificial Sequence
<220> FEATURE:
<223> OTHER INFORMATION: Nanobody sequence

<400> SEQUENCE: 267

Glu Val Gln Leu Val Glu Ser Gly Gly Gly Leu Val Gln Ala Gly Gly
1               5                   10                  15

Ser Leu Arg Leu Ser Cys Val Ala Ser Gly Arg Thr Phe Ser Ser Tyr
            20                  25                  30

Ala Met Gly Trp Phe Arg Gln Ala Pro Gly Lys Glu Arg Ala Phe Val
        35                  40                  45

Ala Gly Ile Ser Gly Ser Ala Ser Arg Lys Tyr Tyr Ala Asp Ser Val
    50                  55                  60

Lys Gly Arg Phe Thr Val Ser Arg Asp Asn Ala Arg Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Asn Ser Tyr Pro Lys Val Gln Phe Asp Tyr Tyr Gly Gln
            100                 105                 110

Gly Thr Gln Val Thr Val Ser Ser Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Ser Lys Val Gln Leu Val
145                 150                 155                 160

Glu Ser Gly Gly Gly Leu Val Gln Pro Gly Gly Ser Leu Arg Leu Ser
                165                 170                 175

Cys Ala Thr Ser Gly Thr Ile Phe Ser Asn Asn Ala Met Gly Trp Tyr
            180                 185                 190

Arg Gln Ala Pro Gly Lys Lys Arg Asp Leu Val Ala Ser Ile Ser Ser
        195                 200                 205

Ser Gly Ser Thr Asn Tyr Ala Asp Ser Val Lys Gly Arg Phe Thr Val
    210                 215                 220

Ser Arg Asp Asn Asp Lys Asn Thr Gly Tyr Leu Gln Met Asn Ser Leu
225                 230                 235                 240

Lys Pro Glu Asp Thr Gly Val Tyr Tyr Cys Thr Leu Asp Ala Arg Arg
                245                 250                 255

Gly Trp Asn Thr Ala Tyr Trp Gly Gln Gly Ala Gln Val Thr Val Ser
            260                 265                 270

Ser

<210> SEQ ID NO 268
<211> LENGTH: 273
<212> TYPE: PRT
<213> ORGANISM: Artificial Sequence
<220> FEATURE:
<223> OTHER INFORMATION: Nanobody sequence

<400> SEQUENCE: 268

Lys Val Gln Leu Val Glu Ser Gly Gly Gly Leu Val Gln Pro Gly Gly
1               5                   10                  15

Ser Leu Arg Leu Ser Cys Ala Thr Ser Gly Thr Ile Phe Ser Asn Asn
            20                  25                  30

Ala Met Gly Trp Tyr Arg Gln Ala Pro Gly Lys Lys Arg Asp Leu Val
        35                  40                  45

Ala Ser Ile Ser Ser Ser Gly Ser Thr Asn Tyr Ala Asp Ser Val Lys
    50                  55                  60

Gly Arg Phe Thr Val Ser Arg Asp Asn Asp Lys Asn Thr Gly Tyr Leu
65                  70                  75                  80

```
Gln Met Asn Ser Leu Lys Pro Glu Asp Thr Gly Val Tyr Tyr Cys Thr
                85                  90                  95

Leu Asp Ala Arg Arg Gly Trp Asn Thr Ala Tyr Trp Gly Gln Gly Ala
            100                 105                 110

Gln Val Thr Val Ser Ser Gly Gly Gly Ser Gly Gly Gly Gly Ser
        115                 120                 125

Gly Gly Gly Gly Ser Gly Gly Gly Ser Gly Gly Gly Ser Gly
        130                 135                 140

Gly Gly Gly Ser Gly Gly Gly Ser Glu Val Gln Leu Val Glu Ser
145                 150                 155                 160

Gly Gly Gly Leu Val Gln Ala Gly Gly Ser Leu Arg Leu Ser Cys Val
                165                 170                 175

Ala Ser Gly Arg Thr Phe Ser Ser Tyr Ala Met Gly Trp Phe Arg Gln
            180                 185                 190

Ala Pro Gly Lys Glu Arg Ala Phe Val Ala Gly Ile Ser Gly Ser Ala
            195                 200                 205

Ser Arg Lys Tyr Tyr Ala Asp Ser Val Lys Gly Arg Phe Thr Val Ser
        210                 215                 220

Arg Asp Asn Ala Arg Asn Thr Val Tyr Leu Gln Met Asn Ser Leu Lys
225                 230                 235                 240

Pro Glu Asp Thr Ala Val Tyr Tyr Cys Ala Ala Ser Asn Ser Tyr Pro
                245                 250                 255

Lys Val Gln Phe Asp Tyr Tyr Gly Gln Gly Thr Gln Val Thr Val Ser
            260                 265                 270

Ser

<210> SEQ ID NO 269
<211> LENGTH: 271
<212> TYPE: PRT
<213> ORGANISM: Artificial Sequence
<220> FEATURE:
<223> OTHER INFORMATION: Nanobody sequence

<400> SEQUENCE: 269

Glu Val Gln Leu Val Glu Ser Gly Gly Gly Ser Val Gln Ala Gly Gly
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Gly Gly Gly Gly Ser Gly Gly Gly Gly Ser Gly
    130                 135                 140

Gly Gly Ser Gly Gly Gly Ser Lys Val Gln Leu Val Glu Ser
145                 150                 155                 160
```

Gly Gly Gly Leu Val Gln Pro Gly Gly Ser Leu Arg Leu Ser Cys Ala
            165                 170                 175

Thr Ser Gly Thr Ile Phe Ser Asn Asn Ala Met Gly Trp Tyr Arg Gln
            180                 185                 190

Ala Pro Gly Lys Lys Arg Asp Leu Val Ala Ser Ile Ser Ser Gly
            195                 200                 205

Ser Thr Asn Tyr Ala Asp Ser Val Lys Gly Arg Phe Thr Val Ser Arg
            210                 215                 220

Asp Asn Asp Lys Asn Thr Gly Tyr Leu Gln Met Asn Ser Leu Lys Pro
225                 230                 235                 240

Glu Asp Thr Gly Val Tyr Tyr Cys Thr Leu Asp Ala Arg Arg Gly Trp
            245                 250                 255

Asn Thr Ala Tyr Trp Gly Gln Gly Ala Gln Val Thr Val Ser Ser
            260                 265                 270

<210> SEQ ID NO 270
<211> LENGTH: 271
<212> TYPE: PRT
<213> ORGANISM: Artificial Sequence
<220> FEATURE:
<223> OTHER INFORMATION: Nanobody sequence

<400> SEQUENCE: 270

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
            35                  40                  45

Ala Val Ile Asn Ser Val Gly Ile Thr Lys Tyr Ala Asp Ser Val Lys
        50                  55                  60

Gly Arg Phe Thr Ile Ser Gly Asp Asn Ala Lys Asn Thr Val Tyr Leu
65                  70                  75                  80

Gln Met Asn Ser Leu Lys Pro Glu Asp Thr Ala Val Tyr Tyr Cys Thr
            85                  90                  95

Ser Asp Ala Arg Arg Gly Trp Asp Thr Arg Tyr Trp Gly Gln Gly Thr
            100                 105                 110

Gln Val Thr Val Ser Ser Gly Gly Gly Ser Gly Gly Gly Gly Ser
            115                 120                 125

Gly Gly Gly Gly Ser Gly Gly Gly Ser Gly Gly Gly Ser Gly
        130                 135                 140

Gly Gly Ser Gly Gly Gly Ser Glu Val Gln Leu Val Glu Ser
145                 150                 155                 160

Gly Gly Gly Ser Val Gln Ala Gly Glu Ser Leu Arg Leu Ser Cys Ala
            165                 170                 175

Ala Ser Gly Ser Ile Phe Ser Ser Asn Ala Met Ala Trp Tyr Arg Gln
            180                 185                 190

Ala Pro Gly Lys Gln Arg Asp Leu Val Ala Val Ile Asn Ser Val Gly
            195                 200                 205

Ile Thr Lys Tyr Ala Asp Ser Val Lys Gly Arg Phe Thr Ile Ser Gly
            210                 215                 220

Asp Asn Ala Lys Asn Thr Val Tyr Leu Gln Met Asn Ser Leu Lys Pro
225                 230                 235                 240

Glu Asp Thr Ala Val Tyr Tyr Cys Thr Ser Asp Ala Arg Arg Gly Trp
            245                 250                 255

```
Asp Thr Arg Tyr Trp Gly Gln Gly Thr Gln Val Thr Val Ser
            260                 265                 270

<210> SEQ ID NO 271
<211> LENGTH: 273
<212> TYPE: PRT
<213> ORGANISM: Artificial Sequence
<220> FEATURE:
<223> OTHER INFORMATION: Nanobody sequence

<400> SEQUENCE: 271

Glu Val Gln Leu Val Glu Ser Gly Gly Gly Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Pro Gly Lys Gln Arg Asp Leu
        35                  40                  45

Val Ala Leu Ile Asn Ser Val Gly Ile Thr Lys Tyr Ala Asp Ser Val
    50                  55                  60

Lys Gly Arg Phe Thr Ile Ser Ser Asp Asn Ala Lys Asn Thr Val Tyr
65                  70                  75                  80

Leu Glu Met Asn Ser Leu Lys Pro Glu Asp Thr Ala Val Tyr Tyr Cys
                85                  90                  95

Thr Ser Asp Gly Arg Arg Gly Trp Asp Thr Arg Tyr Trp Gly Gln Gly
            100                 105                 110

Thr Gln Val Thr Val Ser Ser Gly Gly Gly Ser Gly Gly Gly Gly
        115                 120                 125

Ser Gly Gly Gly Gly Ser Gly Gly Gly Gly Ser Gly Gly Gly Gly Ser
        130                 135                 140

Gly Gly Gly Gly Ser Gly Gly Gly Gly Ser Glu Val Gln Leu Val Glu
145                 150                 155                 160

Ser Gly Gly Gly Ser Val Gln Ala Gly Glu Ser Leu Arg Leu Ser Cys
                165                 170                 175

Ala Ala Ser Gly Ser Ile Phe Ser Ser Asn Ala Met Ala Trp Tyr Arg
            180                 185                 190

Gln Ala Pro Pro Gly Lys Gln Arg Asp Leu Val Ala Leu Ile Asn Ser
        195                 200                 205

Val Gly Ile Thr Lys Tyr Ala Asp Ser Val Lys Gly Arg Phe Thr Ile
    210                 215                 220

Ser Ser Asp Asn Ala Lys Asn Thr Val Tyr Leu Glu Met Asn Ser Leu
225                 230                 235                 240

Lys Pro Glu Asp Thr Ala Val Tyr Tyr Cys Thr Ser Asp Gly Arg Arg
                245                 250                 255

Gly Trp Asp Thr Arg Tyr Trp Gly Gln Gly Thr Gln Val Thr Val Ser
            260                 265                 270

Ser

<210> SEQ ID NO 272
<211> LENGTH: 271
<212> TYPE: PRT
<213> ORGANISM: Artificial Sequence
<220> FEATURE:
<223> OTHER INFORMATION: Nanobody sequence

<400> SEQUENCE: 272

Glu Val Gln Leu Val Glu Ser Gly Gly Gly Ser Val Gln Ala Gly Glu
1               5                   10                  15
```

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser Gly Gly Gly Ser Gly Gly Gly Gly Ser
        115                 120                 125

Gly Gly Gly Gly Ser Gly Gly Gly Ser Gly Gly Gly Gly Ser Gly
    130                 135                 140

Gly Gly Ser Gly Gly Gly Ser Glu Val Gln Leu Val Glu Ser
145                 150                 155                 160

Gly Gly Gly Ser Val Gln Ala Gly Glu Ser Leu Arg Leu Ser Cys Ala
            165                 170                 175

Ala Ser Gly Ser Ile Phe Ser Ser Asn Ala Met Ala Trp Tyr Arg Gln
        180                 185                 190

Ala Pro Gly Lys Arg Arg Asp Leu Val Ala Ala Ile Asn Ser Val Gly
    195                 200                 205

Val Thr Lys Tyr Ala Asp Ser Val Lys Gly Arg Phe Thr Ile Ser Arg
210                 215                 220

Asp Asn Ala Lys Asn Thr Val Tyr Leu Gln Met Asn Ser Leu Lys Pro
225                 230                 235                 240

Glu Asp Thr Ala Val Tyr Tyr Cys Thr Ser Asp Pro Arg Arg Gly Trp
                245                 250                 255

Asp Thr Arg Tyr Trp Gly Gln Gly Thr Gln Val Thr Val Ser Ser
            260                 265                 270

<210> SEQ ID NO 273
<211> LENGTH: 271
<212> TYPE: PRT
<213> ORGANISM: Artificial Sequence
<220> FEATURE:
<223> OTHER INFORMATION: Nanobody sequence

<400> SEQUENCE: 273

Glu Met Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Leu Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
                85                  90                  95

Ser Asp Gly Arg Arg Gly Trp Asp Thr Arg Tyr Trp Gly Gln Gly Thr
            100                 105                 110

```
Gln Val Thr Val Ser Ser Gly Gly Gly Ser Gly Gly Gly Ser
            115                 120                 125

Gly Gly Gly Gly Ser Gly Gly Gly Ser Gly Gly Gly Ser Gly
        130                 135                 140

Gly Gly Gly Ser Gly Gly Gly Ser Glu Met Gln Leu Val Glu Ser
145                 150                 155                 160

Gly Gly Gly Ser Val Gln Ala Gly Glu Ser Leu Arg Leu Ser Cys Ala
                    165                 170                 175

Ala Ser Gly Ser Ile Phe Ser Ser Asn Ala Met Ala Trp Tyr Arg Gln
                180                 185                 190

Ala Pro Gly Lys Gln Arg Asp Leu Val Ala Leu Ile Asn Ser Val Gly
            195                 200                 205

Ile Thr Lys Tyr Ala Asp Ser Val Lys Gly Arg Phe Thr Ile Ser Arg
    210                 215                 220

Asp Asn Ala Lys Asn Thr Val Tyr Leu Gln Met Asn Ser Leu Lys Pro
225                 230                 235                 240

Glu Asp Thr Ala Val Tyr Tyr Cys Thr Ser Asp Gly Arg Arg Gly Trp
                245                 250                 255

Asp Thr Arg Tyr Trp Gly Gln Gly Thr Gln Val Thr Val Ser Ser
            260                 265                 270
```

<210> SEQ ID NO 274
<211> LENGTH: 271
<212> TYPE: PRT
<213> ORGANISM: Artificial Sequence
<220> FEATURE:
<223> OTHER INFORMATION: Nanobody sequence

<400> SEQUENCE: 274

```
Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Gln Arg Asp Leu Val
        35                  40                  45

Ala Gly Ile Asn Ser Val Gly Ile Thr Lys Tyr Ala Asp Ser Val Lys
    50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Leu Val Thr Val Ser Ser Gly Gly Gly Ser Gly Gly Gly Ser
        115                 120                 125

Gly Gly Gly Gly Ser Gly Gly Gly Ser Gly Gly Gly Ser Gly
        130                 135                 140

Gly Gly Ser Gly Gly Gly Ser Glu Val Gln Leu Val Glu Ser
145                 150                 155                 160

Gly Gly Gly Ser Val Gln Ala Gly Glu Ser Leu Arg Leu Ser Cys Ala
                165                 170                 175

Ala Ser Gly Ser Ile Phe Ser Ser Asn Ala Met Ala Trp Tyr Arg Gln
                180                 185                 190

Ala Pro Gly Lys Gln Arg Asp Leu Val Ala Gly Ile Asn Ser Val Gly
            195                 200                 205
```

```
Ile Thr Lys Tyr Ala Asp Ser Val Lys Gly Arg Phe Thr Ile Ser Arg
    210                 215                 220

Asp Asn Ala Lys Asn Thr Ala Tyr Leu Gln Met Asn Ser Leu Lys Pro
225                 230                 235                 240

Glu Asp Thr Ala Val Tyr Tyr Cys Thr Ser Asp Pro Arg Arg Gly Trp
                245                 250                 255

Asp Thr Arg Tyr Trp Gly Gln Gly Thr Leu Val Thr Val Ser Ser
                260                 265                 270
```

<210> SEQ ID NO 275
<211> LENGTH: 273
<212> TYPE: PRT
<213> ORGANISM: Artificial Sequence
<220> FEATURE:
<223> OTHER INFORMATION: Nanobody sequence

<400> SEQUENCE: 275

```
Glu Val Gln Leu Val Glu Ser Gly Gly Gly Leu Val Gln Ala Gly Gly
1               5                   10                  15

Ser Leu Arg Leu Ser Cys Val Ala Ser Gly Arg Thr Phe Ser Ser Tyr
                20                  25                  30

Ala Met Gly Trp Phe Arg Gln Ala Pro Gly Lys Glu Arg Ala Phe Val
            35                  40                  45

Ala Gly Ile Ser Gly Ser Ala Ser Arg Lys Tyr Tyr Ala Asp Ser Val
        50                  55                  60

Lys Gly Arg Phe Thr Val Ser Arg Asp Asn Ala Arg Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Asn Ser Tyr Pro Lys Val Gln Phe Asp Tyr Tyr Gly Gln
            100                 105                 110

Gly Thr Gln Val Thr Val Ser Ser Gly Gly Gly Ser Gly Gly Gly
        115                 120                 125

Gly Ser Gly Gly Gly Ser Gly Gly Gly Ser Gly Gly Gly
    130                 135                 140

Ser Gly Gly Gly Ser Gly Gly Gly Ser Glu Val Gln Leu Val
145                 150                 155                 160

Glu Ser Gly Gly Ser Val Gln Ala Gly Glu Ser Leu Arg Leu Ser
                165                 170                 175

Cys Ala Ala Ser Gly Ser Ile Phe Ser Ser Asn Ala Met Ala Trp Tyr
            180                 185                 190

Arg Gln Ala Pro Gly Lys Arg Arg Asp Leu Val Ala Ala Ile Asn Ser
        195                 200                 205

Val Gly Val Thr Lys Tyr Ala Asp Ser Val Lys Gly Arg Phe Thr Ile
    210                 215                 220

Ser Arg Asp Asn Ala Lys Asn Thr Val Tyr Leu Gln Met Asn Ser Leu
225                 230                 235                 240

Lys Pro Glu Asp Thr Ala Val Tyr Tyr Cys Thr Ser Asp Pro Arg Arg
                245                 250                 255

Gly Trp Asp Thr Arg Tyr Trp Gly Gln Gly Thr Gln Val Thr Val Ser
            260                 265                 270

Ser
```

<210> SEQ ID NO 276
<211> LENGTH: 273
<212> TYPE: PRT

```
<213> ORGANISM: Artificial Sequence
<220> FEATURE:
<223> OTHER INFORMATION: Nanobody sequence

<400> SEQUENCE: 276

Glu Val Gln Leu Val Glu Ser Gly Gly Gly Leu Val Gln Ala Gly Gly
1               5                   10                  15

Ser Leu Arg Leu Ser Cys Val Ala Ser Gly Arg Thr Phe Ser Ser Tyr
            20                  25                  30

Ala Met Gly Trp Phe Arg Gln Ala Pro Gly Lys Glu Arg Ala Phe Val
        35                  40                  45

Ala Gly Ile Ser Gly Ser Ala Ser Arg Lys Tyr Tyr Ala Asp Ser Val
    50                  55                  60

Lys Gly Arg Phe Thr Val Ser Arg Asp Asn Ala Arg Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ser Asn Ser Tyr Pro Lys Val Gln Phe Asp Tyr Tyr Gly Gln
            100                 105                 110

Gly Thr Gln Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Glu Val Gln Leu Val
145                 150                 155                 160

Glu Ser Gly Gly Gly Ser Val Gln Ala Gly Glu Ser Leu Arg Leu Ser
                165                 170                 175

Cys Ala Ala Ser Gly Ser Ile Phe Ser Ser Asn Ala Met Ala Trp Tyr
            180                 185                 190

Arg Gln Ala Pro Gly Lys Gln Arg Asp Leu Val Ala Gly Ile Asn Ser
        195                 200                 205

Val Gly Ile Thr Lys Tyr Ala Asp Ser Val Lys Gly Arg Phe Thr Ile
    210                 215                 220

Ser Arg Asp Asn Ala Lys Asn Thr Ala Tyr Leu Gln Met Asn Ser Leu
225                 230                 235                 240

Lys Pro Glu Asp Thr Ala Val Tyr Tyr Cys Thr Ser Asp Pro Arg Arg
                245                 250                 255

Gly Trp Asp Thr Arg Tyr Trp Gly Gln Gly Thr Leu Val Thr Val Ser
            260                 265                 270

Ser

<210> SEQ ID NO 277
<211> LENGTH: 369
<212> TYPE: PRT
<213> ORGANISM: Artificial Sequence
<220> FEATURE:
<223> OTHER INFORMATION: Nanobody sequence

<400> SEQUENCE: 277

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Ser Val Gly Val Thr Lys Tyr Ala Asp Ser Val Lys
```

```
                    50                  55                  60
Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                 85                  90                  95

Ser Asp Pro Arg Arg Gly Trp Asp Thr Arg Tyr Trp Gly Gln Gly Thr
            100                 105                 110

Gln Val Thr Val Ser Ser Gly Gly Gly Ser Gly Gly Gly Ser Glu
        115                 120                 125

Val Gln Leu Val Glu Ser Gly Gly Ser Val Gln Ala Gly Glu Ser
    130                 135                 140

Leu Arg Leu Ser Cys Ala Ala Ser Gly Ser Ile Phe Ser Ser Asn Ala
145                 150                 155                 160

Met Ala Trp Tyr Arg Gln Ala Pro Gly Lys Arg Arg Asp Leu Val Ala
                165                 170                 175

Ala Ile Asn Ser Val Gly Val Thr Lys Tyr Ala Asp Ser Val Lys Gly
            180                 185                 190

Arg Phe Thr Ile Ser Arg Asp Asn Ala Lys Asn Thr Val Tyr Leu Gln
        195                 200                 205

Met Asn Ser Leu Lys Pro Glu Asp Thr Ala Val Tyr Tyr Cys Thr Ser
    210                 215                 220

Asp Pro Arg Arg Gly Trp Asp Thr Arg Tyr Trp Gly Gln Gly Thr Gln
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Leu Val Gln Pro Gly Asn Ser Leu
            260                 265                 270

Arg Leu Ser Cys Ala Ala Ser Gly Phe Thr Phe Ser Ser Phe Gly Met
        275                 280                 285

Ser Trp Val Arg Gln Ala Pro Gly Lys Gly Leu Glu Trp Val Ser Ser
    290                 295                 300

Ile Ser Gly Ser Gly Ser Asp Thr Leu Tyr Ala Asp Ser Val Lys Gly
305                 310                 315                 320

Arg Phe Thr Ile Ser Arg Asp Asn Ala Lys Thr Thr Leu Tyr Leu Gln
                325                 330                 335

Met Asn Ser Leu Arg Pro Glu Asp Thr Ala Val Tyr Tyr Cys Thr Ile
            340                 345                 350

Gly Gly Ser Leu Ser Arg Ser Ser Gln Gly Thr Leu Val Thr Val Ser
        355                 360                 365

Ser

<210> SEQ ID NO 278
<211> LENGTH: 395
<212> TYPE: PRT
<213> ORGANISM: Artificial Sequence
<220> FEATURE:
<223> OTHER INFORMATION: Nanobody sequence

<400> SEQUENCE: 278

Glu Val Gln Leu Val Glu Ser Gly Gly Gly Ser Val Gln Ala Gly Glu
 1               5                  10                  15

Ser Leu Arg Leu Ser Cys Ala Ala Ser Gly Ser Ile Phe Ser Ser Asn
                20                  25                  30

Ala Met Ala Trp Tyr Arg Gln Ala Pro Gly Lys Arg Arg Asp Leu Val
            35                  40                  45
```

Ala Ala Ile Asn Ser Val Gly Val Thr Lys Tyr Ala Asp Ser Val Lys
            50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                 85                  90                  95

Ser Asp Pro Arg Arg Gly Trp Asp Thr Arg Tyr Trp Gly Gln Gly Thr
                100                 105                 110

Gln Val Thr Val Ser Ser Gly Gly Gly Gly Ser Gly Gly Gly Gly Ser
                115                 120                 125

Gly Gly Gly Gly Ser Gly Gly Gly Ser Gly Gly Gly Gly Ser Gly
130                 135                 140

Gly Gly Ser Gly Gly Gly Ser Glu Val Gln Leu Val Glu Ser
145                 150                 155                 160

Gly Gly Gly Ser Val Gln Ala Gly Glu Ser Leu Arg Leu Ser Cys Ala
                165                 170                 175

Ala Ser Gly Ser Ile Phe Ser Ser Asn Ala Met Ala Trp Tyr Arg Gln
                180                 185                 190

Ala Pro Gly Lys Arg Arg Asp Leu Val Ala Ala Ile Asn Ser Val Gly
                195                 200                 205

Val Thr Lys Tyr Ala Asp Ser Val Lys Gly Arg Phe Thr Ile Ser Arg
210                 215                 220

Asp Asn Ala Lys Asn Thr Val Tyr Leu Gln Met Asn Ser Leu Lys Pro
225                 230                 235                 240

Glu Asp Thr Ala Val Tyr Tyr Cys Thr Ser Asp Pro Arg Arg Gly Trp
                245                 250                 255

Asp Thr Arg Tyr Trp Gly Gln Gly Thr Gln Val Thr Val Ser Ser Gly
                260                 265                 270

Gly Gly Ser Gly Gly Gly Ser Glu Val Gln Leu Val Glu Ser Gly
            275                 280                 285

Gly Gly Leu Val Gln Pro Gly Asn Ser Leu Arg Leu Ser Cys Ala Ala
            290                 295                 300

Ser Gly Phe Thr Phe Ser Ser Phe Gly Met Ser Trp Val Arg Gln Ala
305                 310                 315                 320

Pro Gly Lys Gly Leu Glu Trp Val Ser Ser Ile Ser Gly Ser Gly Ser
                325                 330                 335

Asp Thr Leu Tyr Ala Asp Ser Val Lys Gly Arg Phe Thr Ile Ser Arg
                340                 345                 350

Asp Asn Ala Lys Thr Thr Leu Tyr Leu Gln Met Asn Ser Leu Arg Pro
                355                 360                 365

Glu Asp Thr Ala Val Tyr Tyr Cys Thr Ile Gly Gly Ser Leu Ser Arg
                370                 375                 380

Ser Ser Gln Gly Thr Leu Val Thr Val Ser Ser
385                 390                 395

<210> SEQ ID NO 279
<211> LENGTH: 395
<212> TYPE: PRT
<213> ORGANISM: Artificial Sequence
<220> FEATURE:
<223> OTHER INFORMATION: Nanobody sequence

<400> SEQUENCE: 279

Glu Val Gln Leu Val Glu Ser Gly Gly Gly Ser Val Gln Ala Gly Glu
 1               5                  10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Ser Val Gly Val Thr Lys Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Thr
                85                  90                  95

Ser Asp Pro Arg Arg Gly Trp Asp Thr Arg Tyr Trp Gly Gln Gly Thr
            100                 105                 110

Gln Val Thr Val Ser Ser Gly Gly Gly Gly Ser Gly Gly Gly Ser Glu
        115                 120                 125

Val Gln Leu Val Glu Ser Gly Gly Ser Val Gln Ala Gly Glu Ser
130                 135                 140

Leu Arg Leu Ser Cys Ala Ala Ser Gly Ser Ile Phe Ser Ser Asn Ala
145                 150                 155                 160

Met Ala Trp Tyr Arg Gln Ala Pro Gly Lys Arg Arg Asp Leu Val Ala
            165                 170                 175

Ala Ile Asn Ser Val Gly Val Thr Lys Tyr Ala Asp Ser Val Lys Gly
        180                 185                 190

Arg Phe Thr Ile Ser Arg Asp Asn Ala Lys Asn Thr Val Tyr Leu Gln
    195                 200                 205

Met Asn Ser Leu Lys Pro Glu Asp Thr Ala Val Tyr Tyr Cys Thr Ser
210                 215                 220

Asp Pro Arg Arg Gly Trp Asp Thr Arg Tyr Trp Gly Gln Gly Thr Gln
225                 230                 235                 240

Val Thr Val Ser Ser Gly Gly Gly Ser Gly Gly Gly Ser Gly
            245                 250                 255

Gly Gly Gly Ser Gly Gly Gly Ser Gly Gly Gly Ser Gly Gly
            260                 265                 270

Gly Gly Ser Gly Gly Gly Ser Glu Val Gln Leu Val Glu Ser Gly
        275                 280                 285

Gly Gly Leu Val Gln Pro Gly Asn Ser Leu Arg Leu Ser Cys Ala Ala
        290                 295                 300

Ser Gly Phe Thr Phe Ser Ser Phe Gly Met Ser Trp Val Arg Gln Ala
305                 310                 315                 320

Pro Gly Lys Gly Leu Glu Trp Val Ser Ser Ile Ser Gly Ser Gly Ser
            325                 330                 335

Asp Thr Leu Tyr Ala Asp Ser Val Lys Gly Arg Phe Thr Ile Ser Arg
        340                 345                 350

Asp Asn Ala Lys Thr Thr Leu Tyr Leu Gln Met Asn Ser Leu Arg Pro
    355                 360                 365

Glu Asp Thr Ala Val Tyr Tyr Cys Thr Ile Gly Gly Ser Leu Ser Arg
        370                 375                 380

Ser Ser Gln Gly Thr Leu Val Thr Val Ser Ser
385                 390                 395

<210> SEQ ID NO 280
<211> LENGTH: 421
<212> TYPE: PRT
<213> ORGANISM: Artificial Sequence
<220> FEATURE:

<223> OTHER INFORMATION: Nanobody sequence

<400> SEQUENCE: 280

```
Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
        35                  40                  45

Ala Ala Ile Asn Ser Val Gly Val Thr Lys Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
            85                  90                  95

Ser Asp Pro Arg Arg Gly Trp Asp Thr Arg Tyr Trp Gly Gln Gly Thr
        100                 105                 110

Gln Val Thr Val Ser Ser Gly Gly Gly Ser Gly Gly Gly Gly Gly Ser
        115                 120                 125

Gly Gly Gly Gly Ser Gly Gly Gly Ser Gly Gly Gly Gly Ser Gly
130                 135                 140

Gly Gly Ser Gly Gly Gly Ser Glu Val Gln Leu Val Glu Ser
145                 150                 155                 160

Gly Gly Gly Ser Val Gln Ala Gly Glu Ser Leu Arg Leu Ser Cys Ala
            165                 170                 175

Ala Ser Gly Ser Ile Phe Ser Ser Asn Ala Met Ala Trp Tyr Arg Gln
        180                 185                 190

Ala Pro Gly Lys Arg Arg Asp Leu Val Ala Ala Ile Asn Ser Val Gly
        195                 200                 205

Val Thr Lys Tyr Ala Asp Ser Val Lys Gly Arg Phe Thr Ile Ser Arg
    210                 215                 220

Asp Asn Ala Lys Asn Thr Val Tyr Leu Gln Met Asn Ser Leu Lys Pro
225                 230                 235                 240

Glu Asp Thr Ala Val Tyr Tyr Cys Thr Ser Asp Pro Arg Arg Gly Trp
            245                 250                 255

Asp Thr Arg Tyr Trp Gly Gln Gly Thr Gln Val Thr Val Ser Ser Gly
        260                 265                 270

Gly Gly Ser Gly Gly Gly Gly Ser Gly Gly Gly Ser Gly Gly
            275                 280                 285

Gly Gly Ser Gly Gly Gly Ser Gly Gly Gly Ser Gly Gly Gly
        290                 295                 300

Gly Ser Glu Val Gln Leu Val Glu Ser Gly Gly Leu Val Gln Pro
305                 310                 315                 320

Gly Asn Ser Leu Arg Leu Ser Cys Ala Ala Ser Gly Phe Thr Phe Ser
            325                 330                 335

Ser Phe Gly Met Ser Trp Val Arg Gln Ala Pro Gly Lys Gly Leu Glu
        340                 345                 350

Trp Val Ser Ser Ile Ser Gly Ser Gly Ser Asp Thr Leu Tyr Ala Asp
        355                 360                 365

Ser Val Lys Gly Arg Phe Thr Ile Ser Arg Asp Asn Ala Lys Thr Thr
    370                 375                 380

Leu Tyr Leu Gln Met Asn Ser Leu Arg Pro Glu Asp Thr Ala Val Tyr
385                 390                 395                 400
```

```
Tyr Cys Thr Ile Gly Gly Ser Leu Ser Arg Ser Ser Gln Gly Thr Leu
            405                 410                 415

Val Thr Val Ser Ser
            420

<210> SEQ ID NO 281
<211> LENGTH: 421
<212> TYPE: PRT
<213> ORGANISM: Artificial Sequence
<220> FEATURE:
<223> OTHER INFORMATION: Nanobody sequence

<400> SEQUENCE: 281

Glu Val Gln Leu Val Glu Ser Gly Gly Gly Ser Val Gln Ala Gly Glu
1               5                   10                  15

Ser Leu Arg Leu Ser Cys Ala Ala Ser Gly Ser Ile Phe Ser Ser Asn
            20                  25                  30

Ala Met Ala Trp Tyr Arg Gln Ala Pro Gly Lys Arg Arg Asp Leu Val
            35                  40                  45

Ala Ala Ile Asn Ser Val Gly Val Thr Lys Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Thr
            85                  90                  95

Ser Asp Pro Arg Arg Gly Trp Asp Thr Arg Tyr Trp Gly Gln Gly Thr
            100                 105                 110

Gln Val Thr Val Ser Ser Gly Gly Gly Ser Gly Gly Gly Gly Ser
            115                 120                 125

Gly Gly Gly Gly Ser Gly Gly Gly Ser Gly Gly Gly Ser Gly
            130                 135                 140

Gly Gly Gly Ser Gly Gly Gly Ser Glu Val Gln Leu Val Glu Ser
145                 150                 155                 160

Gly Gly Gly Leu Val Gln Pro Gly Asn Ser Leu Arg Leu Ser Cys Ala
            165                 170                 175

Ala Ser Gly Phe Thr Phe Ser Ser Phe Gly Met Ser Trp Val Arg Gln
            180                 185                 190

Ala Pro Gly Lys Gly Leu Glu Trp Val Ser Ser Ile Ser Gly Ser Gly
            195                 200                 205

Ser Asp Thr Leu Tyr Ala Asp Ser Val Lys Gly Arg Phe Thr Ile Ser
            210                 215                 220

Arg Asp Asn Ala Lys Thr Thr Leu Tyr Leu Gln Met Asn Ser Leu Arg
225                 230                 235                 240

Pro Glu Asp Thr Ala Val Tyr Tyr Cys Thr Ile Gly Gly Ser Leu Ser
            245                 250                 255

Arg Ser Ser Gln Gly Thr Leu Thr Val Ser Ser Gly Gly Gly Gly
            260                 265                 270

Ser Gly Gly Gly Gly Ser Gly Gly Gly Ser Gly Gly Gly Ser
            275                 280                 285
```

```
Gly Gly Gly Ser Gly Gly Gly Ser Gly Gly Gly Ser Glu
    290             295             300
Val Gln Leu Val Glu Ser Gly Gly Ser Val Gln Ala Gly Glu Ser
305             310             315             320
Leu Arg Leu Ser Cys Ala Ala Ser Gly Ser Ile Phe Ser Ser Asn Ala
                325             330             335
Met Ala Trp Tyr Arg Gln Ala Pro Gly Lys Arg Arg Asp Leu Val Ala
            340             345             350
Ala Ile Asn Ser Val Gly Val Thr Lys Tyr Ala Asp Ser Val Lys Gly
            355             360             365
Arg Phe Thr Ile Ser Arg Asp Asn Ala Lys Asn Thr Val Tyr Leu Gln
370             375             380
Met Asn Ser Leu Lys Pro Glu Asp Thr Ala Val Tyr Tyr Cys Thr Ser
385             390             395             400
Asp Pro Arg Arg Gly Trp Asp Thr Arg Tyr Trp Gly Gln Gly Thr Gln
                405             410             415
Val Thr Val Ser Ser
            420

<210> SEQ ID NO 282
<211> LENGTH: 275
<212> TYPE: PRT
<213> ORGANISM: Artificial Sequence
<220> FEATURE:
<223> OTHER INFORMATION: Nanobody sequence

<400> SEQUENCE: 282

Glu Val Gln Leu Val Glu Ser Gly Gly Gly Leu Val Gln Ala Gly Gly
1               5                   10                  15
Ser Leu Arg Leu Ser Cys Val Ala Ser Gly Arg Thr Phe Ser Ser Tyr
            20                  25                  30
Ala Met Gly Trp Phe Arg Gln Ala Pro Gly Lys Glu Arg Ala Phe Val
        35                  40                  45
Ala Gly Ile Ser Gly Ser Ala Ser Arg Lys Tyr Tyr Ala Asp Ser Val
    50                  55                  60
Lys Gly Arg Phe Thr Val Ser Arg Asp Asn Ala Arg Asn Thr Val Tyr
65                  70                  75                  80
Leu Gln Met Asn Ser Leu Lys Pro Glu Asp Thr Ala Val Tyr Tyr Cys
                85                  90                  95
Ala Ala Ser Asn Ser Tyr Pro Lys Val Gln Phe Asp Tyr Tyr Gly Gln
            100                 105                 110
Gly Thr Leu Val Thr Val Ser Ser Gly Gly Gly Ser Gly Gly Gly Gly
        115                 120                 125
Gly Ser Gly Gly Gly Ser Gly Gly Gly Ser Gly Gly Gly Gly
    130                 135                 140
Ser Gly Gly Gly Ser Gly Gly Gly Ser Glu Val Gln Leu Val
145                 150                 155                 160
Glu Ser Gly Gly Gly Leu Val Gln Ala Gly Gly Ser Leu Arg Leu Ser
                165                 170                 175
Cys Val Ala Ser Gly Arg Thr Phe Ser Ser Tyr Ala Met Gly Trp Phe
            180                 185                 190
Arg Gln Ala Pro Gly Lys Glu Arg Ala Phe Val Ala Gly Ile Ser Gly
        195                 200                 205
Ser Ala Ser Arg Lys Tyr Tyr Ala Asp Ser Val Lys Gly Arg Phe Thr
    210                 215                 220
```

-continued

```
Val Ser Arg Asp Asn Ala Arg Asn Thr Val Tyr Leu Gln Met Asn Ser
225                 230                 235                 240

Leu Lys Pro Glu Asp Thr Ala Val Tyr Tyr Cys Ala Ala Ser Asn Ser
                245                 250                 255

Tyr Pro Lys Val Gln Phe Asp Tyr Tyr Gly Gln Gly Thr Leu Val Thr
            260                 265                 270

Val Ser Ser
        275
```